United States Patent
Banville

(10) Patent No.: US 10,214,544 B2
(45) Date of Patent: Feb. 26, 2019

(54) IMIDAZOPYRIDAZINE AND IMIDAZOTHIADIAZOLE COMPOUNDS

(71) Applicant: Universite de Montreal, Montreal (CA)

(72) Inventor: Jacques Banville, Montreal (CA)

(73) Assignee: Universite De Montreal, Montreal, QC (CA)

( * ) Notice: Subject to any disclaimer, the term of this patent is extended or adjusted under 35 U.S.C. 154(b) by 0 days.

(21) Appl. No.: 15/549,257

(22) PCT Filed: Feb. 25, 2016

(86) PCT No.: PCT/CA2016/000050
§ 371 (c)(1),
(2) Date: Aug. 7, 2017

(87) PCT Pub. No.: WO2016/134450
PCT Pub. Date: Sep. 1, 2016

(65) Prior Publication Data
US 2018/0237457 A1    Aug. 23, 2018

Related U.S. Application Data

(60) Provisional application No. 62/120,971, filed on Feb. 26, 2015.

(51) Int. Cl.
*C07D 513/04* (2006.01)
*A61K 31/433* (2006.01)
*A61P 9/00* (2006.01)
*A61K 31/4439* (2006.01)
*A61K 31/497* (2006.01)
*A61K 31/501* (2006.01)
*A61K 31/506* (2006.01)

(52) U.S. Cl.
CPC .......... *C07D 513/04* (2013.01); *A61K 31/433* (2013.01); *A61K 31/4439* (2013.01); *A61K 31/497* (2013.01); *A61K 31/501* (2013.01); *A61K 31/506* (2013.01); *A61P 9/00* (2018.01); *C07B 2200/07* (2013.01); *C07B 2200/09* (2013.01)

(58) Field of Classification Search
CPC .................................................. C07D 513/04
USPC .................................................. 514/252.06
See application file for complete search history.

(56) References Cited

U.S. PATENT DOCUMENTS

| | | |
|---|---|---|
| 8,927,688 B2 | 1/2015 | Kornacker et al. |
| 9,303,065 B2 | 4/2016 | Kornacker et al. |
| 2013/0289238 A1 | 10/2013 | Kornacker et al. |
| 2015/0094297 A1 | 4/2015 | Banville et al. |
| 2015/0119390 A1 | 4/2015 | Martel et al. |
| 2015/0133446 A1 | 5/2015 | Lawrence et al. |
| 2015/0158910 A1 | 6/2015 | Kornacker et al. |

FOREIGN PATENT DOCUMENTS

| | | | |
|---|---|---|---|
| WO | 2013/163241 A1 | 10/2013 | |
| WO | 2013/163244 A1 | 10/2013 | |
| WO | 2013/163248 | * 10/2013 | |
| WO | 2013/163279 A1 | 10/2013 | |

OTHER PUBLICATIONS

International Search Report issued in PCT/CA2016/000050, dated May 6, 2016 (3 pages).
International Written Opinion issued in PCT/CA2016/000050, dated May 6, 2016 (5 pages).

* cited by examiner

*Primary Examiner* — Taofiq A Solola
(74) *Attorney, Agent, or Firm* — Hoffmann & Baron, LLP

(57) ABSTRACT

The present invention provides imidazopyridazine compounds or imidazothiadiazole compounds of Formula I having the structure: (I) wherein $X^1$, $X^2$, $X^3$, $X^4$, $X^5$, Y, W, $R^1$, $R^2$, $R^3$, $R^4$, $R^5$ and (II) are as defined herein, or a stereoisomer, tautomer, pharmaceutically acceptable salt, prodrug ester or solvate form thereof. These compounds are inhibitors of platelet aggregation and thus can be used as medicaments for treating or preventing thromboembolic disorders.

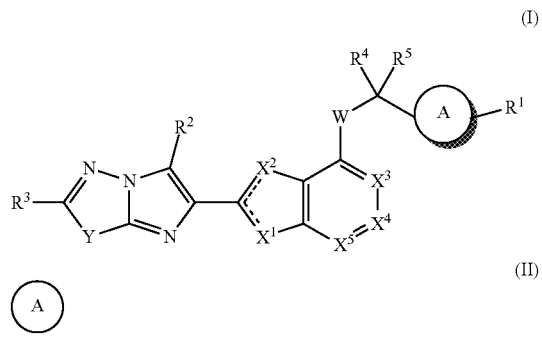

18 Claims, No Drawings

IMIDAZOPYRIDAZINE AND IMIDAZOTHIADIAZOLE COMPOUNDS

CROSS-REFERENCE TO RELATED APPLICATION

This application is the National Stage of International Application No. PCT/CA2016/000050, filed on Feb. 25, 2016, which claims the benefit of priority from U.S. Provisional Patent Application No. 62/120,971, filed on Feb. 26, 2015, the contents of which are incorporated by reference herein in their entirety.

FIELD OF THE INVENTION

The present invention provides novel imidazopyridazine and imidazothiadiazole inhibitors of platelet aggregation which are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.*, 366(1):20-33 (2012). Vorapaxar is currently being marketed as Zontivity® by Merck. Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

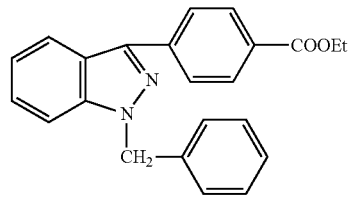

58

"was found to be a selective and potent inhibitor of protease-activated receptor type 4 (PAR4)-dependent platelet activation."

Compound 58 is also referred to as YD-3 in Wu, C-C. et al., "Selective Inhibition of Protease-activated Receptor 4-Dependent Platelet Activation by YD-3", *Thromb. Haemost.*, 87:1026-1033 (2002). Also, see Chen, H. S. et al., "Synthesis and antiplatelet activity of ethyl 4-(1-benzyl-1H-indazol-3-yl)benzoate (YD-3) derivatives", *Bioorg. Med. Chem.*, 16:1262-1278 (2008).

EP1166785 A1 and EP0667345 disclose various pyrazole derivatives which are useful as inhibitors of platelet aggregation.

The PCT publications WO2013/163279, WO2013/163244 and WO2013/163241 disclose various PAR4 antagonists which are useful as inhibitors of platelet aggregation.

SUMMARY OF THE INVENTION

It has been found that compounds of Formula (I) in accordance with the present invention are PAR4 antagonists which inhibit platelet aggregation in gamma-thrombin induced platelet aggregation assays.

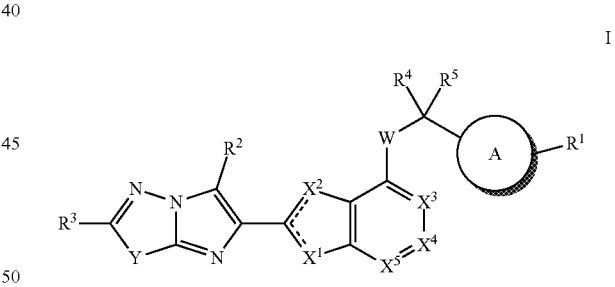

I wherein the various moieties are as defined herein.

Accordingly, the present invention provides novel imidazopyridazine and imidazothiadiazole analogues which are PAR4 antagonists and are useful as selective inhibitors of platelet aggregation, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other features and advantages of the invention will be apparent from the following detailed description and claims.

DETAILED DESCRIPTION

In one embodiment, the present invention provides imidazopyridazine or imidazothiadiazole compounds, stereoisomers, tautomers, salts, solvates or prodrugs thereof, of Formula:

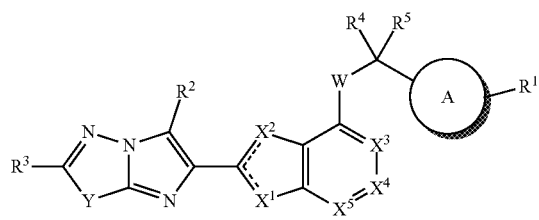

or a stereoisomer, tautomer, pharmaceutically acceptable salt, solvate or prodrug thereof, wherein:

the dashed line represents an optional double-bond with the proviso that only one of the two dashed line double bonds exists at the same time;

$X^1$ is O and $X^2$ is $CR^{1a}$ or N; or
$X^1$ is N and $X^2$ is O; or
$X^1$ is N or $CR^{1a}$, and $X^2$ is S; or
$X^1$ is N and $X^2$ is $NR^8$; or
$X^1$ is $NR^8$ and $X^2$ is N; or
$X^1$ is $NR^8$ and $X^2$ is $CR^{1a}$; or
$X^1$ is $CR^{1a}$ and $X^2$ is $NR^8$;
Y is S or —$CR^{2a}$=$CR^{2a}$—;
$X^3$, $X^4$ and $X^5$ are independently selected from $C(R^9)$ or N;
W is O or S;
$R^1$ is —$N(R^6)$—$C(O)$—$R^7$ or —$N(R^6)$—$S(O)_2$—$R^7$;

is selected from the group consisting of a phenyl ring, a 5-membered heteroaryl ring containing at least one N, S or O as a hetero atom on the ring, or a 6-membered heteroaryl ring containing at least one nitrogen atom, or alternately the moiety

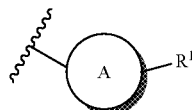

is selected from

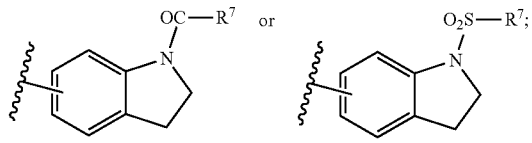

$R^{1a}$ is selected from the group consisting of H, halo, cyano, $C_1$-$C_4$ alkyl, $C_3$-$C_5$ cycloalkyl and $C_1$-$C_4$ alkoxy;

$R^2$ is H, halo, $C_1$-$C_6$ alkyl, $C_1$-$C_3$ alkoxy, CN or $C_3$-$C_7$ cycloalkyl;

$R^{2a}$ is independently at each occurrence selected from the group consisting of H, halo, CN, $C_1$-$C_3$ alkyl, $C_{1-3}$ haloalkyl, $C_1$-$C_3$ alkoxy, and $C_1$-$C_3$ haloalkoxy;

$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^6$ is selected from H, $C_1$-$C_6$ alkyl, $C_1$-$C_3$ haloalkyl, or $C_1$-$C_3$hydroxyalkyl; and $R^7$ is selected from the group consisting of hydrogen, $C_1$-$C_6$ alkyl, $C_6$-$C_{10}$ aryl, $C_1$-$C_7$ alkoxy, 5-7 membered heterocyclic ring containing 1-3 hetero atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, $NR^{10}SO_2R^{11}$, $NR^{10}COR^{11}$, $NR^{10}CONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional heteroatoms selected independently from N, O, or S, wherein each of said monocyclic or bicyclic heterolyic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N they are attached to to form a 4-7 membered heterocycle ring.

$R^8$ is H or $C_1$-$C_4$ alkyl; and $R^9$ is selected from the group consisting of H, halo, $C_1$-$C_6$ alkyl, $C_{1-6}$ haloalkyl, —$C_1$-$C_6$ alkoxy and $C_1$-$C_3$ haloalkoxy; with the proviso that when Y is S and A is

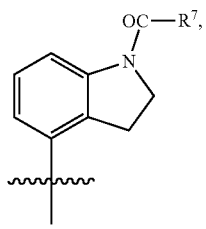

then $R^7$ is not pyridizin-4-yl.

In another embodiment, the present invention provides imidazopyridazine or imidazothiadiazole compounds, stereoisomers, tautomers, salts, solvates or prodrugs thereof, of Formula I having the structure:

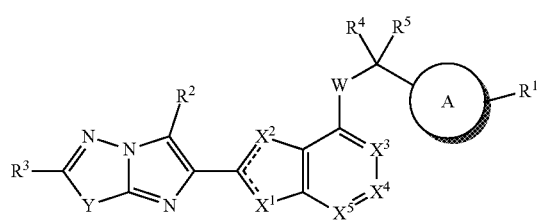

I or a stereoisomer, tautomer, pharmaceutically acceptable salt, solvate or prodrug thereof, wherein:

the dashed line represents an optional double-bond with the proviso that only one of the two dashed line double bonds exists at the same time;

$X^1$ is O and $X^2$ is $CR^{1a}$ or N; or $X^1$ is N and $X^2$ is O; or $X^1$ is N or $CR^{1a}$, and $X^2$ is S; or $X^1$ is N and $X^2$ is $NR^8$; or $X^1$ is $NR^8$ and $X^2$ is N; or $X^1$ is $NR^8$ and $X^2$ is $CR^{1a}$; or $X^1$ is $CR^{1a}$ and $X^2$ is $NR^8$;

Y is S or —$CR^{2a}$=$CR^{2a}$—;

$X^3$, $X^4$ and $X^5$ are independently selected from C($R^9$) or N;

W is O or S;

$R^1$ is —N($R^6$)—C(O)—$R^7$ or —N($R^6$)—S(O)$_2$—$R^7$;

is selected from the group consisting of a phenyl ring, or a 6-membered heteroaryl ring containing at least one nitrogen atom, or alternately the moiety

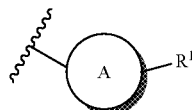

is selected from

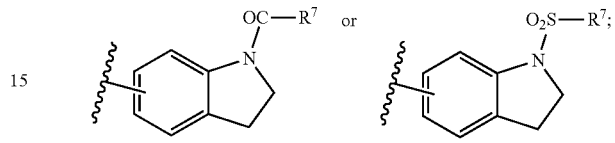

$R^{1a}$ is selected from the group consisting of H, halo, cyano, $C_1$-$C_4$ alkyl, $C_3$-$C_5$ cycloalkyl and $C_1$-$C_4$ alkoxy;

$R^2$ is H, halo, $C_1$-$C_6$ alkyl, $C_1$-$C_3$ alkoxy, CN or $C_3$-$C_7$ cycloalkyl;

$R^{2a}$ is independently at each occurrence selected from the group consisting of H, halo, CN, $C_1$-$C_3$ alkyl, $C_{1-3}$ haloalkyl, $C_1$-$C_3$ alkoxy, and $C_1$-$C_3$ haloalkoxy;

$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^6$ is selected from H, $C_1$-$C_6$ alkyl, $C_1$-$C_3$ haloalkyl, or $C_1$-$C_3$ hydroxyalkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 hetero (ring) atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, $NR^{10}SO_2R^{11}$, $NR^{10}COR^{11}$, $NR^{10}CONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N they are attached to to form a 4-7 membered heterocycle ring.

$R^8$ is H or $C_1$-$C_4$ alkyl; and $R^9$ is selected from the group consisting of H, halo, $C_1$-$C_6$ alkyl, $C_{1-6}$ haloalkyl, —$C_1$-$C_6$ alkoxy and $C_1$-$C_3$ haloalkoxy; with the proviso that when Y is S and A is then $R^7$ is not pyridizin-4-yl.

The term "at least one nitrogen atom" in the definition of the moiety means 1-3 nitrogen atoms.

In an embodiment, $X^1$ is O and $X^2$ is $CR^{1a}$ or N; or $X^1$ is N and $X^2$ is O; or $X^1$ is N or $CR^{1a}$, and $X^2$ is S.

In an embodiment, Y is S.

In an embodiment, Y is —$CR^{2a}$=$CR^{2a}$—, and both $R^{2a}$ are H making Y the moiety-CH=CH—. When Y is S, Formula I is Formula IA:

IA or a stereoisomer, tautomer, pharmaceutically acceptable salt, solvate or prodrug thereof, wherein:

the dashed line represents an optional double-bond with the proviso that only one of the two dashed line double bonds exists at the same time;

$X^1$ is O and $X^2$ is $CR^{1a}$ or N; or $X^1$ is N and $X^2$ is O; or $X^1$ is N or $CR^{1a}$, and $X^2$ is S;

$X^3$, $X^4$ and $X^5$ are independently selected from $C(R^9)$ or N;

W is O or S;

$R^1$ is —$N(R^6)$—$C(O)$—$R^7$ or —$N(R^6)$—$S(O)_2$—$R^7$;

is selected from the group consisting of a phenyl ring, or a 6-membered heteroaryl ring containing at least one nitrogen atom, or alternately the moiety is selected from $R^{1a}$ is selected from the group consisting of H, halo, cyano, $C_1$-$C_4$ alkyl, $C_3$-$C_5$ cycloalkyl and $C_1$-$C_4$ alkoxy;

$R^2$ is H, halo, $C_1$-$C_6$ alkyl, $C_1$-$C_3$ alkoxy, CN or $C_3$-$C_7$ cycloalkyl;

$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{3-6}$ cycloalkyl, $C_{2-3}$ alkenyl, $C_{2-3}$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^8$ is H or $C_1$-$C_4$ alkyl;

$R^9$ is selected from the group consisting of H, halo, $C_1$-$C_6$ alkyl, halo$C_{1-6}$ alkyl, —O—($C_1$-$C_6$ alkyl) and halo$C_{1-3}$ alkoxy;

$R^6$ is selected from H, $C_1$-$C_6$ alkyl, halo$C_{1-3}$alkyl, or hydroxy$C_{1-3}$alkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring, with the proviso that when A is

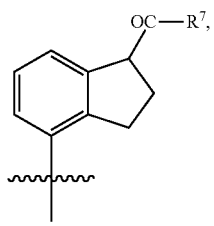

then $R^7$ is not pyridizin-4-yl.

When Y is —CH=CH—, Formula I is Formula IB

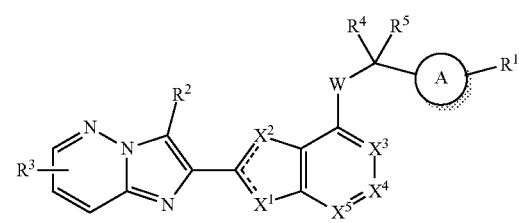

IB wherein:

the dashed line represents an optional double-bond with the proviso that only one of the two dashed line double bonds exists at the same time;

$X^1$ is O and $X^2$ is $CR^{1a}$ or N; or $X^1$ is N and $X^2$ is O; or $X^1$ is N or $CR^{1a}$, and $X^2$ is S;

$X^3$, $X^4$ and $X^5$ are independently selected from $C(R^9)$ or N;

W is O or S;

$R^1$ is —N($R^6$)—C(O)—$R^7$ or —N($R^6$)—S(O)$_2$—$R^7$;

is selected from the group consisting of a phenyl ring, or a 6-membered heteroaryl ring containing at least one nitrogen atom, or alternately the moiety

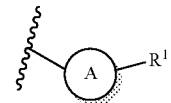

is selected from

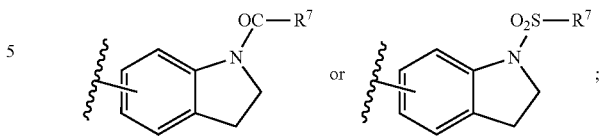

$R^{1a}$ is selected from the group consisting of H, halo, cyano, $C_1$-$C_4$ alkyl, $C_3$-$C_5$ cycloalkyl and $C_1$-$C_4$ alkoxy;

$R^2$ is H, halo, $C_1$-$C_6$ alkyl, $C_1$-$C_3$ alkoxy, CN or $C_3$-$C_7$ cycloalkyl;

$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{3-6}$ cycloalkyl, $C_{2-3}$ alkenyl, $C_{2-3}$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^8$ is H or $C_1$-$C_4$ alkyl;

$R^9$ is selected from the group consisting of H, halo, $C_1$-$C_6$ alkyl, halo$C_{1-6}$ alkyl, —O—($C_1$-$C_6$ alkyl) and halo$C_{1-3}$ alkoxy;

$R^6$ is selected from H, $C_1$-$C_6$ alkyl, halo$C_{1-3}$alkyl, or hydroxy$C_{1-3}$alkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$, CONR$^{12}$R$^{13}$, SONR$^{12}$R$^{13}$, COOH, COOR$^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In another embodiment, the present invention provides imidazopyridazine or imidazothiadiazole compounds, stereoisomers, tautomers, salts, solvates or prodrugs thereof, of Formula:

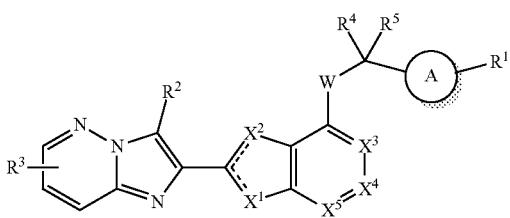

or a stereoisomer, tautomer, pharmaceutically acceptable salt, solvate or prodrug thereof, wherein:

the dashed line represents an optional double-bond with the proviso that only one of the two dashed line double bonds exists at the same time;

$X^1$ is O and $X^2$ is $CR^{1a}$ or N; or
$X^1$ is N and $X^2$ is O; or
$X^1$ is N or $CR^{1a}$, and $X^2$ is S; or
$X^1$ is N and $X^2$ is $NR^8$; or
$X^1$ is NR and $X^2$ is N; or
$X^1$ is $NR^8$ and $X^2$ is $CR^{1a}$; or
$X^1$ is $CR^{1a}$ and $X^2$ is $NR^8$;
Y is S or —$CR^{2a}$=$CR^{2a}$—;
$X^3$, $X^4$ and $X^5$ are independently selected from $C(R^9)$ or N;
W is O or S;
$R^1$ is —$N(R^6)$—C(O)—$R^7$ or —$N(R^6)$—$S(O)_2$—$R^7$;

is selected from the group consisting of a phenyl ring, a 5-membered heteroaryl ring containing at least one N, S or O as a hetero atom on the ring, or a 6-membered heteroaryl ring containing at least one nitrogen atom,
or alternately the moiety

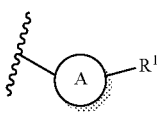

is selected from

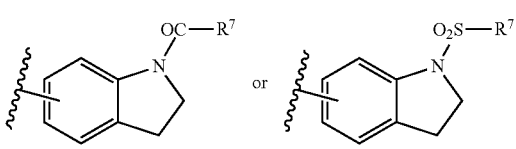

$R^{1a}$ is selected from the group consisting of H, halo, cyano, $C_1$-$C_4$ alkyl, $C_3$-$C_5$ cycloalkyl and $C_1$-$C_4$ alkoxy;

$R^2$ is H, halo, $C_1$-$C_6$ alkyl, $C_1$-$C_3$ alkoxy, CN or $C_3$-$C_7$ cycloalkyl;

$R^{2a}$ is independently at each occurrence selected from the group consisting of H, halo, CN, $C_1$-$C_3$ alkyl, $C_{1-3}$ haloalkyl, $C_1$-$C_3$ alkoxy, and $C_1$-$C_3$ haloalkoxy;

$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^6$ is selected from H, $C_1$-$C_6$ alkyl, $C_1$-$C_3$ haloalkyl, or $C_1$-$C_3$ hydroxyalkyl; and $R^7$ is selected from the group consisting of hydrogen, $C_1$-$C_6$ alkyl, $C_6$-$C_{10}$ aryl, $C_1$-$C_7$ alkoxy, 5-7 membered heterocyclic ring containing 1-3 hetero atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), $N(alkyl)_2$, $CONR^{10}R^{11}$, $SONR^{10}R^{11}$, $NR^{10}SO_2R^{11}$, $NR^{10}COR^{11}$, $NR^{10}CONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional heteroatoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), $N(alkyl)_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N they are attached to to form a 4-7 membered heterocycle ring;

$R^8$ is H or $C_1$-$C_4$ alkyl; and $R^9$ is selected from the group consisting of H, halo, $C_1$-$C_6$ alkyl, $C_{1-6}$ haloalkyl, —$C_1$-$C_6$ alkoxy and $C_1$-$C_3$ haloalkoxy.

In still yet another embodiment, the present invention provides compounds, stereoisomers, tautomers, salts, solvates or prodrugs thereof, wherein the compounds are compounds of Formula IC:

IC

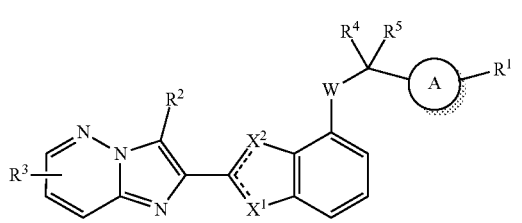

or a stereoisomer, tautomer, pharmaceutically acceptable salt, solvate or prodrug thereof, wherein:

the dashed line represents an optional double-bond with the proviso that only one of the two dashed line double bonds exists at the same time;

$X^1$ is O and $X^2$ is $CR^{1a}$ or N; or
$X^1$ is N and $X^2$ is O; or
$X^1$ is N or $CR^{1a}$, and $X^2$ is S;

W is O;
R$^1$ is —N(R$^6$)—C(O)—R$^7$ or —N(R$^6$)—S(O)$_2$—R$^7$;

is selected from the group consisting of a phenyl ring, or a 6-membered heteroaryl ring containing at least one nitrogen atom,
or alternately the moiety

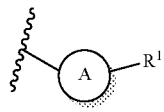

is selected from

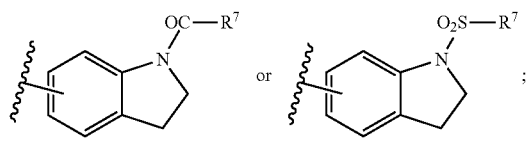

R$^{1a}$ is selected from the group consisting of H, halo, cyano, C$_1$-C$_4$ alkyl, C$_3$-C$_5$ cycloalkyl and C$_1$-C$_4$ alkoxy;
R$^2$ is H, halo, C$_1$-C$_6$ alkyl, C$_1$-C$_3$ alkoxy, CN or C$_3$-C$_7$ cycloalkyl;
R$^3$ is selected from the group consisting of C$_{1-4}$ alkyl, C$_{1-4}$ alkoxy, C$_{1-4}$ alkylthio, C$_{1-2}$ haloalkyl, C$_{1-2}$ haloalkoxy, C$_{3-6}$ cycloalkyl, C$_{2-3}$ alkenyl, C$_{2-3}$ alkynyl and halo;
R$^4$ and R$^5$ are independently selected from H, C$_1$-C$_6$ alkyl, C$_1$-C$_4$ fluoroalkyl, and C$_1$-C$_4$ hydroxyalkyl, or R$^4$ and R$^5$ can be taken together with the carbon to which they are attached to form a C$_3$-C$_7$ cycloalkyl ring;
R$^8$ is H or C$_1$-C$_4$ alkyl;
R$^9$ is selected from the group consisting of H, halo, C$_1$-C$_6$ alkyl, haloC$_{1-6}$ alkyl, —O—(C$_1$-C$_6$ alkyl) and haloC$_{1-3}$ alkoxy;
R$^6$ is selected from H, C$_1$-C$_6$ alkyl, haloC$_{1-3}$alkyl, or hydroxyC$_{1-3}$alkyl; and
R$^7$ is selected from the group consisting of C$_2$-C$_6$ alkyl, C$_6$-C$_{10}$ aryl, C$_1$-C$_7$ alkoxy, 5-7 membered heterocyclic ring containing 1-3 moieties independently selected from N, O or S, C$_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein R$^{10}$ and R$^{11}$ are the same or different and are H or C$_{1-4}$ alkyl or R$^{10}$ and R$^{11}$ can be taken together with the N they are attached to to form a 4-7 membered heterocycle ring;
or R$^6$ and R$^7$ may be taken together to form a monocyclic or bicyclic heterocyclic ring with 0-2 additional hetero (ring) atoms selected independently from N, O, or S, wherein each of said monocyclic or bicyclic heterocyclic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$, CONR$^{12}$R$^{13}$, SONR$^{12}$R$^{13}$, NR$^{12}$SO$_2$R$^{13}$, NR$^{12}$COR$^{13}$, NR$^{12}$CONR$^{12}$R$^{13}$, COOH, COOR$^{12}$, oxo and methylenedioxy, wherein R$^{12}$ and R$^{13}$ are the same or different and are H or C$_{1-4}$ alkyl or R$^{12}$ and R$^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula ID:

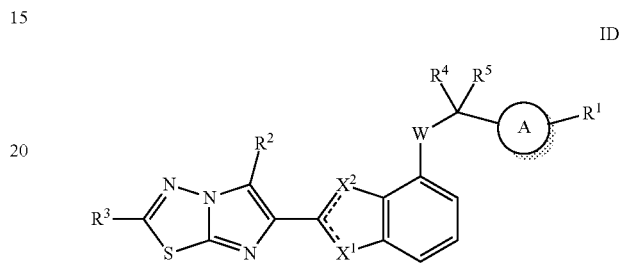

ID or a stereoisomer, tautomer, pharmaceutically acceptable salt, solvate or prodrug thereof, wherein:
the dashed line represents an optional double-bond with the proviso that only one of the two dashed line double bonds exists at the same time;
X$^1$ is O and X$^2$ is CR$^{1a}$ or N; or
X$^1$ is N and X$^2$ is O; or
X$^1$ is N or CR$^{1a}$, and X$^2$ is S;
W is O;
R$^1$ is —N(R$^6$)—C(O)—R$^7$ or —N(R$^6$)—S(O)$_2$—R$^7$

is selected from the group consisting of a phenyl ring, or a 6-membered heteroaryl ring containing at least one nitrogen atom,
or alternately the moiety

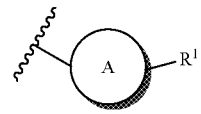

is selected from

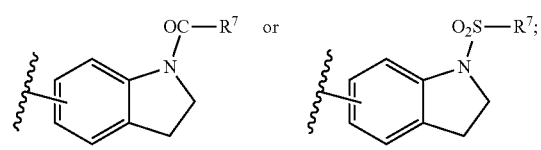

R$^{1a}$ is selected from the group consisting of H, or methyl;
R$^2$ is H, or methyl;
R$^3$ is selected from the group consisting of methyl, ethyl, methoxy, 1,1-difluoroethyl, or 1-fluoroethyl;

$R^4$ and $R^5$ are independently selected from H or methyl;

$R^8$ is H or methyl;

$R^9$ is methoxy;

$R^6$ is selected from H or methyl $R^7$ is selected from the group consisting of $C_1$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocyclic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring, with the proviso that when A is

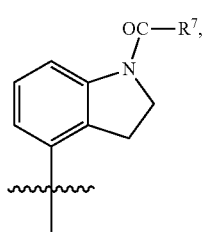

$R^7$ is not pyridizin-4-yl.

In still yet another embodiment, the present invention provides compounds, stereoisomers, tautomers, salts, solvates or prodrugs thereof, wherein the compounds of Formula I are compounds of formulas IE, IF, IG, IH and IJ:

IE
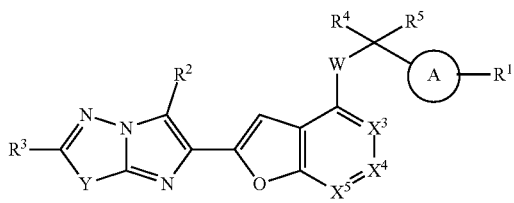

IF
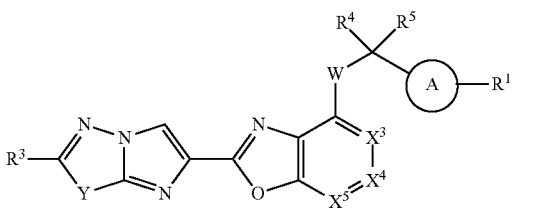

IG
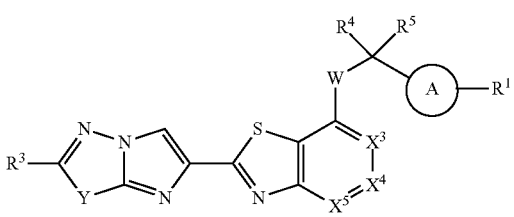

IH
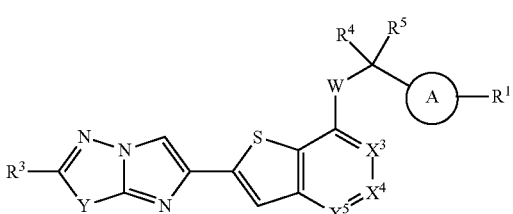

IJ
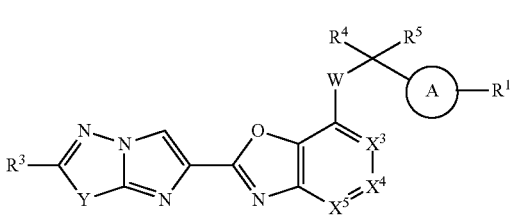

wherein the various moieties are independently selected and are as defined earlier, with the proviso that when Y is S and A is

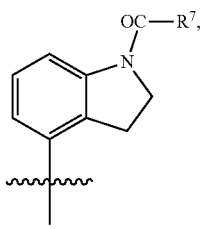

then $R^7$ is not pyridizin-4-yl.

Examples of IE-IJ are:

IE
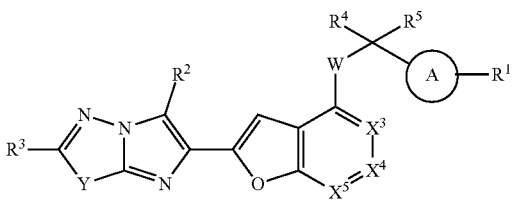

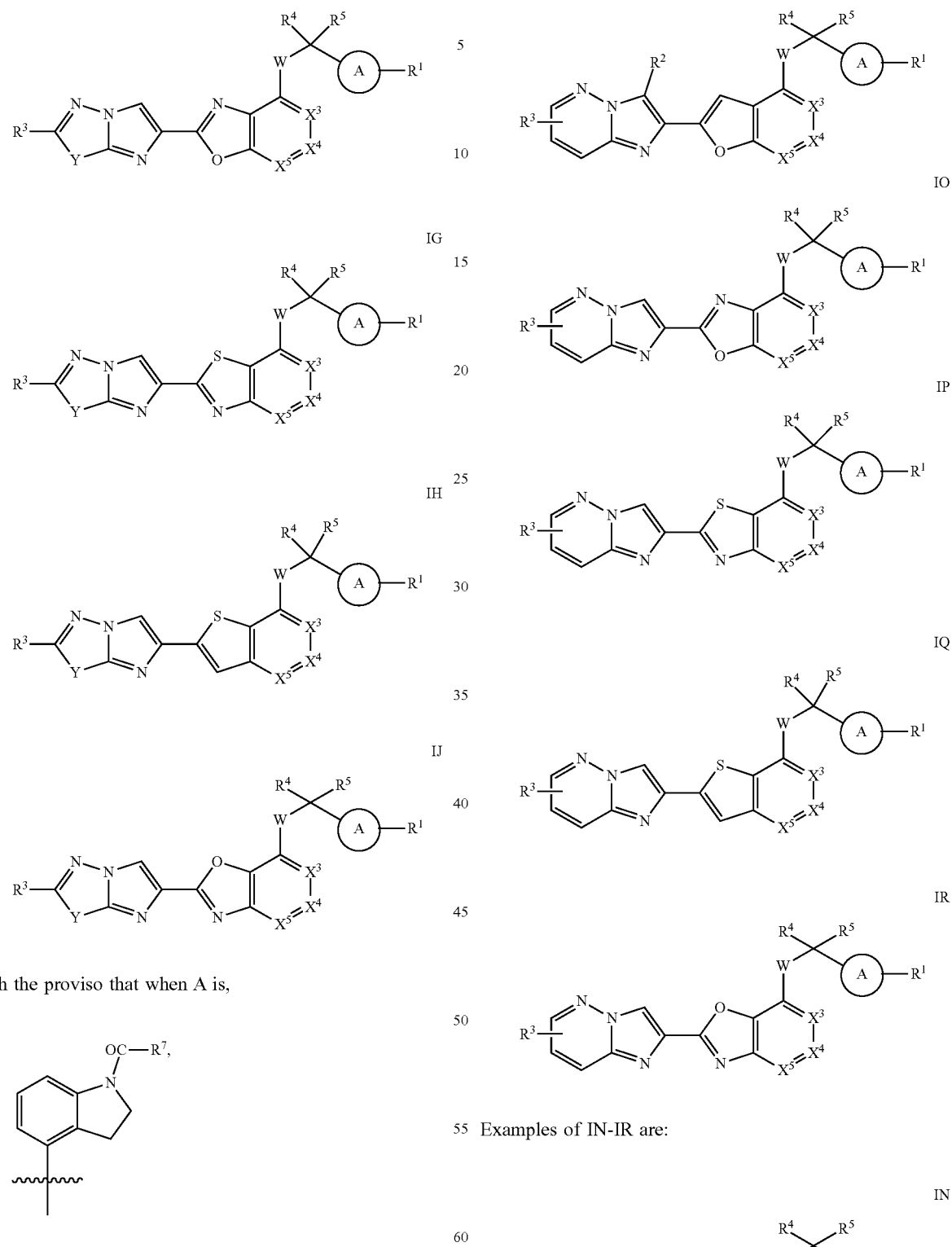
with the proviso that when A is,
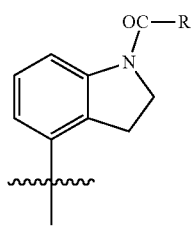
$R^7$ is not pyridizin-4-yl.
In still yet another embodiment, the present invention provides compounds, stereoisomers, tautomers, salts, solvates or prodrugs thereof, wherein the compounds are compounds of Formula I are compounds of formulas IN, IO, IP, IQ and IR:
Examples of IN-IR are:
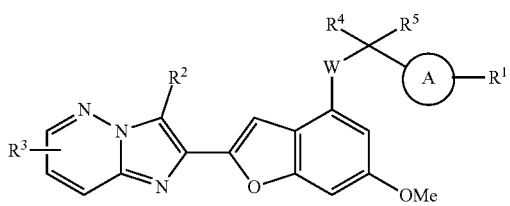

-continued

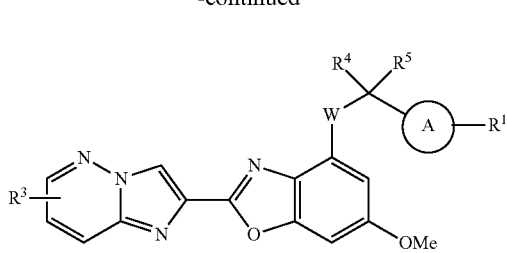

IO

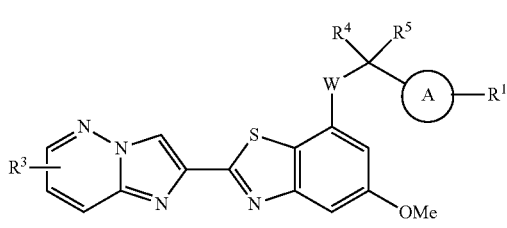

IP

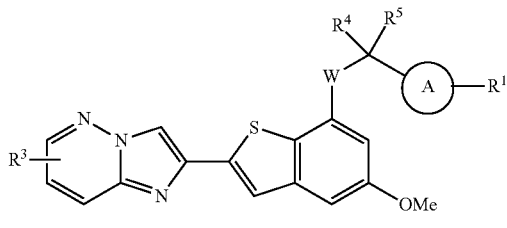

IQ

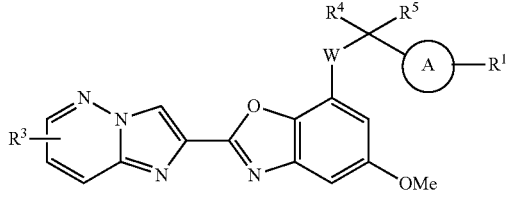

IR wherein the various moieties are independently selected and are as defined earlier. In an embodiment, in the compound of Formula I, the moiety:

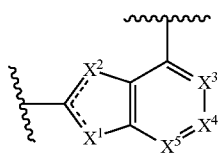

represents the moiety:

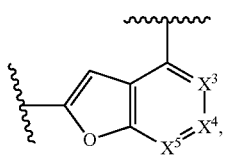

wherein $X^3$, $X^4$ and $X^5$ are as defined under Formula I.

In still yet another embodiment, the present invention provides compounds, stereoisomers, tautomers, salts, solvates or prodrugs thereof, wherein the compounds are compounds of Formula I are compounds of formula:

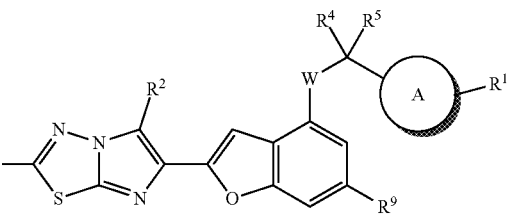

or a stereoisomer, tautomer, pharmaceutically acceptable salt, solvate or prodrug thereof, wherein:

W is O or S;
$R^1$ is —N($R^6$)—C(O)—$R^7$ or —N($R^6$)—S(O)$_2$—$R^7$;

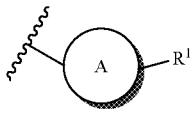

is selected from the group consisting of a phenyl ring, or a 6-membered heteroaryl ring containing at least one nitrogen atom,
or alternately the moiety

is selected from

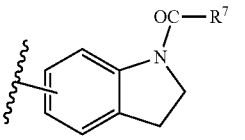 or 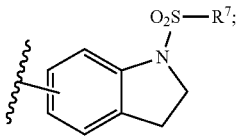

$R^2$ is H, halo, $C_1$-$C_6$ alkyl, $C_1$-$C_3$ alkoxy, CN or $C_3$-$C_7$ cycloalkyl;

$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^6$ is selected from H, $C_1$-$C_6$ alkyl, $C_1$-$C_3$ haloalkyl, or $C_1$-$C_3$ hydroxyalkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 hetero (ring) atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, CON$R^{10}R^{11}$, SON$R^{10}R^{11}$, $NR^{10}SO_2R^{11}$, $NR^{10}COR^{11}$, $NR^{10}CONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), $N(alkyl)_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring; and $R^9$ is selected from the group consisting of H, halo, $C_1$-$C_6$ alkyl, $C_{1-6}$ haloalkyl, —$C_1$-$C_6$ alkoxy and $C_1$-$C_3$ haloalkoxy, with the proviso that when A is

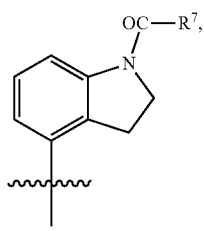

$R^7$ is not pyridizin-4-yl.

In still yet another embodiment, the present invention provides compounds, stereoisomers, tautomers, salts, solvates or prodrugs thereof, wherein the compounds are compounds of Formula I are compounds of formula:

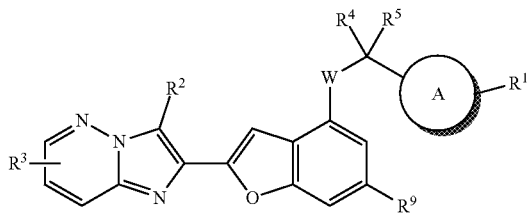

or a stereoisomer, tautomer, pharmaceutically acceptable salt, solvate or prodrug thereof, wherein:

W is O or S;

$R^1$ is —$N(R^6)$—C(O)—$R^7$ or —$N(R^6)$—$S(O)_2$—$R^7$;

is selected from the group consisting of a phenyl ring, or a 6-membered heteroaryl ring containing at least one nitrogen atom, or alternately the moiety

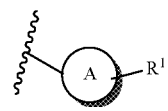

is selected from

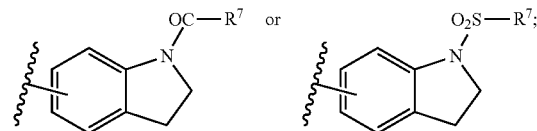

$R^2$ is H, halo, $C_1$-$C_6$ alkyl, $C_1$-$C_3$ alkoxy, CN or $C_3$-$C_7$ cycloalkyl;

$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^6$ is selected from H, $C_1$-$C_6$ alkyl, $C_1$-$C_3$ haloalkyl, or $C_1$-$C_3$ hydroxyalkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 hetero (ring) atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), $N(alkyl)_2$, $CONR^{10}R^{11}$, $SONR^{10}R^{11}$, $NR^{10}SO_2R^{11}$, $NR^{10}COR^{11}$, $NR^{10}CONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), $N(alkyl)_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring; and $R^9$ is selected from the group consisting of H, halo, $C_1$-$C_6$ alkyl, $C_{1-6}$ haloalkyl, —$C_1$-$C_6$ alkoxy and $C_{1-C3}$ haloalkoxy.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:

wherein the various moieties are independently selected and:
$X^3$, and $X^5$ are CH;
$X^4$ is $CR^9$;
W is O;
Y is S or —CH=CH—;
$R^{1a}$ is H;
$R^2$ is H;
$R^3$ is —OCH$_3$;
$R^4$ and $R^5$ are H;
$R^6$ is H or methyl;
$R^9$ is —OCH$_3$;
$R^1$ is —N($R^6$)—C(O)—$R^7$ or —N($R^6$)—S(O)$_2$—$R^7$;

is selected from the group consisting of a phenyl ring, or a 6-membered heteroaryl ring containing at least one nitrogen atom;
or alternately the moiety

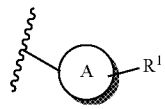

is selected from

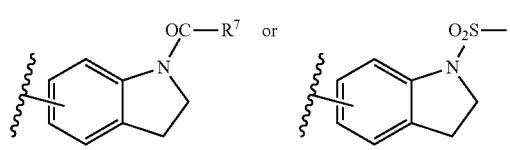

and
$R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein R$^{10}$ and R$^{11}$ are the same or different and are H or C$_{1-4}$ alkyl or R$^{10}$ and R$^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$, CONR$^{12}$R$^{13}$, SONR$^{12}$R$^{13}$, NR$^{12}$SO$_2$R$^{13}$, NR$^{12}$COR$^{13}$, NR$^{12}$CONR$^{12}$R$^{13}$, COOH, COOR$^{12}$, oxo and methylenedioxy, wherein R$^{12}$ and R$^{13}$ are the same or different and are H or C$_{1-4}$ alkyl or R$^{12}$ and R$^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:

wherein the various moieties are independently selected and:
$X^3$=$X^5$=CH;
$X^4$ is $CR^9$;
W is O;
Y is S;
$R^{1a}$ is H;
$R^2$ is H;
$R^3$ is CH$_3$ or methoxy;
$R^4$ and $R^5$ are H;
$R^6$ is H;
$R^9$ is methoxy;
$R^1$ is —N($R^6$)—C(O)—$R^7$ or N($R^6$)—S(O)$_2$—$R^7$;

is selected from the group consisting of a phenyl ring, or a 6-membered heteroaryl ring containing at least one nitrogen atom;
or alternately the moiety

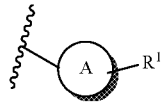

is selected from

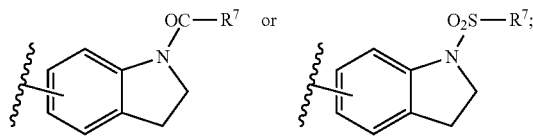

and

R⁷ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:

wherein the various moieties are independently selected and:

$X^3$=$X^5$=CH;
$X^4$ is $CR^9$;
W is O;
Y is S;
$R^{1a}$ is H;
$R^2$ is H or halo;
$R^3$ is $CH_3$ or methoxy;
$R^4$ and $R^5$ are H;
$R^6$ is H;
$R^9$ is methoxy;
$R^1$ is —N($R^6$)—C(O)—$R^7$ or;

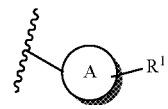

is selected from the group consisting of a phenyl ring, or a 6-membered heteroaryl ring containing at least one nitrogen atom;

or alternately the moiety

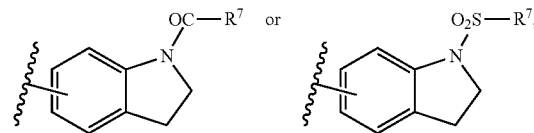

is selected from and

R⁷ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero (ring) atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:

wherein the various moieties are independently selected and:
$X^3$=CH;
$X^4$=$CR^9$;
$X^5$ is N;

W is O;
Y is S;
$R^{1a}$ is selected from the group consisting of H, halo, cyano, $C_1$-$C_4$ alkyl, and $C_1$-$C_4$ alkoxy;
$R^2$ is H;
$R^3$ is $CH_3$ or methoxy;
$R^4$ and $R^5$ are H;
$R^6$ is H;
$R^1$ is —N($R^6$)—C(O)—$R^7$ or N($R^6$)—S(O)$_2$—$R^7$;

is selected from the group consisting of a phenyl ring, or a 6-membered heteroaryl ring containing at least one nitrogen atom;
or alternately the moiety

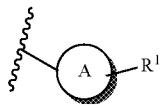

is selected from

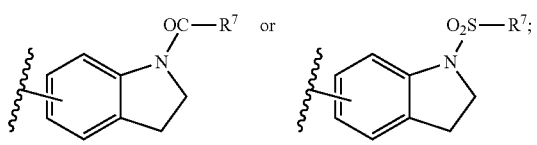

and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, CONR$^{10}$R$^{11}$, SONR$^{10}$R$^{11}$, COOH, COOR$^{10}$, oxo and methylenedioxy, wherein $R^{10}$ and $R^{11}$ are the same or different and are $C_{1-4}$ alkyl or $R^{10}$ and $R^{11}$ can be taken together with the N they are attached to to form a 4-7 membered heterocycle ring;
or $R^6$ and $R^7$ may be taken together to form a monocyclic or bicyclic heterocyclic ring with 0-2 additional hetero atoms selected independently from N, O, or S, wherein each of said monocyclic or bicyclic heterocyclic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, CONR$^{12}$R$^{13}$, SONR$^{12}$R$^{13}$, NR$^{12}$SO$_2$R$^{13}$, NR$^{12}$COR$^{13}$, NR$^{12}$CONR$^{12}$R$^{13}$, COOH, COOR$^{12}$, oxo and methylenedioxy, wherein $R^{12}$ and $R^{13}$ are the same or different and are $C_{1-4}$ alkyl or $R^{12}$ and $R^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:
wherein the various moieties are independently selected and are:
$X^4$=$X^5$=CH;
$X^3$ is N;
W is O;
Y is S;
$R^{1a}$ is H;
$R^2$ is H or halo;
$R^3$ is $CH_3$ or methoxy;
$R^4$ and $R^5$ are H;
$R^6$ is H;
$R^9$ is methoxy;
$R^1$ is —N($R^6$)—C(O)—$R^7$ or;

is selected from the group consisting of a phenyl ring, or a 6-membered heteroaryl ring containing at least one nitrogen atom;
or alternately the moiety

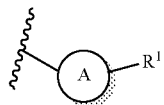

is selected from

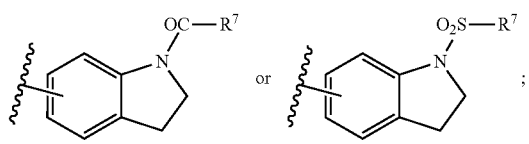

and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), $N(alkyl)_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:

wherein the various moieties are independently selected and:

$X^3=X^4=CH$;

$X^5$ is N;

W is O;

Y is S;

$R^{1a}$ is H;

$R^2$ is H or halo;

$R^3$ is $CH_3$ or methoxy;

$R^4$ and $R^5$ are H;

$R^6$ is H;

$R^9$ is methoxy;

$R^1$ is $-N(R^6)-C(O)-R^7$ or;

(A)

is selected from the group consisting of a phenyl ring, or a 6-membered heteroaryl ring containing at least one nitrogen atom;

or alternately the moiety

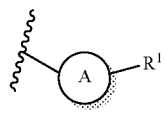

is selected from

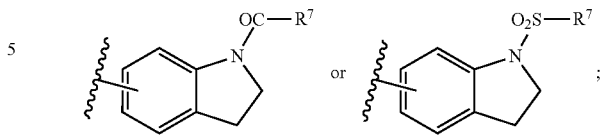

and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), $N(alkyl)_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), $N(alkyl)_2$, $CONR^{12}R^{13}$, $SONR^{12}R^{13}$, $NR^{12}SO_2R^{13}$, $NR^{12}COR^3$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:

wherein the various moieties are independently selected and:

$X^4=X^5=CH$;

$X^3$ is N;

W is O;

Y is S;

$R^{1a}$ is H;

$R^2$ is H or halo;

$R^3$ is $CH_3$ or methoxy;

$R^4$ and $R^5$ are H;

$R^6$ is H;
$R^9$ is methoxy;
$R^1$ is —N($R^6$)—C(O)—$R^7$ or;

is selected from the group consisting of a phenyl ring, or a 6-membered heteroaryl ring containing at least one nitrogen atom;
  or alternately the moiety

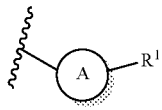

is selected from

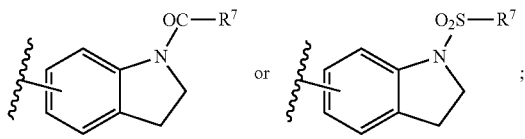

and
  $R^7$ is selected from the group consisting of $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, CONR$^{10}$R$^{11}$, SONR$^{10}$R$^{11}$, COOH, COOR$^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;
  or $R^6$ and $R^7$ may be taken together to form a monocyclic or bicyclic heterocyclic ring with 0-2 additional hetero atoms selected independently from N, O, or S, wherein each of said monocyclic or bicyclic heterocyclic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, CONR$^{12}$R$^{13}$, SONR$^{12}$R$^{13}$, NR$^{12}$SO$_2$R$^{13}$, NR$^{12}$COR$^{13}$, NR$^{12}$CONR$^{12}$R$^{13}$, COOH, COOR$^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In still yet another embodiment, the present invention provides compounds, stereoisomers, tautomers, salts, solvates or prodrugs thereof, wherein the compounds are compounds of Formula I, or they are compounds of Formula IA, or they are compounds of Formula IB, or they are compounds of Formula IC, or they are compounds of Formula ID, or they are compounds of Formula IE, or they are compounds of Formula IF, or they are compounds of Formula IG, or they are compounds of Formula IH, or they are compounds of Formula IJ, or they are compounds of Formula IN, or they are compounds of Formula IO, or they are compounds of Formula IP, or they are compounds of Formula IQ, or they are compounds of Formula IR:
wherein the various moieties are independently selected and:
  $X^3$=$X^4$=$X^5$=CH;
  W is O;
  Y is S;
  $R^{1a}$ is H;
  $R^2$ is H or halo;
  $R^3$ is $CH_3$ or methoxy;
  $R^4$ and $R^5$ are H;
  $R^6$ is H;
  $R^9$ is methoxy;
  $R^1$ is —N($R^6$)—C(O)—$R^7$ or;

is selected from the group consisting of a phenyl ring, or a 6-membered heteroaryl ring containing at least one nitrogen atom;
  or alternately the moiety

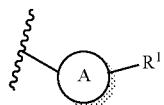

is selected from

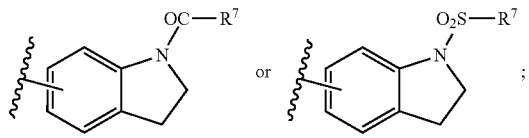

and
  $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, CONR$^{10}$R$^{11}$, SONR$^{10}$R$^{11}$, COOH, COOR$^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to to form a 4-7 membered heterocycle ring;
  or $R^6$ and $R^7$ may be taken together to form a monocyclic or bicyclic heterocyclic ring with 0-2 additional hetero atoms selected independently from N, O, or S, wherein each of said monocyclic or bicyclic heterocyclic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N they are attached to to form a 4-7 membered heterocycle ring.

In another embodiment,

is a phenyl ring;
or alternately the moiety

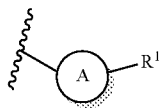

is selected from or

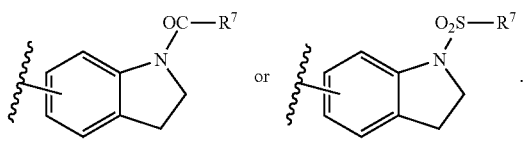

In still yet another embodiment, the present invention provides compounds, stereoisomers, tautomers, salts, solvates or prodrugs thereof, wherein the compounds of Formula I are compounds of formula:

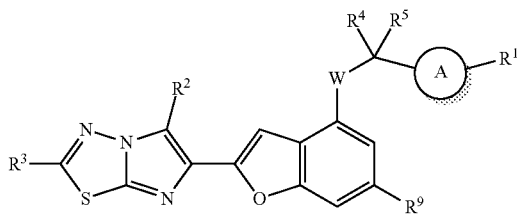

wherein the various moieties are independently selected and:
W is O;
$R^2$ is H;
$R^3$ is $CH_3$ or methoxy;
$R^4$ and $R^5$ are H;
$R^6$ is hydrogen, alkyl, cycloalkyl, cycloalkylalkyl, or arylalkyl;
$R^1$ is —N($R^6$)—C(O)—$R^7$ or N($R^6$)—S(O)$_2$—$R^7$;

is selected from the group consisting of a phenyl ring;

or alternately the moiety

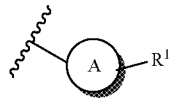

is selected from

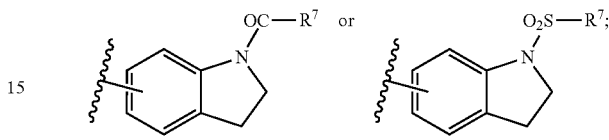

and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, $NR^{10}SO_2R^{11}$, COOH, $COOR^{10}$, oxo and methylenedioxy, wherein $R^{10}$ and $R^{11}$ are the same or different and are $C_{1-4}$ alkyl or $R^{10}$ and $R^{11}$ can be taken together with the N they are attached to to form a 4-7 membered heterocycle ring;

or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are $C_{1-4}$ alkyl or $R^{12}$ and $R^{13}$ can be taken together with the N they are attached to to form a 4-7 membered heterocycle ring, with the proviso that when A is

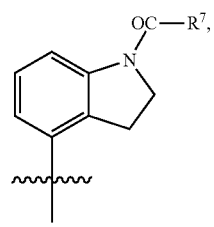

then $R^7$ is not pyridizin-4-yl.

In yet another embodiment, this invention discloses the compounds listed in Table 1.

TABLE 1

Compound

TABLE 1-continued

Compound

TABLE 1-continued

Compound

TABLE 1-continued

| Compound |
|----------|

TABLE 1-continued

Compound

TABLE 1-continued

Compound

TABLE 1-continued

Compound

TABLE 1-continued

Compound

TABLE 1-continued
Compound
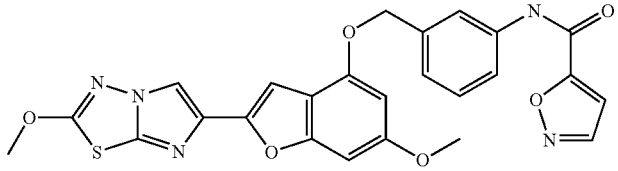
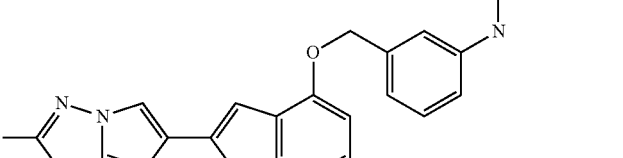
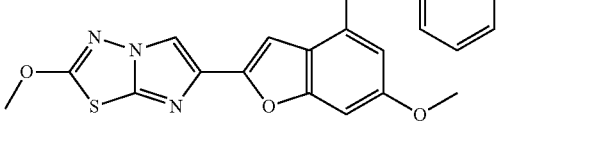

TABLE 1-continued

Compound

TABLE 1-continued
Compound
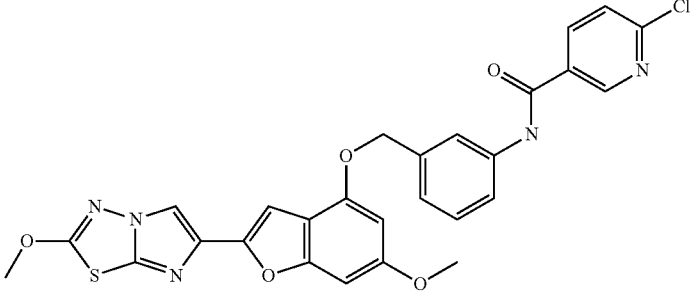 [SMILES: COc1cc(OCc2cccc(NC(=O)c3ccc(Cl)nc3)c2)c2cc(-c3cn4nc(OC)sc4n3)oc2c1]
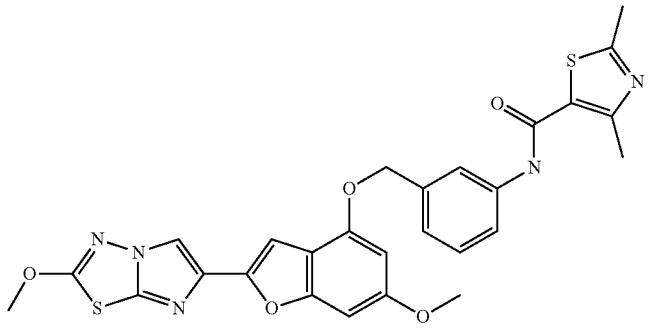 [SMILES: COc1cc(OCc2cccc(NC(=O)c3sc(C)nc3C)c2)c2cc(-c3cn4nc(OC)sc4n3)oc2c1]
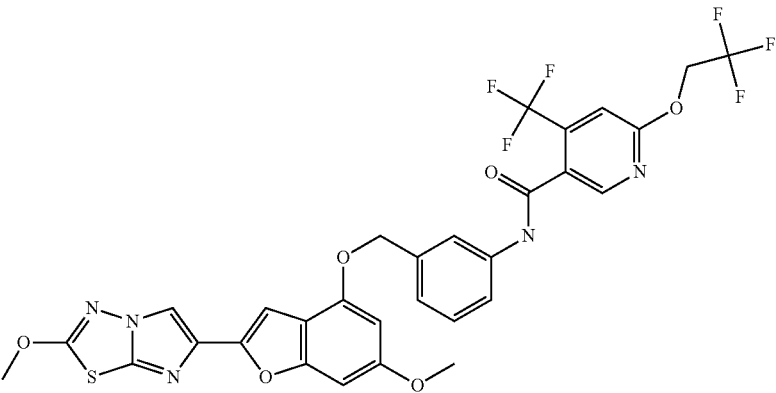 [SMILES: COc1cc(OCc2cccc(NC(=O)c3cnc(OCC(F)(F)F)cc3C(F)(F)F)c2)c2cc(-c3cn4nc(OC)sc4n3)oc2c1]
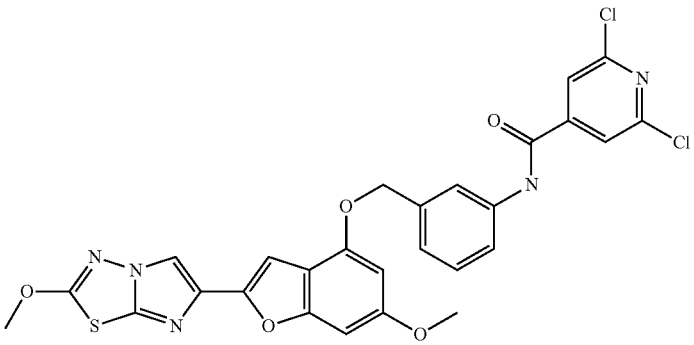 [SMILES: COc1cc(OCc2cccc(NC(=O)c3cc(Cl)nc(Cl)c3)c2)c2cc(-c3cn4nc(OC)sc4n3)oc2c1]

TABLE 1-continued
Compound
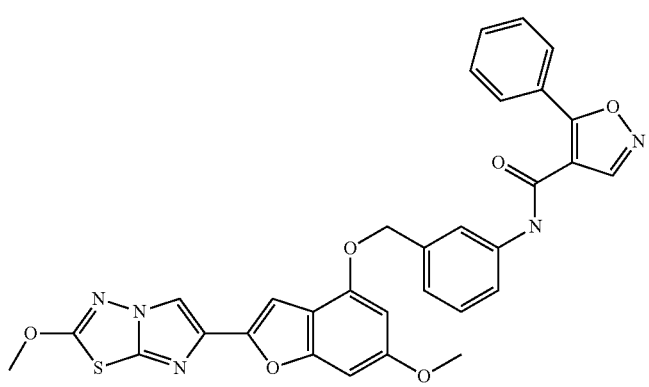 [SMILES: COc1cc(OCc2cccc(NC(=O)c3cnoc3-c3ccccc3)c2)c2cc(-c3cn4nc(OC)sc4n3)oc2c1]
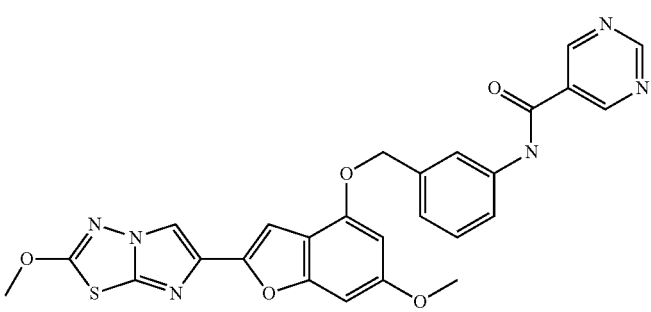 [SMILES: COc1cc(OCc2cccc(NC(=O)c3cncnc3)c2)c2cc(-c3cn4nc(OC)sc4n3)oc2c1]
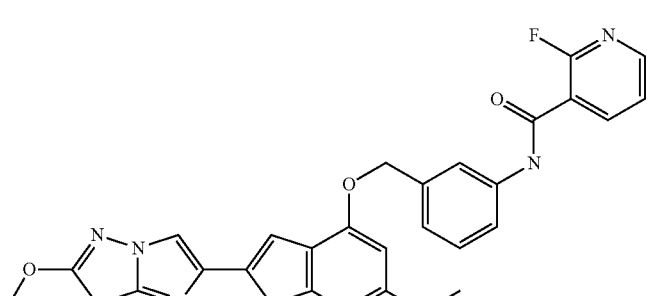
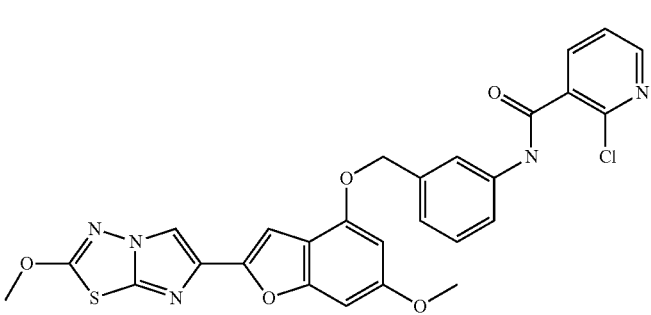 [SMILES: COc1cc(OCc2cccc(NC(=O)c3cccnc3Cl)c2)c2cc(-c3cn4nc(OC)sc4n3)oc2c1]

TABLE 1-continued

Compound

TABLE 1-continued

Compound

TABLE 1-continued

Compound

TABLE 1-continued
Compound
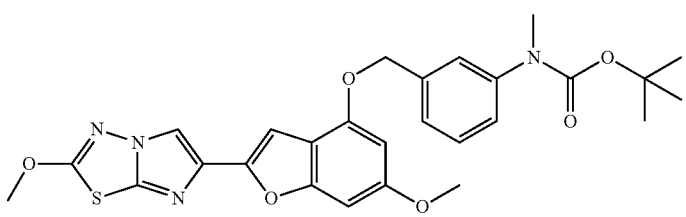 [SMILES: COc1cc(OCc2cccc(N(C)C(=O)OC(C)(C)C)c2)c2cc(-c3cn4nc(OC)sc4n3)oc2c1]
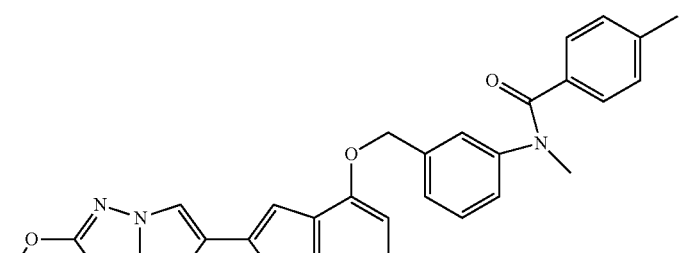
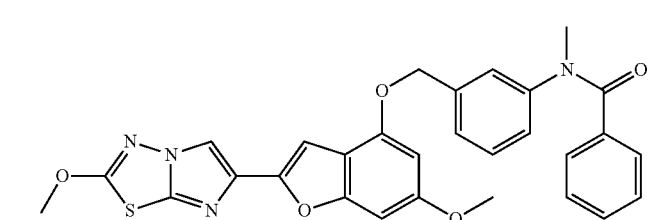
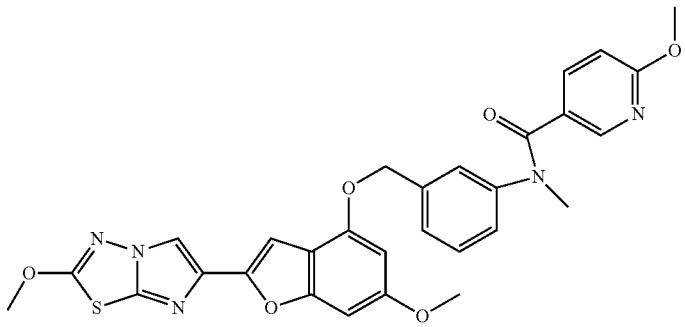
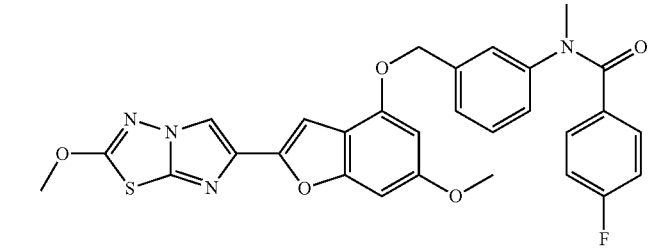 [SMILES: COc1cc(OCc2cccc(N(C)C(=O)c3ccc(F)cc3)c2)c2cc(-c3cn4nc(OC)sc4n3)oc2c1]
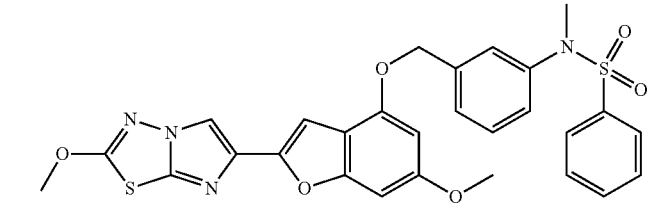 [SMILES: COc1cc(OCc2cccc(N(C)S(=O)(=O)c3ccccc3)c2)c2cc(-c3cn4nc(OC)sc4n3)oc2c1]

TABLE 1-continued

Compound

TABLE 1-continued

Compound

TABLE 1-continued

Compound

TABLE 1-continued
Compound
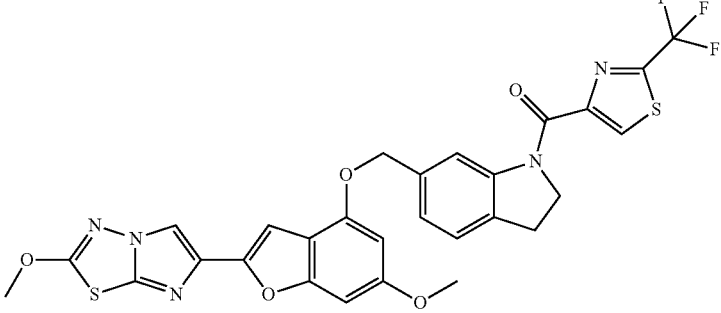
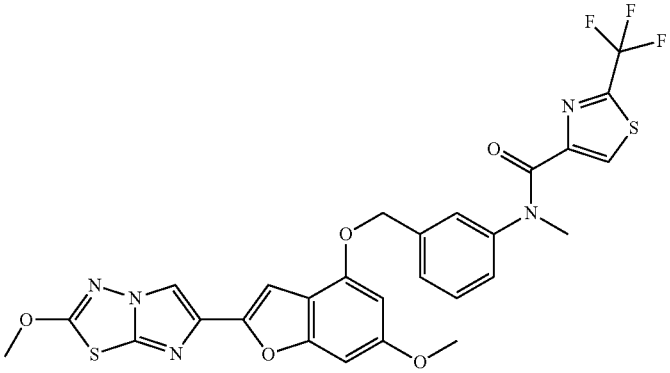 [SMILES: COc1cc(OCc2cccc(N(C)C(=O)c3csc(C(F)(F)F)n3)c2)c2cc(-c3cn4nc(OC)sc4n3)oc2c1]
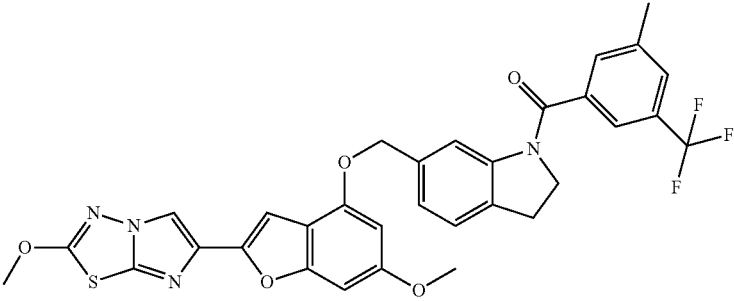 [SMILES: COc1cc(OCc2ccc3c(c2)N(C(=O)c2cc(C)cc(C(F)(F)F)c2)CC3)c2cc(-c3cn4nc(OC)sc4n3)oc2c1]
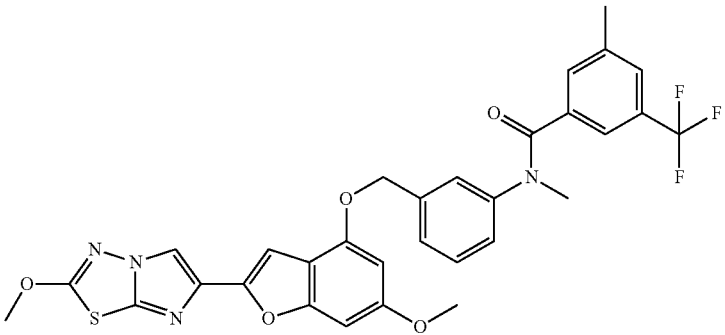 [SMILES: COc1cc(OCc2cccc(N(C)C(=O)c3cc(C)cc(C(F)(F)F)c3)c2)c2cc(-c3cn4nc(OC)sc4n3)oc2c1]

TABLE 1-continued
Compound
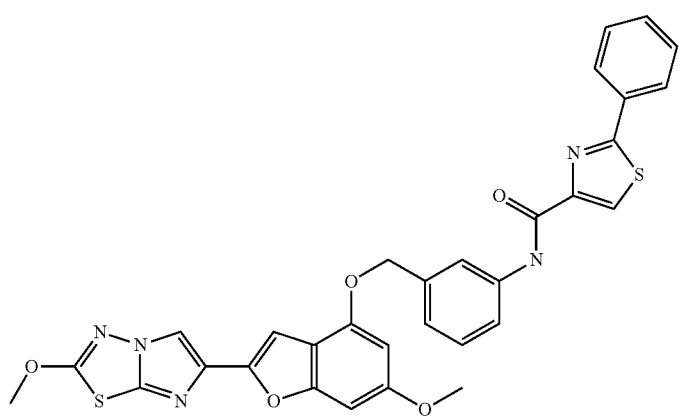 [SMILES: COc1cc(OCc2cccc(NC(=O)c3csc(-c4ccccc4)n3)c2)c2cc(-c3cn4nc(OC)sc4n3)oc2c1]
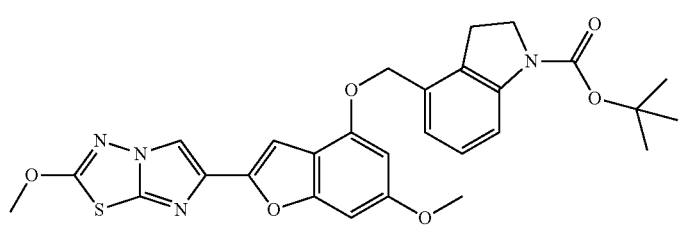 [SMILES: COc1cc(OCc2cccc3c2CCN3C(=O)OC(C)(C)C)c2cc(-c3cn4nc(OC)sc4n3)oc2c1]
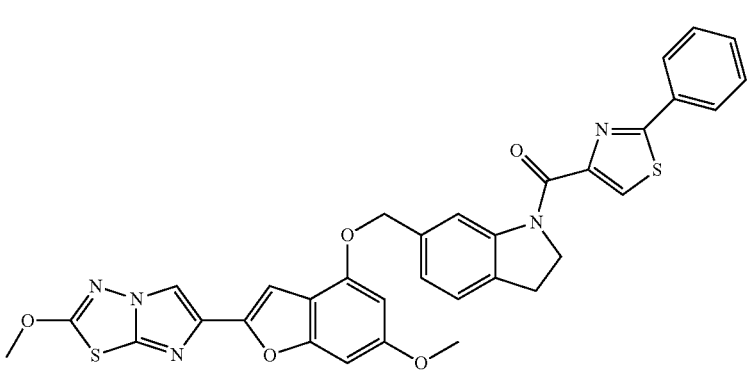 [SMILES: COc1cc(OCc2ccc3c(c2)N(C(=O)c2csc(-c4ccccc4)n2)CC3)c2cc(-c3cn4nc(OC)sc4n3)oc2c1]
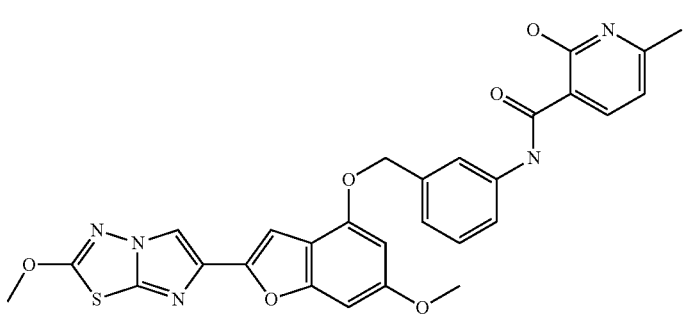

TABLE 1-continued
Compound
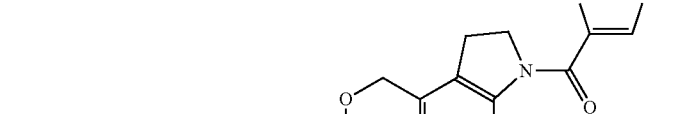
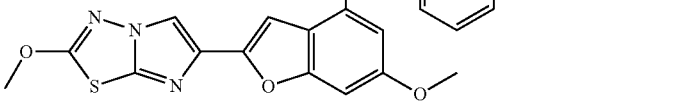
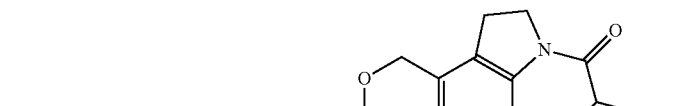
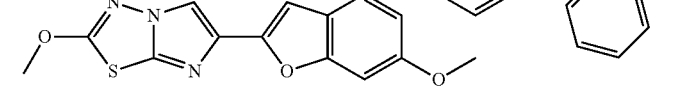
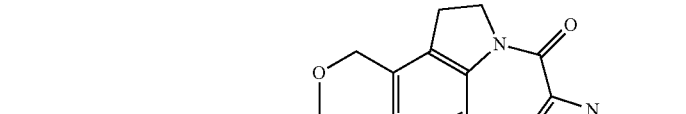

TABLE 1-continued
Compound
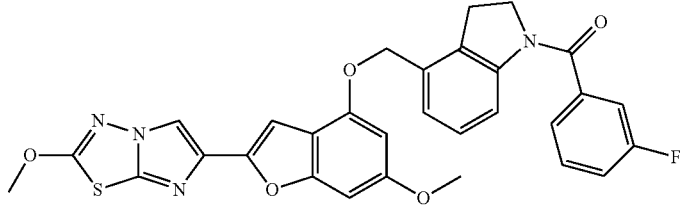 [SMILES: COc1cc(OCc2cccc3c2CCN3C(=O)c2cccc(F)c2)c2cc(-c3cn4nc(OC)sc4n3)oc2c1]
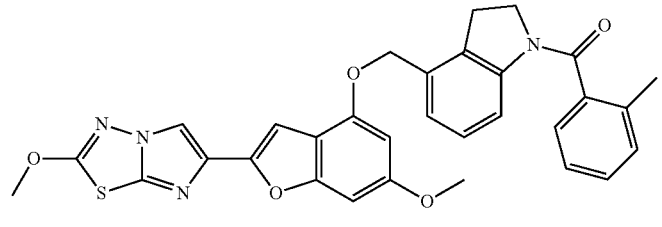
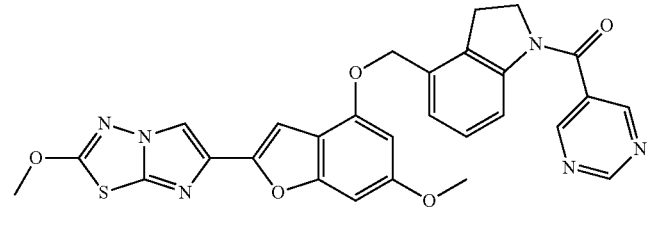 [SMILES: COc1cc(OCc2cccc3c2CCN3C(=O)c2cncnc2)c2cc(-c3cn4nc(OC)sc4n3)oc2c1]
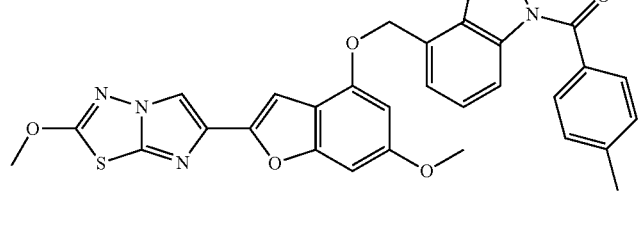
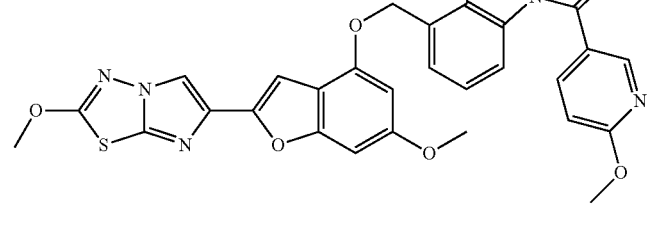
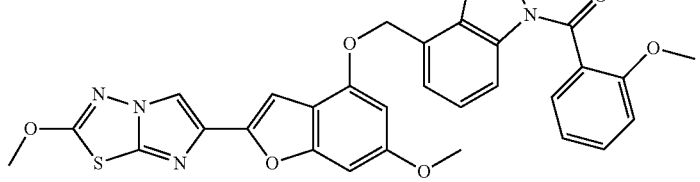

TABLE 1-continued

Compound

TABLE 1-continued

Compound

TABLE 1-continued
Compound
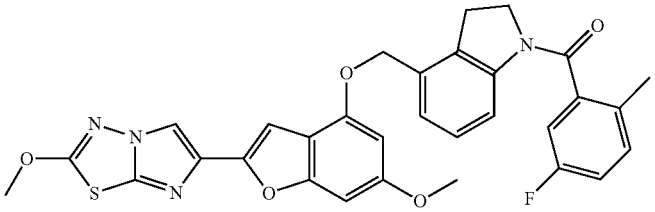
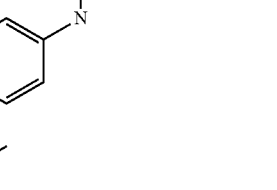
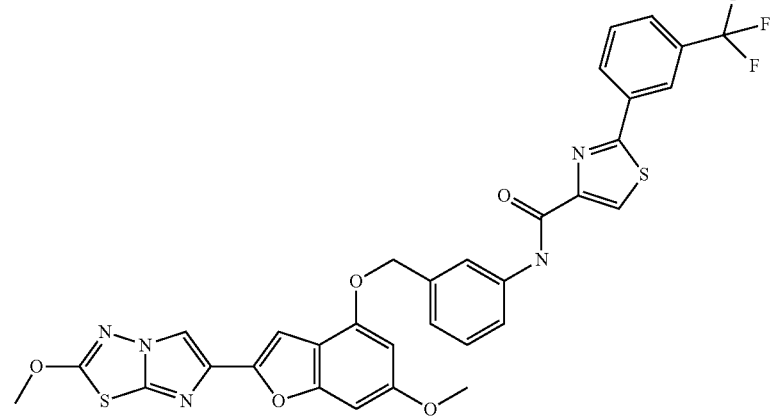
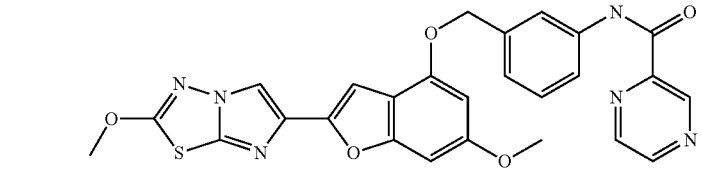 [SMILES: COc1cc(OCc2cccc(NC(=O)c3cnccn3)c2)c2cc(-c3cn4nc(OC)sc4n3)oc2c1]
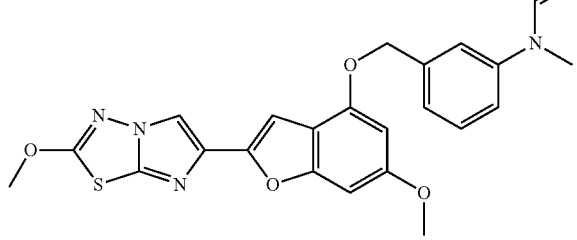

TABLE 1-continued

Compound

TABLE 1-continued

Compound

TABLE 1-continued
Compound
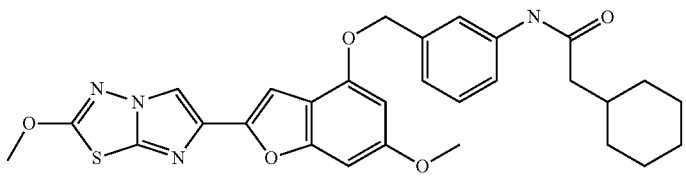 [SMILES: COc1cc(OCc2cccc(NC(=O)CC3CCCCC3)c2)c2cc(-c3cn4nc(OC)sc4n3)oc2c1]
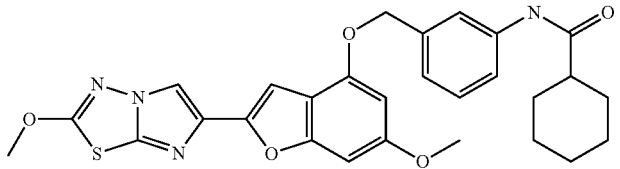 [SMILES: COc1cc(OCc2cccc(NC(=O)C3CCCCC3)c2)c2cc(-c3cn4nc(OC)sc4n3)oc2c1]
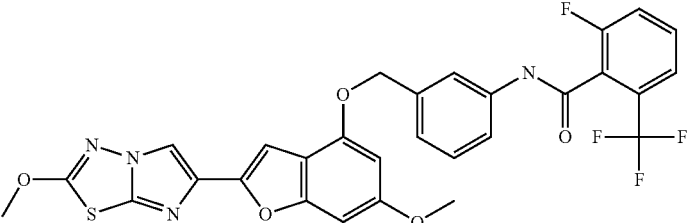
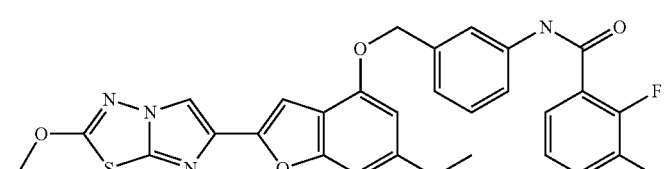
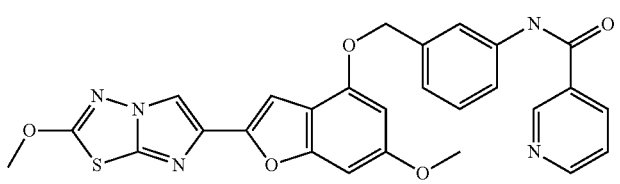 [SMILES: COc1cc(OCc2cccc(NC(=O)c3cccnc3)c2)c2cc(-c3cn4nc(OC)sc4n3)oc2c1]
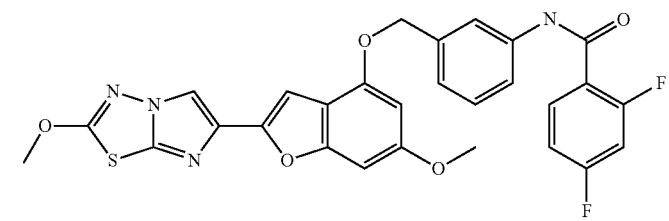 [SMILES: COc1cc(OCc2cccc(NC(=O)c3ccc(F)cc3F)c2)c2cc(-c3cn4nc(OC)sc4n3)oc2c1]
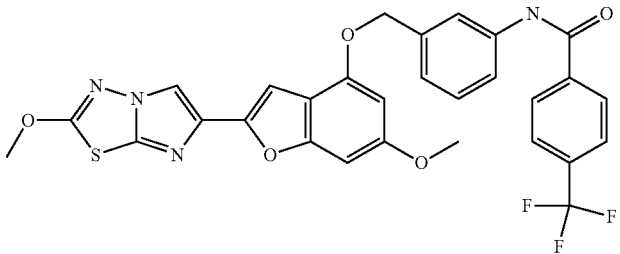 [SMILES: COc1cc(OCc2cccc(NC(=O)c3ccc(C(F)(F)F)cc3)c2)c2cc(-c3cn4nc(OC)sc4n3)oc2c1]

TABLE 1-continued
Compound
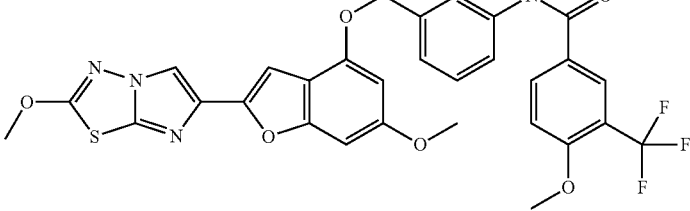
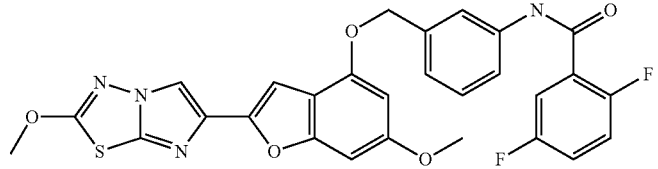 [SMILES: COc1cc(OCc2cccc(NC(=O)c3cc(F)ccc3F)c2)c2cc(-c3cn4nc(OC)sc4n3)oc2c1]
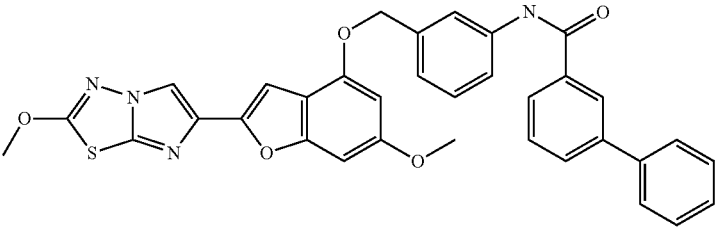 [SMILES: COc1cc(OCc2cccc(NC(=O)c3cccc(-c4ccccc4)c3)c2)c2cc(-c3cn4nc(OC)sc4n3)oc2c1]
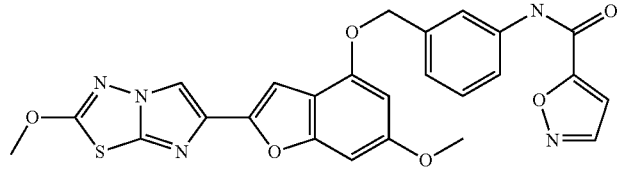 [SMILES: COc1cc(OCc2cccc(NC(=O)c3ccno3)c2)c2cc(-c3cn4nc(OC)sc4n3)oc2c1]
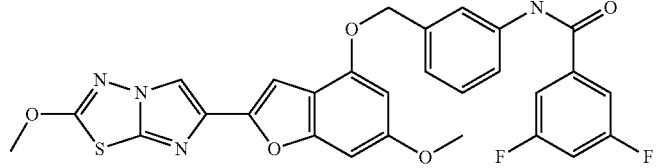 [SMILES: COc1cc(OCc2cccc(NC(=O)c3cc(F)cc(F)c3)c2)c2cc(-c3cn4nc(OC)sc4n3)oc2c1]
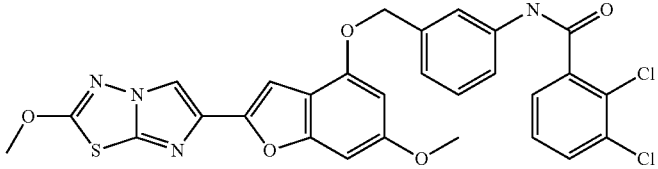
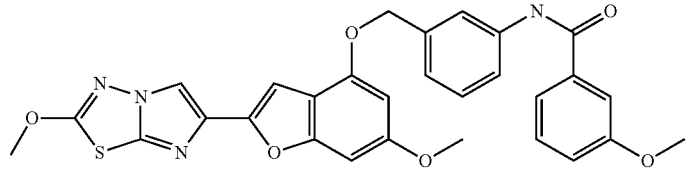

TABLE 1-continued

Compound

TABLE 1-continued

Compound

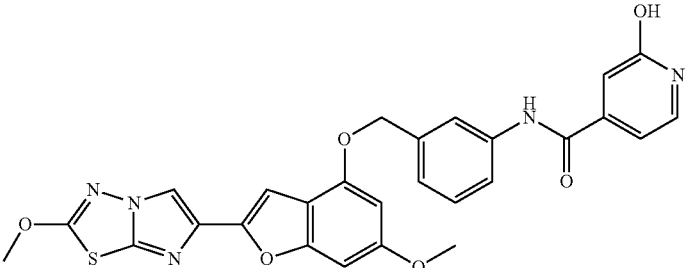

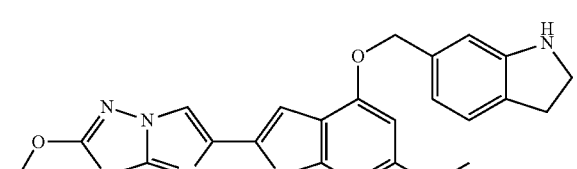

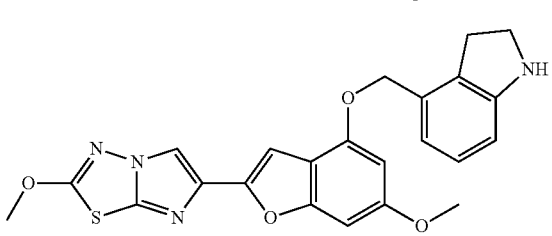

In one embodiment, the present invention provides N compounds, stereoisomers, tautomers, salts, solvates or prodrugs thereof, wherein the compounds are compounds of Formula I.

In one embodiment, the present invention provides compounds, stereoisomers, tautomers, salts, solvates or prodrugs thereof, wherein the compounds are compounds of Formula IA.

In one embodiment, the present invention provides compounds, stereoisomers, tautomers, salts, solvates or prodrugs thereof, wherein the compounds are compounds of Formula IA.

In one embodiment, the present invention provides compounds, stereoisomers, tautomers, salts, solvates or prodrugs thereof, wherein the compounds are compounds of Formula IB.

In one embodiment, the present invention provides compounds, stereoisomers, tautomers, salts, solvates or prodrugs thereof, wherein the compounds are compounds of Formula IC.

In one embodiment, the present invention provides compounds, stereoisomers, tautomers, salts, solvates or prodrugs thereof, wherein the compounds are compounds of Formula ID.

In one embodiment, the present invention provides compounds, stereoisomers, tautomers, salts, solvates or prodrugs thereof, wherein the compounds are compounds of Formula IE.

In one embodiment, the present invention provides compounds, stereoisomers, tautomers, salts, solvates or prodrugs thereof, wherein the compounds are compounds of Formula IF.

In one embodiment, the present invention provides compounds, stereoisomers, tautomers, salts, solvates or prodrugs thereof, wherein the compounds are compounds of Formula IG.

In one embodiment, the present invention provides compounds, stereoisomers, tautomers, salts, solvates or prodrugs thereof, wherein the compounds are compounds of Formula IH.

In one embodiment, the present invention provides compounds, stereoisomers, tautomers, salts, solvates or prodrugs thereof, wherein the compounds are compounds of Formula IJ.

In one embodiment, the present invention provides compounds, stereoisomers, tautomers, salts, solvates or prodrugs thereof, wherein the compounds are compounds of Formula IN.

In one embodiment, the present invention provides compounds, stereoisomers, tautomers, salts, solvates or prodrugs thereof, wherein the compounds are compounds of Formula IO.

In one embodiment, the present invention provides compounds, stereoisomers, tautomers, salts, solvates or prodrugs thereof, wherein the compounds are compounds of Formula IP.

In one embodiment, the present invention provides compounds, stereoisomers, tautomers, salts, solvates or prodrugs thereof, wherein the compounds are compounds of Formula IQ.

In one embodiment, the present invention provides compounds, stereoisomers, tautomers, salts, solvates or prodrugs thereof, wherein the compounds are compounds of Formula IR.

In one embodiment, the present invention provides compounds, stereoisomers, tautomers, salts, solvates or prodrugs thereof, wherein the compounds are the examples.

PAR4 compounds of the invention have $IC_{50}$s in the FLIPR Assay (described hereinafter) of about 10 μM, or 5 μM or less, or 500 nM or less, or 10 nM or less. Activity data for Examples 1-166 are presented in the tables of Example E.

In some embodiments, the present invention provides at least one compound of the present invention or a stereoisomer, tautomer, pharmaceutically acceptable salt, solvate, or prodrug ester thereof.

In some embodiments, the present invention provides one or more compounds of the present invention or a stereoisomer, tautomer, pharmaceutically acceptable salt, solvate, or prodrug ester thereof.

In some embodiments, the present invention provides a pharmaceutical composition, which includes a pharmaceutically acceptable carrier and a therapeutically effective amount of at least one compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or preferably, a compound selected from one of the examples, more preferably, Examples 1 to 166, or stereoisomers, tautomers, pharmaceutically acceptable salts, prodrug esters, or solvates thereof, alone or in combination with another therapeutic agent.

In some embodiments, the present invention provides a pharmaceutical composition which includes a therapeutically effective amount of at least one compound of Formula I, or Formula IA, or Formula IB, or Formula IC, or Formula ID, or Formula IE, or Formula IF, or Formula IG, or Formula IH, or Formula IJ, or Formula IN, or Formula IO, or Formula IP, or Formula IQ, or Formula IR, or and one or more additional therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors or thrombin inhibitors. Preferably, the FXa inhibitors are apixaban or rivaroxaban. Preferably, the thrombin inhibitor is dabigatran.

In some embodiments, the present invention provides a method for the treatment or prophylaxis of a thromboembolic disorder which includes the step of administering to a subject (for example, a human) in need of such treatment or prophylaxis a therapeutically effective amount of at least one compound of Formula I, or Formula IA, or Formula IB, or Formula IC, or Formula ID, or Formula IE, or Formula IF, or Formula IG, or Formula IH, or Formula IJ, or Formula IN, or Formula IO, or Formula IP, or Formula IQ, or Formula IR, or of the Examples herein or stereoisomers, tautomers, pharmaceutically acceptable salts, solvates, or prodrug esters thereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or a compound selected from one of the examples, more preferably, Examples 1 to 166, or stereoisomers, tautomers, pharmaceutically acceptable salts, prodrug esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or a compound selected from one of the examples, more preferably, Examples 1 to 166, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or a compound selected from one of the examples, more preferably, Examples 1 to 166, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or or a compound selected from one of the examples, more preferably, Examples 1 to 166, or stereoisomers, tautomers, pharmaceutically acceptable salts, prodrug esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or or a compound selected from one of the examples, more preferably, Examples 1 to 166, or stereoisomers, tautomers, pharmaceutically acceptable salts, prodrug esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I, or Formula IA, or Formula IB, or Formula IC, or Formula ID, or Formula IE, or Formula IF, or Formula IG, or Formula IH, or Formula IJ, Formula IN, or Formula IO, or Formula IP, or Formula IQ, or Formula IR, or or a compound selected from one of the examples, more preferably, Examples 1 to 166, of the invention.

Other Embodiments of the Invention

In some embodiments, the present invention provides a process for making the compounds of the present invention or a stereoisomer, tautomer, pharmaceutically acceptable salt, solvate or prodrug ester thereof.

In some embodiments, the present invention provides an intermediate for making the compounds of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of at least one compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like. "Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl", (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with at least 1 halogen up to fully substituted with halogens (perhaloalkyl), alternatively 1 to 7 halogens, or 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

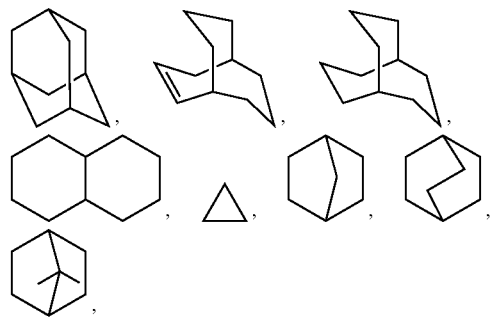

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $C_1$-$C_3$ alkoxy, heterocyclyl, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $S(=O)_2NH_2$, $C_1$-$C_3$ alkyl, $CO_2H$, and $CO_2CH_3$.

As used herein, the term "heterocycle", "heterocyclo" "heterocyclic" or "heterocyclyl" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N—O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, =O, C(=O)CH$_3$, SCH$_3$, S(=O)CH$_3$, S(=O)$_2$CH$_3$, S(=O)$_2$NH$_2$, C$_1$-C$_3$ alkyl, CO$_2$H and CO$_2$CH$_3$. A nitrogen in the heterocycle may optionally be quaternized. The heterocycle may optionally contain a =O. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

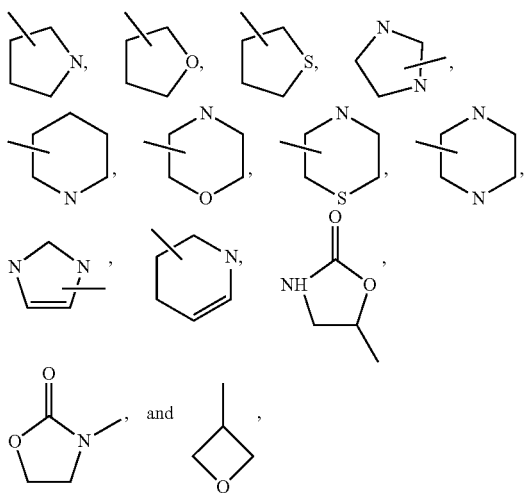

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Heteroaryl groups include, but are not limited to,

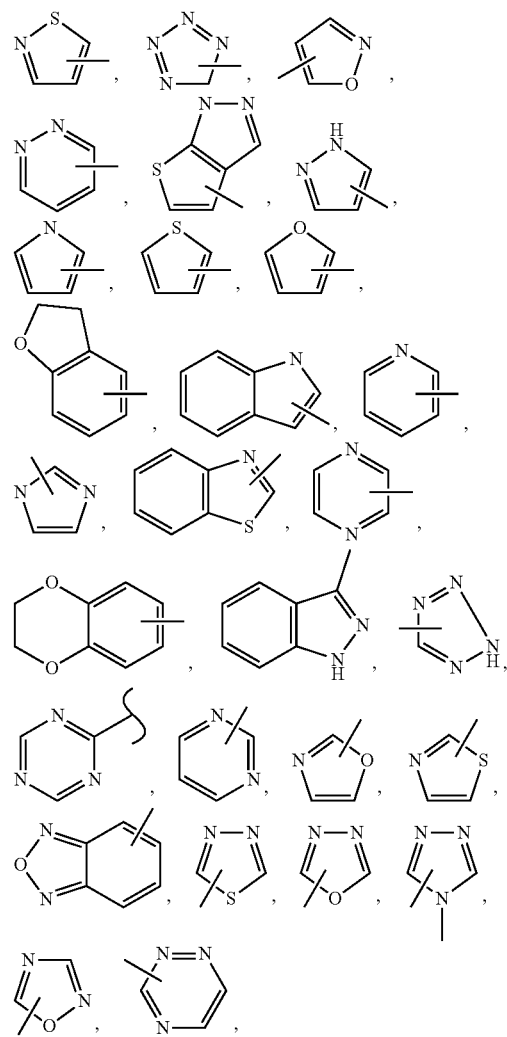

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group C(=O)R$_e$, as well as the bivalent groups —C(=O)— or —C(=O)R$_e$—, which are linked to organic radicals. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation " ∿ " or

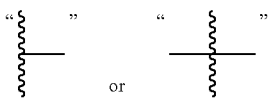

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

The term "at least one" or "one or more" is used to represent one, or suitable multiples thereof such as, for example, two, three, four, five, six and the like.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When a group or moiety in a structure appears to be short on valence, the remaining valences are understood to be filled with hydrogen atoms unless otherwise stated, e.g. (e.g., —N should be considered —NH or —NH$_2$ and —O should be considered —OH, as needed, unless otherwise stated).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 R$^{3a}$, then said group may optionally be substituted with up to three R$^{3a}$ groups, and at each occurrence R$^{3a}$ is selected independently from the definition of R$^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| $Et_2O$ | diethyl ether |
| i-PrOH or IPA | isopropanol |
| HOAc | acetic acid |
| BOP reagent | benzotriazol-1-yloxytris(dimethylamino)phosphonium hexafluorophosphate |
| $BBr_3$ | boron tribromide |
| Boc | tert-butyloxycarbonyl |
| cDNA | complimentary DNA |
| $CDCl_3$ | deuterated chloroform |
| $CH_2Cl_2$ | dichloromethane |
| $CH_3CN$ | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC•HCl) or EDCI (or EDCI•HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperaxine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidinophosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| $K_3PO_4$ | potassium phosphate |
| $MgSO_4$ | magnesium sulfate |
| NaCl | sodium chloride |
| NaH | sodium hydride |
| $NaHCO_3$ | sodium bicarbonate |
| NaOH | sodium hydroxide |
| $Na_2SO_3$ | sodium sulfite |
| $Na_2SO_4$ | sodium sulfate |

| | |
|---|---|
| NH₃ | ammonia |
| NH₄Cl | ammonium chloride |
| NH₄OH | ammonium hydroxide |
| OTs | tosylate, para-toluenesulfonate |
| PBr₃ | phosphorous tribromide |
| Pd(PPh₃)₄ | tetrakis(triphenylphosphine) palladium (0) |
| (S,S)-EtDuPhosRh(I) | (+)-1,2-bis((2S,5S)-2,5-diethylphospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

GENERAL METHODS

The following methods were used in the exemplified Examples, except where noted otherwise.

HPLC Methods:

Method A: Column Zorbax XDB-C18 3.5 microns, 4.6×30 mm; Mobile Phase: A=MeOH:H₂O:TFA (95:5:05), B=MeOH:H₂O:TFA (5:95:05). Grad.: T=0: 100% solv A; T=2:100% solv B; stop time: 4 min. Flow=3.0 mL/min Method B: Agilent Poroshell 120; EC-C18, 2.7 um; 2.1×30 mm; Mobile Phase: Solv A: 5% MeOH: 95% H2O+0.1% AcOH; Solv B: 95% MeOH: 5% H2O+0.1% AcOH; Grad.: T=0: 100% solv A; T=1:100% solv B; stop time: 4 min. Flow=1.0 mL/min Method C: SunfireC18 3.5 microns column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm)

Method D: Eclipse XDB-C18 3.5 microns column (4.6×30 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm)

Method E: Eclipse XDB-C18 3.5 microns column (4.6×30 mm) eluted at 3 mL/min with a 2 min gradient from 100% A to 100% B (A: 5% acetonitrile, 94.95% water, 0.05% TFA; B: 5% water, 94.95% acetonitrile, 0.05% TFA, UV 220 nm)

Method F: Zorbax SB-Phenyl 3.5 microns column (4.6×50 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm).

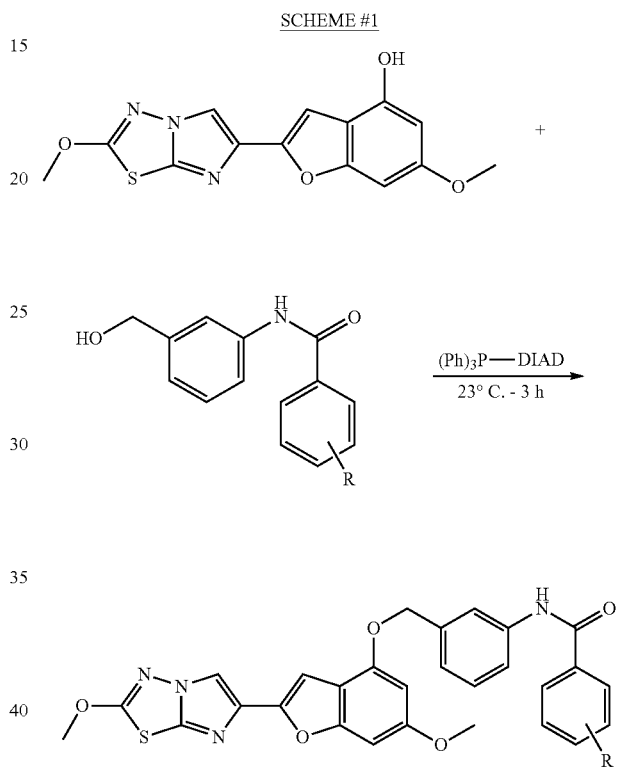

SCHEME #1

Example 1

N-(3-(((6-methoxy-2-(2-methoxyimidazo[2,1-b][1,3,4]thiadiazol-6-yl)benzofuran-4-yl)oxy)methyl)phenyl)benzamide

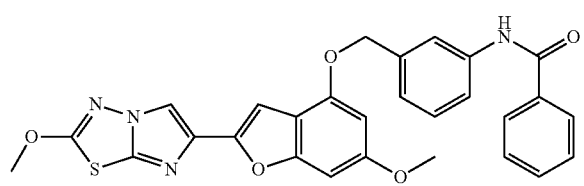 [SMILES: COc1cc(OCc2cccc(NC(=O)c3ccccc3)c2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (0.050 g, 0.157 mmol, see WO13163279, WO13163241, and WO13163244 for preparation of this compound and related intermediates where R³ and Y in Formula I are modified), triphenylphosphine (0.083 g, 0.316 mmol) and N-(3-(hydroxymethyl)phenyl)benzamide (0.072 g, 0.316 mmol) (J. L. Kelly and B. R. Baker, J. Med. Chem., 1982, 25, 600) in a 50 ml flask was maintained under vacuum for 10 min and then purged with nitrogen. Dry tetrahydrofuran (4 ml) was added and the resulting heterogeneous mixture was treated at 22° C. with a solution of diisopropyl azodicarboxylate (0.064 g, 0.316 mmol) in tetrahydrofuran (2 ml) added drop-wise over 10 min. The resulting homogeneous solution was then stirred at 22° C. for 3 h. The reaction mixture was quenched by the addition of dichloromethane and saturated sodium bicarbonate. The organic phase was washed with brine, dried over anhydrous magnesium sulfate and concentrated in vacuo. Chromatography of the residue on silica gel (elution dichloromethane-ethyl acetate 5-10%) followed by crystallization from ethyl acetate gave 0.047 g (56% yield) of the title material as a white solid. HPLC (Method A): 2.348 min. HRMS (ESI) calcd for $C_{28}H_{23}N_4O_5S$ [M+H]⁺ m/z 527.1384, found 527.142. ¹H NMR (CDCl₃, 400 MHz) δ ppm: 7.85-7.90 (m, 2H), 7.84 (br. s, 1H), 7.82 (s, 1H), 7.74 (br. d, J=8.4 Hz, 1H), 7.63 (br. s, 1H), 7.45-7.55 (m, 3H), 7.39 (t, J=7.8 Hz, 1H), 7.25 (overlapping with CHCl₃, 1H), 7.09 (s, 1H), 6.67 (br. s, 1H), 6.36 (br. s, 1H), 5.18 (s, 2H), 4.18 (s, 3H), 3.81 (s, 3H).

Example 2

4-Fluoro-N-(3-(((6-methoxy-2-(2-methoxyimidazo[2,1-b][1,3,4]thiadiazol-6-yl)benzofuran-4-yl)oxy)methyl)phenyl)benzamide Reaction of 6-methoxy-2-(2-methoxyimidazo[2,1-b][1,3,4]thiadiazol-6-yl)benzofuran-4-ol (0.080 g, 0.252 mmol) with 4-fluoro-N-(3-(hydroxymethyl)phenyl)benzamide (0.092 g, 0.378 mmol) as described in example 1 gave 0.099 g (72% yield) of the title material as a white solid. HPLC (Method A): 2.371 min. HRMS (ESI) calcd for $C_{28}H_{22}FN_4O_5S$ [M+H]⁺ m/z 545.1289, found 545.1301. ¹H NMR (CDCl₃, 400 MHz) δ ppm: 7.89-7.92 (m, 3H), 7.82 (s, 1H), 7.76 (br.d, J=7.9 Hz, 1H), 7.61 (s, 1H), 7.39 (t, J=7.9 Hz, 1H), 7.23 (overlapping with CHCl₃, 1H), 7.15 (t, J=8.5 Hz, 2H), 7.09 (s, 1H), 6.67 (br. d, 1H), 6.36 (d, J=1.7 Hz, 1H), 5.18 (s, 2H), 4.19 (s, 3H), 3.82 (s, 3H).

SCHEME #2

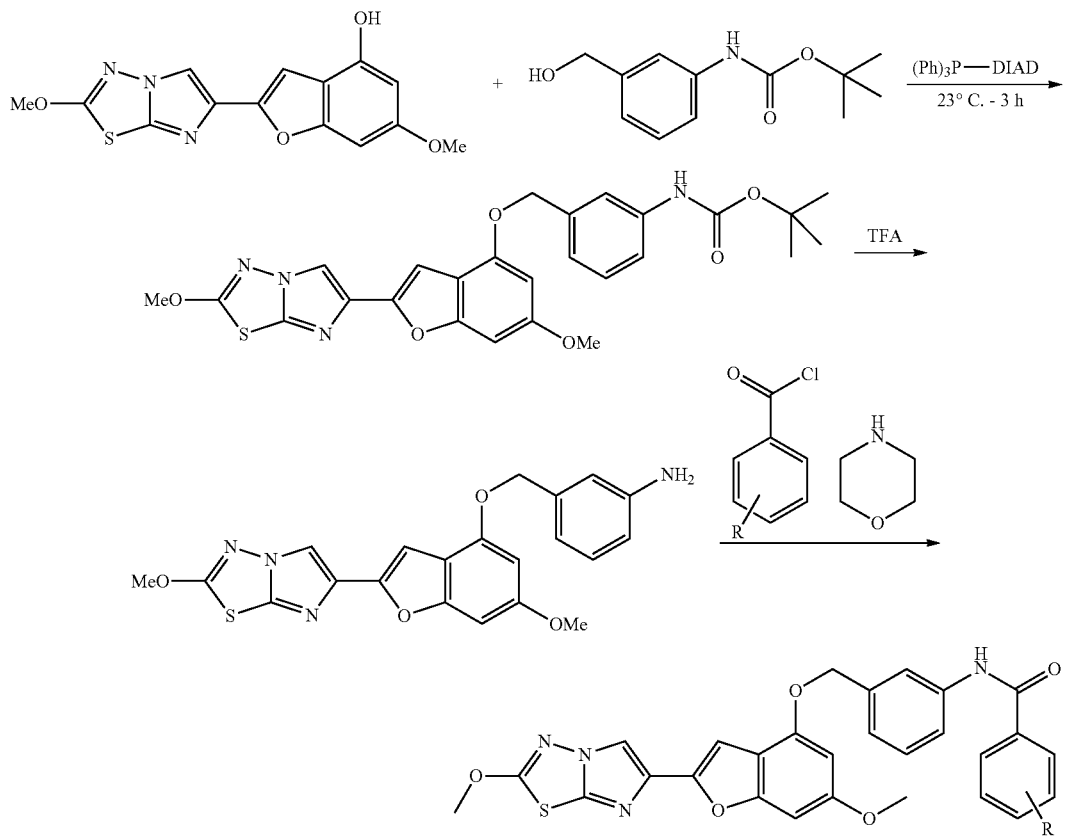

Example 3 tert-Butyl (3-(((6-methoxy-2-(2-methoxyimidazo[2,1-b][1,3,4]thiadiazol-6-yl)benzofuran-4-yl)oxy)methyl)phenyl)carbamate

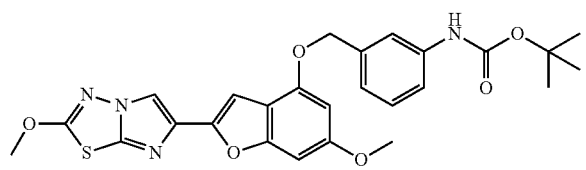 [SMILES: COc1cc(OCc2cccc(NC(=O)OC(C)(C)C)c2)c2cc(-c3cn4nc(OC)sc4n3)oc2c1]

tert-Butyl (3-(hydroxymethyl)phenyl)carbamate

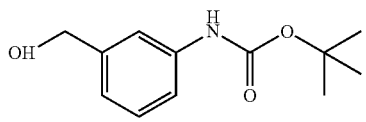 [SMILES: CC(C)(C)OC(=O)Nc1cccc(CO)c1]

A mixture of 3-aminobenzyl alcohol (1.365 g, 11.08 mmol) in dry tetrahydrofuran (15 mL) was treated at 23° C. with di-tert-butyl dicarbonate (2.53 g, 11.59 mmol) and the resulting mixture was stirred for 72 hours (the mixture became homogeneous after 5 min). The reaction mixture was then concentrated under reduced pressure and the oily residue was chromatography on silica gel (elution toluene-ethyl acetate 8:2) to give 2.48 g (100% yield) of the title material as a thick syrup which crystallized to a white solid in the fridge. HPLC (Method A): 1.715 min. $^1$H NMR (CDCl$_3$, 400 MHz) δ ppm: 7.43 (br. s, 1H), 7.26 (t, J=7.9 Hz, 1H), 7.20 (br. d, J=8.0 Hz, 1H), 7.02 (br. d, J=7.5 Hz, 1H), 6.49 (br. s, 1H), 4.65 (d, J=6.0 Hz, 2H), 1.76 (t, J=6.0 Hz, 1H), 1.51 (s, 9H).

tert-Butyl (3-(((6-methoxy-2-(2-methoxyimidazo[2,1-b][1,3,4]thiadiazol-6-yl)benzofuran-4-yl)oxy)methyl)phenyl)carbamate

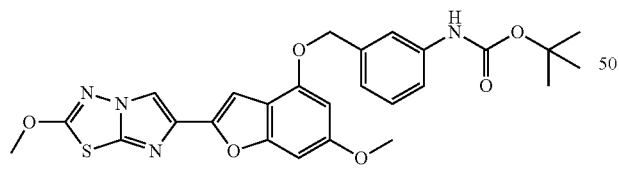

A suspension of 6-methoxy-2-(2-methoxyimidazo[2,1-b][1,3,4]thiadiazol-6-yl)benzofuran-4-ol (2.25 g, 7.09 mmol), tert-butyl (3-(hydroxymethyl)phenyl)carbamate (1.90 g, 8.51 mmol) and triphenylphosphine (2.79 g, 10.63 mmol) in dry tetrahydrofuran (150 mL) was treated at 22° C. and under nitrogen with a solution of diisopropyl azodicarboxylate (2.15 g, 10.63 mmol) in tetrahydrofuran (20 ml) added drop-wise over 2 hours. The heterogeneous mixture was homogeneous at the end of the addition and was stirred for another 3 hours. The reaction mixture was then quenched by the addition of ethyl acetate (400 mL) and saturated sodium bicarbonate. The organic phase was washed with brine, dried over anhydrous magnesium sulfate and concentrated in vacuo. Chromatography of the residue on silica gel (elution toluene-ethyl acetate 9:1) followed by crystallization from ethyl acetate gave 2.595 g (70% yield) of the title material as colorless prisms. HPLC (Method A): 2.413 min. HRMS (ESI) calcd for C$_{26}$H$_{27}$N$_4$O$_6$S [M+H]$^+$ m/z 523.1646, found 523.1676. $^1$H NMR (CDCl$_3$, 400 MHz) δ ppm: 7.83 (s, 1H), 7.42 (br. s, 1H), 7.38 (br. d, J=8 Hz, 1H), 7.30 (t, J=8 Hz, 1H), 7.13 (br. d, J=7.6 Hz, 1H), 7.08 (s, 1H), 6.67 (br. d, 1H),), 6.51 (br. s, 1H), 6.35 (d, J=1.9 Hz, 1H), 5.14 (s, 2H), 4.19 (s, 3H), 3.82 (s, 3H), 1.51 (s, 9H).

Example 4

3-(((6-Methoxy-2-(2-methoxyimidazo[2,1-b][1,3,4]thiadiazol-6-yl)benzofuran-4-yl)oxy)methyl)aniline

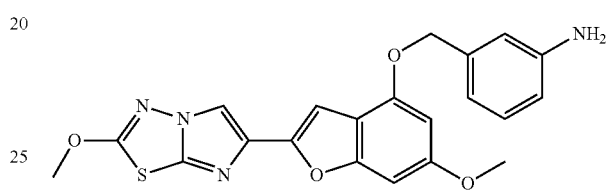

A solution of tert-butyl (3-(((6-methoxy-2-(2-methoxyimidazo[2,1-b][1,3,4]thiadiazol-6-yl)benzofuran-4-yl)oxy)methyl)phenyl)carbamate (2.58 g, 4.93 mmol) in dichloromethane (150 mL) was treated at 22° C. and under nitrogen with trifluoroacetic acid (15 mL) added drop-wise over 5 min. After 2 hours, the solvent and excess reagent were evaporated under reduced pressure and the residue was partitioned between dichloromethane and saturated sodium bicarbonate. The organic phase was washed with brine, dried over anhydrous magnesium sulfate and concentrated under reduced pressure to give a white solid. Trituration of this solid in a small amount of 1,2-dichloroethane followed by filtration gave 1.74 g (83% yield) of the title aniline as a white solid. HPLC (Method A): 1.991 min. HRMS (ESI) calcd for C$_{21}$H$_{19}$N$_4$O$_4$S [M+H]m/z 423.1122, found 423.1129. $^1$H NMR (DMSO-d$_6$, 400 MHz) δ ppm: 8.30 (s, 1H), 6.96 (t, J=7.7 Hz, 1H), 6.89 (s, 1H), 6.73 (br. d, 1H), 6.62 (t, J=1.9 Hz, 1H), 6.53 (br. d, J=7.9 Hz, 1H), 6.43-6.45 (m, 1H), 6.40 (d, J=1.9 Hz, 1H), 5.07 (br. s, 2H), 5.01 (s, 2H), 4.13 (s, 3H), 3.71 (s, 3H).

Example 5

4-Chloro-N-(3-(((6-methoxy-2-(2-methoxyimidazo[2,1-b][1,3,4]thiadiazol-6-yl)benzofuran-4-yl)oxy)methyl)phenyl)benzamide

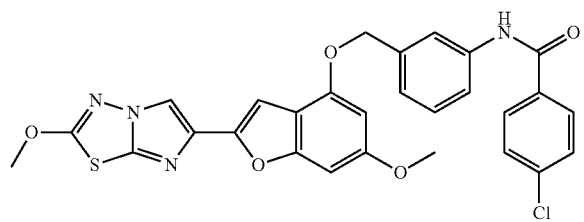 [SMILES: COc1cc(OCc2cccc(NC(=O)c3ccc(Cl)cc3)c2)c2cc(-c3cn4nc(OC)sc4n3)oc2c1]

A solution of 3-(((6-methoxy-2-(2-methoxyimidazo[2,1-b][1,3,4]thiadiazol-6-yl)benzofuran-4-yl)oxy)methyl)aniline (0.058 g, 0.137 mmol) in dry tetrahydrofuran (4 mL) was treated at 22° C. and under nitrogen with 4-methylmorpholine (0.031 g, 0.3 mmol) followed by a solution of 4-chlorobenzoyl chloride (0.035 g, 0.20 mmol) in dry tetrahydrofuran (2 mL) added drop-wise over 2 min. After 1 hour, the reaction mixture was diluted with dichloromethane, washed successively with cold 0.1N hydrochloric acid, saturated sodium bicarbonate and brine. After drying over anhydrous magnesium sulfate, the organic phase was concentrated under reduced pressure. Chromatography of the residue on silica gel (elution dichloromethane-ethyl acetate 9:1) followed by crystallization from ethyl acetate gave 0.046 g (60% yield) of the title material as a white solid. HPLC (Method A): 2.428 min. HRMS (ESI) calcd for $C_{28}H_{22}ClN_4O_5S$ [M+H]+m/z 561.0994, found 561.1023. $^1$H NMR (CDCl$_3$, 400 MHz) δ ppm: 7.80-7.85 (m, 4H), 7.74 (br. d, J=8.6 Hz, 1H), 7.60 (br. s, 1H), 7.45 (d, J=8.6 Hz, 2H), 7.39 (t, J=7.8 Hz, 1H), 7.24 (overlapping with CHCl$_3$, 1H), 7.09 (s, 1H), 6.67 (br. d, 1H), 6.35 (d, J=1.42 Hz, 1H), 5.18 (s, 2H), 4.18 (s, 3H), 3.81 (s, 3H).

Example 6

N-(3-(((6-methoxy-2-(2-methoxyimidazo[2,1-b][1,3,4]thiadiazol-6-yl)benzofuran-4-yl)oxy)methyl)phenyl)-3-(trifluoromethoxy)benzamide

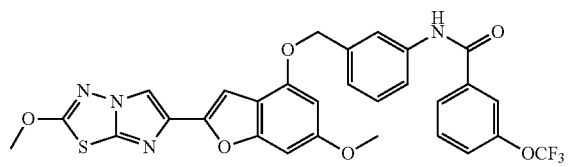 [SMILES: COc1cc(OCc2cccc(NC(=O)c3cccc(OC(F)(F)F)c3)c2)c2cc(-c3cn4nc(OC)sc4n3)oc2c1]

Reaction of 3-(((6-methoxy-2-(2-methoxyimidazo[2,1-b][1,3,4]thiadiazol-6-yl)benzofuran-4-yl)oxy)methyl)aniline (0.056 g, 0.132 mmol) with 3-(trifluoromethoxy)benzoyl chloride (0.040 g, 0.178 mmol) as described in example 5 gave 0.070 g (85% yield) of the title material as a white solid. HPLC (Method A): 2.437 min. HRMS (ESI) calcd for $C_{29}H_{22}F_3N_4O_6S$ [M+H]+ m/z 611.1207, found 611.1186. $^1$H NMR (CDCl$_3$, 400 MHz) δ ppm: 7.85 (s, 1H), 7.81 (s, 1H), 7.77 (d, J=7.7 Hz, 1H), 7.71-7.75 (m, 2H), 7.62 (s, 1H), 7.50 (t, J=8 Hz, 2H), 7.37-7.41 (m, 2H), 7.26 (overlapping with CHCl$_3$, 1H), 6.66 (br. d, 1H), 6.35 (d, J=1.87 Hz, 1H), 5.17 (s, 2H), 4.18 (s, 3H), 3.81 (s, 3H).

Example 7

N-(3-(((6-methoxy-2-(2-methoxyimidazo[2,1-b][1,3,4]thiadiazol-6-yl)benzofuran-4-yl)oxy)methyl)phenyl)benzenesulfonamide

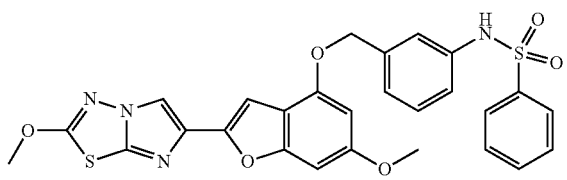 [SMILES: COc1cc(OCc2cccc(NS(=O)(=O)c3ccccc3)c2)c2cc(-c3cn4nc(OC)sc4n3)oc2c1]

Reaction of 3-(((6-methoxy-2-(2-methoxyimidazo[2,1-b][1,3,4]thiadiazol-6-yl)benzofuran-4-yl)oxy)methyl)aniline (0.200 g, 0.473 mmol) with benzenesulfonyl chloride (0.125 g, 0.71 mmol) as described in example 5 gave 0.206 g (77% yield) of the title material as a white solid. HPLC (Method A): 2.28 min. HRMS (ESI) calcd for $C_{27}H_{23}N_4O_6S_2$ [M+H]$^+$ m/z 563.1054, found 563.1045. $^1$H NMR (DMSO-d$_6$, 400 MHz) δ ppm: 10.34 (s, 1H), 8.35 (s, 1H), 7.69-7.71 (m, 2H), 7.53-7.57 (m, 1H), 7.44-7.48 (m, 2H), 7.25 (s, 1H), 7.21 (t, J=7.8 Hz, 1H), 7.09 (d, J=7.8 Hz, 1H), 6.99-7.02 (m, 1H), 6.91 (s, 1H), 6.78 (br. d, 1H), 6.40 (d, J=1.84 Hz, 1H), 5.17 (s, 2H), 4.17 (s, 3H), 3.74 (s, 3H).

Library Approach with Aniline Described in Example 4

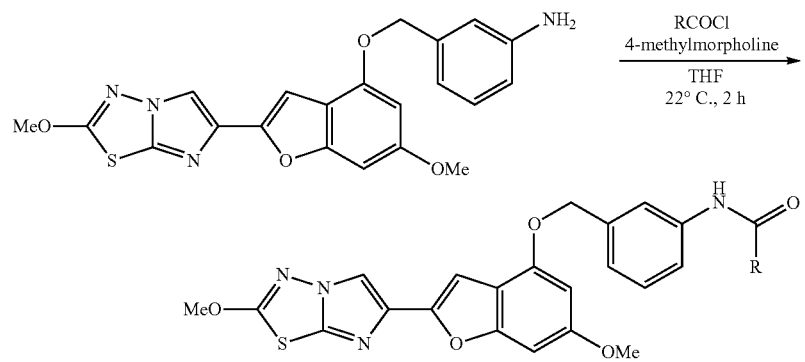

In a 4 mL vial was weighted the 3-(((6-methoxy-2-(2-methoxyimidazo[2,1-b][1,3,4]thiadiazol-6-yl)benzofuran-4-yl)oxy)methyl)aniline (0.025 g, 0.059 mmol). Dry tetrahydrofuran (1 mL) was added, followed by 4-methylmorpholine (25 μL, 0.22 mmol, ~3.7 equivalent). Then the acid chloride (0.082 mmol, 1.4 equivalent) in tetrahydrofuran (0.5 mL) was added all at once. The resulting mixture was stirred on a Heidolph Unimax 1010 shaker (300 rpm) for 2 h. HPLC indicated complete disappearance of the starting aniline. The reaction mixture was then quenched by the addition of water (0.5 mL) and acetic acid (two drops, the solution became homogeneous). The reaction mixture is directly purified by prep HPLC (Zorbax SB-C18 Prep HT 5 um; 21.2×100 mm; solvent A MeOH:H2O/TFA 0.05% (5:95), solvent B MeOH:H2O/TFA 0.05% (95:5), T 0-2 min: 40% solvent B; 8 min gradient to 100% solvent B; stop time 15 min.; 220 nm). The selected fractions are concentrated and the residue was lyophilized from an acetonitrile-water mixture to give ~15-30 mg of the amide as a white solid.

| Ex. | Structure | Formula | HPLC Retention Time (Min)/Method | Calc. [M + H]+ m/z | LCMS [M + H]+ m/z | NMR |
|---|---|---|---|---|---|---|
| 8 | 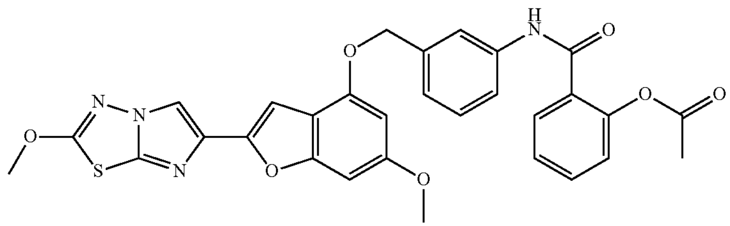 [SMILES: COc1cc(OCc2cccc(NC(=O)c3ccccc3OC(C)=O)c2)c2cc(-c3cn4nc(OC)sc4n3)oc2c1] | C30H24N4O7S | 2.273/A | 585.1438 | 585.1432 | 1H NMR (CDCl3) δ ppm: 8.06 (s, 1H), 7.85 (d, J = 8.3 Hz, 1H), 7.83 (s, 1H), 7.62-7.66 (m, 2H), 7.48-7.52 (m, 1H), 7.33-7.40 (m, 2H), 7.25-7.27 (m, 1H), 7.13-7.15 (m, 2H), 6.66 (br. d, 1H), 6.36 (d, J = 1.9 Hz, 1H), 5.20 (s, 2H), 4.21 (s, 3H), 3.81 (s, 3H), 2.28 (s, 3H). |
| 9 | 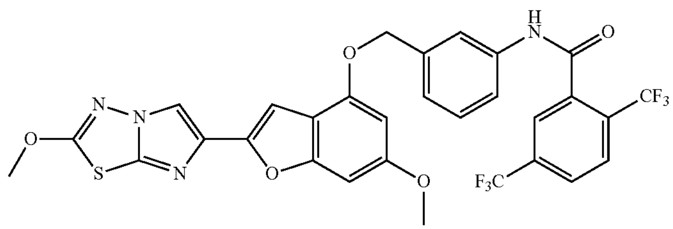 [SMILES: COc1cc(OCc2cccc(NC(=O)c3cc(C(F)(F)F)ccc3C(F)(F)F)c2)c2cc(-c3cn4nc(OC)sc4n3)oc2c1] | C30H20F6N4O5S | 2.373/A | 663.1131 | 663.1132 | 1H NMR (CDCl3) δ ppm: 7.86 (s, 1H), 7.83 (d, J = 8.2 Hz, 1H), 7.78 (d, J = 8.2 Hz, 1H), 7.75 (s, 1H), 7.69 (dd, J = 8.4, 1.3 Hz, 1H), 7.58 (s, 2H), 7.53 (s, 1H), 7.33-7.37 (m, 1H), 7.21 (d, J = 1.85 Hz, 1H), 7.09 (s, 1H), 6.60 (br. d, 1H), 6.31 (d, J = 1.85 Hz, 1H), 5.13 (s, 2H), 4.14 (s, 3H), 3.76 (s, 3H). |
| 10 | 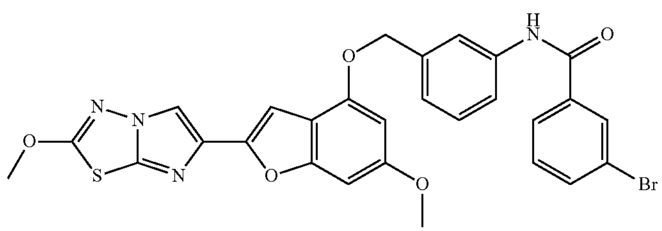 [SMILES: COc1cc(OCc2cccc(NC(=O)c3cccc(Br)c3)c2)c2cc(-c3cn4nc(OC)sc4n3)oc2c1] | C28H21BrN4O5S | 2.438/A | 605.0489 | 605.0475 | 1H NMR (CDCl3) δ ppm: 8.01 (br. s, 1H), 7.82 (s, 1H), 7.81 (br. s, 1H), 7.77-7.80 (m, 1H), 7.71-7.74 (m, 1H), 7.65-7.67 (m, 1H), 7.63 (br. s, 1H), 7.40 (t, J = 7.9 Hz, 1H), 7.35 (t, J = 7.9 Hz, 1H), 7.26 (s, 1H), 7.14 (s, 1H), 6.66 (br. d, 1H), 6.36 (d, J = 1.88 Hz, 1H), 5.19 (s, 2H), 4.20 (s, 3H), 3.82 (s, 3H). |
| 11 | 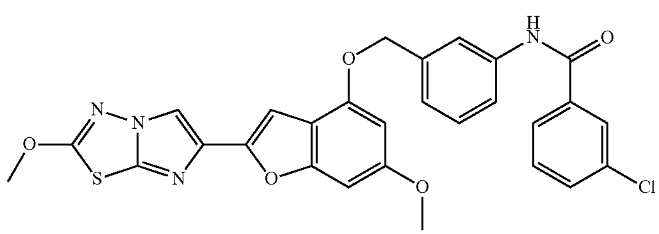 [SMILES: COc1cc(OCc2cccc(NC(=O)c3cccc(Cl)c3)c2)c2cc(-c3cn4nc(OC)sc4n3)oc2c1] | C28H21ClN4O5S | 2.413/A | 561.0994 | 561.0982 | 1H NMR (CDCl3) δ ppm: 7.83 (br. s, 1H), 7.79-7.80 (m, 1H), 7.76 (s, 1H), 7.67 (br. d, J = 7.7 Hz, 2H), 7.57 (s, 1H), 7.42-7.55 (m, 1H), 7.31-7.36 (m, 2H), 7.20 (s, 1H), 7.11 (s, 1H), 6.59 (br. d, 1H), 6.30 (d, J = 1.84 Hz, 1H), 5.13 (s, 2H), 4.14 (s, 3H), 3.75 (s, 3H). |

| Ex. | Structure | Formula | HPLC Retention Time (Min)/Method | Calc. [M+H]+ m/z | LCMS [M+H]+ m/z | NMR |
|---|---|---|---|---|---|---|
| 12 | 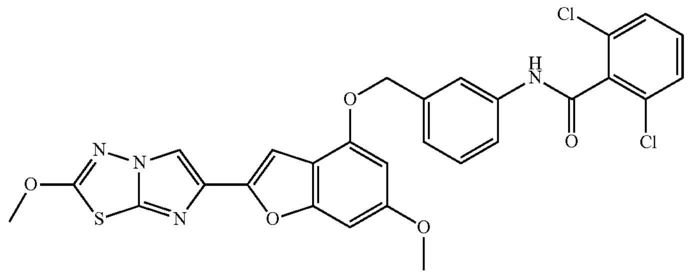 [SMILES: COc1cc(OCc2cccc(NC(=O)c3c(Cl)cccc3Cl)c2)c2cc(-c3cn4nc(OC)sc4n3)oc2c1] | C29H20Cl2N4O5S | 2.327/A | 595.0604 | 595.0596 | 1H NMR (CDCl3) δ ppm: 7.75 (s, 1H), 7.72 (br. d, 1H), 7.57 (br. s, 1H), 7.41 (br. s, 1H), 7.34 (t, J = 7.8 Hz, 1H), 7.29 (d, J = 2.0 Hz, 1H), 7.28 (s, 1H), 7.23 (d, J = 8.5 Hz, 1H), 7.21 (d, J = 9.3 Hz, 1H), 7.09 (s, 1H), 6.60 (br. d, 1H), 6.32 (d, J = 1.86 Hz, 1H), 5.14 (s, 2H), 4.14 (s, 3H), 3.76 (s, 3H). |
| 13 | 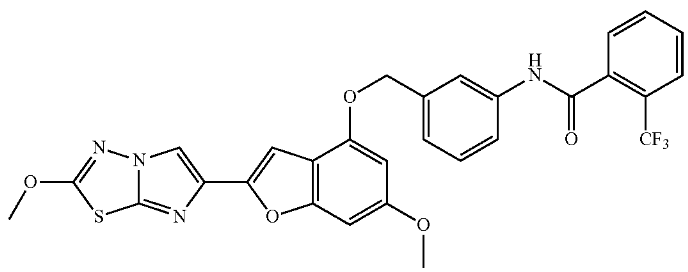 [SMILES: COc1cc(OCc2cccc(NC(=O)c3ccccc3C(F)(F)F)c2)c2cc(-c3cn4nc(OC)sc4n3)oc2c1] | C29H21F3N4O5S | 2.313/A | 595.1258 | 595.126 | 1H NMR (CDCl3) δ ppm: 7.75 (s, 1H), 7.68 (d, J = 7.8 Hz, 1H), 7.63 (br. d, J = 7.9 Hz, 1H), 7.49-7.62 (m, 4H), 7.43 (br. s, 1H), 7.33 (t, J = 7.8 Hz, 1H), 7.21 (d, J = 7.8 Hz, 1H), 7.03 (s, 1H), 6.60 (br. d, 1H), 6.30 (d, J = 1.9 Hz, 1H), 5.12 (s, 2H), 4.12 (s, 3H), 3.75 (s, 3H). |
| 14 | 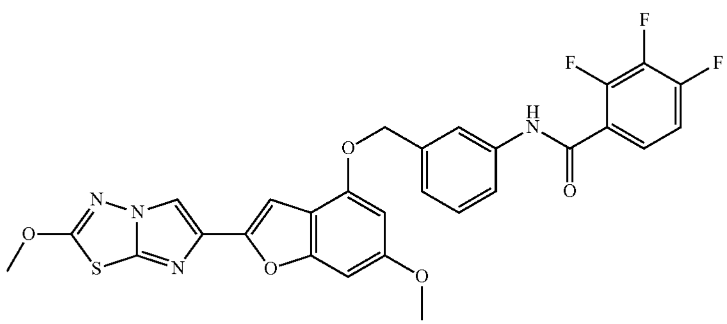 [SMILES: COc1cc(OCc2cccc(NC(=O)c3ccc(F)c(F)c3F)c2)c2cc(-c3cn4nc(OC)sc4n3)oc2c1] | C28H19F3N4O5S | 2.373/A | 581.1101 | 581.1103 | 1H NMR (CDCl3) δ ppm: 8.18 (br. d, 1H), 7.8-7.87 (m, 1H), 7.76 (s, 1H), 7.63 (br. s, 1H), 7.60 (d, J = 8.1 Hz, 1H), 7.34 (t, J = 7.8 Hz, 1H), 7.23 (d, J = 7.8 Hz, 1H), 7.12 (s, 1H), 7.03-7.09 (m, 1H), 6.60 (d, J = 1.8 Hz, 1H), 6.31 (d, J = 1.8 Hz, 1H), 5.14 (s, 2H), 4.15 (s, 3H), 3.76 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 15 | 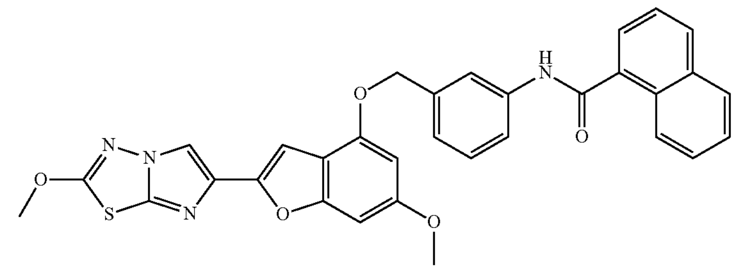 [SMILES: COc1cc(OCc2cccc(NC(=O)c3cccc4ccccc34)c2)c2cc(-c3cn4nc(OC)sc4n3)oc2c1] | C32H24N4O5S | 2.385/A | 577.154 | 577.1535 | 1H NMR (CDCl3) δ ppm: 9.06 (d, J = 8.6 Hz, 1H), 8.35 (d, J = 7.2 Hz, 1H), 8.28 (d, J = 7.4 Hz, 1H), 8.07 (d, J = 7.7 Hz, 1H), 7.41-7.87 (m, 7H), 7.36 (t, J = 7.9 Hz, 1H), 7.22 (d, J = 7.5 Hz, 1H), 7.12 (s, 1H), 6.59 (d, J = 1.8 Hz, 1H), 6.32 (d, J = 1.8 Hz, 1H), 5.16 (s, 2H), 4.15 (s, 3H), 3.76 (s, 3H). |
| 16 | 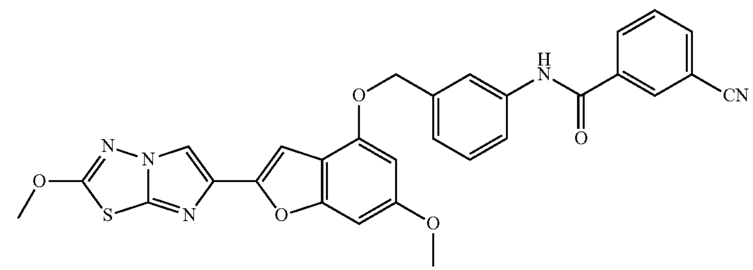 [SMILES: COc1cc(OCc2cccc(NC(=O)c3cccc(C#N)c3)c2)c2cc(-c3cn4nc(OC)sc4n3)oc2c1] | C29H21N5O5S | 2.351/A | 552.1336 | 552.1327 | 1H NMR (CDCl3) δ ppm: 8.21 (s, 1H), 8.16 (br. s, 1H), 8.09 (d, J = 8.0 Hz, 1H), 7.79 (s, 1H), 7.75-7.77 (m, 2H), 7.61 (s, 1H), 7.55 (t, J = 7.8 Hz, 1H), 7.39 (t, J = 7.9 Hz, 1H), 7.24 (d, J = 7.6 Hz, 1H), 7.04 (s, 1H), 6.64 (br. d, 1H), 6.33 (d, J = 1.8 Hz, 1H), 5.16 (s, 2H), 4.17 (s, 3H), 3.80 (s, 3H). |
| 17 | 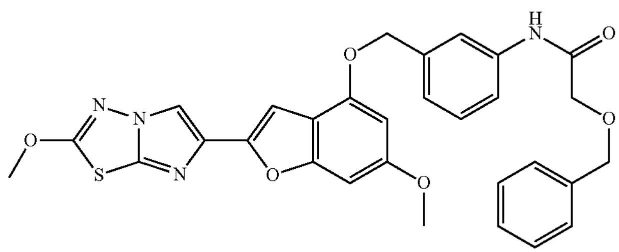 [SMILES: COc1cc(OCc2cccc(NC(=O)COCc3ccccc3)c2)c2cc(-c3cn4nc(OC)sc4n3)oc2c1] | C30H26N4O6S | 2.387/A | 571.1646 | 571.1648 | 1H NMR (CDCl3) δ ppm: 8.26 (br. s, 1H), 7.75 (s, 1H), 7.49-7.52 (m, 2H), 7.25-7.36 (m, 6H), 7.16 (m, overlapping with CHCl3, 1H), 7.00 (s, 1H), 6.61 (br. d, 1H), 6.29 (d, J = 1.8 Hz, 1H), 5.09 (s, 2H), 4.59 (s, 2H), 4.12 (s, 3H), 4.02 (s, 2H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 18 | 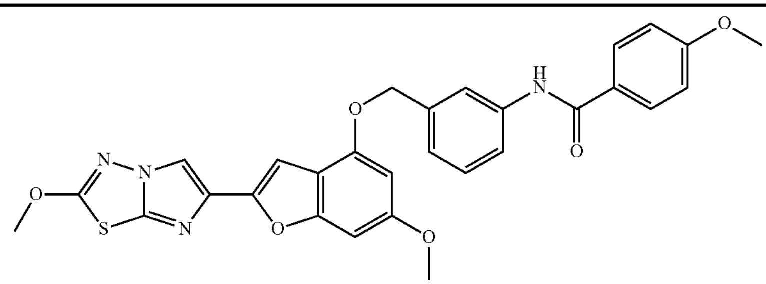 | C29H24N4O6S | 2.337/A | 557.1487 | 557.1514 | 1H NMR (CDCl3) δ ppm: 7.72-7.79 (m, 4H), 7.66 (br. d, 1H), 7.57 (br. s, 1H), 7.32 (t, J = 7.9 Hz, 1H), 7.15-7.16 (m, 1H), 7.11 (s, 1H), 6.89 (br. d, J = 8.8 Hz, 2H), 6.59 (br. d, 1H), 6.30 (d, J = 1.8 Hz, 1H), 5.13 (s, 2H), 4.14 (s, 3H), 3.79 (s, 3H), 3.75 (s, 3H). |
| 19 | 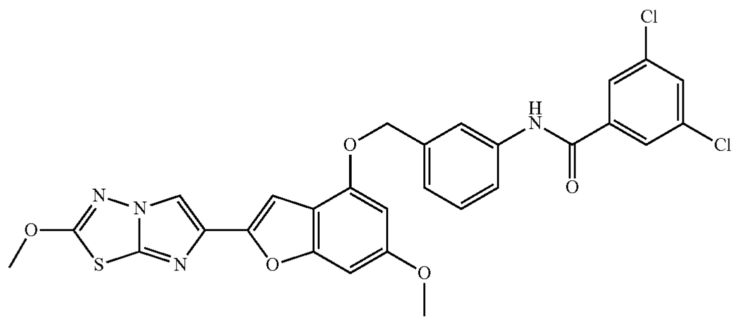 [SMILES: COc1cc(OCc2cccc(NC(=O)c3cc(Cl)cc(Cl)c3)c2)c2cc(-c3cn4nc(OC)sc4n3)oc2c1] | C28H20Cl2N4O5S | 2.540/A | 595.0604 | 595.0627 | 1H NMR (CDCl3) δ ppm: 7.81 (br. s, 1H), 7.75 (s, 1H), 7.67 (d, J = 1.9 Hz, 2H), 7.65 (br. d, 1H), 7.54 (br. s, 1H), 7.44 (t, J = 1.9 Hz, 1H), 7.33 (t, J = 7.9 Hz, 1H), 7.19 (br. d, overlapping with CHCl3, 1H), 7.04 (s, 1H), 6.60 (br. d, 1H), 6.29 (d, J = 1.9 Hz, 1H), 5.12 (s, 2H), 4.13 (s, 3H), 3.75 (s, 3H). |
| 20 | 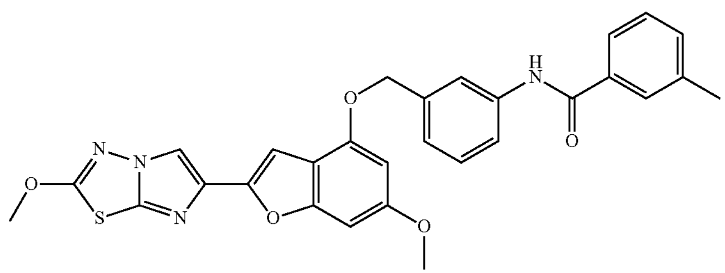 | C29H24N4O5S | 2.387/A | 541.154 | 541.1566 | 1H NMR (CDCl3) δ ppm: 7.77 (br. s, 1H), 7.76 (br. d, 1H), 7.68 (br. d, J = 8 Hz, 1H), 7.62 (s, 1H), 7.57-7.60 (m, 2H), 7.32 (t, J = 7.9 Hz, 1H), 7.26-7.32 (m, 2H), 7.19 (m, overlapping with CHCl3, 1H), 7.06 (s, 1H), 6.60 (br. d, 1H), 6.30 (d, J = 1.9 Hz, 1H), 5.13 (s, 2H), 4.13 (s, 3H), 3.75 (s, 3H), 2.35 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 21 | 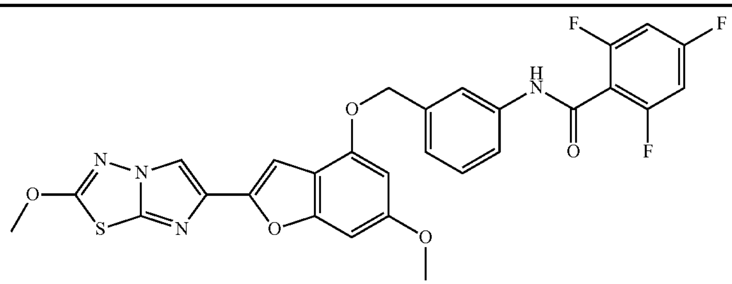 | C28H19F3N4O5S | 2.320/A | 581.1101 | 581.1129 | 1H NMR (CDCl3) δ ppm: 7.77 (s, 1H), 7.70 (br. d, J = 8 Hz, 1H), 7.64 (br. s, 1H), 7.56 (br. s, 1H), 7.34 (t, J = 7.9 Hz, 1H), 7.21 (d, J = 8.2 Hz, 1H), 7.10 (s, 1H), 6.67-6.73 (m, 2H), 6.61 (br. d, 1H), 6.31 (d, J = 1.9 Hz, 1H), 5.13 (s, 2H), 4.15 (s, 3H), 3.77 (s, 3H). |
| 22 | 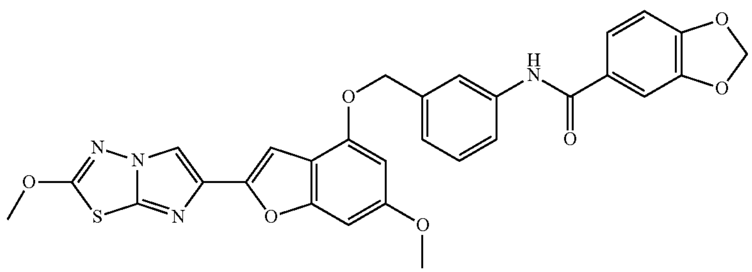 [SMILES: COc1cc(OCc2cccc(NC(=O)c3ccc4c(c3)OCO4)c2)c2cc(-c3cn4nc(OC)sc4n3)oc2c1] | C29H22N4O7S | 2.338/A | 571.1282 | 571.1308 | 1H NMR (CDCl3) δ ppm: 7.76 (s, 1H), 7.7 (br. s, 1H), 7.64 (br. d, J = 8 Hz, 1H), 7.55 (br. s, 1H), 7.29-7.34 (m, 3H), 7.15 (m, overlapping with CHCl3, 1H), 7.09 (s, 1H), 6.79 (d, J = 8.05 Hz, 1H), 6.59 (br. d, 1H), 6.30 (d, J = 1.77 Hz, 1H), 5.97 (s, 2H), 5.12 (s, 2H), 4.14 (s, 3H), 3.75 (s, 3H). |
| 23 | 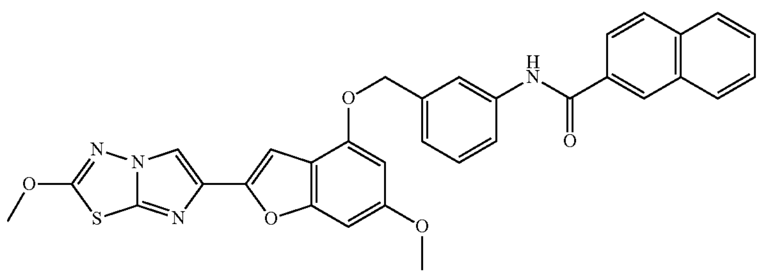 [SMILES: COc1cc(OCc2cccc(NC(=O)c3ccc4ccccc4c3)c2)c2cc(-c3cn4nc(OC)sc4n3)oc2c1] | C32H24N4O5S | 2.428/A | 577.154 | 577.1565 | 1H NMR (CDCl3) δ ppm: 8.32 (s, 1H), 7.96 (br. s, 1H), 7.87-7.90 (m, 3H), 7.81-7.83 (m, 1H), 7.72-7.75 (m, 2H), 7.63 (br. s, 1H), 7.46-7.53 (m, 2H), 7.35 (t, J = 7.9 Hz, 1H), 7.20 (d, J = 8.2 Hz, 1H), 7.06 (s, 1H), 6.60 (br. d, 1H), 6.31 (d, J = 1.86 Hz, 1H), 5.14 (s, 2H), 4.12 (s, 3H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 24 | 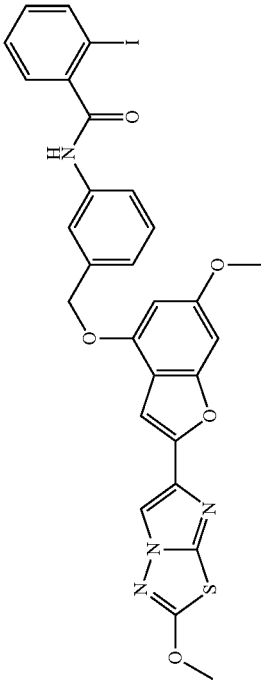 | C28H21IN4O5S | 2.327/A | 653.035 | 653.037 | 1H NMR (CDCl3) δ ppm: 7.83 (d, J = 7.9 Hz, 1H), 7.75 (s, 1H), 7.66 (d, J = 8.3 Hz, 1H), 7.59 (s, 1H), 7.47 (br. d, J = 7.6 Hz, 1H), 7.42 (br. s, 1H), 7.37 (d, J = 8.0 Hz, 1H), 7.33 (d, J = 8.0 Hz, 1H), 7.21 (d, J = 7.5 Hz, 1H), 7.07 (br. t, 1H), 6.91 (s, 1H), 6.60 (br. d, 1H), 6.31 (d, J = 1.4 Hz, 1H), 5.13 (s, 2H), 4.12 (s, 3H), 3.75 (s, 3H). |
| 25 | 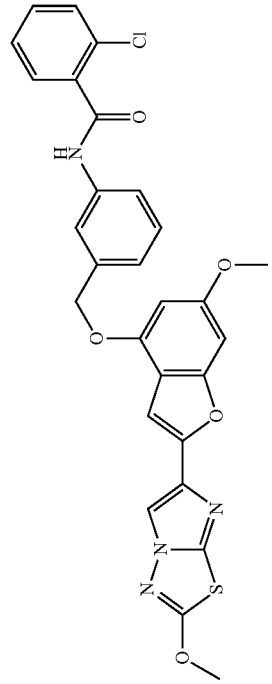 | C28H21ClN4O5S | 2.317/A | 561.0993 | 561.0994 | 1H NMR (CDCl3) δ ppm: 7.80 (br. s, 1H), 7.75 (s, 1H), 7.68 (dd, J = 7.3, 1.9 Hz, 1H), 7.64 (br. d, J = 8.1 Hz, 1H), 7.60 (br. s, 1H), 7.28-7.40 (m, 4H), 7.21 (d, J = 7.8 Hz, 1H), 7.03 (s, 1H), 6.60 (br. d, 1H), 6.31 (d, J = 1.8 Hz, 1H), 5.13 (s, 2H), 4.12 (s, 3H), 3.75 (s, 3H). |
| 26 | 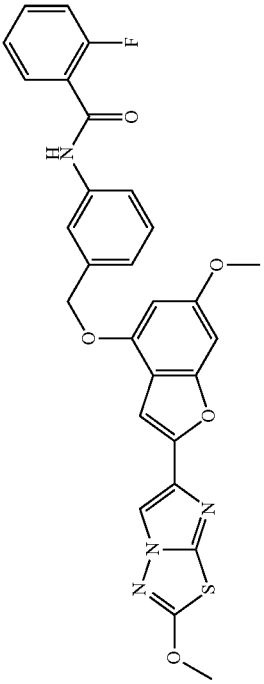 | C28H21FN4O5S | 2.328/A | 545.1289 | 545.1283 | 1H NMR (CDCl3) δ ppm: 8.42 (br. d, J = 15.8 Hz, 1H), 8.09 (dt, J = 8.0, 1.8 Hz, 1H), 7.76 (br. s, 1H), 7.67 (s, 1H), 7.61 (d, J = 8.15 Hz, 1H), 7.41-7.47 (m, 1H), 7.33 (t, J = 7.8 Hz, 1H), 7.21-7.25 (m, 2H), 7.12 (s, 1H), 7.11 (dd, J = 12.4, 8.1 Hz, 1H), 6.59 (br. d, 1H), 6.31 (d, J = 1.8 Hz, 1H), 5.14 (s, 2H), 4.15 (s, 3H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 27 | 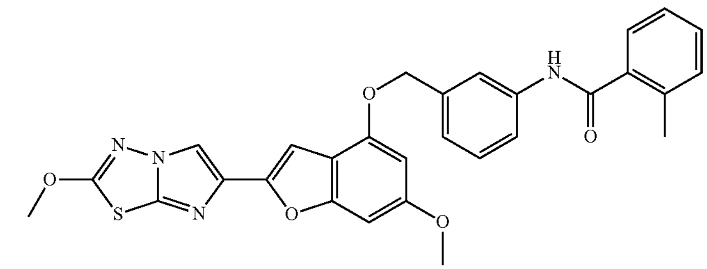 [SMILES: COc1cc(OCc2cccc(NC(=O)c3ccccc3C)c2)c2cc(-c3cn4nc(OC)sc4n3)oc2c1] | C29H24N4O5S | 2.339/A | 541.154 | 541.1538 | 1H NMR (CDCl3) δ ppm: 7.77 (s, 1H), 7.64 (br. d, J = 7.8 Hz, 1H), 7.56 (br. s, 1H), 7.41-7.44 (m, 2H), 7.32 (t, J = 7.8 Hz, 1H), 7.23-7.30 (m, 1H), 7.19-7.20 (m, 3H), 7.02 (s, 1H), 6.60 (br. d, 1H), 6.30 (d, J = 1.8 Hz, 1H), 5.12 (s, 2H), 4.12 (s, 3H), 3.75 (s, 3H), 2.44 (s, 3H). |
| 28 | 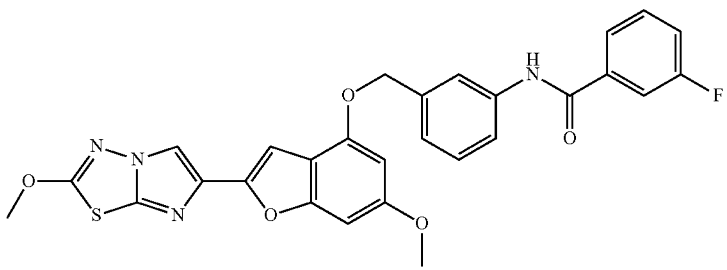 [SMILES: COc1cc(OCc2cccc(NC(=O)c3cccc(F)c3)c2)c2cc(-c3cn4nc(OC)sc4n3)oc2c1] | C28H21FN4O5S | 2.358/A | 545.1289 | 545.1176 | 1H NMR (CDCl3) δ ppm: 7.82 (br. s, 1H), 7.76 (s, 1H), 7.68 (br. d, J = 8.0 Hz, 1H), 7.51-7.57 (m, 3H), 7.37-7.41 (m, 1H), 7.33 (t, J = 7.9 Hz, 1H), 7.13-7.20 (m, 3H), 6.59 (br. d, 1H), 6.30 (d, J = 1.8 Hz, 1H), 5.13 (s, 2H), 4.15 (s, 3H), 3.75 (s, 3H). |
| 29 | 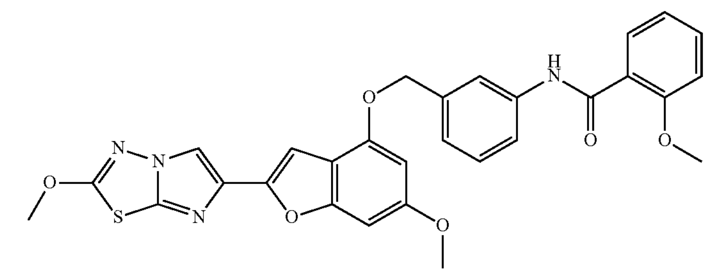 | C29H24F3N4O6S | 2.356/A | 557.1489 | 557.1357 | 1H NMR (CDCl3) δ ppm: 9.75 (br. s, 1H), 8.21 (dd, J = 7.8, 1.8 Hz, 1H), 7.76 (s, 1H), 7.65 (br. s, 1H), 7.62 (br. d, J = 7.9 Hz, 1H), 7.44-7.44 (m, 1H), 7.31 (t, J = 7.8 Hz, 1H), 7.20 (m, 1H), 7.07 (br. d, J = 8 Hz, 1H), 7.04 (s, 1H), 6.96 (d, J = 8.3 Hz, 1H), 6.61 (br. d, 1H), 6.32 (d, J = 1.9 Hz, 1H), 5.13 (s, 2H), 4.12 (s, 3H), 3.98 (s, 3H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 30 | (structure with F, CF3) | C29H20F4N4O5S | 2.424/A | 613.1163 | 613.1188 | 1H NMR (CDCl3) δ ppm: 8.09 (br. dd, J = 6.8, 2.0 Hz, 1H), 8.01-8.04 (m, 1H), 7.86 (br. s, 1H), 7.76 (s, 1H), 7.70 (br. d, J = 8 Hz, 1H), 7.55 (br. s, 1H), 7.34 (t, J = 7.8 Hz, 1H), 7.25 (t, J = 9.2 Hz, 1H), 7.20 (m, 1H), 7.07 (s, 1H), 6.60 (br. d, 1H), 6.30 (d, J = 1.6 Hz, 1H), 5.13 (s, 2H), 4.13 (s, 3H), 3.75 (s, 3H). |
| 31 | (structure with propyl) | C31H28N4O5S | 2.468/A | 569.1853 | 569.1851 | 1H NMR (CDCl3) δ ppm: 7.86 (s, 2H), 7.82 (d, J = 8.2 Hz, 2H), 7.76 (br. d, J = 8 Hz, 1H), 7.67 (br. s, 1H), 7.42 (t, J = 8.0 Hz, 1H), 7.31 (d, J = 8.2 Hz, 2H), 7.25 (m, overlapping with CHCl3, 1H), 7.17 (s, 1H), 6.70 (br. d, 1H), 6.40 (d, J = 2.0 Hz, 1H), 5.22 (s, 2H), 4.23 (s, 3H), 3.85 (s, 3H), 2.67 (t, J = 7.6 Hz, 2H), 1.72-1.75 (m, 2H), 0.96 (t, J = 7.2 Hz, 3H). |
| 32 | (structure with methyl) | C29H24N4O5S | 2.376/A | 541.154 | 541.1565 | 1H NMR (CDCl3) δ ppm: 7.77 (br. s, 1H), 7.76 (s, 1H), 7.70 (br. d, J = 8.0 Hz, 2H), 7.67 (br. dd, J = 7.9, 1.5 Hz, 1H), 7.58 (br. s, 1H), 7.32 (t, J = 7.8 Hz, 1H), 7.20 (br. d, J = 8.0 Hz, 2H), 7.17 (m, overlapping with CHCl3, 1H), 7.10 (s, 1H), 6.60 (br. d, 1H), 6.30 (d, J = 1.9 Hz, 1H), 5.13 (s, 2H), 4.14 (s, 3H), 3.75 (s, 3H), 2.34 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 33 | 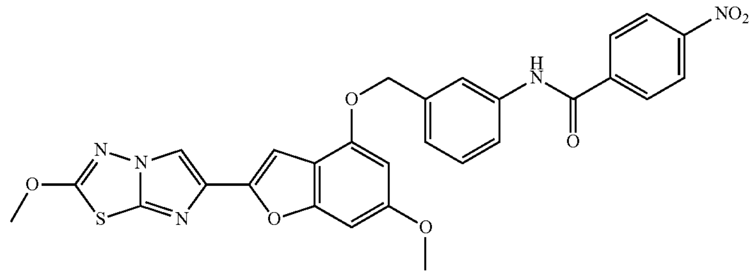 [SMILES: COc1cc(OCc2cccc(NC(=O)c3ccc([N+](=O)[O-])cc3)c2)c2cc(-c3cn4nc(OC)sc4n3)oc2c1] | C28H21N5O7S | 2.358/A | 572.1234 | 572.1255 | 1H NMR (CDCl3) δ ppm: 8.25 (d, J = 8.8 Hz, 2H), 7.99 (s, 1H), 7.98 (d, J = 8.8 Hz, 2H), 7.76 (s, 1H), 7.75 (br. d, J = 7.6 Hz, 1H), 7.55 (br. s, 1H), 7.35 (t, J = 7.9 Hz, 1H), 7.19 (m, overlapping with CHCl3, 1H), 7.10 (s, 1H), 6.60 (br. d, 1H), 6.30 (d, J = 1.8 Hz, 1H), 5.13 (s, 2H), 4.14 (s, 3H), 3.75 (s, 3H). |
| 34 | 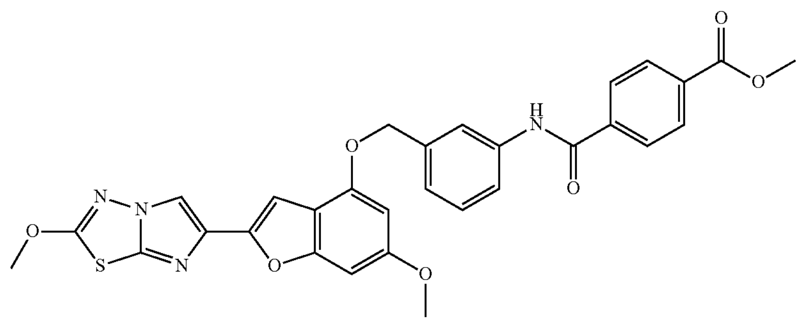 | C30H24N4O7S | 2.367/A | 585.1438 | 585.1454 | 1H NMR (CDCl3) δ ppm: 8.07 (d, J = 8.2 Hz, 2H), 7.87 (d, J = 8.2 Hz, 2H), 7.86 (s, 1H), 7.76 (s, 1H), 7.71 (br. dd, J = 7.6, 1.1 Hz, 1H), 7.58 (br. s, 1H), 7.34 (t, J = 7.9 Hz, 1H), 7.19 (m, overlapping with CHCl3, 1H), 7.09 (s, 1H), 6.60 (br. d, 1H), 6.30 (d, J = 1.86 Hz, 1H), 5.13 (s, 2H), 4.14 (s, 3H), 3.87 (s, 3H), 3.75 (s, 3H). |
| 35 | 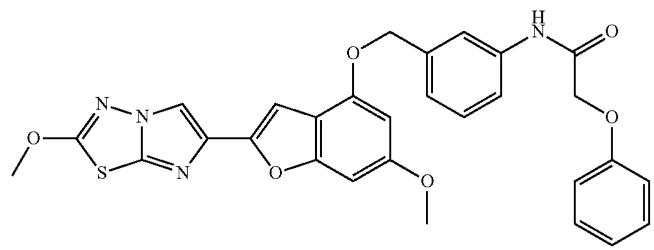 [SMILES: COc1cc(OCc2cccc(NC(=O)COc3ccccc3)c2)c2cc(-c3cn4nc(OC)sc4n3)oc2c1] | C29H24N4O6S | 2.372/A | 557.1489 | 557.1511 | 1H NMR (CDCl3) δ ppm: 8.23 (br. s, 1H), 7.75 (s, 1H), 7.57 (br. s, 1H), 7.54 (br. d, J = 8 Hz, 1H), 7.25-7.32 (m, 3H), 7.20 (d, J = 7.7 Hz, 1H), 7.01 (s, 1H), 6.97 (t, J = 7.4 Hz, 1H), 6.93 (d, J = 8.5 Hz, 2H), 6.61 (br. d, 1H), 6.29 (d, J = 1.6 Hz, 1H), 5.10 (s, 2H), 4.55 (s, 2H), 4.12 (s, 3H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 36 | 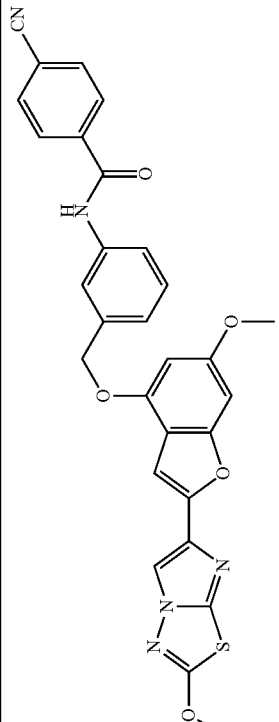 | C29H21N5O5S | 2.315/A | 552.1336 | 552.1254 | 1H NMR (CDCl3) δ ppm: 7.97 (br. d, J = 8.6 Hz, 2H), 7.90 (br. s, 1H), 7.82 (s, 1H), 7.75-7.80 (m, 3H), 7.59 (br. s, 1H), 7.41 (t, J = 7.9 Hz, 1H), 7.24 (m, overlapping with CHCl3, 1H), 7.08 (d, J = 0.7 Hz, 1H), 6.67 (br. d, 1H), 6.35 (d, J = 1.9 Hz, 1H), 5.19 (s, 2H), 4.19 (s, 3H), 3.81 (s, 3H). |
| 37 | 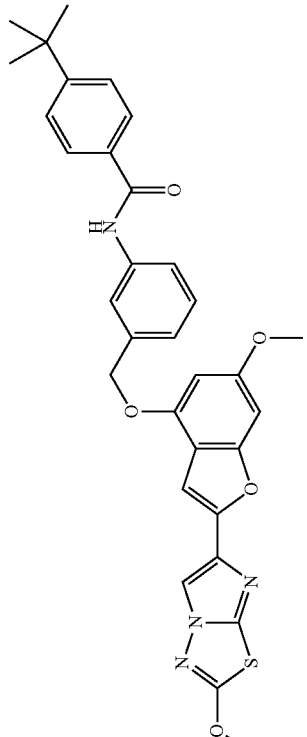 | C32H30N4O5S | 2.405/A | 583.201 | 583.2019 | 1H NMR (CDCl3) δ ppm: 7.78 (br. s, 1H), 7.74 (d, J = 8.4 Hz, 2H), 7.67 (br. d, J = 8.3 Hz, 1H), 7.59 (br. s, 1H), 7.42 (d, J = 8.4 Hz, 2H), 7.32 (t, J = 7.9 Hz, 1H), 7.2 (m, overlapping with CHCl3, 2H), 7.1 (br. s, 1H), 6.61 (br. s, 1H), 6.31 (s, 1H), 5.13 (s, 2H), 4.13 (s, 3H), 3.75 (s, 3H), 1.27 (s, 9H). |
| 38 | 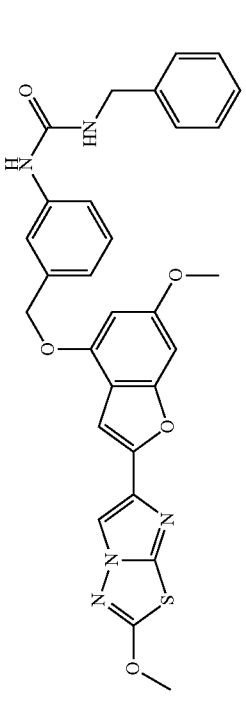 | C29H25N5O5S | 2.346/A | 556.1649 | 556.1556 | 1H NMR (DMSO-d6) δ ppm: 8.60 (s, 1H), 8.34 (s, 1H), 7.50 (t, J = 1.7 Hz, 1H), 7.34-7.36 (br. d, 1H), 7.19-7.32 (m, 7H), 6.99 (d, J = 7.9 Hz, 1H), 6.93 (d, J = 0.7 Hz, 1H), 6.78 (br. d, 1H), 6.56 (t, J = 5.8 Hz, 1H), 6.46 (d, J = 1.9 Hz, 1H), 5.15 (s, 2H), 4.25 (d, J = 5.8 Hz, 1H), 4.16 (s, 3H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 39 | 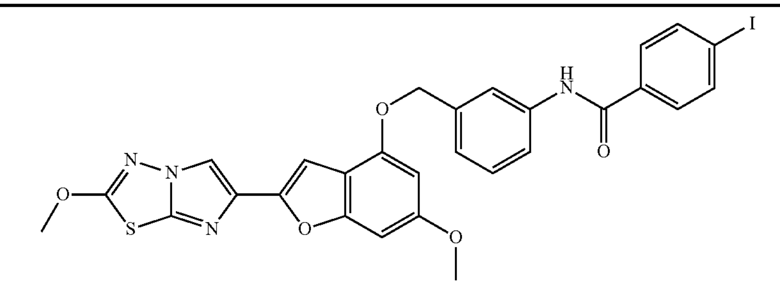 | C28H21IN4O5S | 2.444/A | 653.035 | 653.0362 | 1H NMR (CDCl3) δ ppm: 7.82 (d, J = 8.2 Hz, 2H), 7.75-7.8 (m, 2H), 7.74 (br. d, J = 8.6 Hz, 1H), 7.60 (s, 1H), 7.59 (d, J = 8.2 Hz, 2H), 7.38 (t, J = 7.9 Hz, 1H), 7.2-7.3 (m, 1H), 7.09 (br. s, 1H), 6.66 (br. d, 1H), 6.35 (d, J = 1.5 Hz, 1H), 5.17 (s, 2H), 4.18 (s, 3H), 3.81 (s, 3H). |
| 40 | 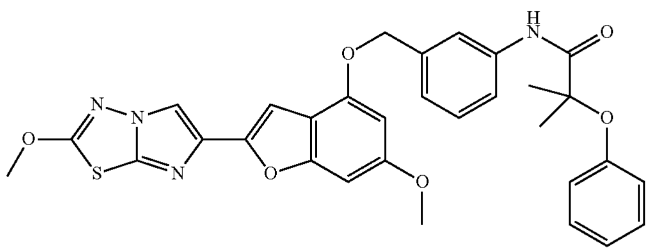 [SMILES: COc1cc(OCc2cccc(NC(=O)C(C)(C)Oc3ccccc3)c2)c2cc(-c3cn4nc(OC)sc4n3)oc2c1] | C31H28N4O6S | 2.453/A | 585.1802 | 585.1812 | 1H NMR (CDCl3) δ ppm: 8.62 (br. s, 1H), 7.81 (s, 1H), 7.64 (br. s, 1H), 7.59 (br. d, J = 8 Hz, 1H), 7.35 (t, J = 7.9 Hz, 1H), 7.25-7.3 (m, 3H), 7.07-7.11 (m, 1H), 7.06 (d, J = 0.53 Hz, 1H), 6.97-7.0 (m, 2H), 6.67 (br. d, 1H), 6.35 (d, J = 1.9 Hz, 1H), 5.15 (s, 2H), 4.18 (s, 3H), 3.81 (s, 3H), 1.57 (s, 6H). |
| 41 | 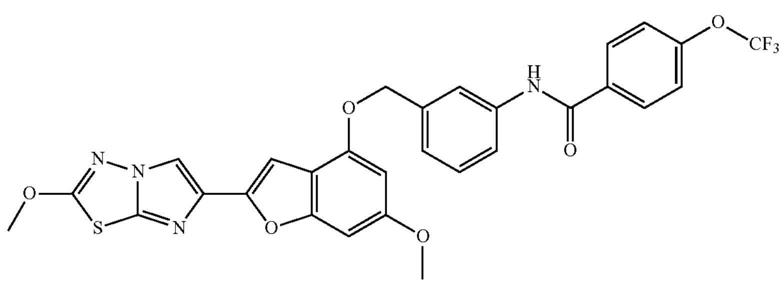 [SMILES: COc1cc(OCc2cccc(NC(=O)c3ccc(OC(F)(F)F)cc3)c2)c2cc(-c3cn4nc(OC)sc4n3)oc2c1] | C29H21F3N4O6S | 2.311/A | 611.1207 | 611.1238 | 1H NMR (CDCl3) δ ppm: 7.93 (d, J = 8.4 Hz, 2H), 7.86 (br. s, 1H), 7.82 (br. s, 1H), 7.76 (d, J = 8.1 Hz, 1H), 7.61 (br. s, 1H), 7.39 (t, J = 7.9 Hz, 1H), 7.31 (d, J = 8.4 Hz, 2H), 7.24 (d, J = 7.2 Hz, 1H), 7.1 (br. s, 1H), 6.67 (br. s, 1H), 6.36 (br. s, 1H), 5.18 (s, 2H), 4.18 (s, 3H), 3.81 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 42 | 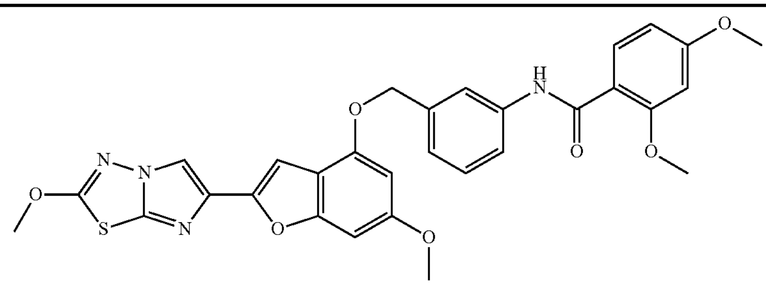 | C30H26N4O7S | 2.392/A | 587.1595 | 587.1626 | 1H NMR (CDCl3) δ ppm: 9.72 (s, 1H), 8.22 (d, J = 8.4 Hz, 1H), 7.8 (br. s, 1H), 7.70 (s, 1H) 7.64 (dd, J = 8.6, 1.0 Hz, 1H), 7.35 (t, J = 8.6 Hz, 1H), 7.1-7.25 (m, 2H), 6.66 (br. s, 1H), 6.62 (dd, J = 8.6, 2.0 Hz, 1H), 6.5 (br. d, 1H), 6.37 (br. d, 1H), 5.19 (s, 2H), 4.19 (s, 3H), 4.0 (s, 3H), 3.85 (s, 3H), 3.81 (s, 3H). |
| 43 | 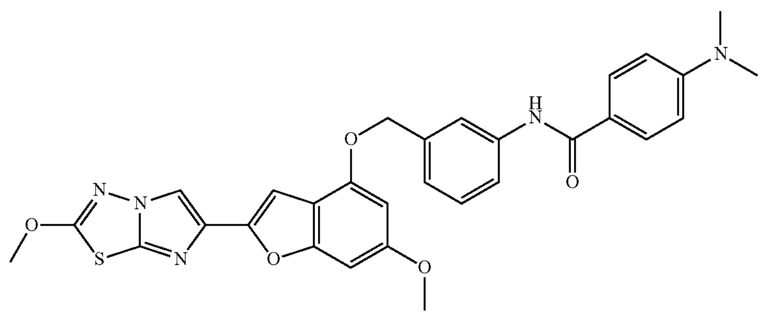 | C30H27N5O5S | 2.351/A | 570.1806 | 570.1837 | 1H NMR (CDCl3) δ ppm: 7.83 (br. s, 1H), 7.80 (br. s, 1H), 7.78 (d, J = 8.9 Hz, 2H), 7.70 (br. d, J = 9 Hz, 1H), 7.65 (br. s, 1H), 7.37 (t, J = 8.6 Hz, 1H), 7.21 (d, J = 7.8 Hz, 1H), 7.19 (br. s, 1H), 6.74 (d, J = 8.9 Hz, 2H), 6.65 (br. d, 1H), 6.37 (d, J = 1.6 Hz, 1H), 5.19 (s, 2H), 4.21 (s, 3H), 3.81 (s, 3H), 3.02 (s, 6H). |
| 44 | 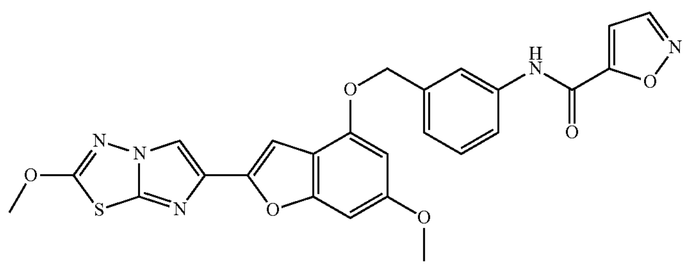 [SMILES: COc1cc(OCc2cccc(NC(=O)c3ccno3)c2)c2cc(-c3cn4nc(OC)sc4n3)oc2c1] | C25H19N5O6S | 2.269/A | 518.1129 | 518.1079 | 1H NMR (CDCl3) δ ppm: 8.3 (d, J = 1.8 Hz, 1H), 8.2 (br. s, 1H), 7.76 (s, 1H), 7.65 (br. s, 1H), 7.61 (br. d, J = 8.0 Hz, 1H), 7.35 (t, J = 7.9 Hz, 1H), 7.25 (d, J = 8.15 Hz, 1H), 7.08 (s, 1H), 6.96 (d, J = 1.8 Hz, 1H), 6.61 (br. d, 1H), 6.30 (d, J = 1.9 Hz, 1H), 5.14 (s, 2H), 4.14 (s, 3H), 3.75 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 45 | 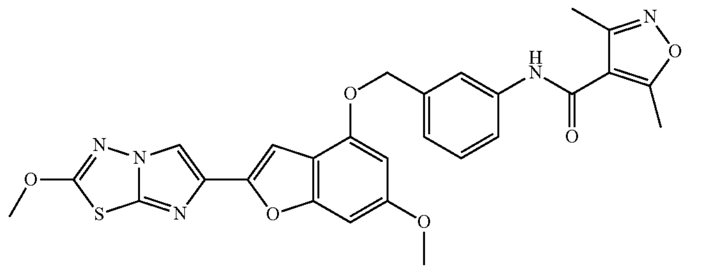 [SMILES: COc1cc(OCc2cccc(NC(=O)c3c(C)noc3C)c2)c2cc(-c3cn4nc(OC)sc4n3)oc2c1] | C27H23N5O6S | 2.281/A | 546.1442 | 546.1399 | 1H NMR (CDCl3) δ ppm: 7.8 (br. s, 1H), 7.51-7.55 (m, 2H), 7.32 (t, J = 8.2 Hz, 1H), 7.26 (br. s, 1H), 7.20 (d, J = 8.2 Hz, 1H), 7.11 (br. s, 1H), 6.60 (br. d, 1H), 6.30 (d, J = 1.6 Hz, 1H), 5.12 (s, 2H), 4.15 (s, 3H), 3.76 (s, 3H), 2.59 (s, 3H), 2.42 (s, 3H). |
| 46 | 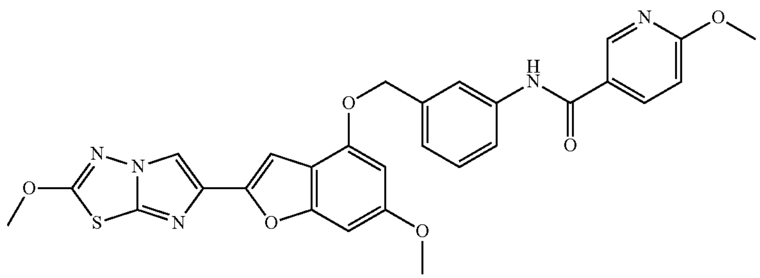 | C28H23N5O6S | 2.370/A | 558.1442 | 558.1408 | 1H NMR (CDCl3) δ ppm: 8.70 (d, J = 2.5 Hz, 1H), 8.06 (dd, J = 8.7, 2.5 Hz, 1H), 7.86 (br. s, 1H), 7.81 (s, 1H), 7.70 (dd, J = 8.1, 1.2 Hz, 1H), 7.61 (br. s, 1H), 7.38 (t, J = 7.9 Hz, 1H), 7.22-7.24 (m, 1H), 7.07 (s, 1H), 6.79 (dd, J = 8.7, 0.65 Hz, 1H), 6.66 (br. d, 1H), 6.35 (d, J = 1.9 Hz, 1H), 5.17 (s, 2H), 4.18 (s, 3H), 3.98 (s, 3H), 3.81 (s, 3H). |
| 47 | 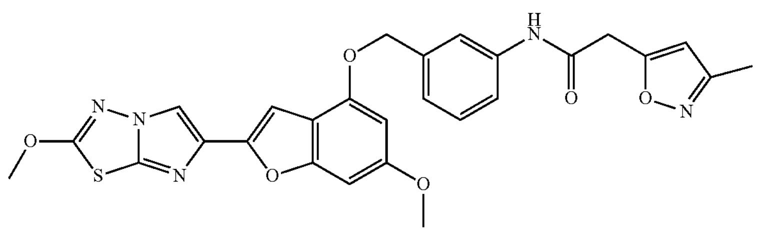 | C27H23N5O6S | 2.255/A | 546.1442 | 546.1469 | 1H NMR (CDCl3) δ ppm: 7.77 (s, 1H), 7.47-7.53 (m, 2H), 7.46 (br. s, 1H), 7.27 (t, J = 7.8 Hz, 1H), 7.14-7.17 (m, 1H), 7.12 (s, 1H), 6.59 (br. d, 1H), 6.29 (d, J = 1.9 Hz, 1H), 6.08 (s, 1H), 5.09 (s, 2H), 4.15 (s, 3H), 3.79 (s, 2H), 3.75 (s, 3H), 2.22 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 48 | 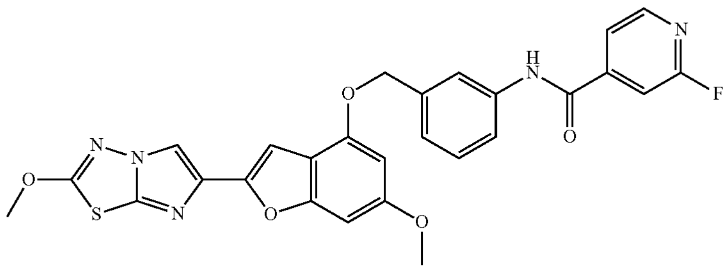 [SMILES: COc1cc(OCc2cccc(NC(=O)c3ccnc(F)c3)c2)c2cc(-c3cn4nc(OC)sc4n3)oc2c1] | C27H20FN5O5S | 2.218/A | 546.1242 | 546.1266 | 1H NMR (CDCl3) δ ppm: 8.32 (d, J = 5.1 Hz, 1H), 7.93 (br. s, 1H), 7.76 (s, 1H), 7.73 (br. d, 1H), 7.52-7.56 (m, 2H), 7.35 (t, J = 7.9 Hz, 1H), 7.32 (br. s, 1H), 7.20 (d, J = 8.5 Hz, 1H), 7.10 (s, 1H), 6.60 (br. d, 1H), 6.30 (d, J = 1.9 Hz, 1H), 5.13 (s, 2H), 4.14 (s, 3H), 3.75 (s, 3H). |
| 49 | 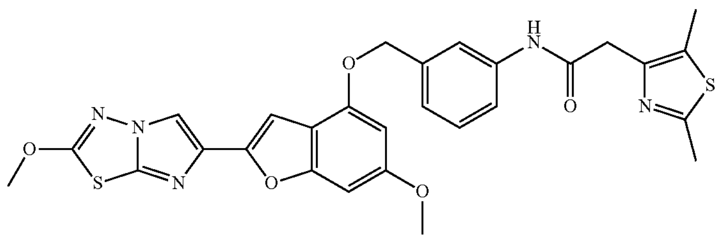 [SMILES: COc1cc(OCc2cccc(NC(=O)Cc3nc(C)sc3C)c2)c2cc(-c3cn4nc(OC)sc4n3)oc2c1] | C28H25N5O5S2 | 2.281/A | 576.137 | 576.1411 | 1H NMR (CDCl3) δ ppm: 9.87 (s, 1H), 7.81 (s, 1H), 7.73 (s, 1H), 7.49 (d, J = 6.5 Hz, 1H), 7.31 (t, J = 7.8 Hz, 1H), 7.20-7.23 (m, 1H), 7.11 (s, 1H), 6.64 (br. d, 1H), 6.34 (d, J = 1.9 Hz, 1H), 5.13 (s, 2H), 4.20 (s, 3H), 3.88 (s, 2H), 3.80 (s, 3H), 2.82 (s, 3H), 2.57 (s, 3H). |
| 50 | 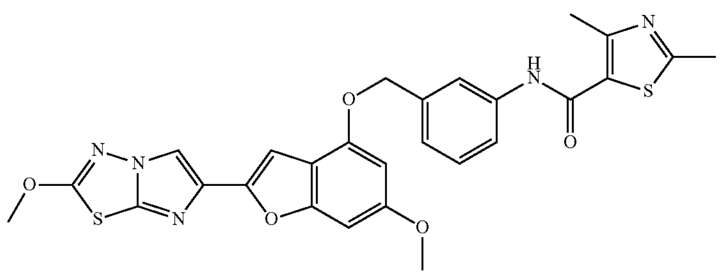 | C27H23N5O5S2 | 2.315/A | 562.1213 | 562.1242 | 1H NMR (CDCl3) δ ppm: 7.82 (s, 1H), 7.60 (br. d, J = 8.3 Hz, 1H), 7.58 (br. s, 1H), 7.45 (br. s, 1H), 7.38 (t, J = 7.8 Hz, 1H), 7.25-7.27 (m, 1H), 7.16 (s, 1H), 6.66 (br. d, 1H), 6.35 (d, J = 1.9 Hz, 1H), 5.18 (s, 2H), 4.21 (s, 3H), 3.81 (s, 3H), 2.70 (s, 3H), 2.65 (br. s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 51 | 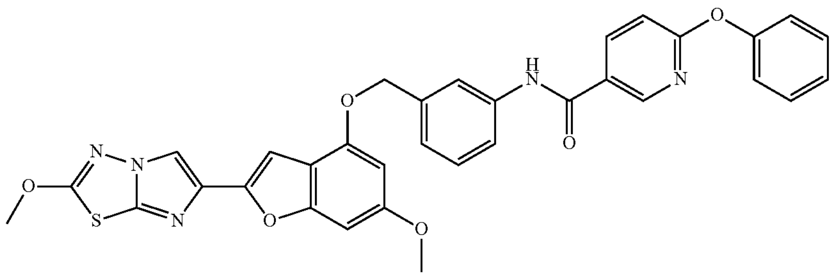 [SMILES: COc1cc(OCc2cccc(NC(=O)c3ccc(Oc4ccccc4)nc3)c2)c2cc(-c3cn4nc(OC)sc4n3)oc2c1] | C₃₃H₂₅N₅O₆S | 2.416/A | 620.1598 | 620.1612 | ¹H NMR (CDCl₃) δ ppm: 8.61 (d, J = 2.5 Hz, 1H), 8.14 (dd, J = 8.6, 2.5 Hz, 1H), 7.80 (br. s, 1H), 7.76 (s, 1H), 7.65 (br. d, J = 8 Hz, 1H), 7.57 (br. s, 1H), 7.31-7.38 (m, 3H), 7.15-7.20 (m, 2H), 7.06-7.13 (m, 3H), 6.91 (d, J = 8.7 Hz, 1H), 6.59 (br. d, 1H), 6.30 (d, J = 1.9 Hz, 1H), 5.13 (s, 2H), 4.15 (s, 3H), 3.75 (s, 3H). |
| 52 | 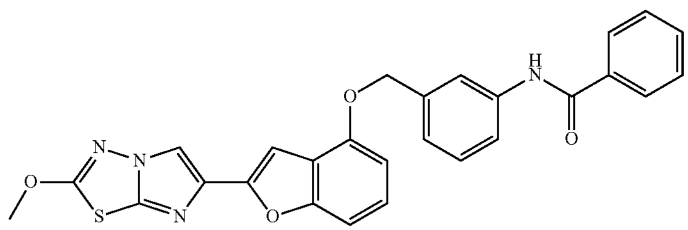 [SMILES: COc1nn2cc(-c3cc4c(OCc5cccc(NC(=O)c6ccccc6)c5)cccc4o3)nc2s1] | C₂₇H₂₀N₄O₄S | 2.361/A | 497.1278 | 497.1291 | ¹H NMR (CDCl₃) δ ppm: 7.80-7.82 (m, 4H), 7.66 (br. d, J = 8 Hz, 1H), 7.60 (br. s, 1H), 7.39-7.47 (m, 3H), 7.32 (t, J = 7.9 Hz, 1H), 7.18 (d, J = 8 Hz, 1H), 7.12 (s, 1H), 7.05-7.12 (m, 2H), 6.63 (dd, J = 7.0, 1.7 Hz, 1H), 5.16 (s, 2H), 4.12 (s, 3H). |
| 53 | 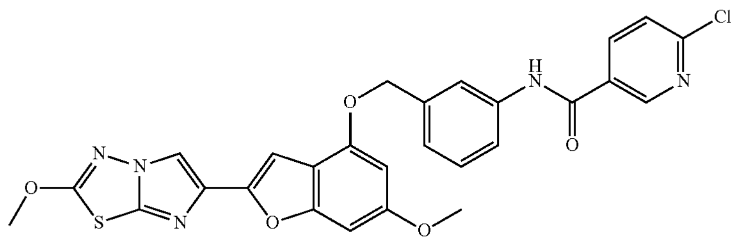 [SMILES: COc1cc(OCc2cccc(NC(=O)c3ccc(Cl)nc3)c2)c2cc(-c3cn4nc(OC)sc4n3)oc2c1] | C₂₇H₂₀ClN₅O₅S | 2.343/A | 562.0946 | 562.0956 | ¹H NMR (DMSO-d₆) δ ppm: 10.49 (s, 1H), 8.88 (d, J = 2.5 Hz, 1H), 8.32 (s, 1H), 8.28 (dd, J = 8.3, 2.5 Hz, 1H), 7.85 (br. s, 1H), 7.69 (dd, J = 8.3, 1.1 Hz, 1H), 7.64 (d, J = 8.3 Hz, 1H), 7.35 (t, J = 7.8 Hz, 1H), 7.20 (d, J = 7.8 Hz, 1H), 6.93 (s, 1H), 6.77 (br. d, 1H), 6.46 (d, J = 1.8 Hz, 1H), 5.20 (s, 2H), 4.13 (s, 3H), 3.72 (s, 3H). |
| 54 | 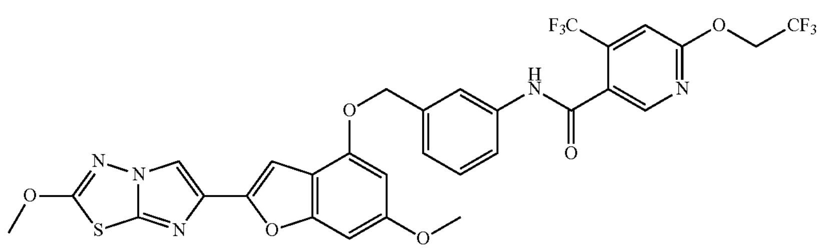 [SMILES: COc1cc(OCc2cccc(NC(=O)c3cnc(OCC(F)(F)F)cc3C(F)(F)F)c2)c2cc(-c3cn4nc(OC)sc4n3)oc2c1] | C₃₀H₂₁F₆N₅O₆S | 2.395/A | 694.1189 | 694.1209 | ¹H NMR (CDCl₃) δ ppm: 8.51 (s, 1H), 7.82 (s, 1H), 7.75 (br. dd, 1H), 7.66 (br. s, 1H), 7.59 (br. s, 1H), 7.40 (t, J = 7.9 Hz, 1H), 7.24-7.27 (m, 1H), 7.21 (s, 1H), 7.16 (s, 1H), 6.66 (br. d, 1H), 6.37 (d, J = 1.6 Hz, 1H), 5.19 (s, 2H), 4.83 (q, J = 8.2 Hz, 2H), 4.20 (s, 3H), 3.82 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 55 | 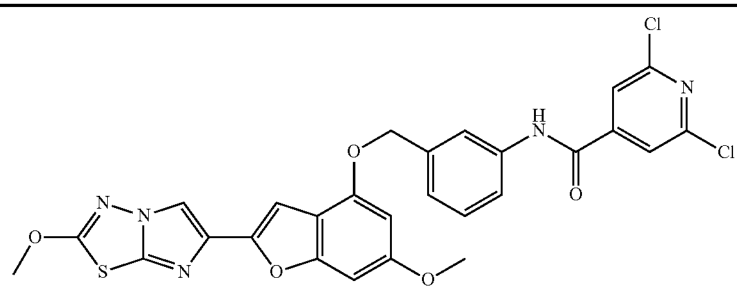 | C27H19Cl2N5O5S2 | 2.453/A | 596.0557 | 596.0567 | 1H NMR (CDCl3) δ ppm: 8.31 (br. s, 1H), 7.73-7.76 (m, 2H), 7.60 (s, 2H), 7.52 (br. s, 1H), 7.33 (t, J = 7.8 Hz, 1H), 7.15-7.18 (m, 1H), 7.1 (s, 1H), 6.56 (br. d, 1H), 6.26 (d, J = 1.7 Hz, 1H), 5.11 (s, 2H), 4.14 (s, 3H), 3.74 (s, 3H). |
| 56 | 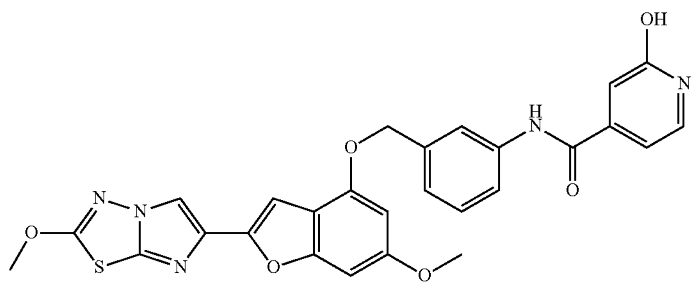 [SMILES: COc1cc(OCc2cccc(NC(=O)c3ccnc(O)c3)c2)c2cc(-c3cn4nc(OC)sc4n3)oc2c1] | C27H21N5O6S | 2.215/A | 544.1285 | 544.1297 | 1H NMR (CDCl3) δ ppm: 8.69 (br. s, 1H), 7.71-7.76 (m, 2H), 7.59 (br. s, 1H), 7.27-7.33 (m, 2H), 7.14 (d, J = 7.5 Hz, 1H), 7.07 (s, 1H), 7.0 (br. s, 1H), 6.72 (br. d, J = 7 Hz, 1H), 6.56 (br. s, 1H), 6.26 (br. s, 1H), 5.10 (s, 2H), 4.11 (s, 3H), 3.73 (s, 3H). |
| 57 | 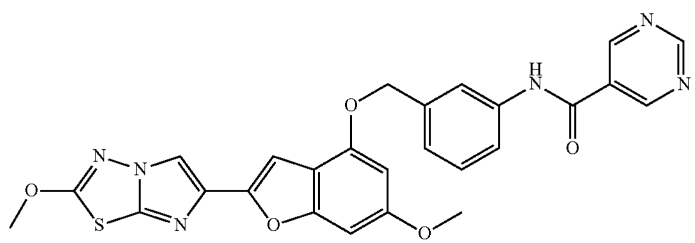 [SMILES: COc1cc(OCc2cccc(NC(=O)c3cncnc3)c2)c2cc(-c3cn4nc(OC)sc4n3)oc2c1] | C26H20N6O5S | 2.273/A | 529.1289 | 529.1306 | 1H NMR (CDCl3) δ ppm: 9.0-9.6 (br. s, 5H), 8.26 (br. s, 1H), 7.78 (br. d, J = 8 Hz, 1H), 7.58 (br. s, 1H), 7.35 (t, J = 7.8 Hz, 1H), 7.18-7.19 (m, 1H), 6.59 (br. s, 1H), 6.30 (s, 1H), 5.14 (s, 2H), 4.15 (s, 3H), 3.75 (s, 3H). |

| Ex. | Structure | Formula | HPLC Retention Time (Min)/Method | Calc. [M+H]+ m/z | LCMS [M+H]+ m/z | NMR |
|---|---|---|---|---|---|---|
| 58 | 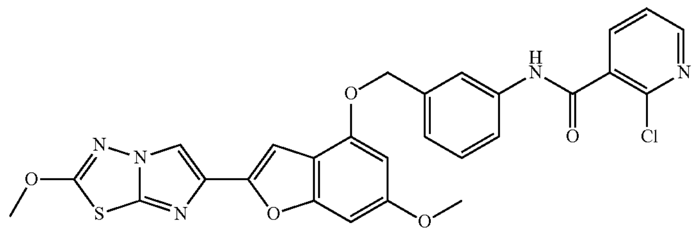 [SMILES: COc1cc(OCc2cccc(NC(=O)c3cccnc3Cl)c2)c2cc(-c3cn4nc(OC)sc4n3)oc2c1] | C27H20ClN5O5S | 2.26I/A | 562.0946 | 562.0948 | 1H NMR (CDCl3) δ ppm: 8.45 (dd, J = 4.8, 1.9 Hz, 1H), 8.12 (dd, J = 7.6, 1.9 Hz, 1H), 8.07 (br. s, 1H), 7.75 (s, 1H), 7.64 (br. d, J = 8 Hz, 1H), 7.61 (br. s, 1H), 7.31-7.37 (m, 2H), 7.23 (br. d, J = 7.8 Hz, 1H), 7.03 (s, 1H), 6.61 (br. d, 1H), 6.31 (d, J = 1.8 Hz, 1H), 5.13 (s, 2H), 4.12 (s, 3H), 3.75 (s, 3H). |
| 59 | 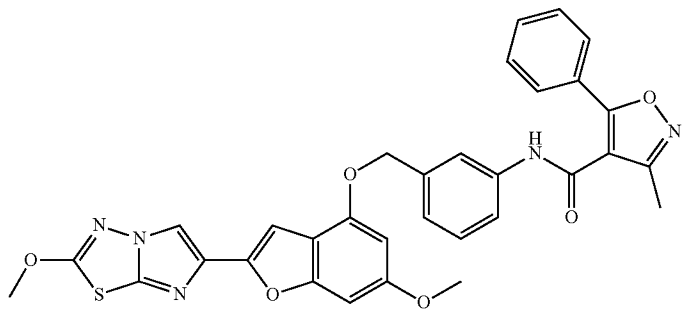 [SMILES: COc1cc(OCc2cccc(NC(=O)c3c(C)noc3-c3ccccc3)c2)c2cc(-c3cn4nc(OC)sc4n3)oc2c1] | C32H25N5O6S | 2.37I/A | 608.1598 | 608.1604 | 1H NMR (CDCl3) δ ppm: 7.83 (s, 1H), 7.73-7.76 (m, 2H), 7.41-7.53 (m, 4H), 7.39 (br. s, 1H), 7.33 (t, J = 7.8 Hz, 1H), 7.31 (br. s, 1H), 7.22-7.24 (m, 1H), 7.09 (s, 1H), 6.66 (br. d, 1H), 6.32 (d, J = 1.8 Hz, 1H), 5.14 (s, 2H), 4.20 (s, 3H), 3.81 (s, 3H), 2.53 (s, 3H). |
| 60 | 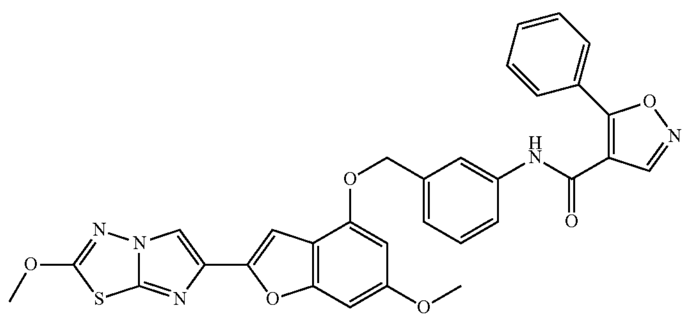 [SMILES: COc1cc(OCc2cccc(NC(=O)c3cnoc3-c3ccccc3)c2)c2cc(-c3cn4nc(OC)sc4n3)oc2c1] | C31H23N5O6S | 2.37I/A | 594.1442 | 594.1445 | 1H NMR (CDCl3) δ ppm: 8.60 (s, 1H), 7.77-7.81 (m, 2H), 7.76 (s, 1H), 7.42-7.51 (m, 5H), 7.35 (br. s, 1H), 7.28 (t, J = 7.9 Hz, 1H), 7.15-7.18 (m, 1H), 7.09 (s, 1H), 6.59 (br. d, 1H), 6.26 (d, J = 1.8 Hz, 1H), 5.09 (s, 2H), 4.15 (s, 3H), 3.75 (s, 3H). |

-continued

| Ex. | Structure | Formula | HPLC Retention Time (Min)/Method | Calc. [M + H]+ m/z | LCMS [M + H]+ m/z | NMR |
|---|---|---|---|---|---|---|
| 61 | 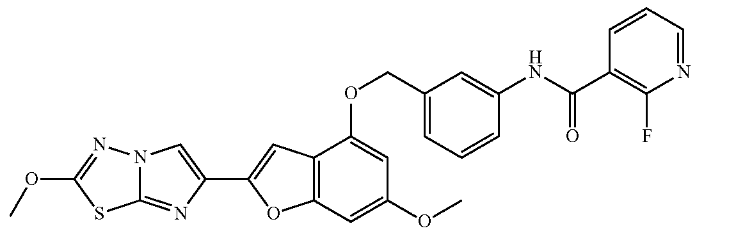 [SMILES: COc1cc(OCc2cccc(NC(=O)c3cccnc3F)c2)c2cc(-c3cn4nc(OC)sc4n3)oc2c1] | C27H20FN5O3S | 2.271/A | 546.1242 | 546.1248 | 1H NMR (CDCl3) δ ppm: 8.55-8.60 (m, 1H), 8.49 (br. d, J = 14 Hz, 1H), 8.29-8.31 (m, 1H), 7.76 (s, 1H), 7.68 (s, 1H), 7.60 (br. d, J = 7.8 Hz, 1H), 7.32-7.37 (m, 2H), 7.25 (d, J = 7.5 Hz, 1H), 7.12 (s, 1H), 6.60 (br. d, 1H), 6.31 (d, J = 1.8 Hz, 1H), 5.14 (s, 2H), 4.15 (s, 3H), 3.75 (s, 3H). |
| 62 | 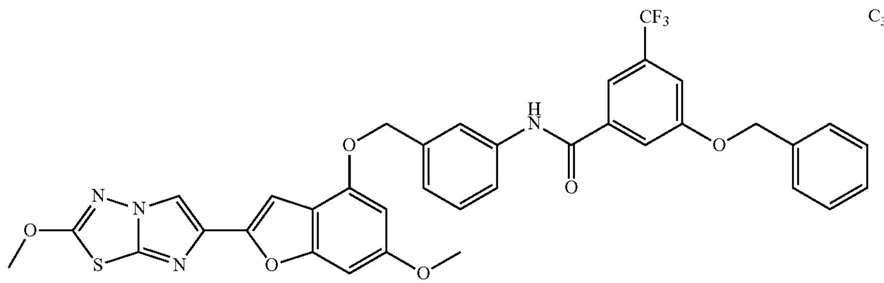 | C36H27F3N4O6S | 2.599/A | 701.1676 | 701.1524 | 1H NMR (CDCl3) δ ppm: 7.88 (br. s, 1H), 7.75 (br. s, 1H), 7.64 (br. d, J = 8.2 Hz, 1H), 7.58-7.62 (m, 3H), 7.25-7.44 (m, 7H), 7.20 (d, J = 7.3 Hz, 1H), 7.03 (br. s, 1H), 6.60 (br. s, 1H), 6.30 (br. s, 1H), 5.12 (s, 2H), 5.06 (s, 2H), 4.12 (s, 3H), 3.74 (s, 3H). |
| 63 | 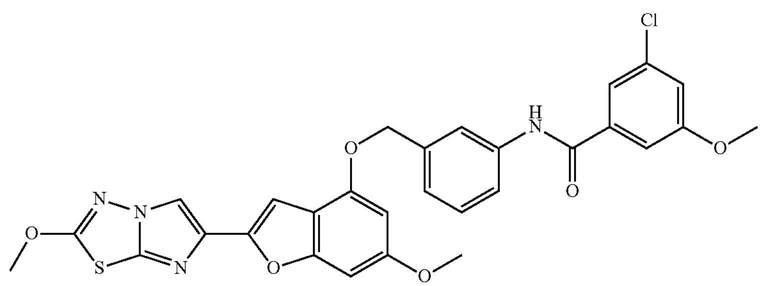 | C29H23ClN4O6S | 2.456/A | 591.11 | 591.0974 | 1H NMR (CDCl3) δ ppm: 7.85 (br. s, 1H), 7.82 (br. s, 1H), 7.73 (br. d, J = 8 Hz, 1H), 7.67 (s, 1H), 7.43 (t, J = 8 Hz, 1H), 7.40 (s, 1H), 7.33 (s, 1H), 7.29 (d, J = 8.6 Hz, 1H), 7.15 (br. s, 1H), 7.08 (s, 1H), 6.70 (br. s, 1H), 6.39 (br. s, 1H), 5.22 (s, 2H), 4.22 (s, 3H), 3.88 (s, 3H), 3.85 (s, 3H). |

-continued

| Ex. | Structure | Formula | HPLC Retention Time (Min)/Method | Calc. [M + H]+ m/z | LCMS [M + H]+ m/z | NMR |
|---|---|---|---|---|---|---|
| 64 | 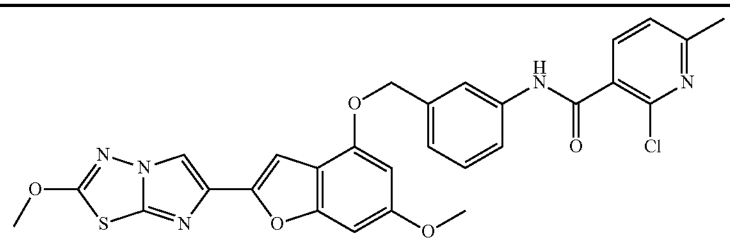 | C28H22ClN5O5S | 2.282/A | 576.1103 | 576.1098 | 1H NMR (DMSO-d6) δ ppm: 10.57 (s, 1H), 8.31 (s, 1H), 7.89 (d, J = 7.6 Hz, 1H), 7.80 (br. s, 1H), 7.62 (br. d, J = 8 Hz, 1H), 7.34 (d, J = 7.7 Hz, 1H), 7.33 (t, J = 7.8 Hz, 1H), 7.18 (br. d, J = 8 Hz, 1H), 6.92 (s, 1H), 6.76 (br. d, 1H), 6.46 (d, J = 1.9 Hz, 1H), 5.19 (s, 2H), 4.13 (s, 3H), 3.73 (s, 3H), 2.42 (s, 3H). |
| 65 | 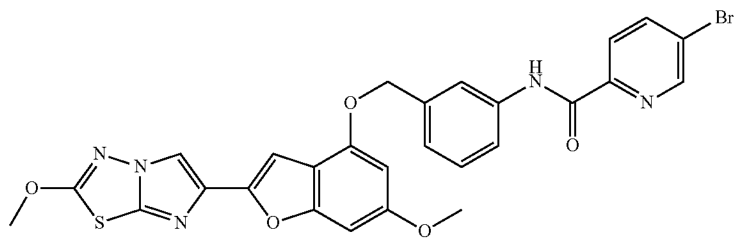 [SMILES: COc1cc(OCc2cccc(NC(=O)c3ccc(Br)cn3)c2)c2cc(-c3cn4nc(OC)sc4n3)oc2c1] | C27H20BrN5O5S | 2.449/A | 606.0441 | 606.0305 | 1H NMR (CDCl3) δ ppm: 9.86 (br. s, 1H), 8.67 (d, J = 1.9 Hz, 1H), 8.17 (d, J = 8.4 Hz, 1H), 8.02 (dd, J = 8.4, 2.3 Hz, 1H), 7.79-7.82 (m, 3H), 7.40 (t, J = 7.8 Hz, 1H), 7.26 (d, J = 7.5 Hz, 1H), 7.11 (s, 1H), 6.67 (br. d, 1H), 6.37 (d, J = 1.9 Hz, 1H), 5.20 (s, 2H), 4.19 (s, 3H), 3.82 (s, 3H). |
| 66 | 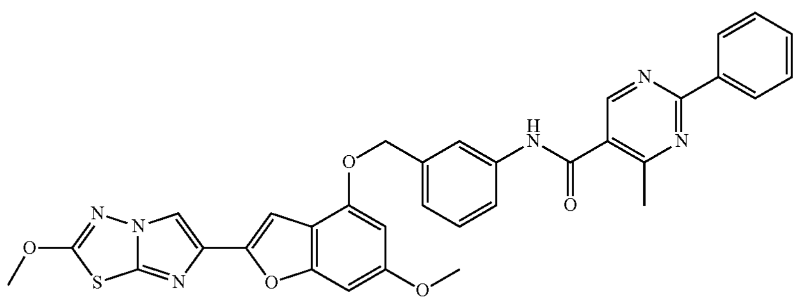 [SMILES: COc1cc(OCc2cccc(NC(=O)c3cnc(-c4ccccc4)nc3C)c2)c2cc(-c3cn4nc(OC)sc4n3)oc2c1] | C33H26N6O5S | 2.467/A | 619.1758 | 619.1575 | 1H NMR (CDCl3) δ ppm: 8.77 (s, 1H), 8.34-8.37 (m, 2H), 7.99 (br. s, 1H), 7.75 (br. d, J = 8 Hz, 1H), 7.73 (s, 1H), 7.56 (br. s, 1H), 7.38-7.43 (m, 3H), 7.34 (t, J = 7.9 Hz, 1H), 7.17-7.19 (m, 1H), 7.14 (s, 1H), 6.53 (br. d, 1H), 6.30 (d, J = 1.9 Hz, 1H), 5.14 (s, 2H), 4.13 (s, 3H), 3.72 (s, 3H), 2.65 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 67 | 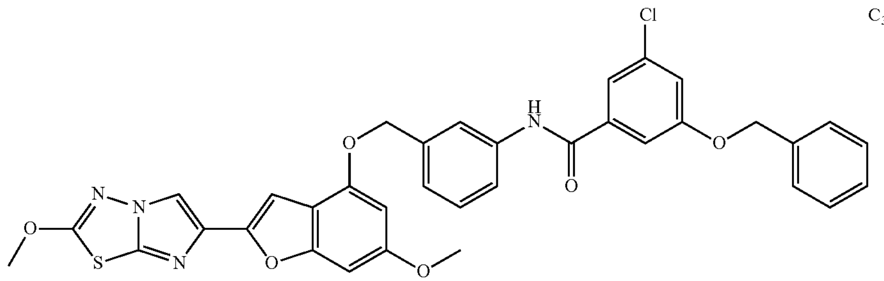 | C35H27ClN4O6S | 2.527/A | 667.1413 | 667.1447 | 1H NMR (CDCl3) δ ppm: 7.82 (s, 1H), 7.76 (br. s, 1H), 7.69 (br. d, J = 8 Hz, 1H), 7.63 (br. s, 1H), 7.31-7.42 (m, 8H), 7.24-7.26 (m, 1H), 7.12 (t, J = 2 Hz, 1H), 7.09 (s, 1H), 6.67 (br. d, 1H), 6.36 (d, J = 1.9 Hz, 1H), 5.18 (s, 2H), 5.09 (s, 2H), 4.18 (s, 3H), 3.81 (s, 3H). |
| 68 | 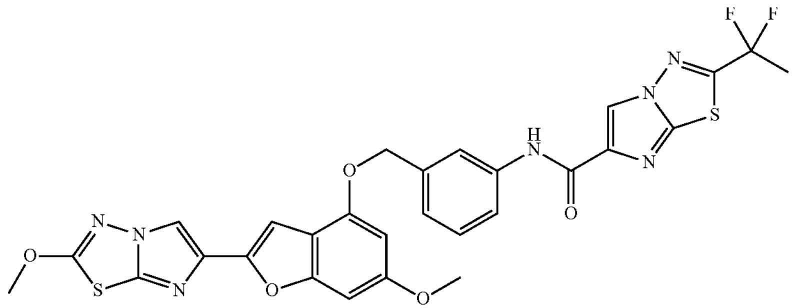 [SMILES: COc1cc(OCc2cccc(NC(=O)c3cn4nc(C(C)(F)F)sc4n3)c2)c2cc(-c3cn4nc(OC)sc4n3)oc2c1] | C28H21F2N7O5S2 | 2.432/A | 638.1086 | 638.112 | 1H NMR (CDCl3) δ ppm: 9.04 (s, 1H), 8.45 (s, 1H), 7.86 (br. s, 1H), 7.75-7.82 (m, 2H), 7.42 (t, J = 8.0 Hz, 1H), 7.27-7.29 (m, 1H), 7.16 (s, 1H), 6.70 (br. d, 1H), 6.40 (d, J = 1.6 Hz, 1H), 5.23 (s, 2H), 4.23 (s, 3H), 3.85 (s, 3H), 2.22 (t, J = 18.4 Hz, 3H). |
| 69 | 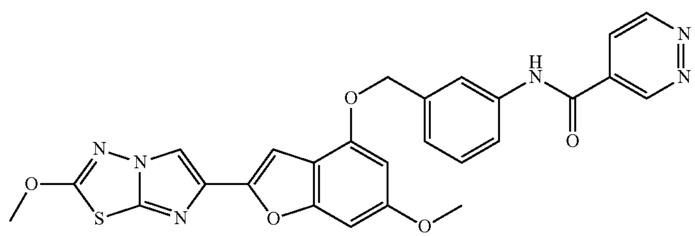 [SMILES: COc1cc(OCc2cccc(NC(=O)c3ccnnc3)c2)c2cc(-c3cn4nc(OC)sc4n3)oc2c1] | C26H20N6O5S | 2.243/A | 529.1289 | 529.1325 | 1H NMR (CDCl3) δ ppm: 9.62 (s, 1H), 9.31 (d, J = 5.2 Hz, 1H), 8.63 (br. s, 1H), 7.88-7.90 (m, 1H), 7.81 (br. d, J = 8 Hz, 1H), 7.79 (s, 1H), 7.58 (br. s, 1H), 7.34 (d, J = 7.9 Hz, 1H), 7.26 (d, J = 8.5 Hz, 1H), 7.0 (s, 1H), 6.63 (br. d, 1H), 6.31 (d, J = 1.7 Hz, 1H), 5.18 (s, 2H), 4.17 (s, 3H), 3.80 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 70 | (structure) | C26H18F3N5O5S2 | 2.180/A | 602.0774 | 602.0797 | 1H NMR (CDCl3) δ ppm: 9.01 (br. s, 1H), 8.38 (s, 1H), 7.76 (s, 1H), 7.73 (br. s, 1H), 7.65 (br. dd, J = 8, 1 Hz, 1H), 7.34 (t, J = 7.8 Hz, 1H), 7.24 (d, J = 7.5 Hz, 1H), 7.08 (s, 1H), 6.61 (br. d, 1H), 6.31 (d, J = 1.9 Hz, 1H), 5.14 (s, 2H), 4.14 (s, 3H), 3.76 (s, 3H). |
| 71 | (structure) | C30H23F3N4O5S | 2.437/A | 609.1414 | 609.1424 | 1H NMR (CDCl3) δ ppm: 7.89 (br. s, 1H), 7.84 (s, 1H), 7.79 (s, 1H), 7.76 (s, 1H), 7.69 (br. d, J = 8.5 Hz, 1H), 7.59 (s, 1H), 7.52 (s, 1H), 7.34 (t, J = 8.0 Hz, 1H), 7.17-7.21 (m, 1H), 7.13 (s, 1H), 6.59 (br. d, 1H), 6.31 (d, J = 1.9 Hz, 1H), 5.14 (s, 2H), 4.15 (s, 3H), 3.76 (s, 3H), 2.41 (s, 3H). |
| 72 | (structure) | C31H23N5O5S2 | 2.494/A | 610.1213 | 610.1229 | 1H NMR (CDCl3) δ ppm: 9.26 (br. s, 1H), 8.12 (s, 1H), 7.90-7.95 (m, 2H), 7.76 (s, 1H), 7.70-7.73 (m, 2H), 7.39-7.44 (m, 3H), 7.34 (t, J = 7.8 Hz, 1H), 7.22 (br. d, J = 8 Hz, 1H), 7.03 (s, 1H), 6.62 (br. d, 1H), 6.32 (d, J = 1.9 Hz, 1H), 5.14 (s, 2H), 4.12 (s, 3H), 3.76 (s, 3H). |

| Ex. | Structure | Formula | HPLC Retention Time (Min)/Method | Calc. [M + H]⁺ m/z | LCMS [M + H]⁺ m/z | NMR |
|---|---|---|---|---|---|---|
| 73 | 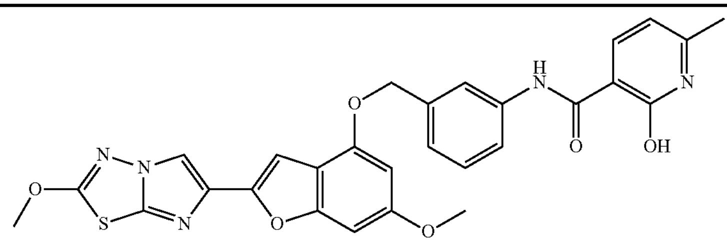 | C₂₈H₂₃N₅O₆S | 2.412/A | 558.1442 | 558.144 | ¹H NMR (DMSO-d₆) δ ppm: 12.64 (s, 1H), 12.14 (s, 1H), 8.31 (s, 1H), 8.28 (d, J = 7.4 Hz, 1H), 7.78 (s, 1H), 7.59 (br. dd, J = 8, 1 Hz, 1H), 7.32 (t, J = 7.8 Hz, 1H), 7.16 (d, J = 7.8 Hz, 1H), 6.92 (s, 1H), 6.76 (br. d, 1H), 6.47 (d, J = 2.0 Hz, 1H), 6.35 (d, J = 7.4 Hz, 1H), 5.19 (s, 2H), 4.13 (s, 3H), 3.73 (s, 3H), 2.27 (s, 3H). |
| 74 | 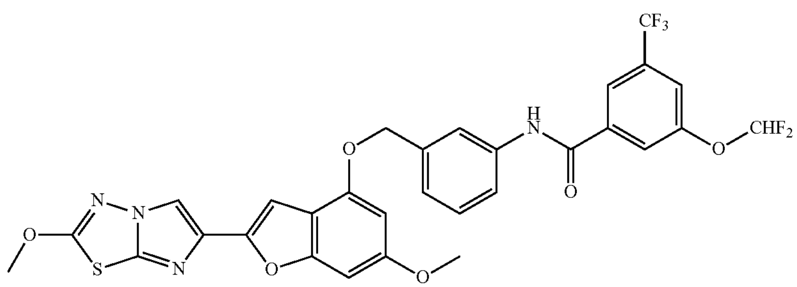 [SMILES: COc1cc(OCc2cccc(NC(=O)c3cc(OC(F)F)cc(C(F)(F)F)c3)c2)c2cc(-c3cn4nc(OC)sc4n3)oc2c1] | C₃₀H₂₁F₅N₄O₅S | 2.061/A | 661.1175 | 661.1154 | ¹H NMR (CDCl₃) δ ppm: 8.06 (br. s, 1H), 7.90 (s, 1H), 7.79 (s, 1H), 7.75 (s, 1H), 7.69 (br. d, J = 7.8 Hz, 1H), 7.59 (s, 1H), 7.47 (s, 1H), 7.34 (t, J = 8 Hz, 1H), 7.20 (d, J = 8.1 Hz, 1H), 7.05 (s, 1H), 6.60 (br. d, 1H), 6.56 (t, J = 72 Hz, 1H), 6.30 (d, J = 1.5 Hz, 1H), 5.12 (s, 2H), 4.13 (s, 3H), 3.75 (s, 3H). |
| 75 | 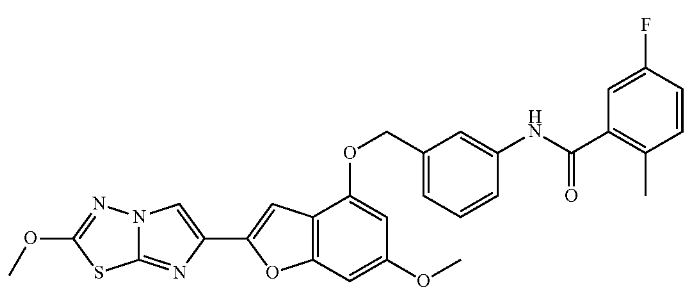 [SMILES: COc1cc(OCc2cccc(NC(=O)c3cc(F)ccc3C)c2)c2cc(-c3cn4nc(OC)sc4n3)oc2c1] | C₂₉H₂₃FN₄O₅S | 2.018/A | 559.1446 | 559.1467 | ¹H NMR (CDCl₃) δ ppm: 7.82 (s, 1H), 7.70 (br. d, J = 7.6 Hz, 1H), 7.62 (br. s, 1H), 7.49 (br. s, 1H), 7.39 (t, J = 7.8 Hz, 1H), 7.2–7.3 (m, 3H), 7.08 (s, 1H), 7.05 (dt, J = 8.3, 2.7 Hz, 1H), 6.67 (br. s, 1H), 6.37 (br. s, 1H), 5.18 (s, 2H), 4.18 (s, 3H), 3.82 (s, 3H), 2.45 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 76 | 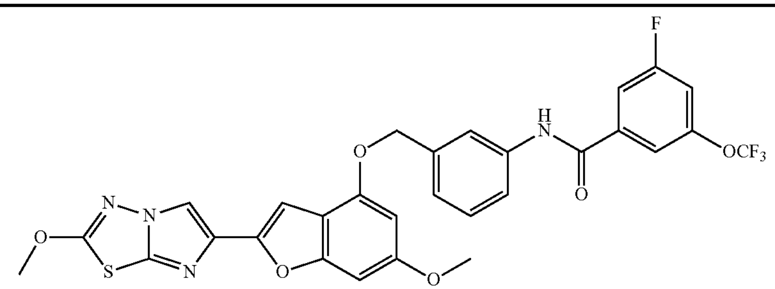 | C29H20F4N4O6S | 2.152/A | 629.1112 | 629.1133 | 1H NMR (CDCl3) δ ppm: 7.82 (br. s, 2H), 7.72 (br. d, J = 7.8 Hz, 1H), 7.62 (br. s, 1H), 7.53 (br. s, 2H), 7.40 (t, J = 7.8 Hz, 1H), 7.27 (d, J = 7.8 Hz, 1H), 7.13 (br. d, J = 8.6 Hz, 1H), 7.08 (s, 1H), 6.67 (br. s, 1H), 6.36 (br. s, 1H), 5.19 (s, 2H), 4.19 (s, 3H), 3.82 (s, 3H). |
| 77 | 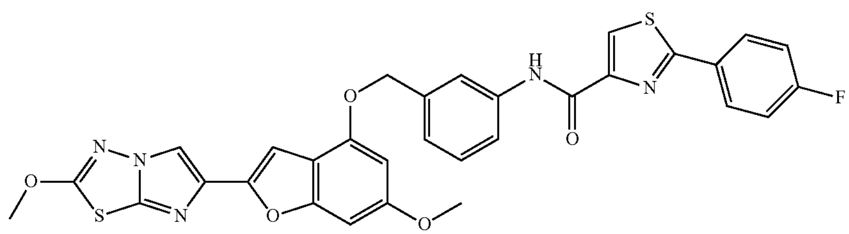 [SMILES: COc1cc(OCc2cccc(NC(=O)c3csc(-c4ccc(F)cc4)n3)c2)c2cc(-c3cn4nc(OC)sc4n3)oc2c1] | C31H22FN5O5S2 | 2.793/B | 628.1119 | 628.113 | 1H NMR (CDCl3) δ ppm: 9.23 (s, 1H), 8.13 (s, 1H), 7.91-7.95 (m, 2H), 7.77 (s, 1H), 7.74 (br. d, J = 8.2 Hz, 1H), 7.71 (br. s, 1H), 7.36 (t, J = 7.6 Hz, 1H), 7.22 (d, J = 7.9 Hz, 1H), 7.11 (t, J = 8.4 Hz, 2H), 7.04 (s, 1H), 6.63 (br. d, 1H), 6.33 (d, J = 1.8 Hz, 1H), 5.15 (s, 2H), 4.13 (s, 3H), 3.77 (s, 3H). |
| 78 | 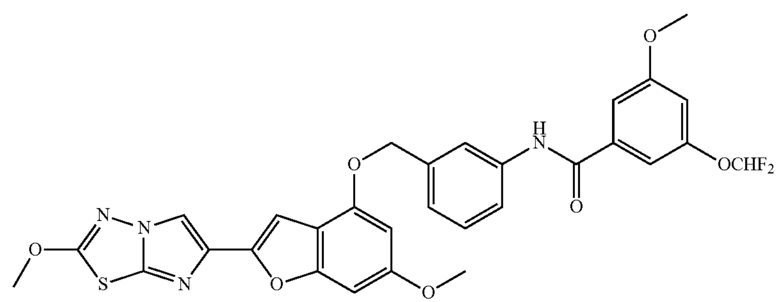 [SMILES: COc1cc(OC(F)F)cc(C(=O)Nc2cccc(COc3cc(OC)cc4oc(-c5cn6nc(OC)sc6n5)cc34)c2)c1] | C30H24F2N4O7S | 2.648/B | 623.1407 | 623.1436 | 1H NMR (CDCl3) δ ppm: 7.85 (s, 1H), 7.83 (br. s, 1H), 7.72 (br. d, J = 8.2 Hz, 1H), 7.67 (br. s, 1H), 7.42 (t, J = 7.8 Hz, 1H), 7.25-7.3 (m, 2H), 7.19 (br. s, 1H), 7.11 (s, 1H), 6.85 (t, J = 2.2 Hz, 1H), 6.70 (d, J = 2 Hz, 1H), 6.58 (t, J = 73 Hz, 1H), 6.39 (d, J = 2 Hz, 1H), 5.21 (s, 2H), 4.21 (s, 3H), 3.88 (s, 3H), 3.85 (s, 3H). |

| Ex. | Structure | Formula | HPLC Retention Time (Min)/Method | Calc. [M + H]+ m/z | LCMS [M + H]+ m/z | NMR |
|---|---|---|---|---|---|---|
| 79 | (2-chlorophenyl thiazole carboxamide-benzyl-methoxybenzofuran-methoxyimidazothiadiazole) | C31H22ClN5O5S2 | 3.048/B | 644.0824 | 644.0847 | 1H NMR (CDCl3) δ ppm: 9.26 (br. s, 1H), 8.28 (s, 1H), 8.18 (dd, J = 7.4, 2.4 Hz, 1H), 7.76 (s, 1H), 7.7-7.73 (m, 2H), 7.47 (dd, J = 7.5, 1.5 Hz, 1H), 7.31-7.39 (m, 3H), 7.22 (d, J = 7.3 Hz, 1H), 7.03 (s, 1H), 6.62 (br. d, 1H), 6.32 (d, J = 2.0 Hz, 1H), 5.14 (s, 2H), 4.12 (s, 3H), 3.76 (s, 3H). |
| 80 | (3-trifluoromethylphenyl thiazole carboxamide-benzyl-methoxybenzofuran-methoxyimidazothiadiazole) | C32H22F3N5O5S2 | 2.562/A | 678.1087 | 678.1111 | 1H NMR (CDCl3) δ ppm: 9.21 (br. s, 1H), 8.21 (s, 1H), 8.18 (br. s, 1H), 8.12 (br. d, J = 7.9 Hz, 1H), 7.77 (br. s, 2H), 7.71 (br. d, J = 7.5 Hz, 1H), 7.67 (br. d, J = 8.2 Hz, 1H), 7.57 (t, J = 8 Hz, 1H), 7.36 (t, J = 7.8 Hz, 1H), 7.24 (d, J = 7.4 Hz, 1H), 7.04 (s, 1H), 6.63 (br. d, 1H), 6.34 (d, J = 2.0 Hz, 1H), 5.16 (s, 2H), 4.13 (s, 3H), 3.77 (s, 3H). |

SCHEME #3

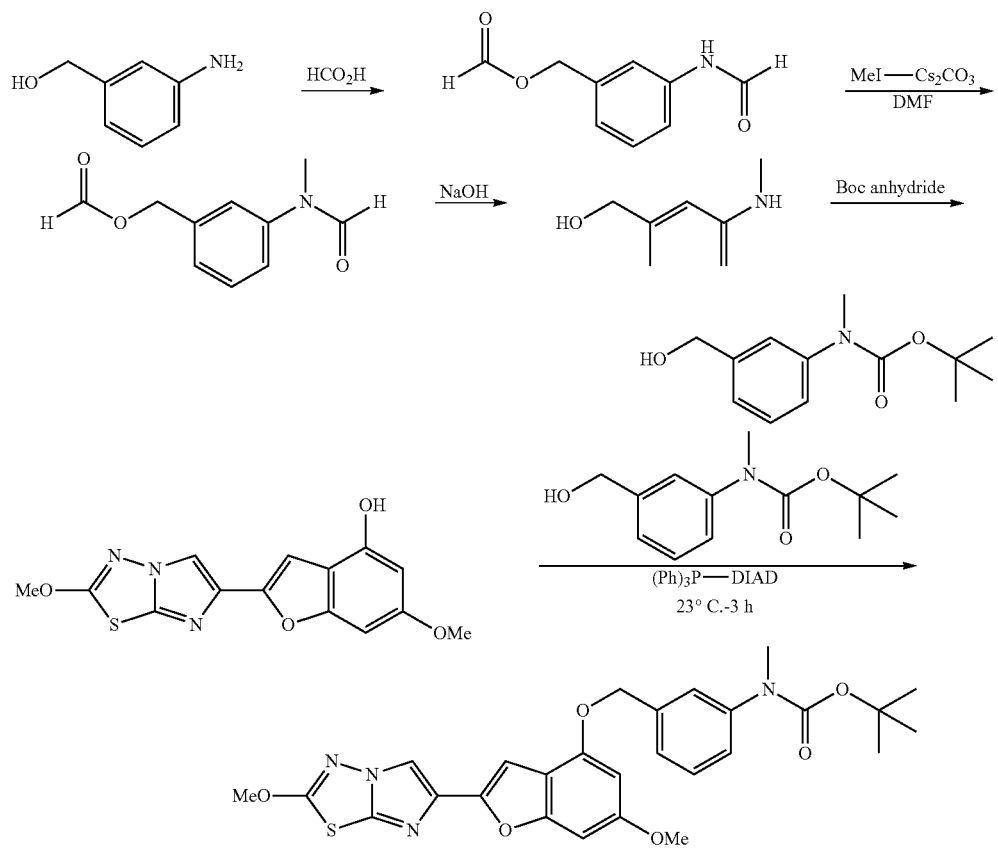

Example 81 tert-Butyl (3-(((6-methoxy-2-(2-methoxyimidazo[2,1-b][1,3,4]thiadiazol-6-yl)benzofuran-4-yl)oxy)methyl)phenyl)(methyl)carbamate

3-Formamidobenzyl formate

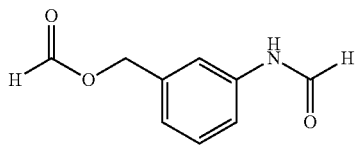

A solution of 3-aminobenzyl alcohol (2.00 g, 16.24 mmol) in formic acid (30 mL) was heated under reflux (bath temperature 110° C.) for 2 hours. The excess formic acid was evaporated under reduced pressure and the residual oil was chromatographed on silica gel (elution toluene-ethyl acetate 7:3) to give 2.47 g (85% yield) of the title material as a clear oil. HPLC (Method A): 1.255 min. $^1$H NMR (CDCl$_3$, 400 MHz) δ ppm: (mixture of rotamers) 8.72 and 8.69 (two s, 0.4H), 8.38 (two s, 0.5H), 8.13 and 8.14 (two s, 0.9H), 8.0 (broad s, 0.4 H), 7.61 (br. s, 0.5H), 7.49 (br. d, 0.6H), 7.32-7.38 (m, 1.5H), 7.19 (d, J=7.7 Hz, 0.5H), 7.14 (d, J=7.5 Hz, 0.5H), 7.05-7.09 (m, 1H), 5.18 and 5.19 (two s, ratio 1:1, 2H).

3-(N-methylformamido)benzyl formate

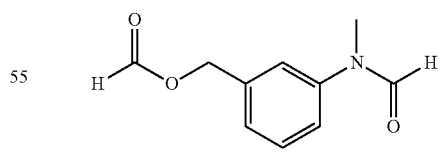

A solution of 3-formamidobenzyl formate (2.068 g, 11.54 mmol) in N,N-dimethylformamide (40 mL) was treated at 23° C. and under nitrogen with cesium carbonate (5.64 g, 17.31 mmol) followed by methyl iodide (0.80 mL, 12.8 mmol) added drop wise over 5 min. After 24 h, the solid carbonate was filtered and the filtrate was concentrated under reduced pressure. The residual oil was chromatographed on silica gel (gradient of ethyl acetate in toluene) to

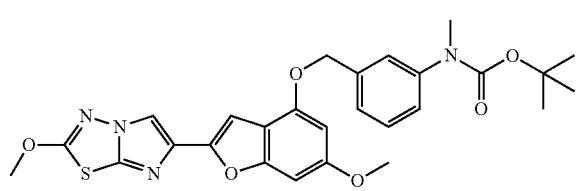 [SMILES: COc1cc(OCc2cccc(N(C)C(=O)OC(C)(C)C)c2)c2cc(-c3cn4nc(OC)sc4n3)oc2c1]

give 1.780 g (80% yield) of the title material as a clear oil which solidified to a white solid in the fridge. HPLC (Method A): 1.376 min. HRMS (ESI) calcd for $C_{10}H_{12}NO_3$ $[M+H]^+$ m/z 194.0812, found 194.0809. $^1$H NMR (CDCl$_3$, 400 MHz) δ ppm: 8.47 (s, 1H), 8.13 (d, J=0.8 Hz, 1H), 7.40 (tr, J=7.8 Hz, 1H), 7.26 (d, J=7.6 Hz, 1H), 7.17 (br. s, 1H), 7.13 (dd, J=7.9, 2.2 Hz, 1H), 5.20 (s, 2H), 3.30 (s, 3H).

(3-(Methylamino)phenyl)methanol

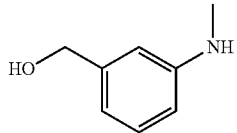

A solution of 3-(N-methylformamido)benzyl formate (1.76 g, 9.1 mmol) in methanol (11 mL) was treated at 23° C. and under nitrogen with 5 N aqueous sodium hydroxide (8 mL, 40 mmol) and the resulting mixture was heated to 70° C. for 4 hours. The methanol was then evaporated under reduced pressure and the residue was diluted with saturated aqueous ammonium chloride (10 mL). The aqueous phase was extracted three times with ether and the combined organic extract was dried over anhydrous sodium sulfate and concentrated under reduced pressure to give a light brown oil. Distillation under vacuum (bulb to bulb distillation, bp 75-85° C./0.1 torr, air bath temperature) gave 1.18 g (95% yield) of a clear oil. HPLC (Method A): 0.146 min. HRMS (ESI) calcd for $C_8H_{12}NO$ $[M+H]^+$ m/z 138.0913, found 138.088. $^1$H NMR (DMSO-d$_6$, 400 MHz) δ ppm: 6.97 (t, J=7.7 Hz, 1H), 6.46 (br. s, 1H), 6.43 (br. d, J=7 Hz, 1H), 6.33-6.36 (m, 1H), 5.50 (br. s, 1H), 4.95 (t, J=5.6 Hz, 1H), 4.33 (d, J=5.6 Hz, 2H), 2.61 (s, 3H).

tert-Butyl (3-(hydroxymethyl)phenyl)(methyl)carbamate

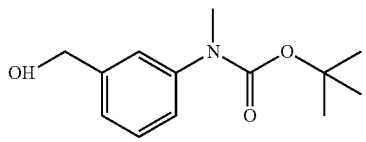 [SMILES: CN(C(=O)OC(C)(C)C)c1cccc(CO)c1]

A solution of (3-(methylamino)phenyl)methanol (1.17 g, 8.53 mmol) in dry tetrahydrofuran (15 mL) was treated at 23° C. with di-tert-butyl dicarbonate (2.15 g, 9.85 mmol) and the resulting mixture was stirred for 72 hours. The reaction mixture was then concentrated under reduced pressure and the oily residue was purified by chromatography on silica gel (elution toluene-ethyl acetate 8:2) to give 1.97 g (97% yield) of the title material as a thick syrup. HPLC (Method A): 1.836 min. $^1$H NMR (CDCl$_3$, 400 MHz) δ ppm: 7.29 (t, J=7.8 Hz, 1H), 7.25 (br. s, 1H), 7.14 (dd, J=7.8, 1.6 Hz, 2H), 4.67 (d, J=6.0 Hz, 2H), 3.24 (s, 3H), 1.74 (t, J=6.0 Hz, 1H), 1.43 (s, 9H).

tert-Butyl (3-(((6-methoxy-2-(2-methoxyimidazo[2, 1-b][1,3,4]thiadiazol-6-yl)benzofuran-4-yl)oxy) methyl)phenyl)(methyl)carbamate

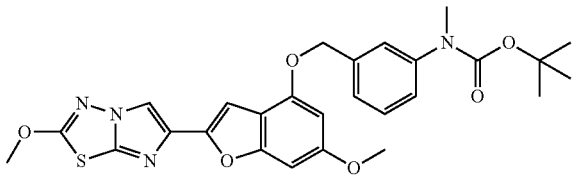 [SMILES: COc1cc(OCc2cccc(N(C)C(=O)OC(C)(C)C)c2)c2cc(-c3cn4nc(OC)sc4n3)oc2c1]

A suspension of 6-methoxy-2-(2-methoxyimidazo[2,1-b][1,3,4]thiadiazol-6-yl)benzofuran-4-ol (2.00 g, 6.30 mmol), tert-butyl (3-(hydroxymethyl)phenyl)(methyl)carbamate (1.90 g, 8.0 mmol) and triphenylphosphine (2.47 g, 9.41 mmol) in dry tetrahydrofuran (200 mL) was treated at 22° C. and under nitrogen with a solution of diisopropyl azodicarboxylate (1.70 g, 8.40 mmol) in tetrahydrofuran (15 ml) added drop-wise over 2 hours. The heterogeneous mixture was homogeneous at the end of the addition and was stirred for another 3 hours. The reaction mixture was then quenched by the addition of ethyl acetate (400 mL) and saturated sodium bicarbonate. The organic phase was washed with brine, dried over anhydrous magnesium sulfate and concentrated in vacuo. Chromatography of the residue on silica gel (elution dichloromethane-ethyl acetate 5-10%) followed by crystallization from ethyl acetate gave 2.35 g (70% yield) of the title material as colorless crystals. HPLC (Method A): 2.443 min. HRMS (ESI) calcd for $C_{27}H_{29}N_4O_6S$ $[M+H]^+$ m/z 537.1802, found 537.1848. $^1$H NMR (CDCl$_3$, 400 MHz) δ ppm: 7.82 (s, 1H), 7.31-7.35 (m, 2H), 7.26 (br. d, J=7.5 Hz, 1H), 7.19 (br. d, J=7.5 Hz, 1H), 7.06 (s, 1H), 6.68 (br. d, 1H),), 6.37 (d, J=1.9 Hz, 1H), 5.14 (s, 2H), 4.18 (s, 3H), 3.81 (s, 3H), 3.25 (s, 3H), 1.42 (s, 9H).

Example 82

3-(((6-Methoxy-2-(2-methoxyimidazo[2,1-b][1,3,4] thiadiazol-6-yl)benzofuran-4-yl)oxy)methyl)-N-methylaniline

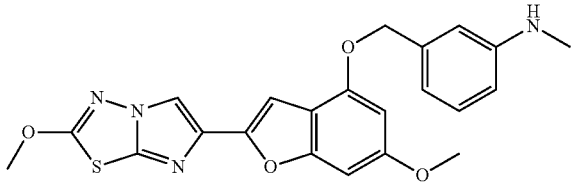

A solution of tert-butyl (3-(((6-methoxy-2-(2-methoxy-imidazo[2,1-b][1,3,4]thiadiazol-6-yl)benzofuran-4-yl)oxy) methyl)phenyl)(methyl)carbamate (2.20 g, 4.10 mmol) in dichloromethane (100 mL) was treated at 22° C. and under nitrogen with trifluoroacetic acid (15 mL) added drop-wise over 5 min. After 2 hours, the solvent and excess reagent were evaporated under reduced pressure and the residue was partitioned between dichloromethane and saturated sodium bicarbonate. The organic phase was washed with brine, dried over anhydrous magnesium sulfate and concentrated under reduced pressure to give a white solid. Crystallization from 1,2-dichloroethane (10 mL, −15° C., 18 h) gave 1.66 g (92% yield) of the title aniline as white cubes. HPLC (Method A): 2.037 min. HRMS (ESI) calcd for $C_{22}H_{21}N_4O_4S$ [M+H]$^+$ m/z 438.1307, found 438.1344. $^1$H NMR (DMSO-d$_6$, 400 MHz) δ ppm: 8.30 (s, 1H), 7.03 (t, J=7.8 Hz, 1H), 6.89 (s, 1H), 6.73 (br. d, 1H), 6.58 (s, 1H), 6.57 (br. d, J=7 Hz, 1H), 6.42 (d, J=1.8 Hz, 1H), 6.41 (br. dd, J=7, 1.5 Hz, 1H), 5.65 (br. s, 1H), 5.05 (s, 2H), 4.13 (s, 3H), 3.71 (s, 3H), 2.59 (s, 3H).

Example 83

N-(3-(((6-methoxy-2-(2-methoxyimidazo[2,1-b][1,3,4]thiadiazol-6-yl)benzofuran-4-yl)oxy)methyl)phenyl)-N-methylbenzamide

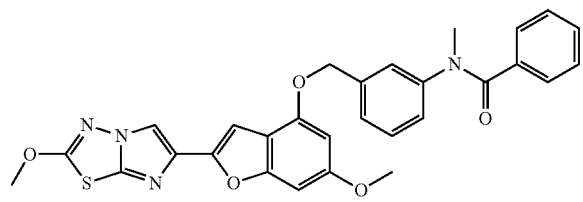 [SMILES: COc1cc(OCc2cccc(N(C)C(=O)c3ccccc3)c2)c2cc(-c3cn4nc(OC)sc4n3)oc2c1]

A solution of 3-(((6-methoxy-2-(2-methoxyimidazo[2,1-b][1,3,4]thiadiazol-6-yl)benzofuran-4-yl)oxy)methyl)-N-methylaniline (0.100 g, 0.23 mmol) in dry tetrahydrofuran (4 mL) was treated at 22° C. and under nitrogen with 4-methylmorpholine (0.070 g, 0.69 mmol) followed by a solution of benzoyl chloride (0.040 g, 0.28 mmol) in dry tetrahydrofuran (2 mL) added drop-wise over 2 min. After 1 hour, the reaction mixture was diluted with dichloromethane, washed successively with cold 0.1N hydrochloric acid, saturated sodium bicarbonate and brine. After drying over anhydrous magnesium sulfate, the organic phase was concentrated under reduced pressure. Chromatography of the residue on silica gel (elution dichloromethane-ethyl acetate 15-20%) followed by crystallization from ethyl acetate gave 0.096 g (78% yield) of the title material as colorless prisms. HPLC (Method A): 2.343 min. HRMS (ESI) calcd for $C_{29}H_{25}N_4O_5S$ [M+H]$^+$ m/z 541.154, found 541.1545. $^1$H NMR (CDCl$_3$, 400 MHz) δ ppm: 7.77 (s, 1H), 7.04-7.20 (m, 8H), 6.95 (s, 1H), 6.86-6.89 (m, 1H), 6.61 (br. d, 1H), 6.19 (d, J=1.8 Hz, 1H), 4.99 (s, 2H), 4.12 (s, 3H), 3.75 (s, 3H), 3.43 (s, 3H).

The following compounds were prepared using the methodology described for preparation of example 83

| Ex. | Structure | Formula | HPLC Retention Time (Min)/ Method | Calc. [M + H]$^+$ m/z | LCMS [M + H]$^+$ m/z | NMR |
|---|---|---|---|---|---|---|
| 84 | 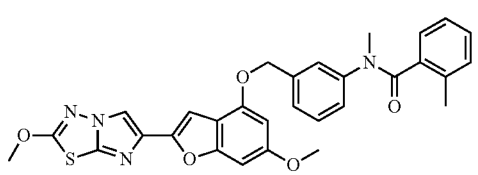 [SMILES: COc1cc(OCc2cccc(N(C)C(=O)c3ccccc3C)c2)c2cc(-c3cn4nc(OC)sc4n3)oc2c1] | $C_{30}H_{26}N_4O_5S$ | 2.398/B | 555.1697 | 555.1695 | $^1$H NMR (CDCl$_3$) δ ppm: 7.87 (s, 1H), 7.10-7.27 (m, 3H), 7.12 (s, 1H), 6.8-7.1 (m, 5H), 6.71 (d, J = 2 Hz, 1H), 6.26 (br. s, 1H), 5.08 (br. s, 2H), 4.24 (s, 3H), 3.84 (s, 3H), 3.51 (br. s, 3H), 2.29 (br. s, 3H). |
| 85 | 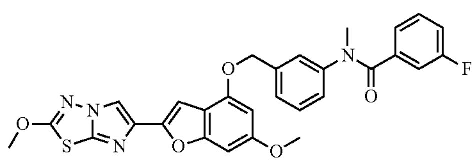 [SMILES: COc1cc(OCc2cccc(N(C)C(=O)c3cccc(F)c3)c2)c2cc(-c3cn4nc(OC)sc4n3)oc2c1] | $C_{29}H_{23}FN_4O_5S$ | 2.363/B | 559.1446 | 559.1443 | $^1$H NMR (CDCl$_3$) δ ppm: 7.78 (s, 1H), 7.19 (s, 1H), 7.16-7.19 (m, 1H), 7.09 (br. s, 1H), 7.03 (s, 1H), 6.91-7.0 (m, 2H), 6.90 (s, 1H), 6.88 (br. s, 1H), 6.80 (dt, J = 8.5, 2.5 Hz, 1H), 6.60 (br. d, 1H), 6.18 (d, J = 1.7 Hz, 1H), 5.02 (s, 2H), 4.15 (s, 3H), 3.75 (s, 3H), 3.42 (s, 3H). |
| 86 | 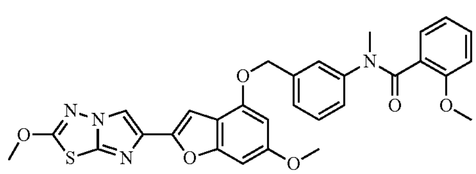 | $C_{30}H_{26}N_4O_6S$ | 2.343/B | 571.1646 | 571.1639 | $^1$H NMR (CDCl$_3$) δ ppm: 7.78 (s, 1H), 7.0-7.2 (m, 6H), 6.90 (br. s, 1H), 6.67 (br. t, 1H), 6.60 (br. s, 1H), 6.49 (br. d, 1H), 6.16 (br. s, 1H), 4.94 (br. s, 2H), 4.15 (s, 3H), 3.75 (s, 3H), 3.48 (br. s, 3H), 3.42 (br. s, 3H). |
| 87 | 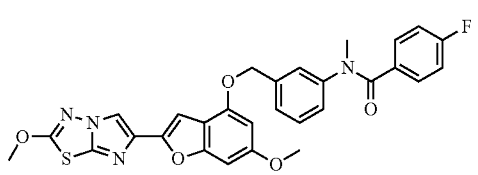 [SMILES: COc1cc(OCc2cccc(N(C)C(=O)c3ccc(F)cc3)c2)c2cc(-c3cn4nc(OC)sc4n3)oc2c1] | $C_{29}H_{23}FN_4O_5S$ | 2.349/A | 559.1446 | 559.1435 | $^1$H NMR (CDCl$_3$) δ ppm: 7.78 (s, 1H), 7.15-7.2 (m, 4H), 7.09 (br. s, 1H), 6.95 (s, 1H), 6.85-6.87 (m, 1H), 6.72 (br. t, J = 8.8 Hz, 2H), 6.61 (br. d, 1H), 6.16 (d, J = 1.9 Hz, 1H), 5.02 (s, 2H), 4.12 (s, 3H), 3.75 (s, 3H), 3.41 (s, 3H). |

| Ex. | Structure | Formula | HPLC Retention Time (Min)/ Method | Calc. [M + H]+ m/z | LCMS [M + H]+ m/z | NMR |
|---|---|---|---|---|---|---|
| 88 | 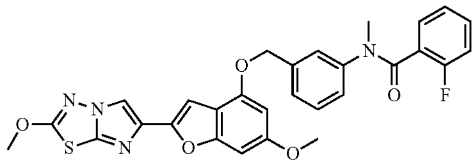 [SMILES: COc1cc(OCc2cccc(N(C)C(=O)c3ccccc3F)c2)c2cc(-c3cn4nc(OC)sc4n3)oc2c1] | C29H23FN4O5S | 2.365/B | 559.1446 | 559.1469 | 1H NMR (CDCl3) δ ppm: 7.77 (s, 1H), 7.0-7.18 (m, 5H), 7.00 (s, 1H), 6.93 (br. s, 1H), 6.85 (br. s, 1H), 6.70 (br. s, 1H), 6.61 (s, 1H), 6.17 (br. s, 1H), 4.97 (s, 2H), 4.14 (s, 3H), 3.75 (s, 3H), 3.42 (br. s, 3H). |
| 89 | 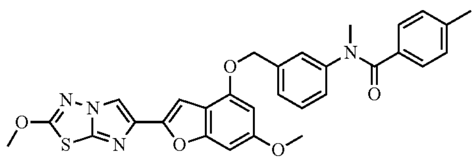 | C30H26N4O5S | 2.427/B | 555.1697 | 555.1728 | 1H NMR (CDCl3) δ ppm: 7.77 (s, 1H), 7.17-7.19 (m, 1H), 7.14 (t, J = 7.4 Hz, 1H), 7.12 (br. s, 1H), 7.09 (br. d, J = 8.2 Hz, 2H), 7.03 (s, 1H), 6.84-6.87 (m, 3H), 6.61 (br. d, 1H), 6.21 (d, J = 1.9 Hz, 1H), 5.02 (s, 2H), 4.14 (s, 3H), 3.75 (s, 3H), 3.41 (s, 3H), 2.15 (s, 3H). |
| 90 | 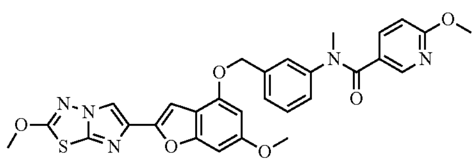 | C29H25N5O6S | 2.337/B | 572.1598 | 572.1627 | 1H NMR (CDCl3) δ ppm: 8.07 (br. s, 1H), 7.79 (s, 1H), 7.36 (br. d, 1H), 7.17-7.25 (m, 2H), 7.15 (s, 1H), 7.04 (s, 1H), 6.89-6.91 (m, 1H), 6.60 (br. s, 1H), 6.40 (d, J = 9 Hz, 1H), 6.21 (br. s, 1H), 5.05 (s, 2H), 4.15 (s, 3H), 3.77 (s, 3H), 3.76 (s, 3H), 3.41 (s, 3H). |
| 91 | 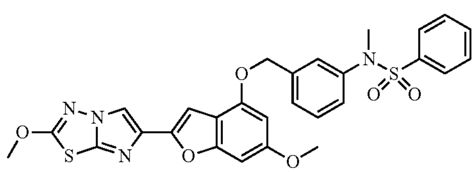 [SMILES: COc1cc(OCc2cccc(N(C)S(=O)(=O)c3ccccc3)c2)c2cc(-c3cn4nc(OC)sc4n3)oc2c1] | C28H24N4O6S2 | 2.326/A | 577.121 | 577.122 | 1H NMR (CDCl3) δ ppm: 7.77 (s, 1H), 7.44-7.48 (m, 3H), 7.30-7.35 (m, 3H), 7.25 (t, J = 8 Hz, 1H), 7.02-7.04 (m, 2H), 6.92 (s, 1H), 6.62 (br. d, 1H), 6.24 (d, J = 1.9 Hz, 1H), 5.03 (s, 2H), 4.13 (s, 3H), 3.75 (s, 3H), 3.11 (s, 3H). |
| 92 | 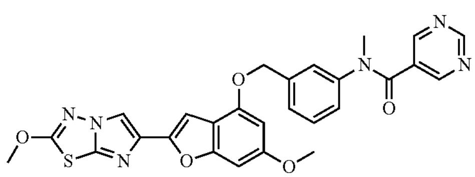 [SMILES: COc1cc(OCc2cccc(N(C)C(=O)c3cncnc3)c2)c2cc(-c3cn4nc(OC)sc4n3)oc2c1] | C27H22N6O5S | 2.190/B | 543.1445 | 543.1451 | 1H NMR (CDCl3) δ ppm: 8.94 (br. s, 1H), 8.53 (br. s, 2H), 7.80 (s, 1H), 7.22-7.28 (m, 2H), 7.16-7.18 (m, 1H), 7.04 (s, 1H), 6.91-6.94 (m, 1H), 6.61 (br. d, 1H), 6.18 (d, J = 1.8 Hz, 1H), 5.04 (s, 2H), 4.15 (s, 3H), 3.76 (s, 3H), 3.45 (s, 3H). |
| 93 | 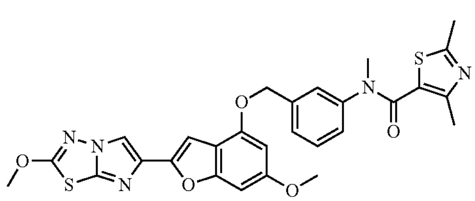 [SMILES: COc1cc(OCc2cccc(N(C)C(=O)c3sc(C)nc3C)c2)c2cc(-c3cn4nc(OC)sc4n3)oc2c1] | C28H25N5O5S2 | 2.289/B | 576.137 | 576.1392 | 1H NMR (CDCl3) δ ppm: 7.79 (s, 1H), 7.33 (br. d, J = 7.8 Hz, 1H), 7.27 (t, J = 7.7 Hz, 1H), 7.20 (br. s, 1H), 7.05 (s, 1H), 6.96 (br. d, J = 7.5 Hz, 1H), 6.60 (br. d, 1H), 6.23 (d, J = 1.8 Hz, 1H), 5.11 (s, 2H), 4.15 (s, 3H), 3.74 (s, 3H), 3.36 (s, 3H), 2.42 (s, 3H), 2.38 (s, 3H). |
| 94 | 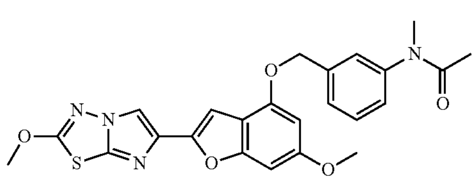 [SMILES: COc1cc(OCc2cccc(N(C)C(C)=O)c2)c2cc(-c3cn4nc(OC)sc4n3)oc2c1] | C24H22N4O5S | 2.232/A | 479.1384 | 479.1375 | 1H NMR (CDCl3) δ ppm: 7.83 (s, 1H), 7.4-7.44 (m, 2H), 7.28 (s, 1H), 7.12-7.14 (m, 1H), 7.05 (s, 1H), 6.68 (br. d, 1H), 6.36 (br. d, J = 1.1 Hz, 1H), 5.18 (s, 2H), 4.18 (s, 3H), 3.82 (s, 3H), 3.26 (s, 3H), 1.85 (s, 3H). |

-continued
| Ex. | Structure | Formula | HPLC Retention Time (Min)/ Method | Calc. [M + H]⁺ m/z | LCMS [M + H]⁺ m/z | NMR |
|---|---|---|---|---|---|---|
| 95 | 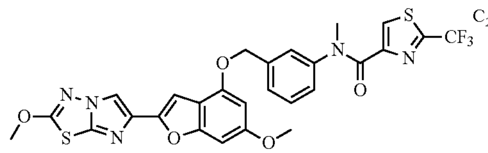 | C₂₇H₂₀F₃N₅O₅S₂ | 2.053/A | 616.0931 | 616.0969 | ¹H NMR (CDCl₃) δ ppm: 7.77 (s, 1H), 7.6 (br. s, 1H), 7.4-7.5 (m, 2H), 7.16 (br. s, 1H), 7.03 (s, 1H), 6.98 (br. s, 1H), 6.60 (br. d, 1H), 6.21 (br. d, 1H), 5.06 (s, 2H), 4.15 (s, 3H), 3.75 (s, 3H), 3.45 (s, 3H). |
| 96 | 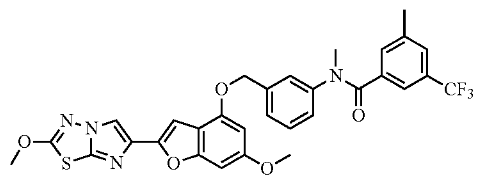 [SMILES: COc1cc(OCc2cccc(N(C)C(=O)c3cc(C)cc(C(F)(F)F)c3)c2)c2cc(-c3cn4nc(OC)sc4n3)oc2c1] | C₃₁H₂₅F₃N₄O₅S | 2.150/A | 623.1571 | 623.1612 | ¹H NMR (CDCl₃) δ ppm: 8.1, 8.07, 8.05, 8.0, 7.68 and 7.58 (six broad s, 1H), 7.7 (s, 1H), 7.15-7.25 (m, 4H), 7.12 (br. s, 1H), 7.01 (s, 1H), 6.87-6.92 (m, 1H), 6.60 (d, J = 1.6 Hz, 1H), 6.20 (d, J = 1.6 Hz, 1H), 5.01 (s, 2H), 4.15 (s, 3H), 3.75 (s, 3H), 3.44 (s, 3H), 2.14 (s, 3H). |
| 97 | 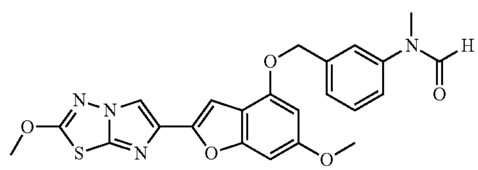 [SMILES: COc1cc(OCc2cccc(N(C)C=O)c2)c2cc(-c3cn4nc(OC)sc4n3)oc2c1] | C₂₃H₂₀N₄O₅S | 2.547/A | 465.1227 | 465.1231 | ¹H NMR (CDCl₃) δ ppm: 8.51 (s, 1H), 7.86 (s, 1H), 7.37-7.48 (m, 2H), 7.30 (br. s, 1H), 7.14 (d, J = 7.8 Hz, 1H), 7.08 (s, 1H), 6.72 (br. d, 1H), 6.39 (br. d, 1H), 5.21 (s, 2H), 4.21 (s, 3H), 3.85 (s, 3H), 3.35 (s, 3H). |
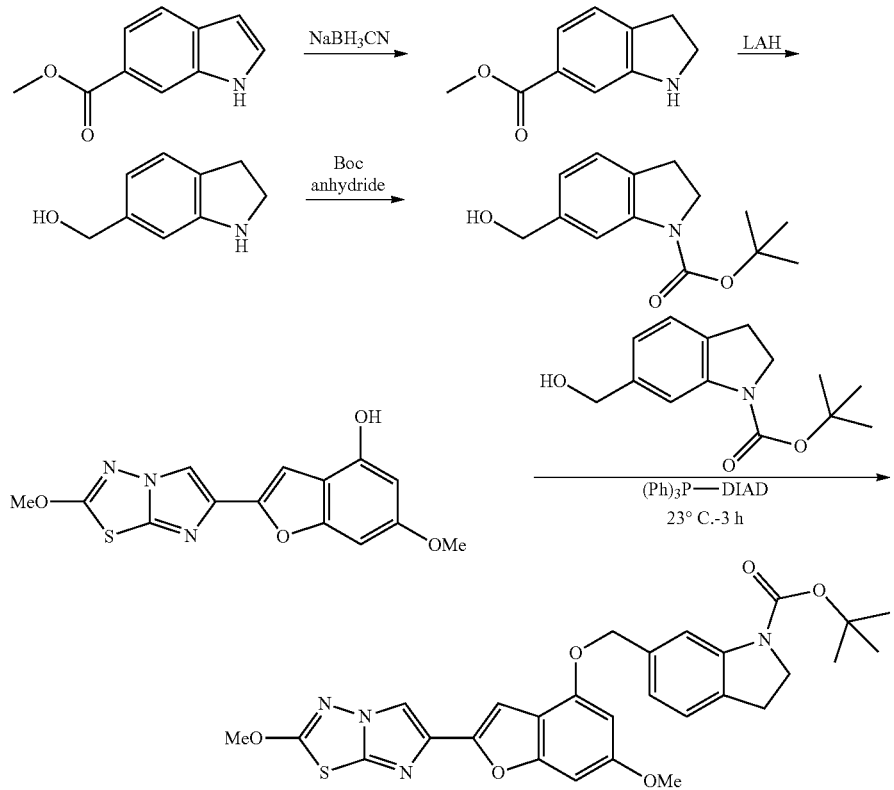
SCHEME #4

Example 98 tert-Butyl 6-(((6-methoxy-2-(2-methoxyimidazo[2,1-b][1,3,4]thiadiazol-6-yl)benzofuran-4-yl)oxy)methyl)indoline-1-carboxylate

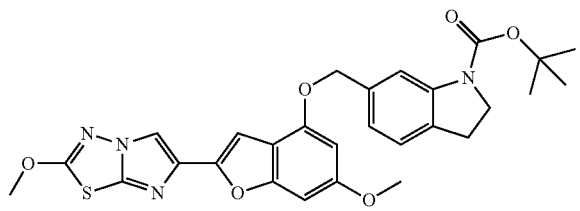 [SMILES: COc1cc(OCc2ccc3c(c2)N(C(=O)OC(C)(C)C)CC3)c2cc(-c3cn4nc(OC)sc4n3)oc2c1]

Methyl indoline-6-carboxylate

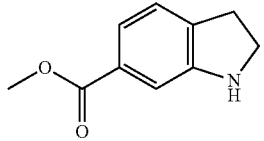

A solution of methyl 1H-indole-6-carboxylate (4.80 g, 27.4 mmol) in acetic acid (40 mL) was cooled to 15° C. and then treated with sodium cyanoborohydride (6.90 g, 0.11 mmol) added in small portions over 30 min. After 5 h at 15° C., the reaction mixture was diluted with a mixture of ice and water (200 mL) and carefully adjusted to pH 9-10 with solid potassium carbonate. The aqueous phase was extracted three times with dichloromethane and the combined organic phase was washed with brine and dried over anhydrous magnesium sulfate. The solvent was evaporated under reduced pressure and the residual oil was chromatographed on silica gel (elution toluene-ethyl acetate 8:2) to give 3.54 g (73% yield) of the title material as yellowish solid. HPLC (Method A): 0.9 min (tailing). HRMS (ESI) calcd for $C_{10}H_{12}NO_2$ [M+H]$^+$ m/z 178.0863, found 178.0882. $^1$H NMR (CDCl$_3$, 400 MHz) δ ppm: 7.40 (dd, J=7.6, 1.5 Hz, 1H), 7.25 (d, J=1.5 Hz, 1H), 7.12 (br. d, J=7.6 Hz, 1H), 3.85 (s, 3H), 3.59 (t, J=8.5 Hz, 2H), 3.05 (t, J=8.5 Hz, 2H).

Indolin-6-ylmethanol

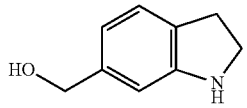 [SMILES: OCc1ccc2c(c1)NCC2]

A solution of methyl indoline-6-carboxylate (0.830 g, 4.68 mmol) in dry tetrahydrofuran (20 mL) was treated at 23° C. and under nitrogen with lithium aluminum hydride (0.23 g, 6.08 mmol) and the resulting mixture was stirred for 3.5 h. The reaction mixture was carefully quenched by successive addition of ethyl acetate (1 mL), water (0.2 mL), 15% aqueous sodium hydroxide (0.2 mL) and water (0.6 mL). The solid formed was filtered and the filtrate was concentrated under reduced pressure. Chromatography of the residual oil on silica gel (elution ethyl acetate) followed by distillation under vacuum (bulb to bulb distillation, bp 95-105° C./0.1 torr, air bath temperature) gave 0.460 g (57% yield) of a clear oil which crystallized to a white solid. HPLC (Method A): 0.132 min. HRMS (ESI) calcd for $C_9H_{12}NO$ [M+H]$^+$ m/z 150.0913, found 150.0932. $^1$H NMR (CDCl$_3$, 400 MHz) δ ppm: 7.4 (d, J=7.4 Hz, 1H), 6.66 (dd, J=7.4, 1.5 Hz, 1H), 6.63 (br. s, 1H), 4.55 (s, 2H), 3.54 (t, J=8.4 Hz, 2H), 2.99 (t, J=8.4 Hz, 2H).

tert-Butyl 6-(hydroxymethyl)indoline-1-carboxylate

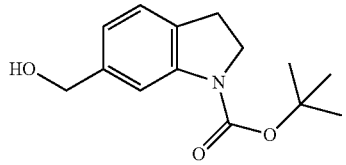 [SMILES: CC(C)(C)OC(=O)N1CCc2ccc(CO)cc21]

A solution of indolin-6-ylmethanol (0.630 g, 4.22 mmol) in dry tetrahydrofuran (15 mL) was treated at 23° C. with di-tert-butyl dicarbonate (0.99 g, 4.53 mmol) and the resulting mixture was stirred for 18 hours. The reaction mixture was then concentrated under reduced pressure and the oily residue was purified by chromatography on silica gel (elution toluene-ethyl acetate 7:3) to give 1.052 g (100% yield) of the title material as a thick syrup which crystallized to a white solid in the fridge. HPLC (Method A): 1.905 min. $^1$H NMR (CDCl$_3$, 400 MHz) δ ppm: 7.84 (br. s, 1H), 7.10 (d, J=7.5 Hz, 1H), 6.93 (br. d, J=7.5 Hz, 1H), 4.62 (d, J=6.0 Hz, 2H), 3.96 (t, J=8.7 Hz, 2H), 3.05 (t, J=8.7 Hz, 2H), 1.57 (t, J=6.0 Hz, 1H), 1.54 (s, 9H).

tert-Butyl 6-(((6-methoxy-2-(2-methoxyimidazo[2,1-b][1,3,4]thiadiazol-6-yl)benzofuran-4-yl)oxy)methyl)indoline-1-carboxylate

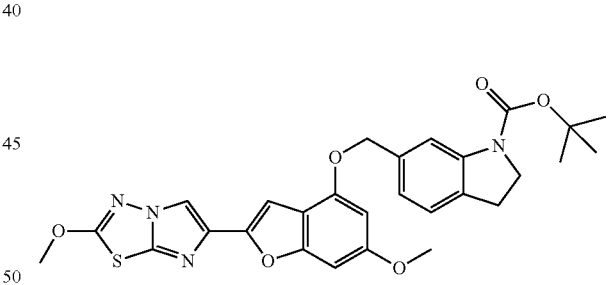

A suspension of 6-methoxy-2-(2-methoxyimidazo[2,1-b][1,3,4]thiadiazol-6-yl)benzofuran-4-ol (0.500 g, 1.57 mmol), tert-butyl 6-(hydroxymethyl)indoline-1-carboxylate (0.500 g, 2.0 mmol) and triphenylphosphine (0.62 g, 2.36 mmol) in dry tetrahydrofuran (50 mL) was treated at 22° C. and under nitrogen with a solution of diisopropyl azodicarboxylate (0.47 g, 2.32 mmol) in tetrahydrofuran (10 ml) added drop-wise over 2 hours. The heterogeneous mixture was homogeneous at the end of the addition and was stirred for another 3 hours. The reaction mixture was then quenched by the addition of ethyl acetate and saturated sodium bicarbonate. The organic phase was washed with brine, dried over anhydrous magnesium sulfate and concentrated in vacuo. Chromatography of the residue on silica gel (elution toluene-ethyl acetate 10-15%) gave 0.582 g (67% yield) of the title material as a white solid. HPLC (Method A): 2.523 min.

HRMS (ESI) calcd for $C_{28}H_{29}N_4O_6S$ [M+H]$^+$ m/z 549.1802, found 549.1793. $^1$H NMR (CDCl$_3$, 400 MHz) δ ppm: 7.86 (br. s, 1H), 7.74 (s, 1H), 7.06 (d, J=7.5 Hz, 1H), 6.98-7.04 (m, 2H), 6.59 (br. d, 1H), 6.29 (d, J=1.8 Hz, 1H), 5.06 (s, 2H), 4.11 (s, 3H), 3.91 (t, J=8.7 Hz, 2H), 3.74 (s, 3H), 3.0 (t, J=8.7 Hz, 2H), 1.46 (s, 9H).

Example 99

6-(4-(Indolin-6-ylmethoxy)-6-methoxybenzofuran-2-yl)-2-methoxyimidazo[2,1-b][1,3,4]thiadiazole

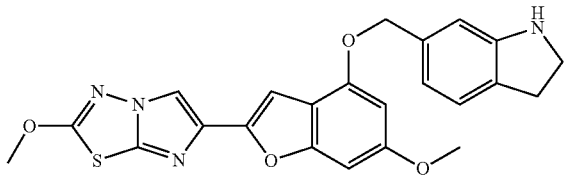 [SMILES: COc1cc(OCc2ccc3c(c2)NCC3)c2cc(-c3cn4nc(OC)sc4n3)oc2c1]

A solution of tert-butyl 6-(((6-methoxy-2-(2-methoxyimidazo[2,1-b][1,3,4]thiadiazol-6-yl)benzofuran-4-yl)oxy)methyl)indoline-1-carboxylate (0.379 g, 0.69 mmol) in dichloromethane (15 mL) was treated at 22° C. and under nitrogen with trifluoroacetic acid (1.5 mL) added drop-wise over 2 min. After 2 hours, the solvent and excess reagent were evaporated under reduced pressure and the residue was partitioned between dichloromethane and saturated sodium bicarbonate. The organic phase was washed with brine, dried over anhydrous magnesium sulfate and concentrated under reduced pressure to give 0.259 g (83% yield) of a white solid. HPLC (Method A): 1.948 min. HRMS (ESI) calcd for $C_{23}H_{21}N_4O_4S$ [M+H]$^+$ m/z 449.1278, found 449.1284. $^1$H NMR (CDCl$_3$, 400 MHz) δ ppm: 7.75 (s, 1H), 7.03 (d, J=7.9 Hz, 1H), 7.01 (s, 1H), 6.71 (d, J=7.2 Hz, 1H), 6.70 (s, 1H), 6.60 (br. d, 1H), 6.31 (d, J=1.9 Hz, 1H), 5.01 (s, 2H), 4.13 (s, 3H), 3.75 (s, 3H), 3.74 (br. s, 1H), 3.50 (t, J=8.3 Hz, 2H), 2.95 (t, J=8.3 Hz, 2H).

Example 100

(6-(((6-Methoxy-2-(2-methoxyimidazo[2,1-b][1,3,4]thiadiazol-6-yl)benzofuran-4-yl)oxy)methyl)indolin-1-yl)(phenyl)methanone

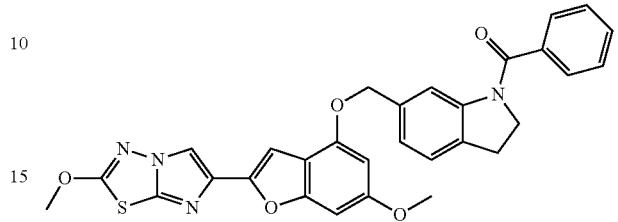

A solution of 6-(4-(indolin-6-ylmethoxy)-6-methoxybenzofuran-2-yl)-2-methoxyimidazo[2,1-b][1,3,4]thiadiazole (0.065 g, 0.145 mmol) in dry tetrahydrofuran (4 mL) was treated at 22° C. and under nitrogen with 4-methylmorpholine (0.050 g, 0.49 mmol) followed by a solution of benzoyl chloride (0.025 g, 0.18 mmol) in dry tetrahydrofuran (1 mL) added drop-wise over 2 min. After 1 hour, the reaction mixture was diluted with dichloromethane, washed successively with cold 0.1N hydrochloric acid, saturated sodium bicarbonate and brine. After drying over anhydrous magnesium sulfate, the organic phase was concentrated under reduced pressure. Chromatography of the residue on silica gel (elution dichloromethane-ethyl acetate 10-15%) gave 0.053 g (66% yield) of the title material as a white solid. HPLC (Method A): 2.354 min. HRMS (ESI) calcd for $C_{30}H_{25}N_4O_5S$ [M+H]$^+$ m/z 553.154, found 553.154. $^1$H NMR (CDCl$_3$, 400 MHz) δ ppm: 7.76 (s, 1H), 7.4-7.5 (m, 2H), 7.3-7.4 (m, 3H), 7.13 (br. d, J=7.0 Hz, 1H), 7.08 (br. s, 2H), 6.94 (br. s, 1H), 6.65 (br. s, 1H), 6.24 (br. s, 1H), 5.05 (br. s, 2H), 4.12 (s, 3H), 4.03 (br. s, 2H), 3.75 (s, 3H), 3.04 (t, J=8.3 Hz, 2H).

The following compounds were prepared using the methodology described for preparation of example 100

| Ex. | Structure | Formula | HPLC Retention Time (Min)/ Method | Calc. [M + H]+ m/z | LCMS [M + H]+ m/z | NMR |
|---|---|---|---|---|---|---|
| 101 | 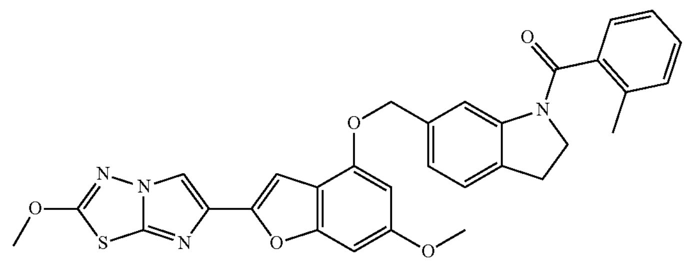 [SMILES: COc1cc(OCc2ccc3c(c2)N(C(=O)c2ccccc2C)CC3)c2cc(-c3cn4nc(OC)sc4n3)oc2c1] | C31H26N4O5S | 2.495/B | 567.1697 | 567.1704 | 1H NMR (CDCl3) δ ppm: (mixture of rotamers) 8.47 (br. s, 0.7H), 7.88 (br. s, 1.2 H), 7.2-7.4 (m, 4H), 7.0-7.15 (m, 1.6H), 6.69 and 6.67 (two s, 1.1H), 6.44 (s, 0.7H), 6.10 (s, 0.6H), 5.67 (s, 0.65H), 5.24 (s, 1.3H), 4.84 (s, 1H), 4.34 (br. t, 1H), 4.25 (s, 3H), 3.86 and 3.83 (two s, 3H), 3.75-3.83 (m, 1.4H), 3.10-3.2 (m, 2H), 2.16 and 2.39 (two s, 3H). |
| 102 | 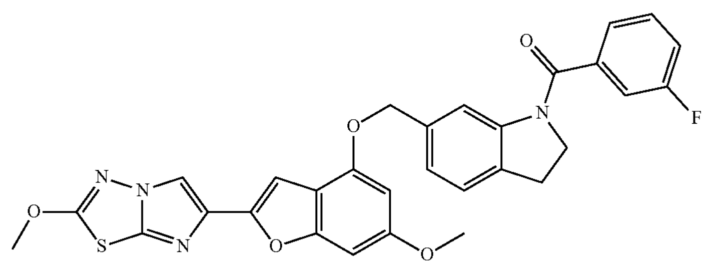 [SMILES: COc1cc(OCc2ccc3c(c2)N(C(=O)c2cccc(F)c2)CC3)c2cc(-c3cn4nc(OC)sc4n3)oc2c1] | C30H23FN4O5S | 2.017/A | 571.1446 | 571.1453 | 1H NMR (CDCl3) δ ppm: 7.76 (s, 1H), 7.31 (br. s, 1H), 7.24 (br. s, 1H), 7.06-7.22 (m, 4H), 7.05 (br. t, 1H), 6.95 (br. s, 1H), 6.60 (br. d, 1H), 6.25 (br. s, 1H), 5.02 (br. s, 2H), 4.12 (s, 3H), 4.0 (br. s, 2H), 3.75 (s, 3H), 3.05 (t, J = 8.3 Hz, 2H). |
| 103 | 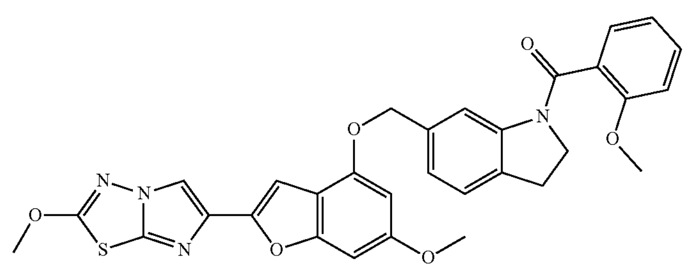 [SMILES: COc1cc(OCc2ccc3c(c2)N(C(=O)c2ccccc2OC)CC3)c2cc(-c3cn4nc(OC)sc4n3)oc2c1] | C31H26N4O6S | 1.999/A | 583.1646 | 583.1658 | 1H NMR (CDCl3) δ ppm: (mixture of rotamers) 8.36 (s, 0.7H), 7.75 and 7.77 (two s, 1H), 7.05-7.35 (m, 3H), 7.01 (s, 0.7H), 6.95 (t, J = 7.5 Hz, 0.7H), 6.85-6.9 (m, 2H), 6.65 (d, J = 8 Hz, 0.3H), 6.55-6.55 (m, 1H), 6.34 (s, 0.7H), 6.04 (s, 0.3H), 5.82 (s, 0.3H), 5.13 (s, 1.3H), 4.77 (s, 0.6H), 4.2-4.35 (m, 0.6H), 4.11 and 4.13 (two s, 3H), 3.7-3.8 (m, 7H), 3.44 (s, 0.9H), 3.01 (br. t, J = 8.4 Hz, 2H). |

| Ex. | Structure | Formula | HPLC Retention Time (Min)/ Method | Calc. [M + H]+ m/z | LCMS [M + H]+ m/z | NMR |
|---|---|---|---|---|---|---|
| 104 | 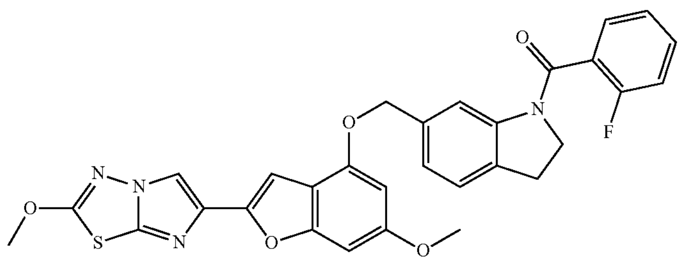 [SMILES: COc1cc(OCc2ccc3c(c2)N(C(=O)c2ccccc2F)CC3)c2cc(-c3cn4nc(OC)sc4n3)oc2c1] | C30H23FN4O5S | 2.042/A | 571.1446 | 571.1447 | 1H NMR (CDCl3) δ ppm: (mixture of rotamers) 8.33 (s, 0.8H), 7.76 (broad s, 1H), 6.9-7.4 (m, 7H), 6.61 (br. s, 1H), 6.34 (s, 0.8H), 5.95 and 6.06 (two br. s, 0.4H), 5.14 and 4.78 (two s, 2H), 4.32 and 4.18 (two br. s, 0.6H), 4.12 (s, 3H), 3.8 (t, J = 8.2 Hz, 1.4H), 3.76 and 3.74 (two s, 3H), 3.06 (br. t, J = 8.2 Hz, 2H). |
| 105 | 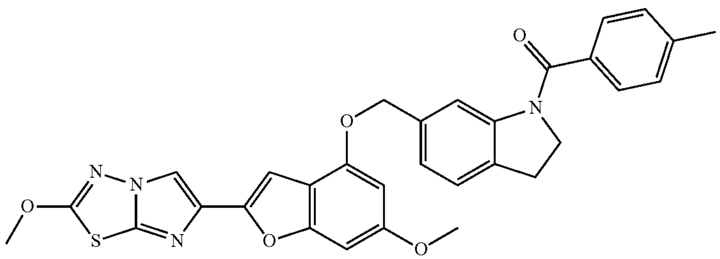 | C31H26N4O5S | 2.083/A | 567.1697 | 567.1698 | 1H NMR (CDCl3) δ ppm: 7.76 (s, 1H), 7.37 (d, J = 8.0 Hz, 2H), 7.14 (d, J = 8.0 Hz, 2H), 7.1-7.15(m, 2H), 7.09 (br. s, 1H), 6.96 (br. s, 1H), 6.60 (br. d, 1H), 6.26 (br. s, 1H), 5.01 (br. s, 2H), 4.12 (s, 3H), 4.04 (br. t, 2H), 3.75 (s, 3H), 3.03 (t, J = 8.3 Hz, 2H), 2.28 (br. s, 3H). |
| 106 | 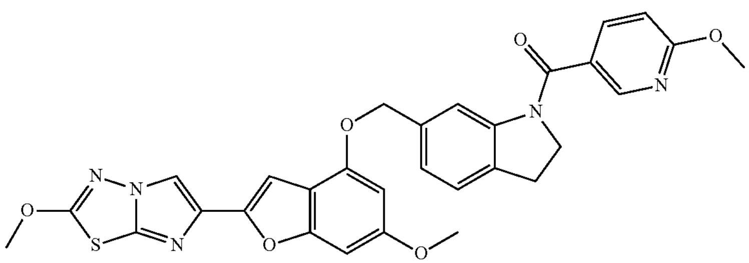 | C30H25N5O6S | 2.000/A | 584.1598 | 584.1601 | 1H NMR (CDCl3) δ ppm: 8.38 (d, J = 1.6 Hz, 1H), 7.77 (s, 1H), 7.72 (dd, J = 8.2, 2.1 Hz, 1H), 7.08-7.15 (m, 2H), 6.99 (s, 1H), 6.59 (br. d, 1H), 6.30 (d, J = 1.9 Hz, 1H), 5.06 (br. s, 2H), 4.13 (s, 3H), 4.08 (t, J = 8.2 Hz, 2H), 3.89 (s, 3H), 3.76 (s, 3H), 3.07 (t, J = 8.2 Hz, 2H). |

| Ex. | Structure | Formula | HPLC Retention Time (Min)/ Method | Calc. [M + H]+ m/z | LCMS [M + H]+ m/z | NMR |
|---|---|---|---|---|---|---|
| 107 | 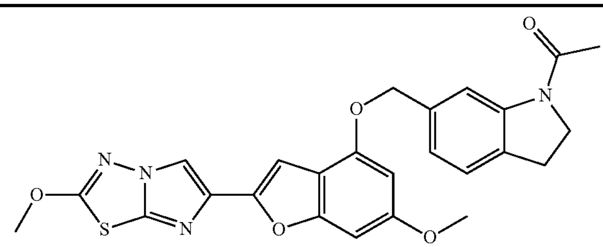 | $C_{25}H_{22}N_4O_5S$ | 2.266/A | 491.1384 | 491.1389 | 1H NMR (CDCl3) δ ppm: 8.31 (s, 1H), 7.84 (s, 1H), 7.15-7.22 (m, 2H), 7.09 (s, 1H), 6.69 (br. d, 1H), 6.40 (d, J = 1.6 Hz, 1H), 5.17 (s, 2H), 4.21 (s, 3H), 4.09 (t, J = 8.5 Hz, 2H), 3.84 (s, 3H), 3.21 (t, J = 8.5 Hz, 2H), 2.25 (s, 3H). |
| 108 | 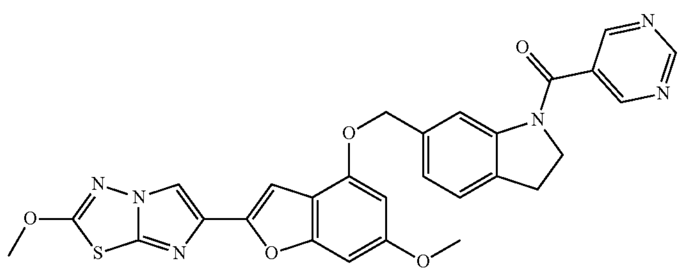 [SMILES: COc1cc(OCc2ccc3c(c2)N(C(=O)c2cncnc2)CC3)c2cc(-c3cn4nc(OC)sc4n3)oc2c1] | $C_{28}H_{22}N_6O_5S$ | 1.935/A | 555.1445 | 555.1449 | 1H NMR (CDCl3) δ ppm: 9.25 (s, 1H), 8.90 (s, 2H), 8.25 (br. s, 1H), 7.77 (broad s, 1H), 7.15-7.2 (m, 2H), 6.99 (br. s, 1H), 6.61 (s, 1H), 6.30 (br. s, 1H), 5.12 (br. s, 2H), 4.12 (s, 3H), 3.90-4.1 (m, 2H), 3.76 (s, 3H), 3.12 (t, J = 8.2 Hz, 2H). |
| 109 | 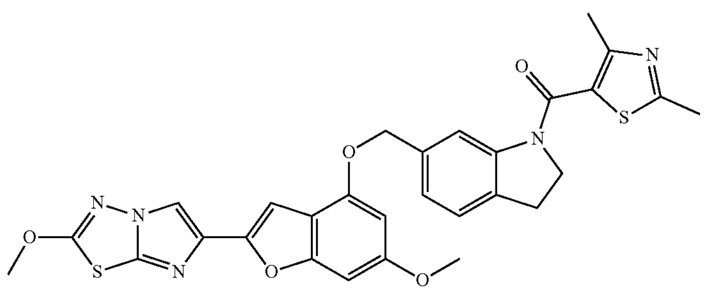 | $C_{29}H_{25}N_5O_5S_2$ | 1.992/A | 588.137 | 588.1386 | 1H NMR (CDCl3) δ ppm: 7.77 (s, 1H), 7.15-7.2 (m, 3H), 6.99 (s, 1H), 6.61 (d, J = 2H, 1H), 6.28 (d, J = 2 Hz, 1H), 5.06 (s, 2H), 4.12 (s, 3H), 4.05 (t, J = 8.2 Hz, 2H), 3.76 (s, 3H), 3.08 (t, J = 8.2 Hz, 2H), 2.60 (s, 3H), 2.38 (s, 3H). |

| Ex. | Structure | Formula | HPLC Retention Time (Min)/ Method | Calc. [M + H]+ m/z | LCMS [M + H]+ m/z | NMR |
|---|---|---|---|---|---|---|
| 110 | 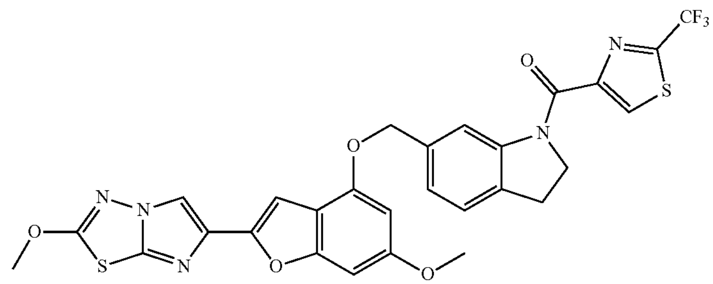 [SMILES: COc1cc(OCc2ccc3c(c2)N(C(=O)c2csc(C(F)(F)F)n2)CC3)c2cc(-c3cn4nc(OC)sc4n3)oc2c1] | C28H20F3N5O5S2 | 2.382/A | 628.0931 | 628.0951 | 1H NMR (CDCl3) δ ppm: 8.35 (d, J = 7.4 Hz, 2H), 7.75 (s, 1H), 7.15-7.22 (m, 2H), 7.01 (s, 1H), 6.60 (s, 1H), 6.30 (br. s, 1H), 5.12 (s, 2H), 4.54 (br. t, J = 8.2 Hz, 2H), 4.12 (s, 3H), 3.75 (s, 3H), 3.15 (t, J = 8.2 Hz, 2H). |
| 111 | 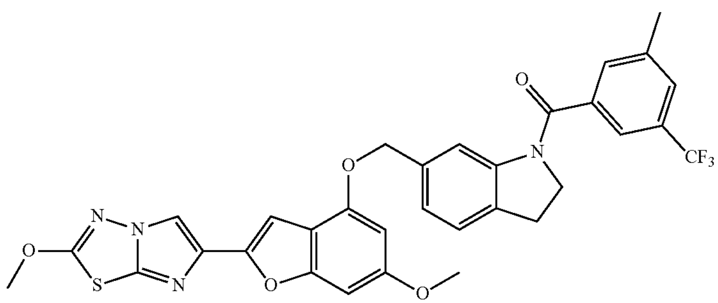 [SMILES: COc1cc(OCc2ccc3c(c2)N(C(=O)c2cc(C)cc(C(F)(F)F)c2)CC3)c2cc(-c3cn4nc(OC)sc4n3)oc2c1] | C32H25F3N4O5S | 2.274/A | 635.1571 | 635.1589 | 1H NMR (CDCl3) δ ppm: (mixture of rotamers) 8.11, 8.07, 8.05 and 8.0 (four s, 0.6H), 7.76 (broad s, 1H), 7.4-7.7 (m, 4H), 7.15-7.20 (m, 2H), 7.05 (br. s, 1H), 6.59 (s, 1H), 6.30 (br. s, 1H), 5.08 (br. s, 1H), 4.14 (s, 3H), 4.0 (br. s, 2H), 3.76 (s, 3H), 3.07 (t, J = 8.2 Hz, 2H), 2.36 br. s, 3H). |
| 112 | 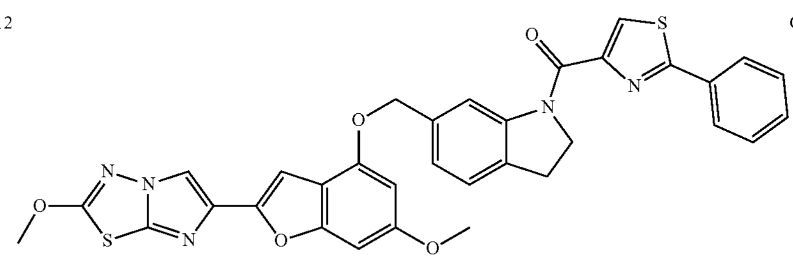 | C33H25N5O5S2 | 2.587/A | 636.137 | 636.1378 | 1H NMR (CDCl3) δ ppm: 8.39 (br. s, 1H), 8.36 (broad s, 1H), 7.90 (br. s, 2H), 7.75 (s, 1H), 7.39 (br. s, 3H), 7.15-7.2 (m, 2H), 7.01 (br. s, 1H), 6.60 (s, 1H), 6.33 (br. s, 1H), 5.13 (br. s, 2H), 4.62 (br. t, 2H), 4.12 (s, 3H), 3.75 (s, 3H), 3.15 (t, J = 8.4 Hz, 2H). |

SCHEME #5

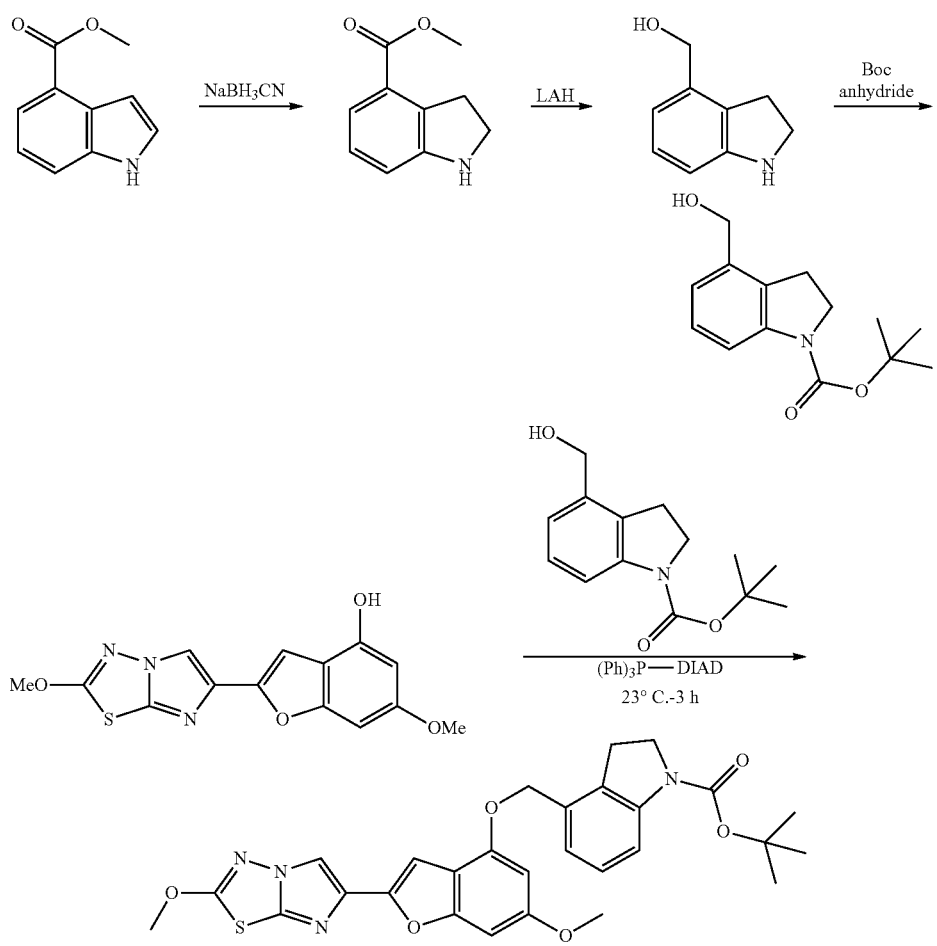

Example 113 tert-Butyl 4-(((6-methoxy-2-(2-methoxyimidazo[2,1-b][1,3,4]thiadiazol-6-yl)benzofuran-4-yl)oxy)methyl)indoline-1-carboxylate

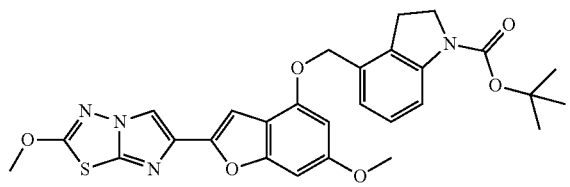 [SMILES: COc1cc(OCc2cccc3c2CCN3C(=O)OC(C)(C)C)c2cc(-c3cn4nc(OC)sc4n3)oc2c1]

Methyl indoline-4-carboxylate

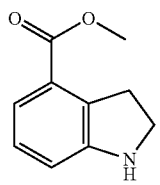

A solution of methyl 1H-indole-4-carboxylate (2.60 g, 14.84 mmol) in acetic acid (26 mL) was cooled to 15° C. and then treated with sodium cyanoborohydride (3.82 g, 0.061 mmol) added in small portions over 30 min. After 5 h at 15° C., the reaction mixture was diluted with a mixture of ice and water (200 mL) and carefully adjusted to pH 9-10 with solid potassium carbonate. The aqueous phase was extracted three times with dichloromethane and the combined organic phase was washed with brine and dried over anhydrous magnesium sulfate. The solvent was evaporated under reduced pressure and the residual oil was chromatographed on silica gel (elution dichloromethane-ethyl acetate 5-10%) to give 1.26 g (48% yield) of the title material as white solid. HPLC (Method A): 0.9 min (tailing). HRMS (ESI) calcd for $C_{10}H_{12}NO_2$ $[M+H]^+$ m/z 178.0863, found 178.0867. $^1$H NMR (CDCl$_3$, 400 MHz) δ ppm: 7.32 (br. d, J=7.9 Hz, 1H), 7.05 (br. t, J=8 Hz, 1H), 6.77 (d, J=7.8 Hz, 1H), 3.86 (s, 3H), 3.57 (t, J=8.4 Hz, 2H), 3.37 (t, J=8.4 Hz, 2H).

Indolin-4-ylmethanol

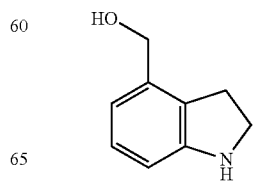

A solution of methyl indoline-4-carboxylate (1.20 g, 6.77 mmol) in dry tetrahydrofuran (20 mL) was treated at 23° C. and under nitrogen with lithium aluminum hydride (0.35 g, 6.08 mmol) added in small portions over 20 min and the resulting mixture was stirred for 3 h. The reaction mixture was carefully quenched by successive addition of ethyl acetate (1 mL), water (0.4 mL), 15% aqueous sodium hydroxide (0.4 mL) and water (1.2 mL). The solid formed was filtered and the filtrate was concentrated under reduced pressure. Chromatography of the residual oil on silica gel (elution ethyl acetate) followed by distillation under vacuum (bulb to bulb distillation, bp 105-110° C./0.1 torr, air bath temperature) gave 0.62 g (61% yield) of a white solid. HPLC (Method A): 0.13 min. HRMS (ESI) calcd for $C_9H_{12}NO$ $[M+H]^+$ m/z 150.0913, found 150.0932. $^1H$ NMR (CDCl$_3$, 400 MHz) δ ppm: 7.05 (t, J=7.6 Hz, 1H), 6.74 (d, J=7.1 Hz, 1H), 6.62 (d, J=7.7 Hz, 1H), 4.64 (s, 2H), 3.60 (t, J=8.4 Hz, 2H), 3.06 (t, J=8.4 Hz, 2H).

tert-Butyl 4-(hydroxymethyl)indoline-1-carboxylate

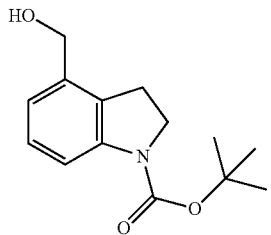 [SMILES: CC(C)(C)OC(=O)N1CCc2c(CO)cccc21]

A solution of indolin-4-ylmethanol (0.57 g, 3.82 mmol) in dry tetrahydrofuran (15 mL) was treated at 23° C. with di-tert-butyl dicarbonate (0.92 g, 4.2 mmol) and the resulting mixture was stirred for 18 hours. The reaction mixture was then concentrated under reduced pressure and the residue was purified by chromatography on silica gel (elution toluene-ethyl acetate 7:3) to give 0.95 g (100% yield) of the title material as a thick syrup which crystallized to a white solid in the fridge. HPLC (Method A): 1.901 min. $^1H$ NMR (CDCl$_3$, 400 MHz) δ ppm: 7.8 (br. s, 1H), 7.19 (t, J=7.9 Hz, 1H), 6.97 (d, J=7.4 Hz, 1H), 4.64 (d, J=5.9 Hz, 2H), 4.01 (br. t, J=8.7 Hz, 2H), 3.11 (t, J=8.7 Hz, 2H), 1.58 (s, 9H).

tert-Butyl 4-(((6-methoxy-2-(2-methoxyimidazo[2,1-b][1,3,4]thiadiazol-6-yl)benzofuran-4-yl)oxy)methyl)indoline-1-carboxylate

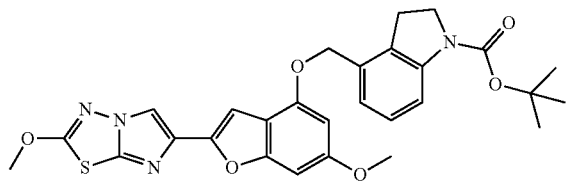 [SMILES: COc1cc(OCc2cccc3c2CCN3C(=O)OC(C)(C)C)c2cc(-c3cn4nc(OC)sc4n3)oc2c1]

A suspension of 6-methoxy-2-(2-methoxyimidazo[2,1-b][1,3,4]thiadiazol-6-yl)benzofuran-4-ol (0.529 g, 1.67 mmol), tert-butyl 6-(hydroxymethyl)indoline-1-carboxylate (0.462 g, 1.85 mmol) and triphenylphosphine (0.66 g, 2.5 mmol) in dry tetrahydrofuran (40 mL) was treated at 22° C. and under nitrogen with a solution of diisopropyl azodicarboxylate (0.41 g, 2.0 mmol) in tetrahydrofuran (10 ml) added drop-wise over 2 hours. The heterogeneous mixture was homogeneous at the end of the addition and was stirred for another 3 hours. The reaction mixture was then quenched by the addition of ethyl acetate and saturated sodium bicarbonate. The organic phase was washed with brine, dried over anhydrous magnesium sulfate and concentrated in vacuo. Chromatography of the residue on silica gel (elution dichloromethane-ethyl acetate 2-5%) followed by crystallization from ethyl acetate gave 0.621 g (68% yield) of the title material as a white solid. HPLC (Method A): 2.543 min. HRMS (ESI) calcd for $C_{28}H_{29}N_4O_6S$ $[M+H]^+$ m/z 549.1802, found 549.182. $^1H$ NMR (CDCl$_3$, 400 MHz) δ ppm: 7.7-8.0 (br. s, 1H), 7.84 (s, 1H), 7.21 (t, J=7.8 Hz, 1H), 7.07 (d, J=7.8 Hz, 1H), 7.05 (s, 1H), 6.70 (br. d, 1H), 6.39 (d, J=2.0 Hz, 1H), 5.12 (s, 2H), 4.21 (s, 3H), 4.02 (br. t, 2H), 3.85 (s, 3H), 3.16 (t, J=8.6 Hz, 2H), 1.58 (s, 9H).

Example 114

6-(4-(Indolin-4-ylmethoxy)-6-methoxybenzofuran-2-yl)-2-methoxyimidazo[2,1-b][1,3,4]thiadiazole

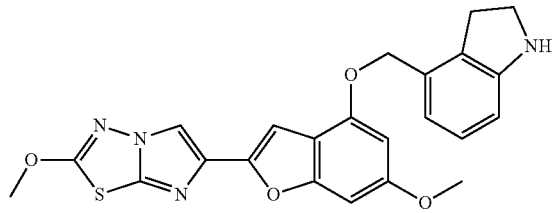 [SMILES: COc1cc(OCc2cccc3c2CCN3)c2cc(-c3cn4nc(OC)sc4n3)oc2c1]

A suspension of tert-butyl 4-(((6-methoxy-2-(2-methoxyimidazo[2,1-b][1,3,4]thiadiazol-6-yl)benzofuran-4-yl)oxy)methyl)indoline-1-carboxylate (0.600 g, 1.09 mmol) in dichloromethane (20 mL) was treated at 22° C. and under nitrogen with trifluoroacetic acid (5 mL) added drop-wise over 2 min and the resulting solution was stirred for 2 hours. The solvent and excess reagent were evaporated under reduced pressure and the residue was partitioned between dichloromethane and saturated sodium bicarbonate. The organic phase was washed with brine, dried over anhydrous magnesium sulfate and concentrated under reduced pressure to give 0.490 g (99% yield) of a white solid. HPLC (Method A): 1.981 min. HRMS (ESI) calcd for $C_{23}H_{21}N_4O_4S$ $[M+H]^+$ m/z 449.1278, found 449.1293. $^1H$ NMR (CDCl$_3$, 400 MHz) δ ppm: 7.84 (s, 1H), 7.07 (s, 1H), 7.06 (t, J=7.8 Hz, 1H), 6.84 (d, J=7.5 Hz, 1H), 6.69 (br. d, 1H), 6.65 (d, J=7.9 Hz, 1H), 6.42 (d, J=1.9 Hz, 1H), 5.12 (s, 2H), 4.21 (s, 3H), 3.85 (s, 3H), 3.50 (t, J=8.4 Hz, 2H), 3.12 (t, J=8.4 Hz, 2H).

Example 115

(4-(((6-Methoxy-2-(2-methoxyimidazo[2,1-b][1,3,4]thiadiazol-6-yl)benzofuran-4-yl)oxy)methyl)indolin-1-yl)(phenyl)methanone

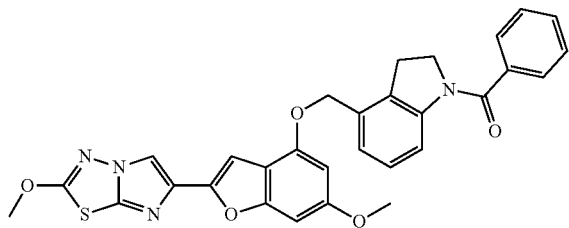 [SMILES: COc1cc(OCc2cccc3c2CCN3C(=O)c2ccccc2)c2cc(-c3cn4nc(OC)sc4n3)oc2c1]

A solution of 6-(4-(indolin-4-ylmethoxy)-6-methoxybenzofuran-2-yl)-2-methoxyimidazo[2,1-b][1,3,4]thiadiazole (0.080 g, 0.178 mmol) in dry tetrahydrofuran (5 mL) was treated at 22° C. and under nitrogen with 4-methylmorpholine (0.054 g, 0.535 mmol) followed by a solution of benzoyl chloride (0.030 g, 0.23 mmol) in dry tetrahydrofuran (1 mL) added drop-wise over 2 min. After 1 hour, the reaction mixture was diluted with dichloromethane, washed successively with cold 0.1N hydrochloric acid, saturated sodium bicarbonate and brine. After drying over anhydrous magnesium sulfate, the organic phase was concentrated under reduced pressure. Chromatography of the residue on silica gel (elution dichloromethane-ethyl acetate 5-15%) gave 0.087 g (84% yield) of the title material as a white solid. HPLC (Method A): 2.449 min. HRMS (ESI) calcd for $C_{30}H_{25}N_4O_5S$ [M+H]$^+$ m/z 553.154, found 553.155. $^1$H NMR (CDCl$_3$, 400 MHz) δ ppm: 7.84 (s, 1H), 7.54-7.6 (m, 2H), 7.4-7.5 (m, 3H), 7.1-7.3 (m, 3H), 7.04 (d, J=0.8 Hz, 1H), 6.71 (br. d, 1H), 6.40 (d, J=2.0 Hz, 1H), 5.15 (s, 2H), 4.21 (s, 3H), 4.12 (br. s, 2H), 3.85 (s, 3H), 3.20 (t, J=8.2 Hz, 2H).

The following compounds were prepared using the methodology described for preparation of Example 115

| Ex. | Structure | Formula | HPLC Retention Time (Min)/ Method | Calc. [M + H]+ m/z | LCMS [M + H]+ m/z | NMR |
|---|---|---|---|---|---|---|
| 116 | 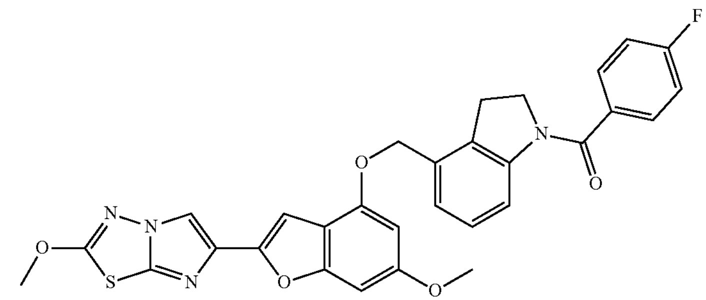 [SMILES: COc1cc(OCc2cccc3c2CCN3C(=O)c2ccc(F)cc2)c2cc(-c3cn4nc(OC)sc4n3)oc2c1] | C30H23FN4O5S | 2.394/A | 571.1446 | 571.1462 | 1H NMR (CDCl3) δ ppm: 7.85 (s, 1H), 7.55-7.65 (m, 2H), 7.11-7.21 (m, 5H), 7.04 (s, 1H), 6.70 (br. d, 1H), 6.40 (d, J = 2.0 Hz, 1H), 5.16 (s, 2H), 4.21 (s, 3H), 4.12 (br. t, 2H), 3.85 (s, 3H), 3.21 (t, J = 8.2 Hz, 2H). |
| 117 | 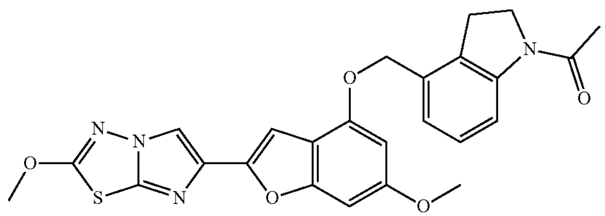 [SMILES: COc1cc(OCc2cccc3c2CCN3C(C)=O)c2cc(-c3cn4nc(OC)sc4n3)oc2c1] | C25H22N4O3S | 2.285/A | 491.1384 | 491.1401 | 1H NMR (CDCl3) δ ppm: 8.09 (d, J = 8.2 Hz, 1H), 7.75 (s, 1H), 7.12 (br. t, J = 7.8 Hz, 1H), 7.03 (d, J = 7.8 Hz, 1H), 6.91 (s, 1H), 6.58 (br. d, 1H), 6.29 (d, J = 1.6 Hz, 1H), 5.03 (s, 2H), 4.11 (s, 3H), 3.73 (s, 3H), 3.17 (t, J = 8.5 Hz, 2H), 2.13 (s, 3H). |
| 118 | 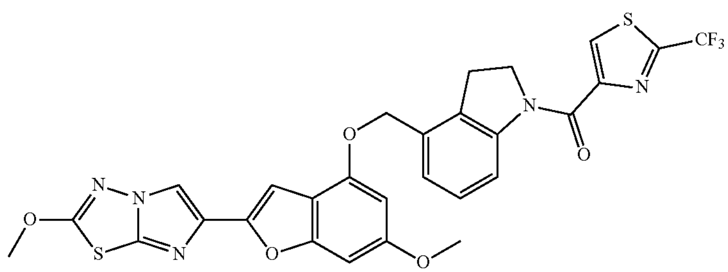 [SMILES: COc1cc(OCc2cccc3c2CCN3C(=O)c2csc(C(F)(F)F)n2)c2cc(-c3cn4nc(OC)sc4n3)oc2c1] | C28H20F3N5O5S2 | 2.185/A | 628.0931 | 628.0946 | 1H NMR (CDCl3) δ ppm: 8.35 (br. s, 1H), 8.24 (br. d, J = 9 Hz, 1H), 7.76 (s, 1H), 7.23 (br. t, J = 7.8 Hz, 1H), 7.15 (d, J = 7.7 Hz, 1H), 6.96 (s, 1H), 6.62 (br. d, 1H), 6.32 (d, J = 2.0 Hz, 1H), 5.09 (s, 2H), 4.52 (t, J = 8.2 Hz, 2H), 4.12 (s, 3H), 3.76 (s, 3H), 3.21 (t, J = 8.2 Hz, 2H). |

| Ex. | Structure | Formula | HPLC Retention Time (Min)/ Method | Calc. [M + H]+ m/z | LCMS [M + H]+ m/z | NMR |
|---|---|---|---|---|---|---|
| 119 | 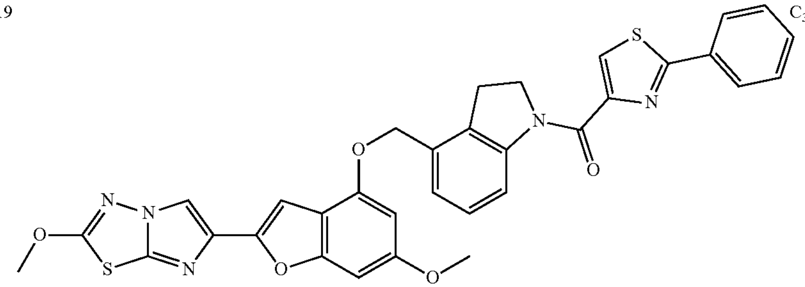 | C33H25N5O5S2 | 2.328/A | 636.137 | 636.1383 | 1H NMR (CDCl3) δ ppm: 8.27 (br. s, 1H), 8.07 (br. s, 1H), 7.85-7.95 (m, 2H), 7.76 (s, 1H), 7.35-7.45 (m, 3H), 7.15-7.25 (m, 1H), 7.13 (d, J = 7.4 Hz, 1H), 6.98 (s, 1H), 6.62 (br. d, 1H), 6.33 (d, J = 1.5 Hz, 1H), 5.1 (s, 2H), 4.64 (br. t, 2H), 4.12 (s, 3H), 3.77 (s, 3H), 3.22 (t, J = 8.2 Hz, 2H). |
| 120 | 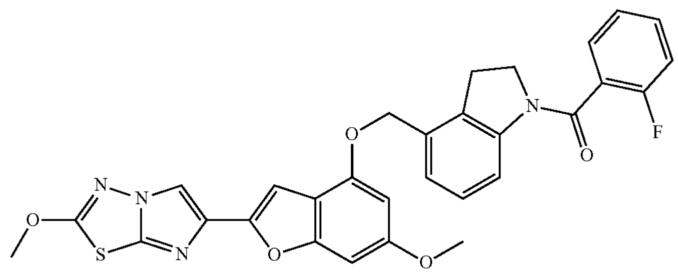 [SMILES: COc1cc(OCc2cccc3c2CCN3C(=O)c2ccccc2F)c2cc(-c3cn4nc(OC)sc4n3)oc2c1] | C30H23FN4O5S | 2.030/A | 571.1446 | 571.1465 | 1H NMR (CDCl3) δ ppm: 8.24 (br. d, J = 7.4 Hz, 1H), 7.75 (s, 1H), 7.3-7.45 (m, 2H), 7.2-7.25 (m, 1H), 7.13-7.18 (m, 2H), 7.07 (t, J = 9.0 Hz, 1H), 6.94 (s, 1H), 6.61 (br. d, 1H), 6.29 (d, J = 1.9 Hz, 1H), 5.07 (s, 2H), 4.12 (s, 3H), 3.88 (t, J = 8.2 Hz, 2H), 3.76 (s, 3H), 3.13 (t, J = 8.5 Hz, 2H). |
| 121 | 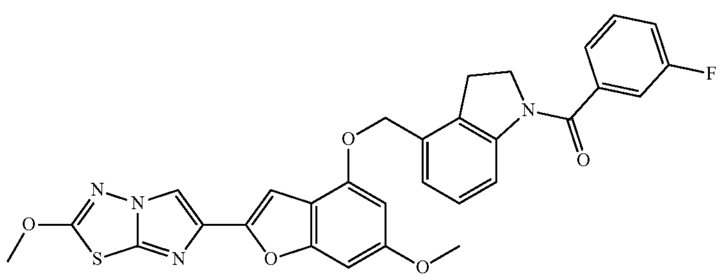 [SMILES: COc1cc(OCc2cccc3c2CCN3C(=O)c2cccc(F)c2)c2cc(-c3cn4nc(OC)sc4n3)oc2c1] | C30H23FN4O5S | 2.045/A | 571.1446 | 571.1455 | 1H NMR (CDCl3) δ ppm: 8.1 (br. s, 1H), 7.76 (s, 1H), 7.3-7.38 (m, 1H), 7.26 (br. d, J = 7.6 Hz, 1H), 7.15-7.2 (m, 2H), 7.08-7.12 (m, 2H), 6.95 (s, 1H), 6.61 (br. d, 1H), 6.31 (d, J = 2.0 Hz, 1H), 5.07 (s, 2H), 4.12 (s, 3H), 4.02 (br. t, 2H), 3.76 (s, 3H), 3.12 (t, J = 8.3 Hz, 2H). |

-continued

| Ex. | Structure | Formula | HPLC Retention Time (Min)/ Method | Calc. [M + H]+ m/z | LCMS [M + H]+ m/z | NMR |
|---|---|---|---|---|---|---|
| 122 | 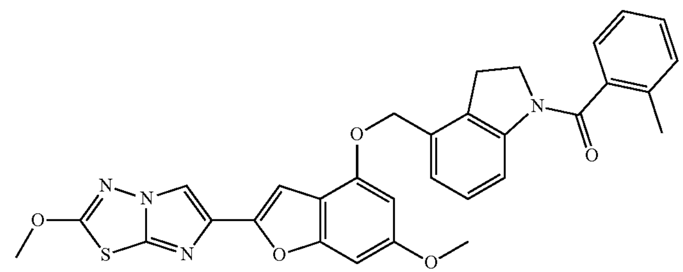 [SMILES: COc1cc(OCc2cccc3c2CCN3C(=O)c2ccccc2C)c2cc(-c3cn4nc(OC)sc4n3)oc2c1] | C₃₁H₂₆N₄O₅S | 2.136/A | 567.1697 | 567.1695 | ¹H NMR (CDCl₃) δ ppm: (mixture of rotamers) 8.31 (br. d, J = 8.2 Hz, 0.5H), 7.93 (br. dd, J = 8.3, 1.6 Hz, 0.2H), 7.05-7.4 (m, 7H), 6.95 (br. s, 1H), 6.75 (br. s, 0.3H), 6.62 (br. s, 1H), 6.31 (d, J = 2 Hz, 1H), 5.56 (br. s, 0.3 H), 5.05 (br. s, 2H), 4.27 and 3.68 (two br. t, 2H), 4.12 (s, 3H), 3.76 (s, 3H), 3.1 (br. t, 2H), 2.19 and 2.3 (two broad s, 3H). |
| 123 | 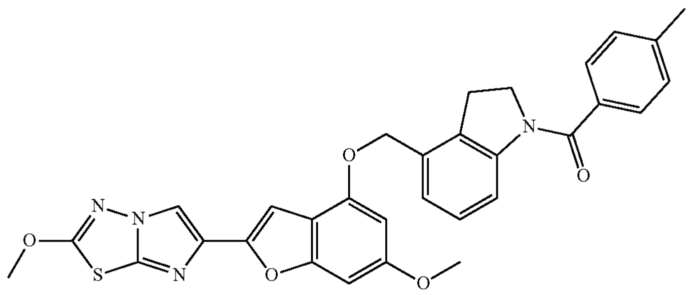 | C₃₁H₂₆N₄O₅S | 2.125/A | 567.1697 | 567.1693 | ¹H NMR (CDCl₃) δ ppm: 7.75 (s, 1H), 7.38 (d, J = 8.1 Hz, 2H), 7.1-7.2 (m, 4H), 7.06 (br. s, 1H), 6.95 (s, 1H), 6.61 (br. d, 1H), 6.31 (d, J = 1.6 Hz, 1H), 5.06 (br. s, 2H), 4.12 (s, 3H), 4.04 (br. t, J = 8 Hz, 2H), 3.76 (s, 3H), 3.1 (t, J = 8.1 Hz, 2H), 2.33 (s, 3H). |
| 124 | 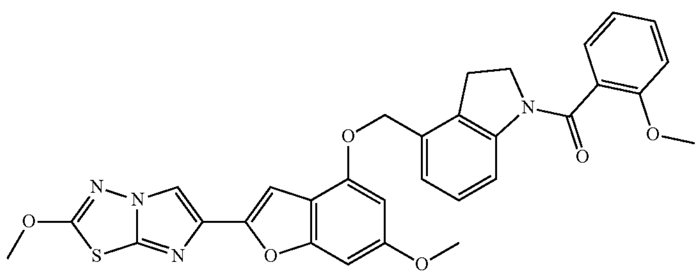 | C₃₁H₂₆N₄O₆S | 2.042/A | 583.1646 | 583.1634 | ¹H NMR (CDCl₃) δ ppm: (mixture of rotamers) 8.29 (br. d, J = 7.9 Hz, 0.7H), 7.75 (s, 1H), 7.2-7.4 (m, 3 H), 7.10 (d, J = 7.8 Hz, 0.7H), 6.9-7.0 (m, 2.3H), 6.87 (d, J = 8.3 Hz, 1H), 6.75 (br. s, 0.3H), 6.61 (br. s, 1H), 6.31 (br.s, 1H), 5.05 (s, 2H), 4.2 and 3.8 (two br. s, 2H), 4.12 (s, 3H), 3.78 (s, 3H), 3.76 (s, 3H), 3.08 (br. t, J = 8.3 Hz, 2H). |

-continued

| Ex. | Structure | Formula | HPLC Retention Time (Min)/ Method | Calc. [M + H]+ m/z | LCMS [M + H]+ m/z | NMR |
|---|---|---|---|---|---|---|
| 125 | 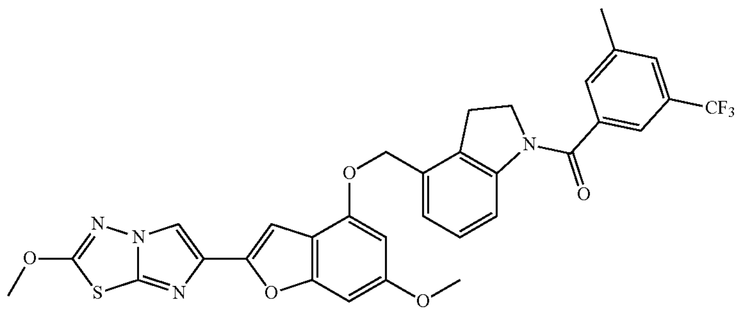 [SMILES: COc1cc(OCc2cccc3c2CCN3C(=O)c2cc(C)cc(C(F)(F)F)c2)c2cc(-c3cn4nc(OC)sc4n3)oc2c1] | C₃₂H₂₅F₃N₄O₅S | 2.163/A | 635.1571 | 635.157 | ¹H NMR (CDCl₃) δ ppm: 8.2 (br. s, 1H), 7.76 (s, 1H), 7.54 (s, 1H), 7.47 (br. s, 2H), 7.1-7.2 (m, 2H), 6.95 (s, 1H), 6.61 (br. d, 1H), 6.31 (d, J = 1.6 Hz, 1H), 5.07 (s, 2H), 4.12 (s, 3H), 3.98 (br. s, 2H), 3.76 (s, 3H), 3.13 (t, J = 8.2 Hz, 2H), 2.39 (s, 3H). |
| 126 | 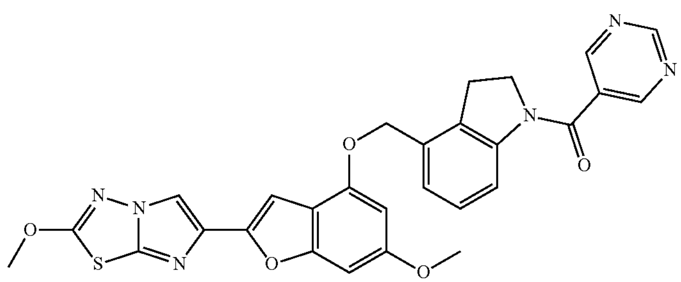 [SMILES: COc1cc(OCc2cccc3c2CCN3C(=O)c2cncnc2)c2cc(-c3cn4nc(OC)sc4n3)oc2c1] | C₂₈H₂₂N₆O₃S | 1.926/A | 555.1445 | 555.1431 | ¹H NMR (CDCl₃) δ ppm: 9.25 (s, 1H), 8.89 (s, 2H), 8.15 (br. s, 1H), 7.75 (s, 1H), 7.0-7.25 (m, 2H), 6.94 (s, 1H), 6.62 (br. d, 1H), 6.30 (d, J = 2.0 Hz, 1H), 5.09 (s, 2H), 4.12 (s, 3H), 4.06 (br. s, 2H), 3.76 (s, 3H), 3.19 (t, J = 8.2 Hz, 2H). |
| 127 | 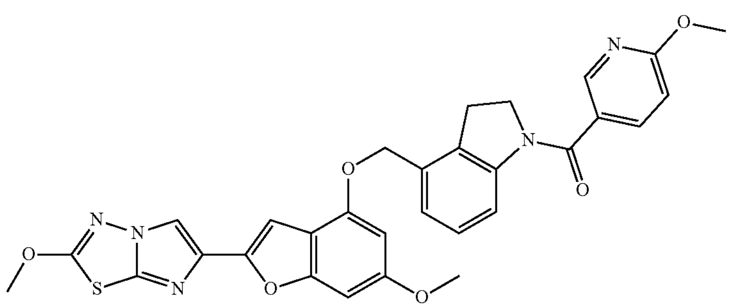 | C₃₀H₂₅N₅O₆S | 2.005/A | 584.1598 | 584.1595 | ¹H NMR (CDCl₃) δ ppm: 8.36 (d, J = 2.3 Hz, 2H), 7.76 (s, 1H), 7.73 (dd, J = 8.6, 2.3 Hz, 1H), 7.07-7.18 (m, 2H), 6.95 (s, 1H), 6.72 (d, J = 8.6 Hz, 1H), 6.61 (br. d, 1H), 6.31 (d, J = 1.8 Hz, 1H), 5.07 (s, 2H), 4.12 (s, 3H), 4.08 (t, J = 8.2 Hz, 2H), 3.92 (s, 3H), 3.76 (s, 3H), 3.13 (t, J = 8.2 Hz, 2H). |

| Ex. | Structure | Formula | HPLC Retention Time (Min)/ Method | Calc. [M + H]+ m/z | LCMS [M + H]+ m/z | NMR |
|---|---|---|---|---|---|---|
| 128 | 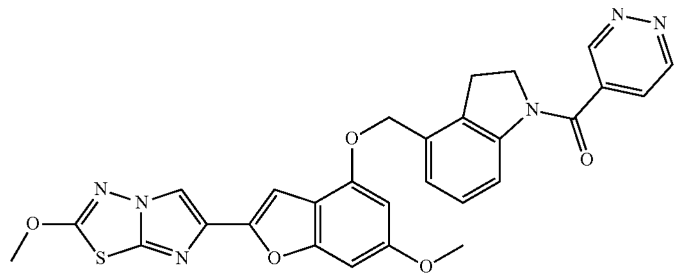 [SMILES: COc1cc(OCc2cccc3c2CCN3C(=O)c2ccnnc2)c2cc(-c3cn4nc(OC)sc4n3)oc2c1] | C28H22N6O5S | 1.880/A | 555.1445 | 555.1435 | 1H NMR (CDCl3) δ ppm: 9.30 (d, J = 5 Hz, 1H), 9.29 (s, 1H), 8.15 (br. s, 1H), 7.76 (s, 1H), 7.54 (dd, J = 5, 2.4 Hz, 1H), 7.25 (br. s, 1H), 7.1-7.2 (m, 1H), 6.92 (s, 1H), 6.62 (br. d, 1H), 6.30 (d, J = 1.5 Hz, 1H), 5.08 (s, 2H), 4.13 (s, 3H), 3.95 (br. s, 2H), 3.76 (s, 3H), 3.19 (t, J = 8.4 Hz, 2H). |
| 129 | 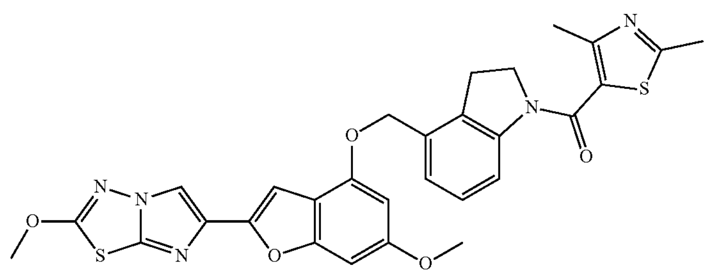 | C29H25N5O5S2 | 2.043/A | 588.137 | 588.1355 | 1H NMR (CDCl3) δ ppm: 7.76 (s, 1H), 7.7 (br. s, 1H), 7.1-7.2 (m, 2H), 6.92 (s, 1H), 6.62 (br. d, 1H), 6.31 (d, J = 2.0 Hz, 1H), 5.06 (s, 2H), 4.13 (s, 3H), 4.05 (t, J = 8.3 Hz, 2H), 3.77 (s, 3H), 3.15 (t, J = 8.3 Hz, 2H), 2.64 (s, 3H), 2.39 (s, 3H). |
| 130 | 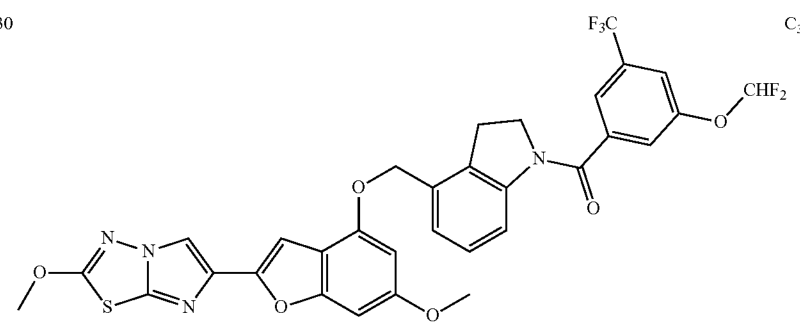 | C32H23F5N4O6S | 2.074/A | 687.1331 | 687.1334 | 1H NMR (CDCl3) δ ppm: 8.1 (br. s, 1H), 7.76 (s, 1H), 7.61 (s, 1H), 7.44 (s, 1H), 7.42 (s, 1H), 7.1-7.2 (m, 2H), 6.95 (s, 1H), 6.62 (br. d, 1H), 6.52 (t, J = 72 Hz, 1H), 6.31 (d, J = 2.0 Hz, 1H), 5.07 (s, 2H), 4.12 (s, 3H), 3.98 (br. s, 2H), 3.76 (s, 3H), 3.1 (t, J = 8.2 Hz, 2H). |

| Ex. | Structure | Formula | HPLC Retention Time (Min)/ Method | Calc. [M + H]+ m/z | LCMS [M + H]+ m/z | NMR |
|---|---|---|---|---|---|---|
| 131 | 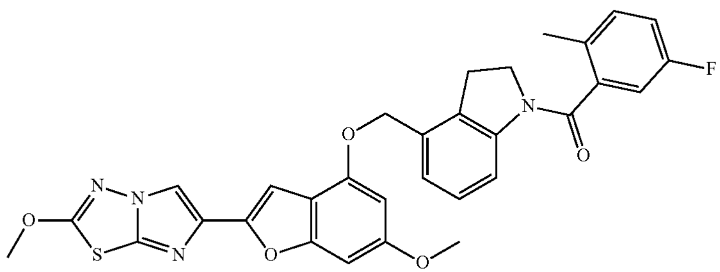 [SMILES: COc1cc(OCc2cccc3c2CCN3C(=O)c2cc(F)ccc2C)c2cc(-c3cn4nc(OC)sc4n3)oc2c1] | C31H25FN4O5S | 2.109/A | 585.1602 | 585.1605 | 1H NMR (CDCl3) δ ppm: (mixture of rotamers) 8.33 (br. d, J = 7.1 Hz, 0.5H), 7.82 (s, 1H), 7.2-7.4 (m, 2.5H), 7.0-7.15 (m, 3.5H), 6.85 (br. s, 0.5H), 6.68 (br. s, 1H), 6.37 (d, J = 1.5 Hz, 1H), 5.28 (br. s, 2H), 4.32 and 3.76 (two br. t, 2H), 4.19 (s, 3H), 3.83 (s, 3H), 3.15-3.23 (m, 2H), 2.2 and 2.32 (two broad s, 3H). |

General Synthetic Procedure for Examples 132-166

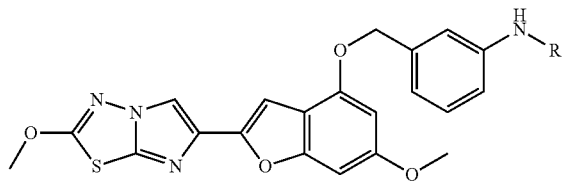

Procedure:

Into a reaction vessel containing acylating reagent (0.091 mmol) was added 3-((((6-Methoxy-2-(2-methoxyimidazo[2,1-b][1,3,4]thiadiazol-6-yl)benzofuran-4-yl)oxy)methyl)aniline (Example 4, 18 mg, 0.043 mmol) dissolved in THF (0.076 M) and N-methylmorpholine (20 µl, 0.182 mmol). The reaction mixture was stirred at rt for 3 h. Upon complete conversion as monitored by LC-MS, to the reaction mixture was added water (0.1 mL), acetic acid (5 µl) and DMF (0.5 mL). The reaction mixture was subjected to reverse-phase HPLC purification to afford the desired product.

Purification:

The crude material was purified via preparative LC/MS with the following conditions: Column: XBridge C18, 19×100 mm, 5-µm particles;

Mobile Phase A: 5:95 acetonitrile: water with 0.05% TFA;

Mobile Phase B: 95:5 acetonitrile: water with 0.05% TFA. Gradient: 0-100% B over 15 minutes; Flow: 20 mL/min. Fractions containing the desired product were combined and dried via centrifugal evaporation.

QC Analysis:

Analytical Method G: Column: Supelco Ascentris Express 4.6×50 mm, 2.7 µm particles; Mobile Phase A: 5:95 acetonitrile:water with 10 mM NH4OAc; Mobile Phase B: 95:5 acetonitrile:water with 10 mM NH4OAc; Gradient: 0-100% B over 4 minutes, 4.0 mL/min; Detection: UV at 220 nm.

| Example # | Structure | FW | % Purity | HPLC RT | Observed MS Ion | Analytical Method |
|---|---|---|---|---|---|---|
| 132 | 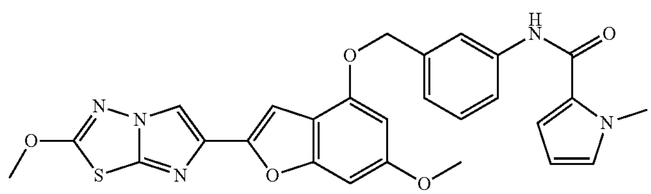 | 529.57 | 98.95 | 2.93 | 530.04 | G |
| 133 | 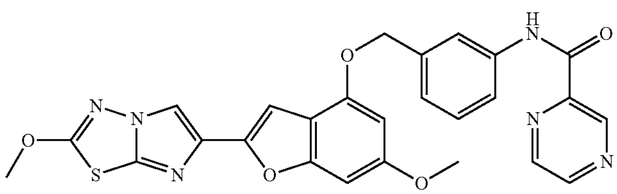 [SMILES: COc1cc(OCc2cccc(NC(=O)c3cnccn3)c2)c2cc(-c3cn4nc(OC)sc4n3)oc2c1] | 528.54 | 100.00 | 2.70 | 529.00 | G |
| 134 | 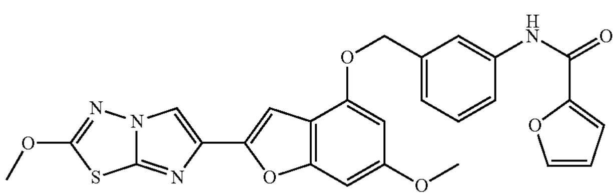 [SMILES: COc1cc(OCc2cccc(NC(=O)c3ccco3)c2)c2cc(-c3cn4nc(OC)sc4n3)oc2c1] | 516.53 | 95.10 | 2.74 | 517.01 | G |
| 135 | 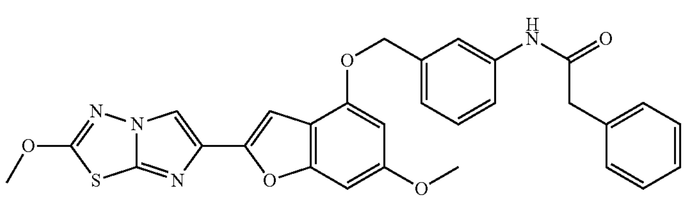 [SMILES: COc1cc(OCc2cccc(NC(=O)Cc3ccccc3)c2)c2cc(-c3cn4nc(OC)sc4n3)oc2c1] | 540.59 | 98.33 | 2.92 | 541.07 | G |
| 136 | 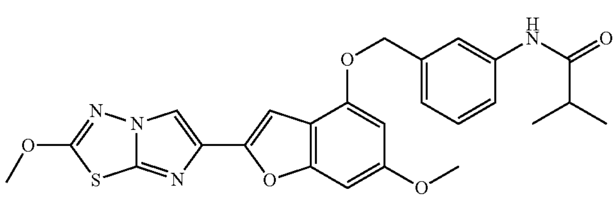 [SMILES: COc1cc(OCc2cccc(NC(=O)C(C)C)c2)c2cc(-c3cn4nc(OC)sc4n3)oc2c1] | 492.55 | 97.72 | 2.76 | 493.06 | G |

| Example # | Structure | FW | % Purity | HPLC RT | Observed MS Ion | Analytical Method |
|---|---|---|---|---|---|---|
| 137 | 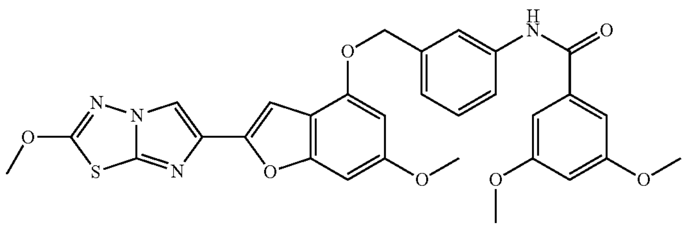 | 586.62 | 96.69 | 3.02 | 587.08 | G |
| 138 | 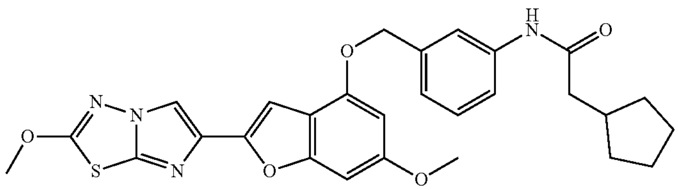 [SMILES: COc1cc(OCc2cccc(NC(=O)CC3CCCC3)c2)c2cc(-c3cn4nc(OC)sc4n3)oc2c1] | 532.61 | 98.41 | 3.11 | 533.10 | G |
| 139 | 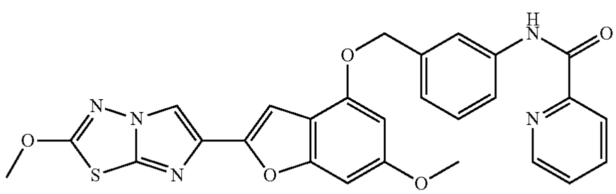 [SMILES: COc1cc(OCc2cccc(NC(=O)c3ccccn3)c2)c2cc(-c3cn4nc(OC)sc4n3)oc2c1] | 527.55 | 98.38 | 3.00 | 528.03 | G |
| 140 | 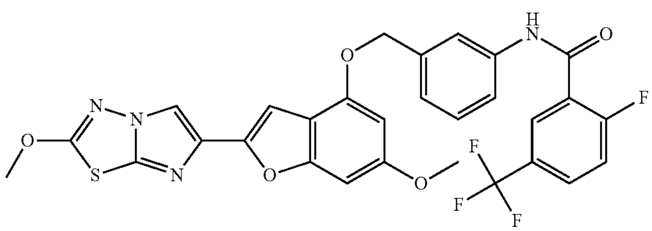 [SMILES: COc1cc(OCc2cccc(NC(=O)c3cc(C(F)(F)F)ccc3F)c2)c2cc(-c3cn4nc(OC)sc4n3)oc2c1] | 612.55 | 90.68 | 3.25 | 613.05 | G |
| 141 | 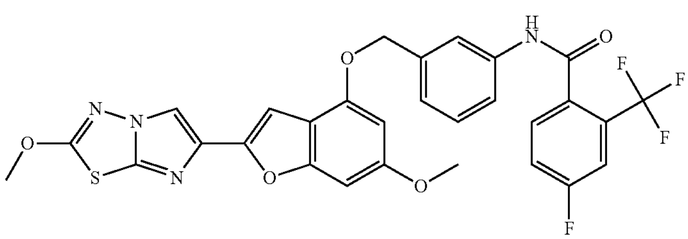 [SMILES: COc1cc(OCc2cccc(NC(=O)c3ccc(F)cc3C(F)(F)F)c2)c2cc(-c3cn4nc(OC)sc4n3)oc2c1] | 612.55 | 100.00 | 3.07 | 613.05 | G |
| 142 | 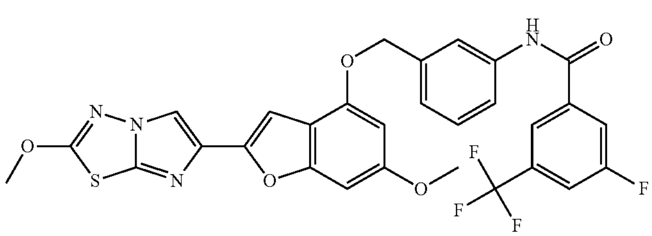 [SMILES: COc1cc(OCc2cccc(NC(=O)c3cc(F)cc(C(F)(F)F)c3)c2)c2cc(-c3cn4nc(OC)sc4n3)oc2c1] | 612.55 | 98.30 | 3.36 | 613.05 | G |

| Example # | Structure | FW | % Purity | HPLC RT | Observed MS Ion | Analytical Method |
|---|---|---|---|---|---|---|
| 143 | 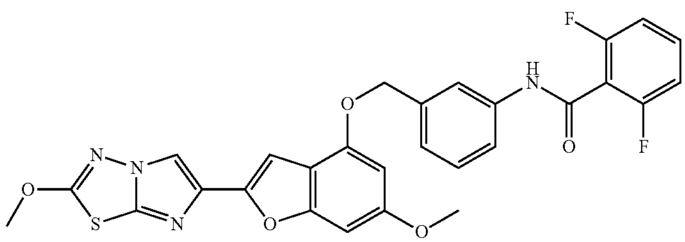 [SMILES: COc1cc(OCc2cccc(NC(=O)c3c(F)cccc3F)c2)c2cc(-c3cn4nc(OC)sc4n3)oc2c1] | 562.54 | 95.62 | 2.91 | 563.04 | G |
| 144 | 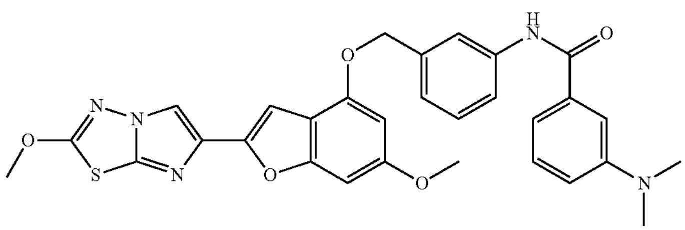 | 569.63 | 92.71 | 3.08 | 570.10 | G |
| 145 | 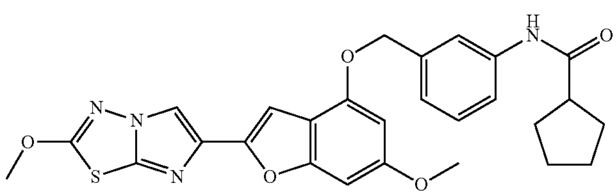 [SMILES: COc1cc(OCc2cccc(NC(=O)C3CCCC3)c2)c2cc(-c3cn4nc(OC)sc4n3)oc2c1] | 518.58 | 96.32 | 2.99 | 519.09 | G |
| 146 | 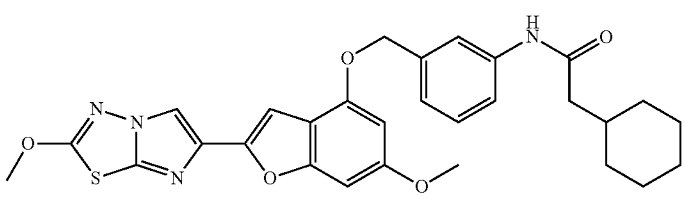 [SMILES: COc1cc(OCc2cccc(NC(=O)CC3CCCCC3)c2)c2cc(-c3cn4nc(OC)sc4n3)oc2c1] | 546.64 | 98.10 | 3.23 | 547.12 | G |
| 147 | 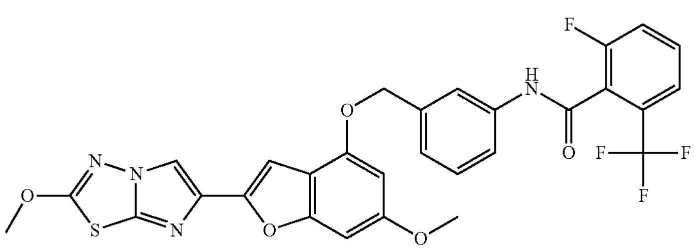 [SMILES: COc1cc(OCc2cccc(NC(=O)c3c(F)cccc3C(F)(F)F)c2)c2cc(-c3cn4nc(OC)sc4n3)oc2c1] | 612.55 | 97.37 | 3.02 | 613.06 | G |
| 148 | 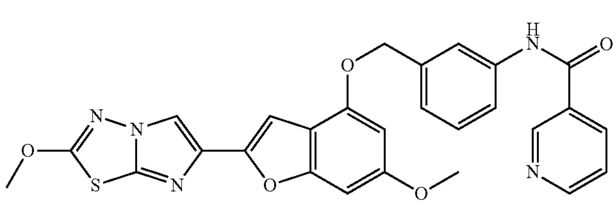 [SMILES: COc1cc(OCc2cccc(NC(=O)c3cccnc3)c2)c2cc(-c3cn4nc(OC)sc4n3)oc2c1] | 527.55 | 100.00 | 2.55 | 528.02 | G |

-continued
| Example # | Structure | FW | % Purity | HPLC RT | Observed MS Ion | Analytical Method |
|---|---|---|---|---|---|---|
| 149 | 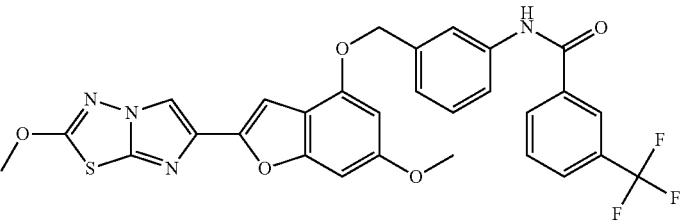 [SMILES: COc1cc(OCc2cccc(NC(=O)c3cccc(C(F)(F)F)c3)c2)c2cc(-c3cn4nc(OC)sc4n3)oc2c1] | 594.56 | 97.37 | 3.25 | 595.03 | G |
| 150 | 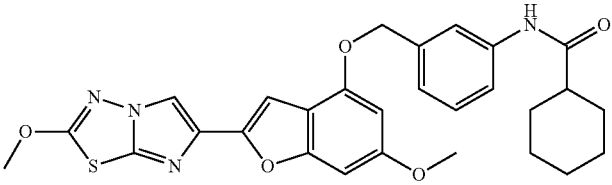 [SMILES: COc1cc(OCc2cccc(NC(=O)C3CCCCC3)c2)c2cc(-c3cn4nc(OC)sc4n3)oc2c1] | 532.61 | 98.88 | 3.12 | 533.10 | G |
| 151 | 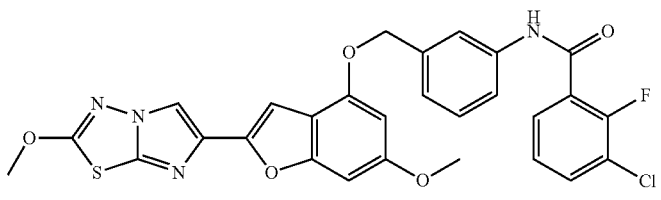 | 579.00 | 100.00 | 3.16 | 579.01 | G |
| 152 | 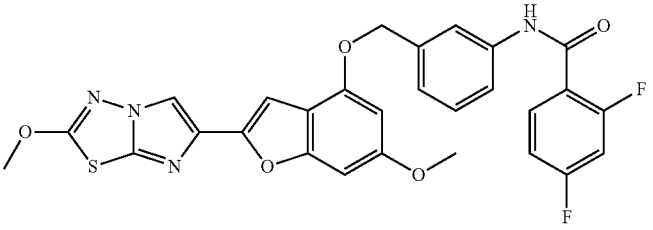 [SMILES: COc1cc(OCc2cccc(NC(=O)c3ccc(F)cc3F)c2)c2cc(-c3cn4nc(OC)sc4n3)oc2c1] | 562.54 | 94.40 | 3.05 | 563.04 | G |
| 153 | 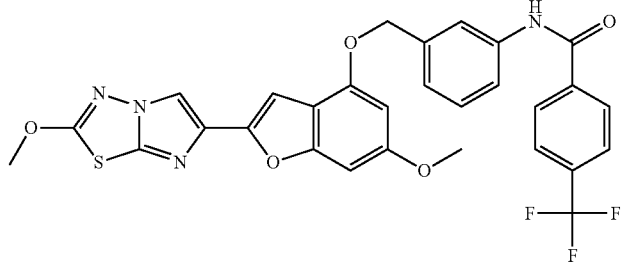 [SMILES: COc1cc(OCc2cccc(NC(=O)c3ccc(C(F)(F)F)cc3)c2)c2cc(-c3cn4nc(OC)sc4n3)oc2c1] | 594.56 | 98.93 | 3.24 | 595.05 | G |
| 154 | 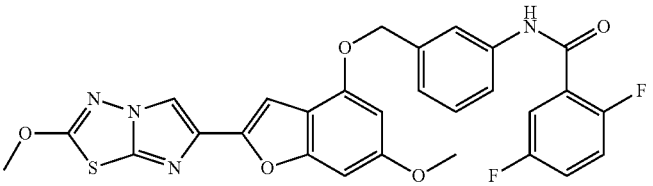 [SMILES: COc1cc(OCc2cccc(NC(=O)c3cc(F)ccc3F)c2)c2cc(-c3cn4nc(OC)sc4n3)oc2c1] | 562.54 | 93.83 | 3.05 | 563.04 | G |

| Example # | Structure | FW | % Purity | HPLC RT | Observed MS Ion | Analytical Method |
|---|---|---|---|---|---|---|
| 155 | 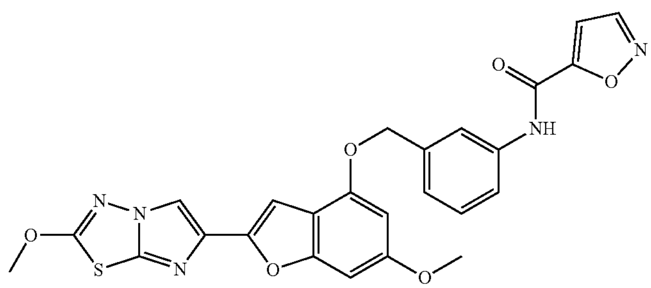 [SMILES: COc1cc(OCc2cccc(NC(=O)c3ccno3)c2)c2cc(-c3cn4nc(OC)sc4n3)oc2c1] | 517.51 | 96.05 | 2.68 | 518.00 | G |
| 156 | 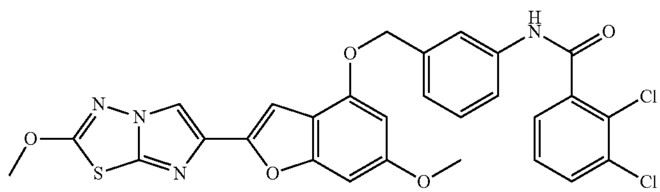 [SMILES: COc1cc(OCc2cccc(NC(=O)c3cccc(Cl)c3Cl)c2)c2cc(-c3cn4nc(OC)sc4n3)oc2c1] | 595.45 | 97.45 | 3.13 | 594.98 | G |
| 157 | 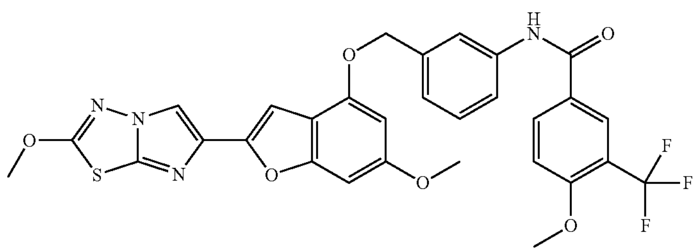 [SMILES: COc1cc(OCc2cccc(NC(=O)c3ccc(OC)c(C(F)(F)F)c3)c2)c2cc(-c3cn4nc(OC)sc4n3)oc2c1] | 624.59 | 98.83 | 3.21 | 625.10 | G |
| 158 | 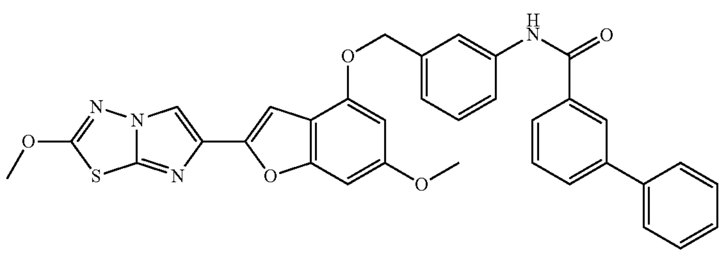 [SMILES: COc1cc(OCc2cccc(NC(=O)c3cccc(-c4ccccc4)c3)c2)c2cc(-c3cn4nc(OC)sc4n3)oc2c1] | 602.66 | 97.95 | 3.40 | 603.10 | G |
| 159 | 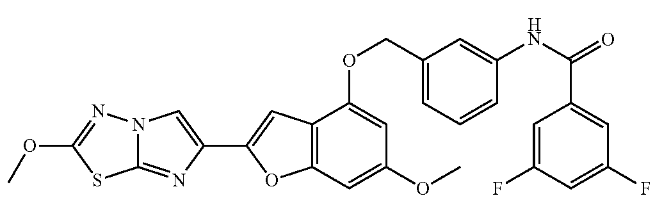 [SMILES: COc1cc(OCc2cccc(NC(=O)c3cc(F)cc(F)c3)c2)c2cc(-c3cn4nc(OC)sc4n3)oc2c1] | 562.54 | 97.47 | 3.13 | 563.03 | G |
| 160 | 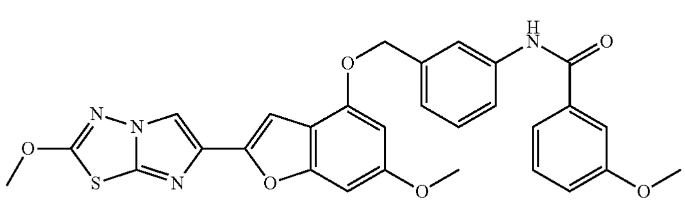 | 556.59 | 95.06 | 2.98 | 557.03 | G |

US 10,214,544 B2

219                                                      220

-continued

| Example # | Structure | FW | % Purity | HPLC RT | Observed MS Ion | Analytical Method |
|---|---|---|---|---|---|---|
| 161 | 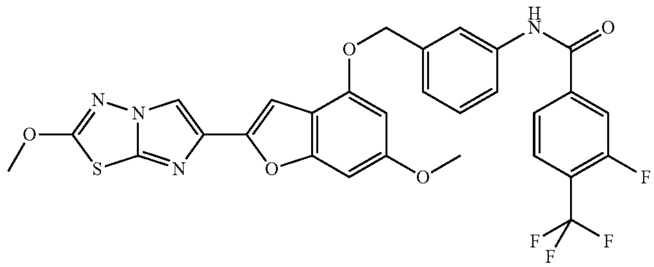 [SMILES: COc1cc(OCc2cccc(NC(=O)c3ccc(C(F)(F)F)c(F)c3)c2)c2cc(-c3cn4nc(OC)sc4n3)oc2c1] | 612.55 | 98.67 | 3.32 | 613.03 | G |
| 162 | 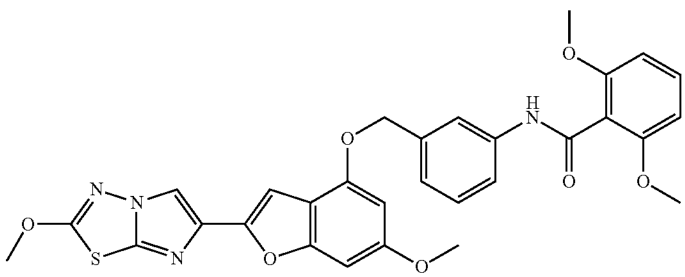 | 586.62 | 97.75 | 2.78 | 587.08 | G |
| 163 | 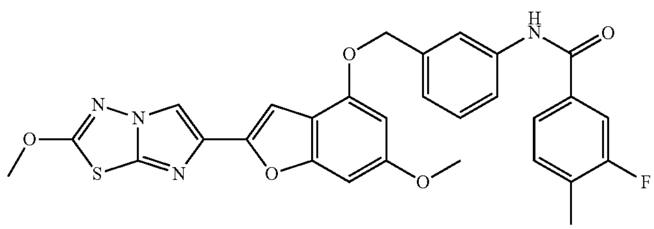 [SMILES: COc1cc(OCc2cccc(NC(=O)c3ccc(C)c(F)c3)c2)c2cc(-c3cn4nc(OC)sc4n3)oc2c1] | 558.58 | 100.00 | 3.16 | 559.06 | G |
| 164 | 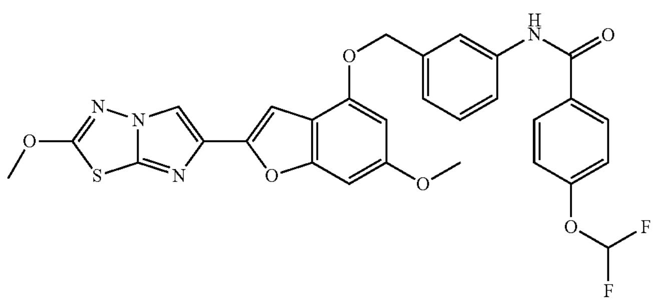 [SMILES: COc1cc(OCc2cccc(NC(=O)c3ccc(OC(F)F)cc3)c2)c2cc(-c3cn4nc(OC)sc4n3)oc2c1] | 592.57 | 96.58 | 3.05 | 593.05 | G |
| 165 | 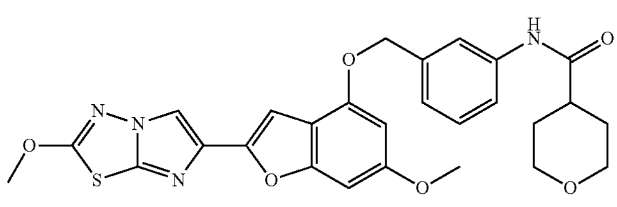 [SMILES: COc1cc(OCc2cccc(NC(=O)C3CCOCC3)c2)c2cc(-c3cn4nc(OC)sc4n3)oc2c1] | 534.58 | 97.36 | 2.53 | 535.06 | G |
| 166 | 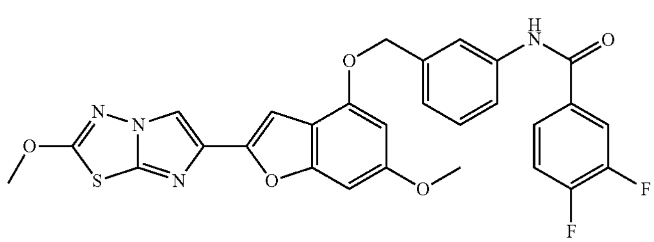 [SMILES: COc1cc(OCc2cccc(NC(=O)c3ccc(F)c(F)c3)c2)c2cc(-c3cn4nc(OC)sc4n3)oc2c1] | 562.54 | 100.00 | 3.10 | 563.04 | G |

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, or Formula IA, or Formula IB, or Formula IC, or Formula ID, or Formula IE, or Formula IF, or Formula IG, or Formula IH, or Formula IJ, or Formula IN, or Formula IO, or Formula IP, or Formula IQ, or Formula IR, or a compound selected from one of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-NH$_2$. H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example B. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Example C is an alpha-thrombin-induced platelet aggregation assay. Alpha-thrombin activates both PAR1 and PAR4.

Example D is a tissue factor-induced platelet aggregation assay. The conditions in this assay mimic the physiological events during thrombus formation. In this assay, platelet aggregation in human PRP was initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example F describes an in vivo model of arterial thrombosis in cynolmolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

Assays

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-NH$_2$ were synthesized. H-Ala-Phe(4-F)-Pro-Gly-Trp-Leu-Val-Lys-Asn-Gly-NH$_2$ showed improved PAR4 agonist activity over AYPGKF in the FLIPR assay (EC$_{50}$ value of 8 µM for H-Ala-Phe(4-F)-Pro-Gly-Trp-Leu-Val-Lys-Asn-Gly-NH$_2$ and 60 µM for AYPGKF) and in washed platelet aggregation assay (EC$_{50}$ value of 0.9 µM for H-Ala-Phe(4-F)-Pro-Gly-Trp-Leu-Val-Lys-Asn-Gly-NH$_2$ and 12 µM for AYPGKF).

2) PAR4 Expressing Cells

HEK293 cells stably expressing PAR4 were generated by a standard method of transfection of human PAR4 (F2R23) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader; Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, N.J.), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~2.5×10$^8$/ml in Tyrode's Buffer (137 mM NaCl, 2 mM KCl, 1.0 mM MgCl$_2$, 1 mM CaCl$_2$, 5 mM glucose, 20 mM HEPES pH 7.4).

Example A

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-NH$_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, N.Y.) containing 10% heat-inactivated FBS, 1% Penicillin-Streptomycin, 10 µg/mL blasticidin, and 100 µg/mL Zeocin at 37° C. with 5% CO$_2$. Cells were plated overnight prior to the experiment in a black 384-well Purecoat Amine clear bottom plate (Becton Dickinson Biosciences, San Jose, Calif.) at 10,000 cells/well in 30 µL growth medium and incubated in a humidified chamber at 37° C. with 5% CO$_2$ overnight. Prior to compound addition, the cell medium was replaced with 40 L of 1× calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C. and a further 30 minute incubation and equilibration period at room temperature, 20 µL test compound (diluted in 1× HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 µL of agonist peptide for antagonist activity measurement. The PAR4 agonist peptide (H-Ala-Phe(4-F)-Pro-Gly-Trp-Leu-Val-Lys-Asn-Gly-NH$_2$) and the PAR1 agonist peptide (SFFLRR) were routinely tested to ensure a proper response at the EC$_{50}$ value in the assay (~5 µM for PAR4 agonist peptide and ~2 µM for PAR1 agonist peptide). Compound potency was derived from 11-point concentration-response curves.

Example B

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 µL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 µL of gamma-thrombin (Haematologic Technologies, Inc. Essex Junction, Vt.) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100−100*[ODcompound−ODminimum]/[ODmaximum−ODminimum]). The $IC_{50}$ value of the test compound was calculated by fitting the % IPA values to the one-site concentration response equation: Y=A+(B−A)/{1+(C/X)^D] }, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example C

Alpha-thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, Vt.) to 300 µl of washed platelets at stirring speed of 1000 rpm. Platelet aggregation is monitored using an Optical Aggregometer (Chrono-Log, Havertown, Pa.) and the area under the curve (AUC) at 6 min was measured. $IC_{50}$ values are calculated using vehicle control as 0% inhibition.

Example D

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of $CaCl_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example E

The following Table sets out results obtained employing various compounds of the invention tested in the FLIPR assay. As indicated above, the FLIPR assay, an in vitro assay, measures the PAR4 antagonist activity of compounds tested as described in Example A.

TABLE 2

| Example | PAR4 FLIPR assay ($EC_{50}$, nM) |
|---|---|
| 1 | 1.1 |
| 2 | 1.0 |
| 3 | 2.6 |
| 4 | 17 |
| 5 | 1.3 |
| 6 | 1.4 |
| 7 | 10 |
| 8 | 1.6 |
| 9 | 2.0 |
| 10 | 1.9 |
| 11 | 1.7 |
| 12 | 1.5 |
| 13 | 1.9 |
| 14 | 1.4 |
| 15 | 1.7 |
| 16 | 1.4 |
| 17 | 0.55 |
| 18 | 0.91 |
| 19 | 3.3 |
| 20 | 1.4 |
| 21 | 1.5 |
| 22 | 1.1 |
| 23 | 1.8 |
| 24 | 1.4 |
| 25 | 1.7 |
| 26 | 0.75 |
| 27 | 0.87 |
| 28 | 2.0 |
| 29 | 1.1 |
| 30 | 1.8 |
| 31 | 1.3 |
| 32 | 1.6 |
| 33 | 1.8 |
| 34 | 1.2 |
| 35 | 1.0 |
| 36 | 2.5 |
| 37 | 2.5 |
| 38 | 4.8 |
| 39 | 2.4 |
| 40 | 1.4 |
| 41 | 1.4 |
| 42 | 2.3 |
| 43 | 1.6 |
| 44 | 2.3 |
| 45 | 2.8 |
| 46 | 1.1 |
| 47 | 6.9 |
| 48 | 2.7 |
| 49 | 0.85 |
| 50 | 7.4 |
| 51 | 2.3 |
| 52 | 0.41 |
| 53 | 3.5 |
| 54 | NT |
| 55 | 1.1 |
| 56 | 5.5 |
| 57 | 1.8 |
| 58 | 0.74 |
| 59 | 3.5 |
| 60 | 2.9 |
| 61 | 1.5 |
| 62 | 57 |
| 63 | 1.4 |
| 64 | 1.4 |
| 65 | 1.1 |
| 66 | 5.7 |
| 67 | 680 |
| 68 | 8.9 |
| 69 | 12 |
| 70 | 1.0 |
| 71 | 1.9 |
| 72 | 2.2 |
| 73 | 3.6 |
| 74 | 0.95 |
| 75 | 1.7 |
| 76 | 2.5 |
| 77 | 120 |

TABLE 2-continued

| Example | PAR4 FLIPR assay (EC$_{50}$, nM) |
|---|---|
| 78 | 2.3 |
| 79 | NT |
| 80 | 94 |
| 81 | 4.8 |
| 82 | 5.2 |
| 83 | 4.1 |
| 84 | 2.5 |
| 85 | 6.1 |
| 86 | 1.8 |
| 87 | 5.7 |
| 88 | 3.3 |
| 89 | 3.5 |
| 90 | 1.1 |
| 91 | 2.0 |
| 92 | 3.5 |
| 93 | 4.8 |
| 94 | 3.8 |
| 95 | NT |
| 96 | NT |
| 97 | 2.5 |
| 98 | NT |
| 99 | NT |
| 100 | NT |
| 101 | 3.1 |
| 102 | 4.1 |
| 103 | 4.5 |
| 104 | 2.2 |
| 105 | 3.4 |
| 106 | 1.5 |
| 107 | 26 |
| 108 | NT |
| 109 | NT |
| 110 | 0.52 |
| 111 | 6.0 |
| 112 | 0.55 |
| 113 | NT |
| 114 | 37 |
| 115 | 96 |
| 116 | 140 |
| 117 | >3300 |
| 118 | 16 |
| 119 | 1700 |
| 120 | 4.2 |
| 121 | 140 |
| 122 | 5.0 |
| 123 | 5.0 |
| 124 | 190 |
| 125 | 3.9 |
| 126 | 260 |
| 127 | 2.9 |
| 128 | >3300 |
| 129 | 4.2 |
| 130 | 5.2 |
| 131 | NT |
| 132 | 3.8 |
| 133 | 2.7 |
| 134 | 5.0 |
| 135 | 5.0 |
| 136 | 3.9 |
| 137 | 3.4 |
| 138 | 2.5 |
| 139 | 2.7 |
| 140 | 1.5 |
| 141 | 1.9 |
| 142 | 1.3 |
| 143 | 5.9 |
| 144 | 3.8 |
| 145 | 6.8 |
| 146 | 7.5 |
| 147 | 1.6 |
| 148 | 6.8 |
| 149 | 2.0 |
| 150 | 2.3 |
| 151 | 3.4 |
| 152 | 1.3 |
| 153 | 0.99 |
| 154 | 2.2 |
| 155 | 2.3 |
| 156 | 1.7 |
| 157 | 2.8 |
| 158 | 12 |
| 159 | 1.6 |
| 160 | 36 |
| 161 | 1.5 |
| 162 | 11 |
| 163 | 2.1 |
| 164 | 2.0 |
| 165 | 4.6 |
| 166 | 2.3 |

Data in Table 2 are reported with two significant figures. NT indicates the compound was not tested in the FLIPR assay.

EXAMPLE F

Cynomolgus Monkey Electrolytic Injury-Induced Carotid Artery Thrombosis Model Healthy cynomolgus monkeys can be used in the study. These monkeys are retired from other pharmacokinetic and pharmacodynamic studies and had at least a 4-week washout period.

On the day of the study, compounds or vehicles are administered orally at 1 to 2 hours before the experiment. Monkeys are then sedated by intramuscular administration of 0.2 mg/kg atropine, 5 mg/kg TELAZOL® (tiletamine/zolazepam) and 0.1 mg/kg hydromorphone to facilitate placement of an endotracheal tube. An intravenous catheter is placed in the left cephalic vein for fluid administration to prevent dehydration. Animals are then administered with an inhalant anesthetic, isoflurane (1-5% to effect) and oxygen, ventilated, and placed on a thermostatically controlled heating pad to maintain the body temperature at 37° C. General anesthesia is maintained at a surgical plane using inhaled isoflurane and oxygen. The left brachial artery is cannulated to record blood pressure and heart rate. Blood pressure and heart rate are monitored to maintain normal vital signs.

The carotid arterial thrombosis model in monkeys is based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", *J. Pharmacol. Exp. Ther.*, 295:212-218 (2002).) Thrombosis is induced by electrical stimulation of the carotid artery for 5 min at 10 mA using an external stainless-steel bipolar electrode. Carotid blood flow is measured with an appropriately sized TRANSONIC® flow probe and a TRANSONIC® perivascular flowmeter (TS420 Model, Transonic Systems Inc., Ithaca, N.Y.). It is continuously recorded over a 90-min period to monitor thrombosis-induced occlusion. Integrated carotid blood flow is measured by the area under the flow-time curve. It is expressed as percent of total control carotid blood flow, which would result if control blood flow had been maintained continuously for 90 min. In addition, thrombus from the injured artery is removed, blotted twice on a weighing paper to remove residual fluid, and weighed.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:

1. A compound of Formula I:

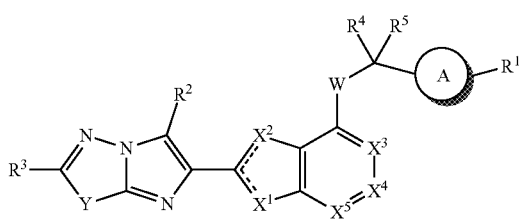

or a stereoisomer, tautomer, or pharmaceutically acceptable salt thereof, wherein:
the dashed line represents an optional double-bond with the proviso that only one of the two dashed line double bonds exists at the same time;
$X^1$ is O and $X^2$ is $CR^{1a}$ or N; or
$X^1$ is N and $X^2$ is O; or
$X^1$ is N or $CR^{1a}$, and $X^2$ is S; or
$X^1$ is N and $X^2$ is $NR^8$; or
$X^1$ is $NR^8$ and $X^2$ is N; or
$X^1$ is $NR^8$ and $X^2$ is $CR^{1a}$; or
$X^1$ is $CR^{1a}$ and $X^2$ is $NR^8$;
Y is S or —$CR^{2a}$=$CR^{2a}$—;
$X^3$, $X^4$ and $X^5$ are independently selected from $C(R^9)$ or N;
W is O or S;
$R^1$ is —$N(R^6)$—C(O)—$R^7$ or —$N(R^6)$—$S(O)_2$—$R^7$;

is selected from the group consisting of a phenyl ring, or a 6-membered heteroaryl ring containing at least one nitrogen atom,
or alternately the moiety

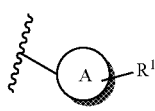

is selected from

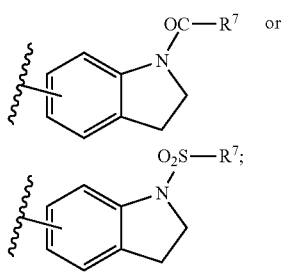

$R^{1a}$ is selected from the group consisting of H, halo, cyano, $C_1$-$C_4$ alkyl, $C_3$-$C_5$ cycloalkyl and $C_1$-$C_4$ alkoxy;
$R^2$ is H, halo, $C_1$-$C_6$ alkyl, $C_1$-$C_3$ alkoxy, CN or $C_3$-$C_7$ cycloalkyl;
$R^{2a}$ is independently at each occurrence selected from the group consisting of H, halo, CN, $C_1$-$C_3$ alkyl, $C_{1-3}$ haloalkyl, $C_1$-$C_3$ alkoxy, and $C_1$-$C_3$ haloalkoxy;
$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;
$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;
$R^6$ is selected from H, $C_1$-$C_6$ alkyl, $C_1$-$C_3$haloalkyl, or $C_1$-$C_3$hydroxyalkyl; and
$R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 hetero atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, $NR^{10}SO_2R^{11}$, $NR^{10}COR^{11}$, $NR^{10}CONR^{10}R^{11}$COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N to which they are attached to form a 4-7 membered heterocycle ring;
or $R^6$ and $R^7$ may be taken together to form a monocyclic or bicyclic heterocyclic ring with 0-2 additional heteroatoms selected independently from N, O, or S, wherein each of said monocyclic or bicyclic heterocyclic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{12}SO_2R^{13}$, $NR^{12}COR^{13}$, $NR^{12}CONR^{12}R^{13}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N to which they are attached to form a 4-7 membered heterocycle ring,
$R^8$ is H or $C_1$-$C_4$ alkyl; and
$R^9$ is selected from the group consisting of H, halo, $C_1$-$C_6$ alkyl, $C_{1-6}$ haloalkyl, - $C_1$-$C_6$ alkoxy and $C_1C_3$ haloalkoxy;
with the proviso that when Y is S and A is

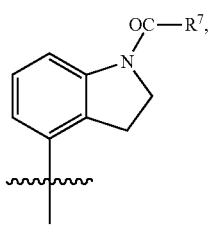

then $R^7$ is not pyridizin-4-yl.

2. The compound of claim 1, or a stereoisomer, tautomer, or pharmaceutically acceptable salt thereof, wherein:
$X^1$ is O and $X^2$ is $CR^{1a}$ or N; or
$X^1$ is N and $X^2$ is O; or
$X^1$ is N or $CR^{1a}$, and $X^2$ is S.

3. The compound of claim 1, or a stereoisomer, tautomer, or pharmaceutically acceptable salt thereof, wherein the compound has Formula IA:

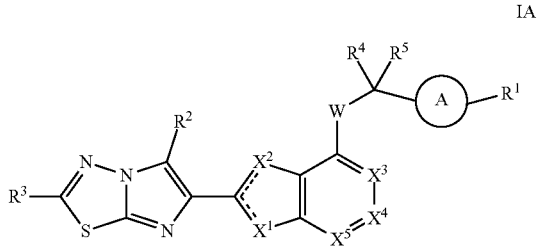

IA or a stereoisomer, tautomer, or pharmaceutically acceptable salt thereof, wherein:
the dashed line represents an optional double-bond with the proviso that only one of the two dashed line double bonds exists at the same time;
$X^1$ is O and $X^2$ is $CR^{1a}$ or N; or
$X^1$ is N and $X^2$ is O; or
$X^1$ is N or $CR^{1a}$, and $X^2$ is S;
$X^3$, $X^4$ and $X^5$ are independently selected from $C(R^9)$ or N;
W is O or S;
$R^1$ is —$N(R^6)$—C(O)—$R^7$ or —$N(R^6)$—$S(O)_2$—$R^7$;

is selected from the group consisting of a phenyl ring, or a 6-membered heteroaryl ring containing at least one nitrogen atom,
or alternately the moiety

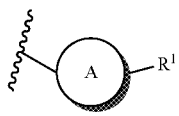

is selected from

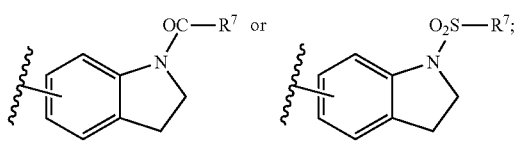

$R^{1a}$ is selected from the group consisting of H, halo, cyano, $C_1$-$C_4$ alkyl, $C_3$-$C_5$ cycloalkyl and $C_1$-$C_4$ alkoxy;
$R^2$ is H, halo, $C_1$-$C_6$ alkyl, $C_1$-$C_3$ alkoxy, CN or $C_3$-$C_7$ cycloalkyl;
$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{3-6}$ cycloalkyl, $C_{2-3}$ alkenyl, $C_{2-3}$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;
$R^8$ is H or $C_1$-$C_4$ alkyl;
$R^9$ is selected from the group consisting of H, halo, $C_1$-$C_6$ alkyl, halo$C_{1-6}$ alkyl, —O—($C_1$-$C_6$ alkyl) and halo$C_{1-3}$ alkoxy;
$R^6$ is selected from H, $C_1$-$C_6$ alkyl, halo$C_{1-3}$alkyl, or hydroxy$C_{1-3}$alkyl; and
$R^7$ is selected from the group consisting of hydrogen, $C_1$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), $N(alkyl)_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl or $R^{10}$ and $R^{11}$ can be taken together with the N they are attached to form a 4-7 membered heterocycle ring;

or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), $N(alkyl)_2$, $CONR^{12}R^{13}$, $SONR^{12}R^{13}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N to which they are attached to form a 4-7 membered heterocycle ring,
with the proviso that when A is

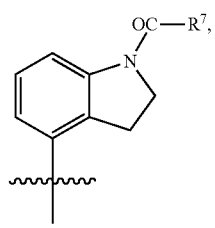

then $R^7$ is not pyridizin-4-yl.

4. The compound of claim 1, or a stereoisomer, tautomer, or pharmaceutically acceptable salt thereof, wherein the compound has Formula IB:

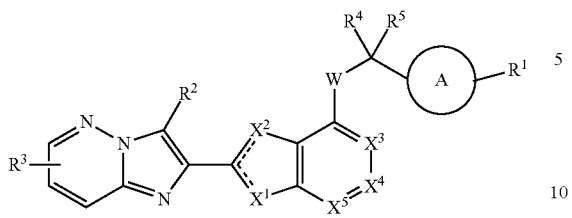

wherein:
the dashed line represents an optional double-bond with the proviso that only one of the two dashed line double bonds exists at the same time;
$X^1$ is O and $X^2$ is $CR^{1a}$ or N; or
$X^1$ is N and $X^2$ is O; or
$X^1$ is N or $CR^{1a}$, and $X^2$ is S;
$X^3$, $X^4$ and $X^5$ are independently selected from $C(R^9)$ or N;
W is O or S;
$R^1$ is —$N(R^6)$—$C(O)$—$R^7$ or —$N(R^6)$—$S(O)_2$—$R^7$;

is selected from the group consisting of a phenyl ring, or a 6-membered heteroaryl ring containing at least one nitrogen atom,
or alternately the moiety

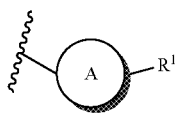

is selected from

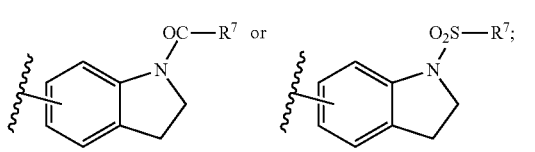

$R^{1a}$ is selected from the group consisting of H, halo, cyano, $C_1$-$C_4$ alkyl, $C_{3-5}$ cycloalkyl and $C_1$-$C_4$ alkoxy;
$R^2$ is H, halo, $C_1$-$C_6$ alkyl, $C_1$-$C_3$ alkoxy, CN or $C_3$-$C_7$ cycloalkyl;
$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{3-6}$ cycloalkyl, $C_{2-3}$ alkenyl, $C_{2-3}$ alkynyl and halo;
$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;
$R^8$ is H or $C_1$-$C_4$ alkyl;
$R^9$ is selected from the group consisting of H, halo, $C_1$-$C_6$ alkyl, halo$C_{1-6}$ alkyl, —O—($C_1$-$C_6$ alkyl) and halo$C_{1-3}$ alkoxy;
$R^6$ is selected from H, $C_1$-$C_6$ alkyl, halo$C_{1-3}$alkyl, or hydroxy$C_{1-3}$alkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl, or $R^{10}$ and $R^{11}$ can be taken together with the N to which they are attached to form a 4-7 membered heterocycle ring;
or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, COOH, $COOR^{12}$, oxo and methylenedioxy, wherein $R^{12}$ and $R^{13}$ are the same or different and are H or $C_{1-4}$ alkyl or $R^{12}$ and $R^{13}$ can be taken together with the N to which they are attached to form a 4-7 membered heterocycle ring.

5. The compound of claim 1 wherein the compound has Formula IC:

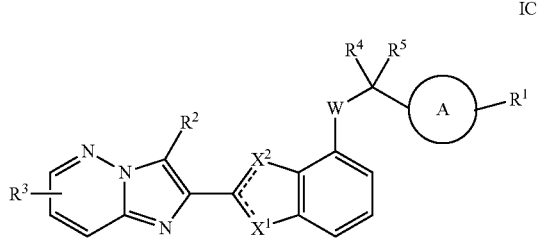

or a stereoisomer, tautomer, or pharmaceutically acceptable salt thereof, wherein:
the dashed line represents an optional double-bond with the proviso that only one of the two dashed line double bonds exists at the same time;
$X^1$ is O and $X^2$ is $CR^{1a}$ or N; or
$X^1$ is N and $X^2$ is O; or
$X^1$ is N or $CR^{1a}$, and $X^2$ is S;
W is O;
$R^1$ is —$N(R^6)$—$C(O)$—$R^7$ or —$N(R^6)$—$S(O)_2$—$R^7$;

is selected from the group consisting of a phenyl ring, or a 6-membered heteroaryl ring containing at least one nitrogen atom, or alternately the moiety

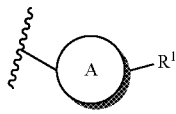

is selected from

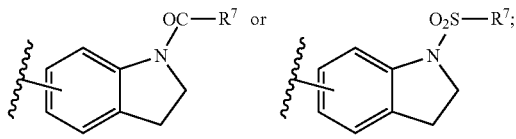

$R^{1a}$ is selected from the group consisting of H, halo, cyano, $C_1$-$C_4$ alkyl, $C_3$-$C_5$ cycloalkyl and $C_1$-$C_4$ alkoxy;
$R^2$ is H, halo, $C_1$-$C_6$ alkyl, $C_1$-$C_3$ alkoxy, CN or $C_3$-$C_7$ cycloalkyl;
$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{3-6}$ cycloalkyl, $C_{2-3}$ alkenyl, $C_{2-3}$ alkynyl and halo;
$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;
$R^8$ is H or $C_1$-$C_4$ alkyl;
$R^9$ is selected from the group consisting of H, halo, $C_1$-$C_6$ alkyl, halo$C_{1-6}$ alkyl, —O—($C_1$-$C_6$ alkyl) and halo$C_{1-3}$ alkoxy;
$R^6$ is selected from H, $C_1$-$C_6$ alkyl, halo$C_{1-3}$alkyl, or hydroxy$C_{1-3}$alkyl; and
$R^7$ is selected from the group consisting of hydrogen, $C_1$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein R$^{10}$ and R$^{11}$ are the same or different and are H or $C_{1-4}$ alkyl or R$^{10}$ and R$^{11}$ can be taken together with the N to which they are attached to form a 4-7 membered heterocycle ring;
or $R^6$ and $R^7$ may be taken together to form a monocyclic or bicyclic heterocyclic ring with 0-2 additional hetero atoms selected independently from N, O, or S, wherein each of said monocyclic or bicyclic heterocyclic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$, CONR$^{12}$R$^{13}$, SONR$^{12}$R$^{13}$, COOH, COOR$^{12}$, oxo and methylenedioxy, wherein R$^{12}$ and R$^{13}$ are the same or different and are H or $C_{1-4}$ alkyl, or R$^{12}$ and R$^{13}$ can be taken together with the N to which they are attached to form a 4-7 membered heterocycle ring.

6. The compound of claim 1, wherein the compound has Formula ID:

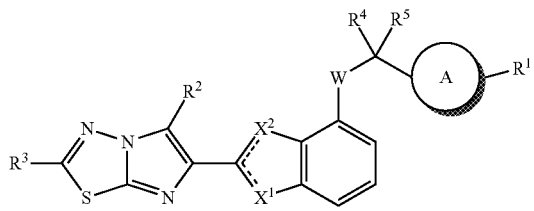

ID or a stereoisomer, tautomer, or pharmaceutically acceptable salt thereof, wherein:
the dashed line represents an optional double-bond with the proviso that only one of the two dashed line double bonds exists at the same time;
$X^1$ is O and $X^2$ is CR$^{1a}$ or N; or
$X^1$ is N and $X^2$ is O; or
$X^1$ is N or CR$^{1a}$, and $X^2$ is S;
W is O;
$R^1$ is —N(R$^6$)—C(O)—R$^7$ or —N(R$^6$)—S(O)$_2$—R$^7$;

is selected from the group consisting of a phenyl ring, or a 6-membered heteroaryl ring containing at least one nitrogen atom,
or alternately the moiety

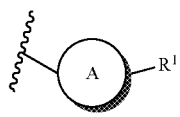

is selected from

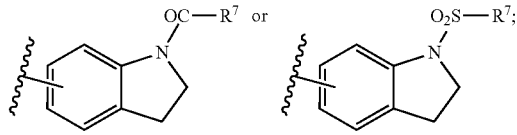

$R^{1a}$ is selected from the group consisting of H, or methyl;
$R^2$ is H, or methyl;
$R^3$ is selected from the group consisting of methyl, ethyl, methoxy, 1,1-difluoroethyl, or 1-fluoroethyl;
$R^4$ and $R^5$ are independently selected from H or methyl;
$R^8$ is H or methyl;
$R^9$ is methoxy;
$R^6$ is selected from H or methyl;
$R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, COOH, $COOR^{10}$, oxo and methylenedioxy, wherein $R^{10}$ and $R^{11}$ are the same or different and are H or $C_{1-4}$ alkyl, or $R^{10}$ and $R^{11}$ can be taken together with the N to which they are attached to form a 4-7 membered heterocycle ring;

or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N to which they are attached to form a 4-7 membered heterocycle ring, with the proviso that when A is

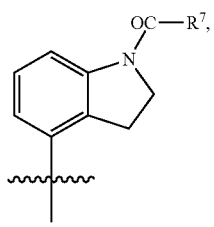

then $R^7$ is not pyridizin-4-yl.

7. The compound of claim 1, or a stereoisomer, tautomer, or pharmaceutically acceptable salt thereof, wherein the compound of Formula I is selected from the compounds of formulas IE, IF, IG, IH and IJ:

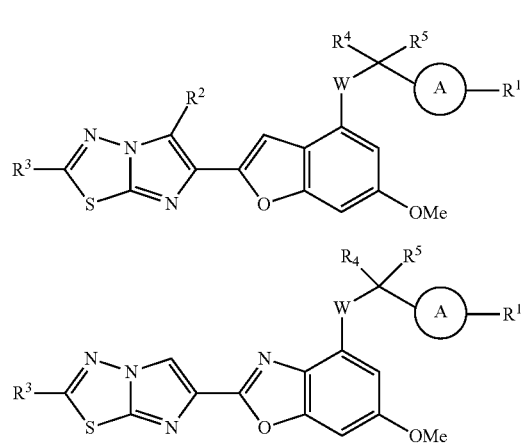

IE

IF

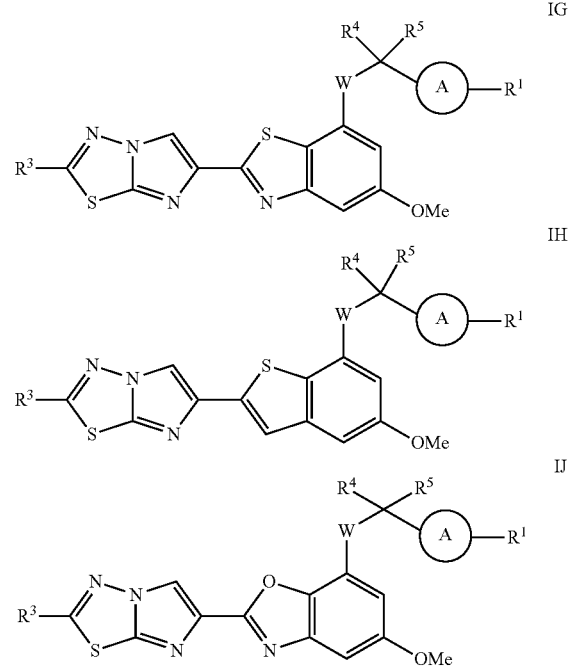

IG

IH

IJ wherein the various moieties are independently selected and are as defined earlier in claim 1, with the proviso that when A is

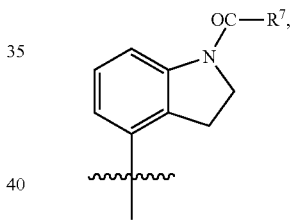

then $R^7$ is not pyridizin-4-yl.

8. The compound of claim 1, or a stereoisomer, tautomer, or pharmaceutically acceptable salt thereof, wherein the compound of Formula I is selected from the compounds of formulas IN, IO, IP, IQ and IR:

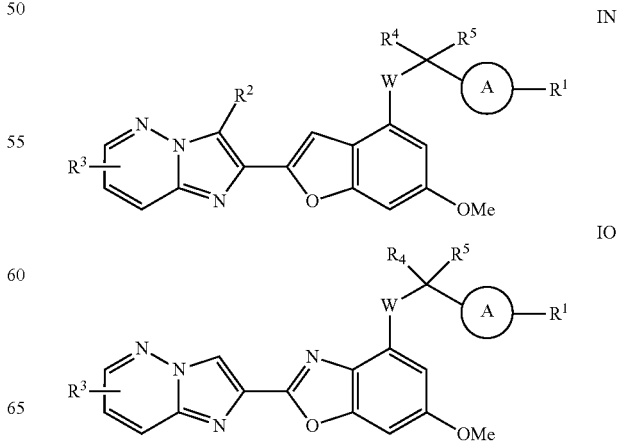

IN

IO

245
-continued

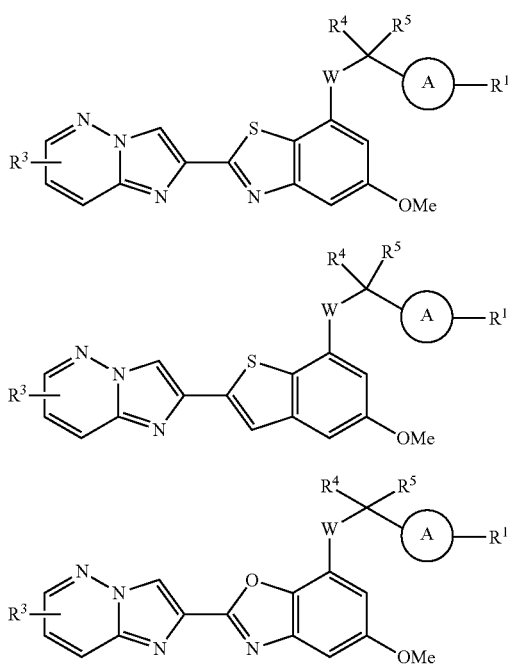

IP

IQ

IR wherein the various moieties are independently selected and are as defined earlier in claim 1.

9. The compound of claim 1, or a stereoisomer, tautomer, or pharmaceutically acceptable salt thereof, wherein the various moieties are independently selected, and $X^3$, and $X^5$ are CH;
$X^4$ is $CR^9$;
W is O;
Y is S or —CH=CH—;
$R^{1a}$ is H;
$R^2$ is H;
$R^3$ is —OCH$_3$ or CH$_3$;
$R^4$ and $R^5$ are H;
$R^6$ is H or methyl;
$R^9$ is —OCH$_3$;
$R^1$ is —N($R^6$)—C(O)—$R^7$ or —N($R^6$)—S(O)$_2$—$R^7$;

is selected from the group consisting of a phenyl ring, or a 6-membered heteroaryl ring containing at least one nitrogen atom;
or alternately the moiety

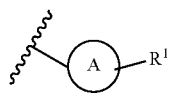

246 is selected from

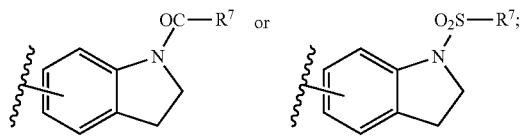

and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 moieties independently selected from N, O or S, $C_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein R$^1$ and R$^{11}$ are the same or different and are H or C$_{1-4}$ alkyl, or R$^1$ and R$^{11}$ can be taken together with the N to which they are attached to form a 4-7 membered heterocycle ring;

or R$^6$ and R$^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$, CONR$^{12}$R$^{13}$, SONR$^{12}$R$^{13}$, COOH, COOR$^{12}$, oxo and methylenedioxy, wherein R$^{12}$ and R$^{13}$ are the same or different and are H or C$_{1-4}$ alkyl, or R$^{12}$ and R$^{13}$ can be taken together with the N to which they are attached to form a 4-7 membered heterocycle ring.

10. The compound of claim 1, or a stereoisomer, tautomer, or pharmaceutically acceptable salt thereof, wherein the various moieties are independently selected, and $X^3$=$X^5$=CH;
$X^4$ is $CR^9$;
W is O;
Y is S;
$R^{1a}$ is H;
$R^2$ is H;
$R^3$ is CH$_3$ or methoxy;
$R^4$ and $R^5$ are H;
$R^6$ is H;
$R^9$ is methoxy;
$R^1$ is —N($R^6$)—C(O)—$R^7$ or —N($R^6$)—S(O)$_2$—$R^7$;

is selected from the group consisting of a phenyl ring, or a 6-membered heteroaryl ring containing at least one nitrogen atom;

or alternately the moiety

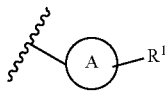

is selected from

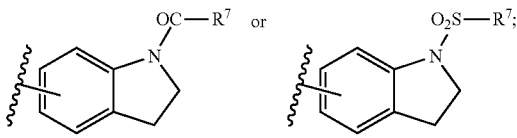

and

R$^7$ is selected from the group consisting of hydrogen, C$_2$-C$_6$ alkyl, C$_6$-C$_{10}$ aryl, C$_1$-C$_7$ alkoxy, 5-7 membered heterocyclic ring containing 1-3 moieties independently selected from N, O or S, C$_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein R$^1$ and R$^{11}$ are the same or different and are H or C$_{1-4}$ alkyl, or R$^{10}$ and R$^{11}$ can be taken together with the N to which they are attached to form a 4-7 membered heterocycle ring;

or R$^6$ and R$^7$ may be taken together to form a monocyclic or bicyclic heterocyclic ring with 0-2 additional hetero atoms selected independently from N, O, or S, wherein each of said monocyclic or bicyclic heterolytic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$, CONR$^{12}$R$^{13}$, SONR$^{12}$R$^{13}$, COOH, COOR$^{12}$, oxo and methylenedioxy, wherein R$^{12}$ and R$^{13}$ are the same or different and are H or C$_{1-4}$ alkyl, or R$^{12}$ and R$^{13}$ can be taken together with the N to which they are attached to form a 4-7 membered heterocycle ring.

11. The compound of claim 1, or a stereoisomer, tautomer, or pharmaceutically acceptable salt thereof, wherein the various moieties are independently selected, and X$^3$ =X$^5$ =CH;
X$^4$ is CR$^9$;
W is O;
Y is S;
R$^{1a}$ is H;
R$^2$ is H;
R$^3$ is CH$_3$ or methoxy;
R$^4$ and R$^5$ are H;
R$^6$ is H;
R$^9$ is methoxy;
R$^1$ is —N(R$^6$)—C(O)—R$^7$;

is selected from the group consisting of a phenyl or pyridyl ring; and
R$^7$ is selected from the group consisting of hydrogen, C$_2$-C$_6$ alkyl, C$_6$-C$_{10}$ aryl, C$_1$-C$_7$ alkoxy, 5-7 membered heterocyclic ring containing 1-3 moieties independently selected from N, O or S, C$_{3-7}$ cycloalkyl, and 6-10 membered heteroaryl, wherein each of said alkyl, aryl, heterocylic and heteroaryl is independently unsubstituted or substituted with 1-3 moieties which can be the same or different and being independently selected from the group consisting of halo, alkyl, aryl, heteroaryl, alkoxy, aryloxy, arylalkyloxy, alkyloxycarbonyl, alkylcarboxy, aryloxycarbonyl, arylcarboxy, nitro, cyano, OH, NH$_2$, NH(alkyl), N(alkyl)$_2$, CONR$^{10}$R$^{11}$, SONR$^{10}$R$^{11}$, COOH, COOR$^{10}$, oxo and methylenedioxy, wherein R$^{10}$ and R$^{11}$ are the same or different and are H or C$_{1-4}$ alkyl, or R$^{10}$ and R$^{11}$ can be taken together with the N to which they are attached to form a 4-7 membered heterocycle ring;

or R$^6$ and R$^7$ may be taken together to form a monocyclic or bicyclic heterocyclic ring with 0-2 additional hetero atoms selected independently from N, O, or S, wherein each of said monocyclic or bicyclic heterolytic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, NH$_2$, NH(alkyl), N(alkyl)$_2$ , CONR$^{12}$R$^{13}$, SONR$^{12}$R$^{13}$, COOH, COOR$^{12}$, oxo and methylenedioxy, wherein R$^{12}$ and R$^{13}$ are the same or different and are H or C$_{1-4}$ alkyl, or R$^{12}$ and R$^{13}$ can be taken together with the N to which they are attached to form a 4-7 membered heterocycle ring.

12. A compound, or a stereoisomer, tautomer, or pharmaceutically acceptable salt thereof, wherein the compound has the formula:

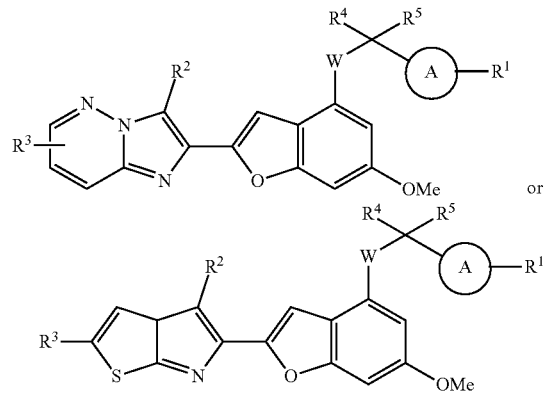

wherein:
X$^3$, X$^4$ and X$^5$ are independently selected from C(R$^9$) or N;
W is O or S;
R$^1$ is —N(R$^6$)—C(O)—R$^7$ or —N(R$^6$)—S(O)$_2$—R$^7$;

is selected from the group consisting of a phenyl ring, or a 6-membered heteroaryl ring containing at least one nitrogen atom,
or alternately the moiety

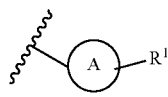

is selected from

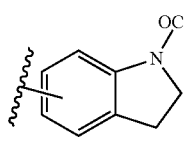 or 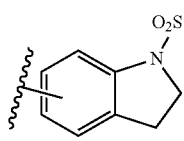;

$R^2$ is H, halo, $C_1$-$C_6$ alkyl, $C_1$-$C_3$ alkoxy, CN or $C_3$-$C_7$ cycloalkyl;

$R^3$ is selected from the group consisting of $C_1$-$C_4$ alkyl, $C_1$-$C_4$ alkoxy, $C_1$-$C_4$ alkylthio, $C_1$-$C_2$ haloalkyl, $C_1$-$C_2$ haloalkoxy, $C_3$-$C_6$ cycloalkyl, $C_2$-$C_3$ alkenyl, $C_2$-$C_3$ alkynyl and halo;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

$R^6$ is selected from H, $C_1$-$C_6$ alkyl, $C_1$-$C_3$ haloalkyl, or $C_1$-$C_3$ hydroxyalkyl; and $R^7$ is selected from the group consisting of hydrogen, $C_2$-$C_6$ alkyl, $C_6$-$C_{10}$ aryl, $C_1$-$C_7$ alkoxy, 5-7 membered heterocyclic ring containing 1-3 atoms independently selected from N, O or S, $C_{3-7}$ cycloalkyl, and 6-10 membered heteroaryl, wherein each of said alkyl, cycloalkyl, aryl, heterocylic and heteroaryl group is independently unsubstituted or substituted with 1-3 moieties which can be the same or different and being independently selected from the group consisting of halo, alkyl, haloalkyl, aryl, heteroaryl, alkoxy, haloalkoxy, aryloxy, arylalkyloxy, alkyloxycarbonyl, alkylcarboxy, aryloxycarbonyl, arylcarboxy, nitro, cyano, OH, $NH_2$, NH(alkyl), N(alkyl)$_2$, $CONR^{10}R^{11}$, $SONR^{10}R^{11}$, $NR^{10}SO_2R^{11}$, $NR^{10}COR^{11}$, $NR^{10}CONR^{10}R^{11}$, COOH, $COOR^{10}$, oxo and methylenedioxy, wherein $R^{10}$ and $R^{11}$ are the same or different and are H or $C_{1-4}$ alkyl, or $R^{10}$ and $R^{11}$ can be taken together with the N to which they are attached to form a 4-7 membered heterocycle ring;

or $R^6$ and $R^7$ may be taken together to form a monocyclic or bicyclic heterocyclic ring with 0-2 additional hetero atoms selected independently from N, O, or S, wherein each of said monocyclic or bicyclic heterocylic ring can be independently unsubstituted or substituted with 1-3 moieties which can be the same or different and being independently selected from the group consisting of halo, alkyl, aryl, heteroaryl, alkoxy, aryloxy, arylalkyoxy, alkyloxycarbonyl, alkylcarboxy, aryloxycarbonyl, arylcarboxy, nitro, cyano, OH, $NH_2$, NH(alkyl), N(alkyl)$_2$, $CONR^{12}R^{13}$, $SONR^{12}R^{13}$, $NR^{10}SO_2R^{11}$, $NR^{10}COR^{11}$, $NR^{10}$ $CONR^{10}$ $R^{11}$, COOH, $COOR^{12}$, oxo and methylenedioxy, wherein $R^{12}$ and $R^{13}$ are the same or different and are H or $C_{1-4}$ alkyl, or $R^{12}$ and $R^{13}$ can be taken together with the N to which they are attached to form a 4-7 membered heterocycle ring;

$R^8$ is H or $C_1$-$C_4$ alkyl; and $R^9$ is selected from the group consisting of H, halo, $C_1$-$C_6$ alkyl, $C_{1-6}$ haloalkyl, - $C_1$-$C_6$ alkoxy and $C_1$-$C_3$ haloalkoxy, with the proviso that when the compound is:

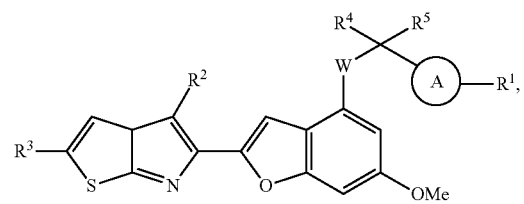

and A is

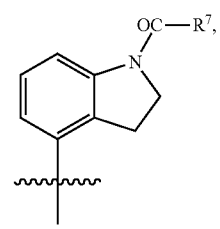

then
$R^7$ is not pyridizin-4-yl.

13. The compound as defined in claim 1, wherein the compound is selected from the following:

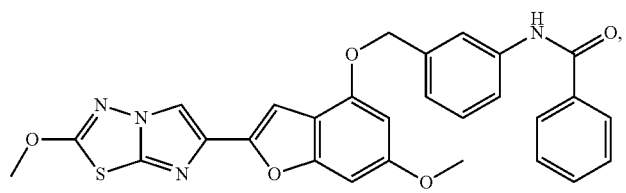

-continued
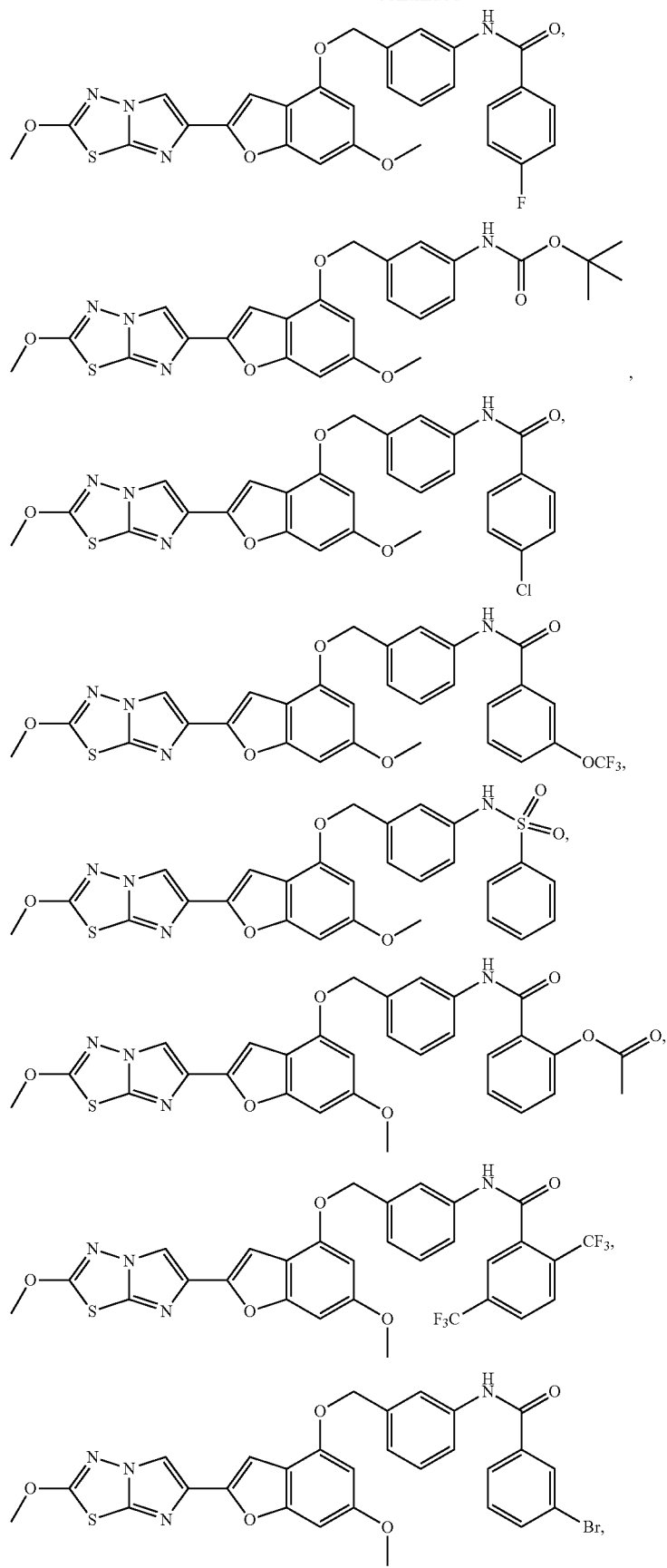

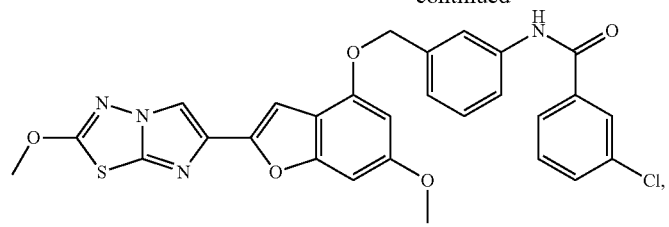
,
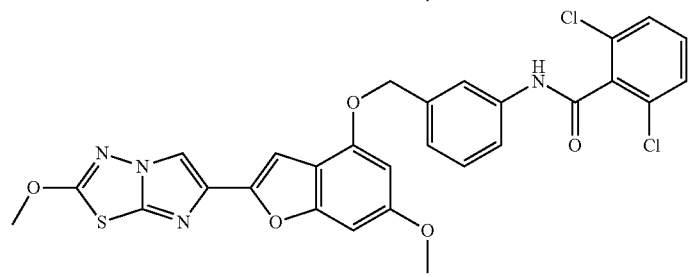
,
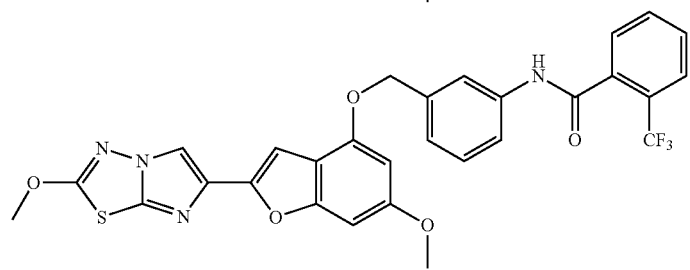
,
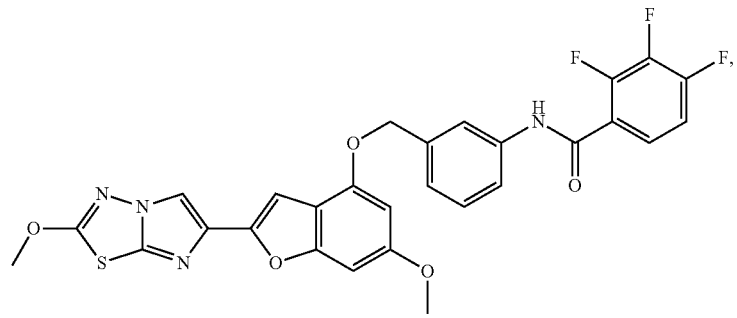
,
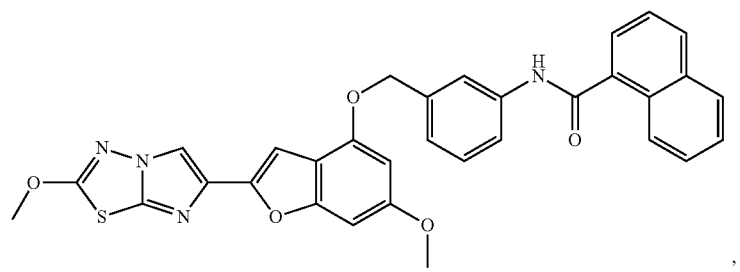
,
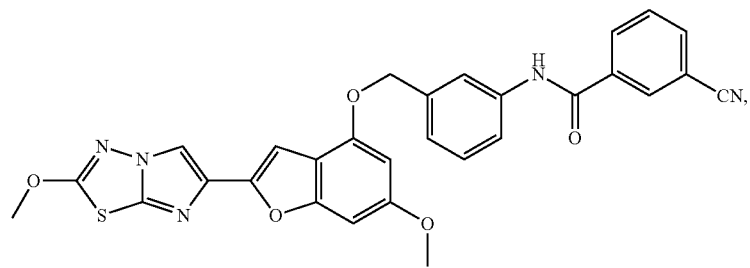

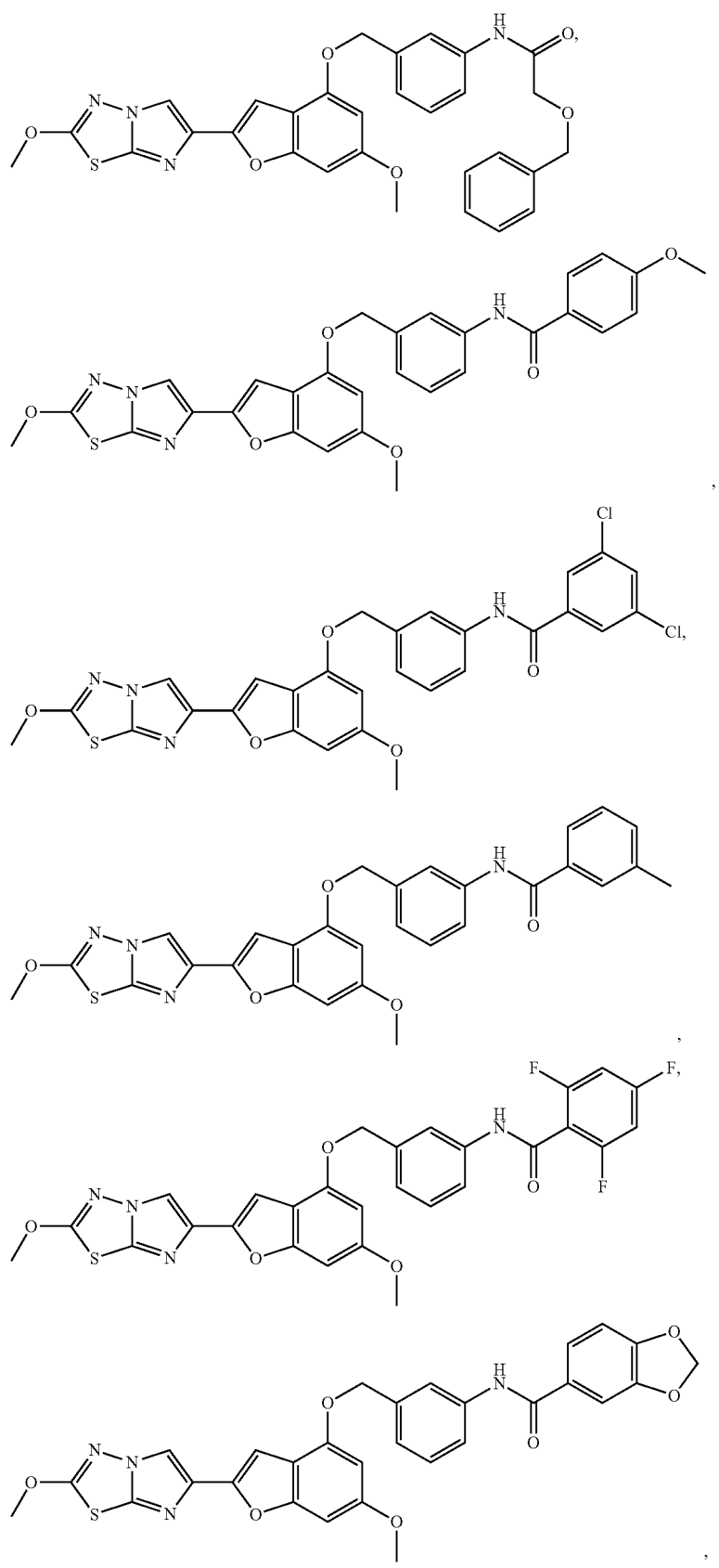

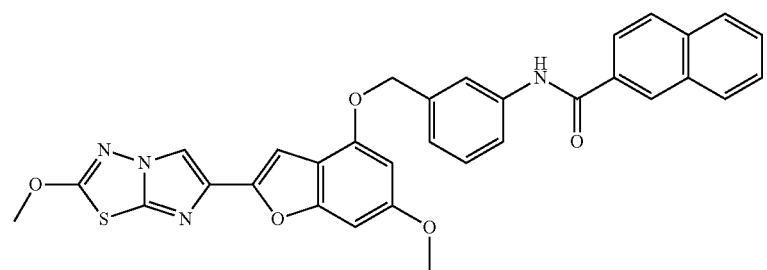,
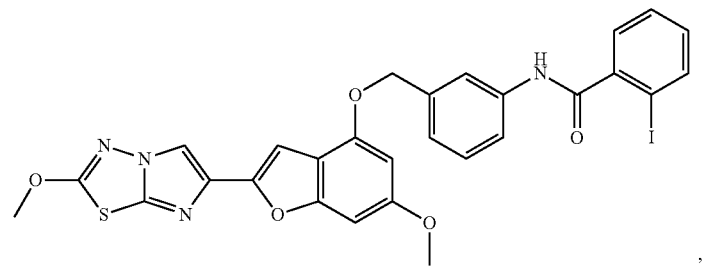,
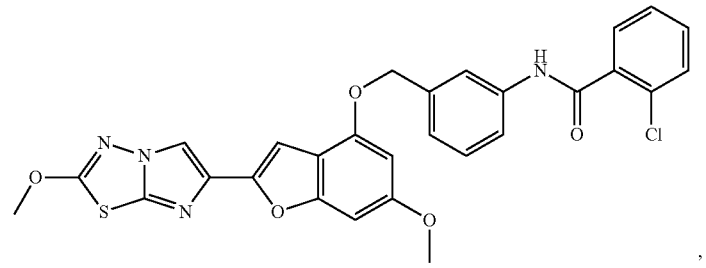,
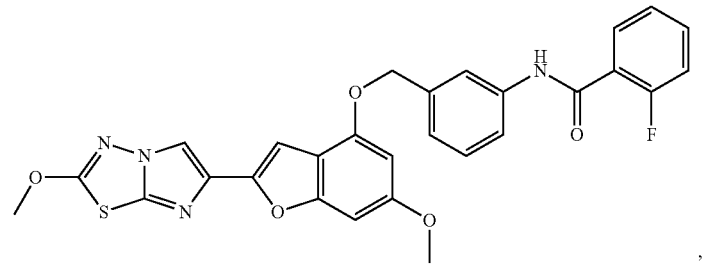,
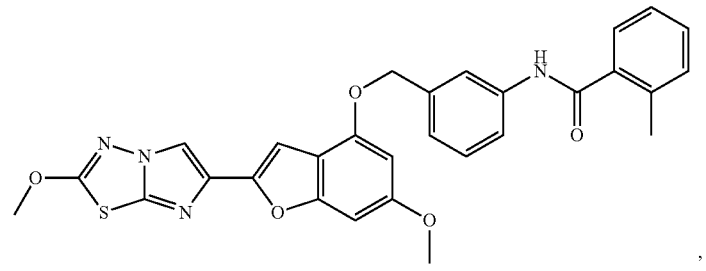,
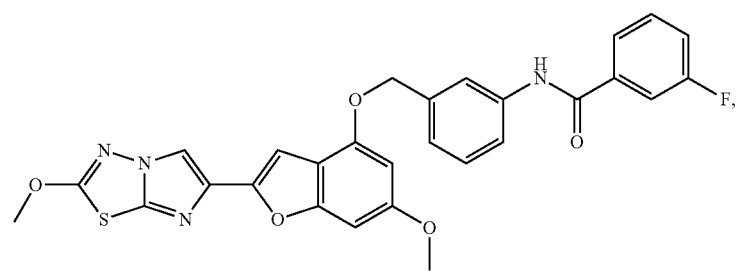

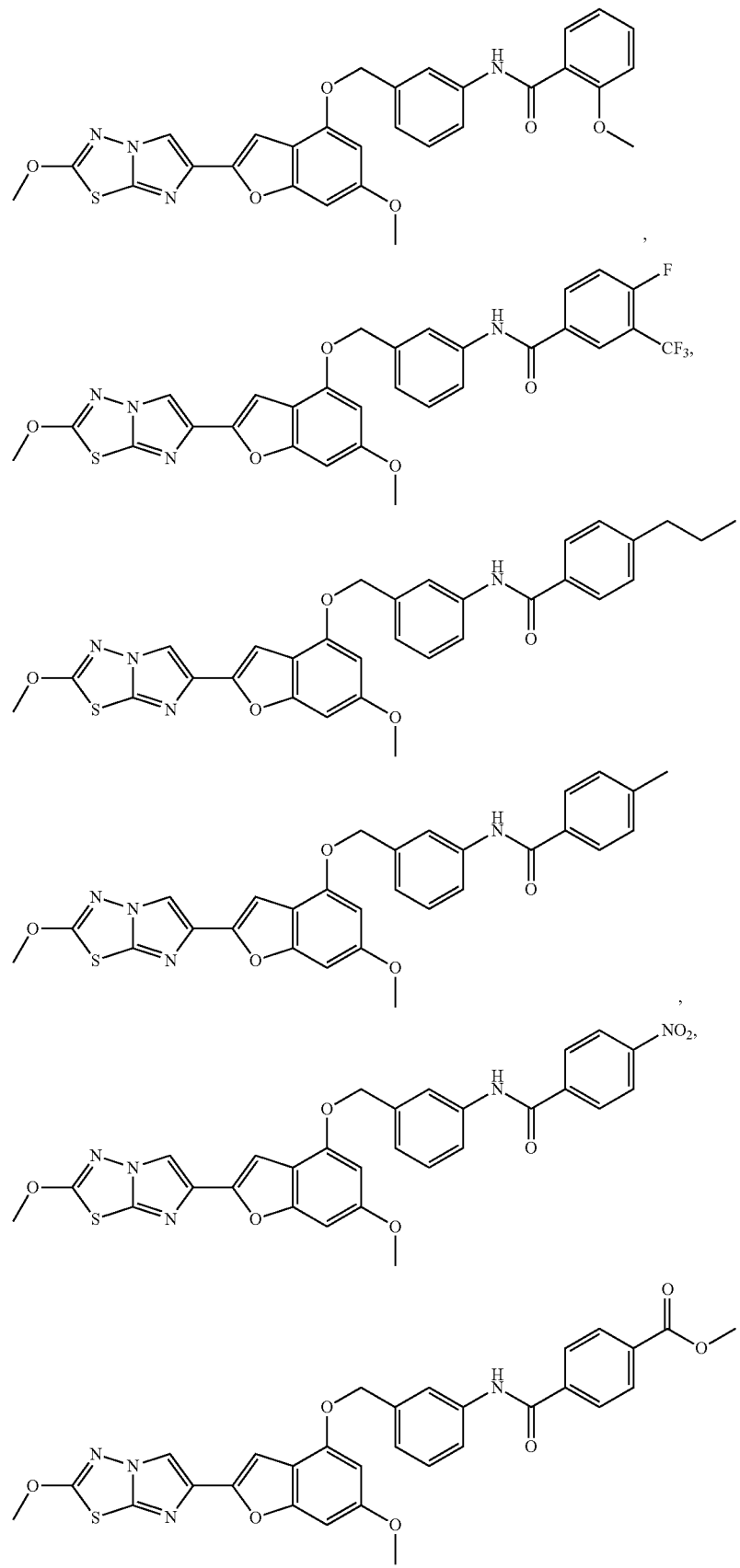

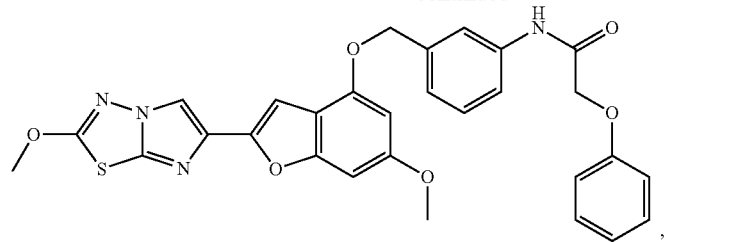
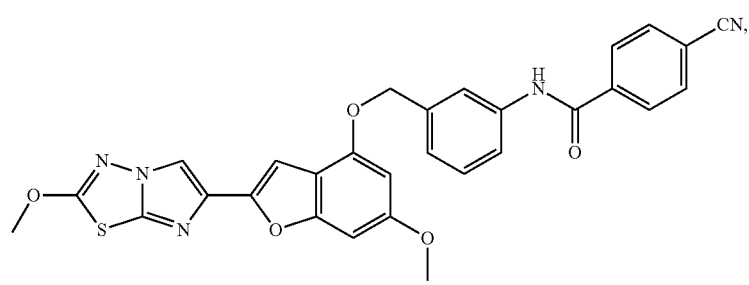
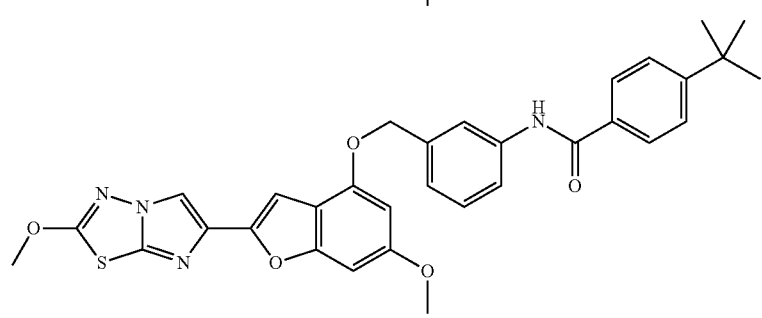
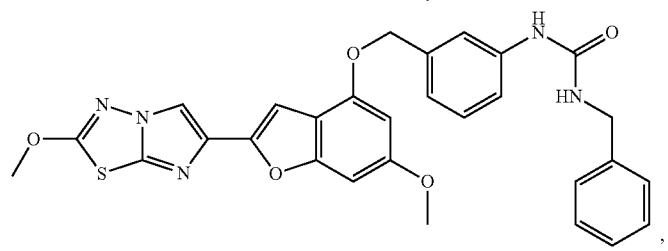
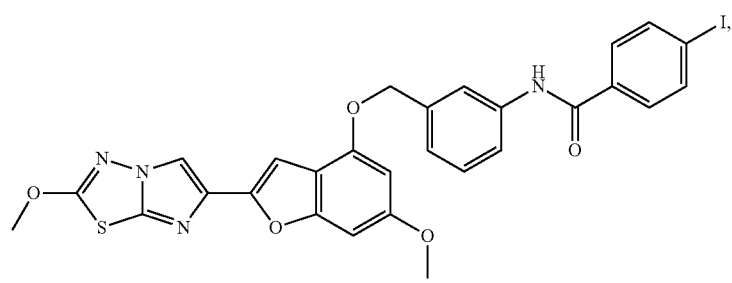
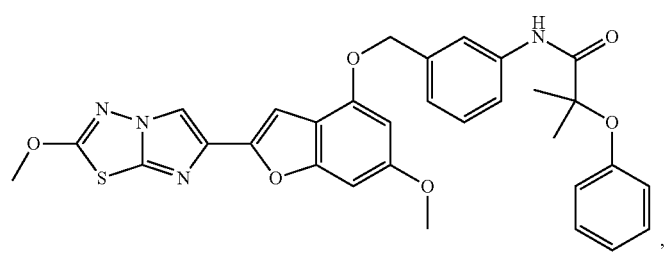

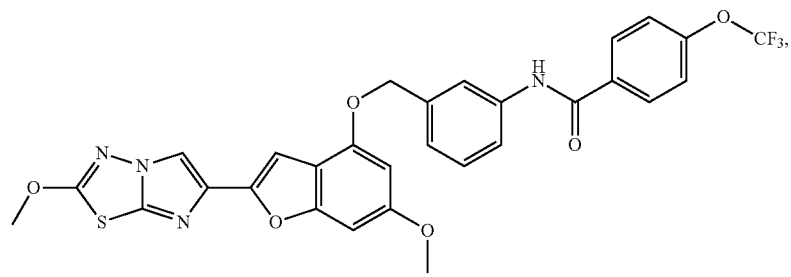
,
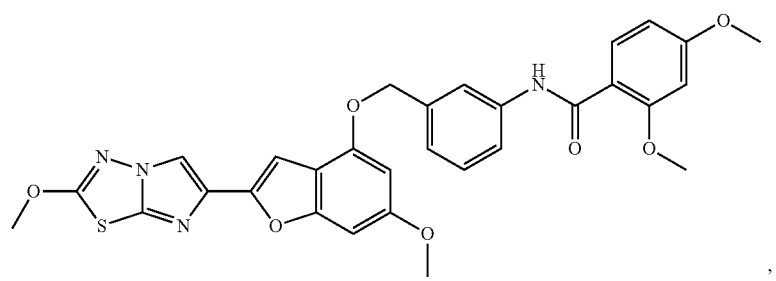
,
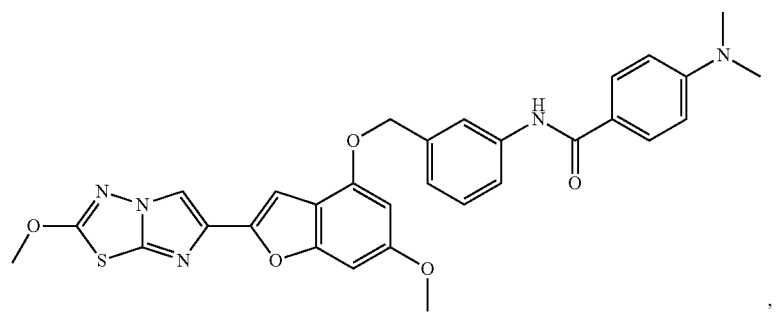
,
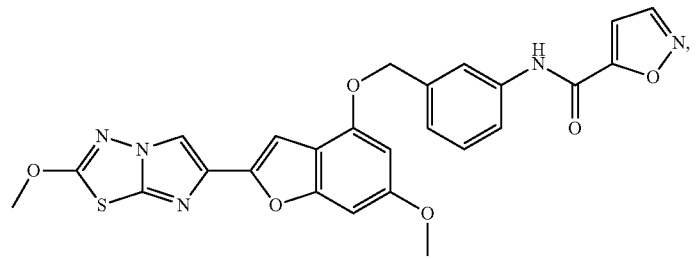
,
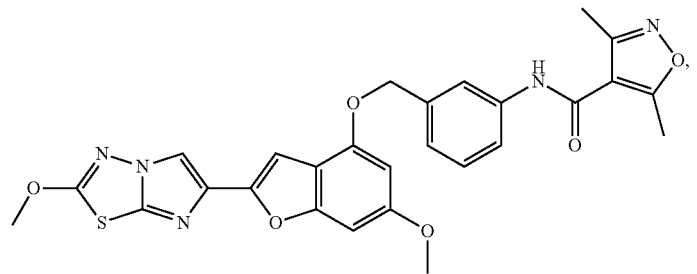
,
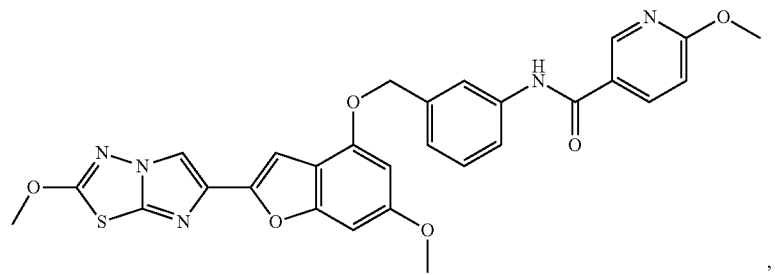
,

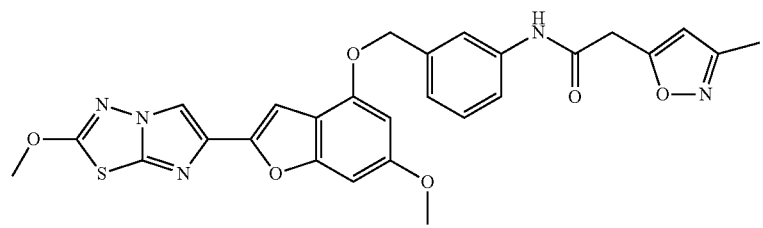
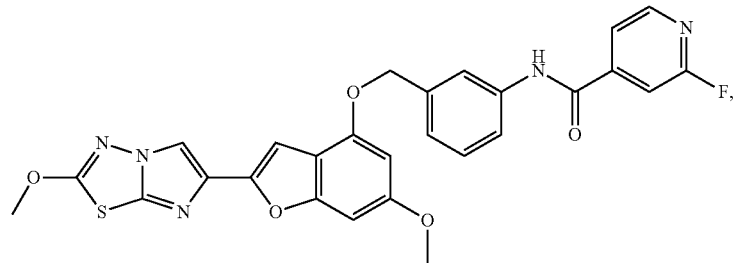
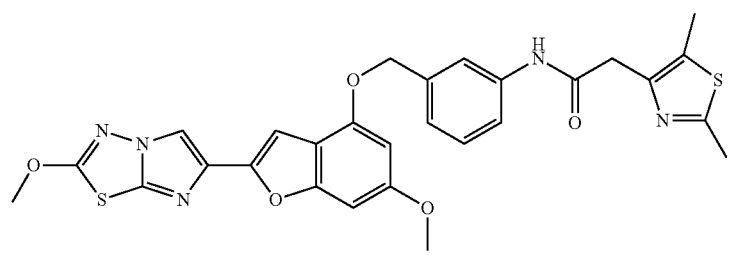
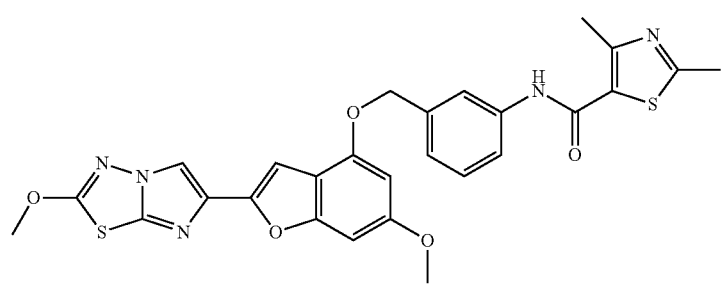
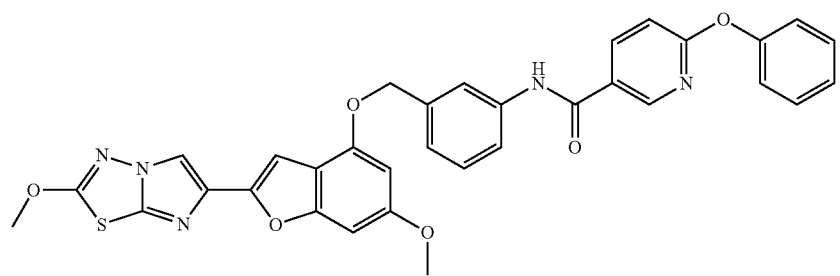
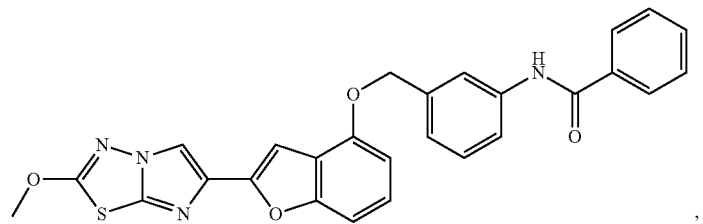

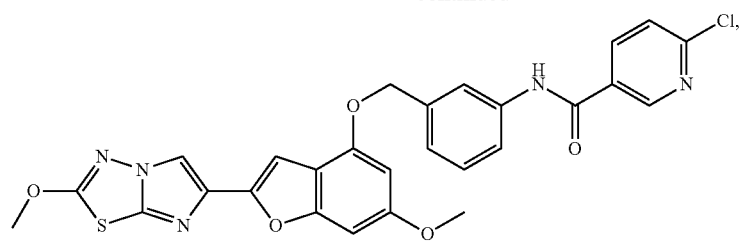
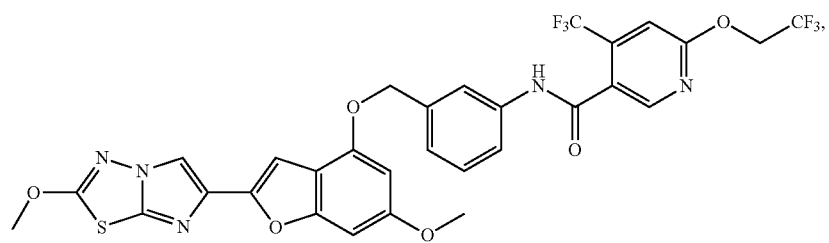
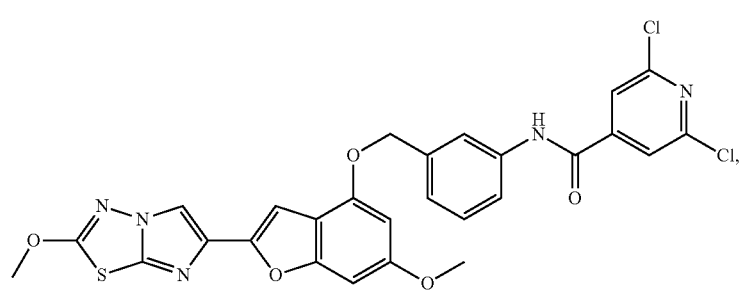
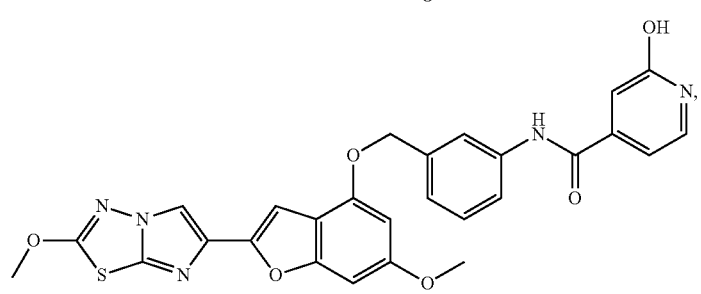
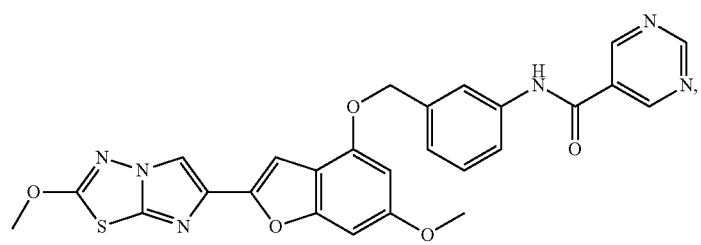
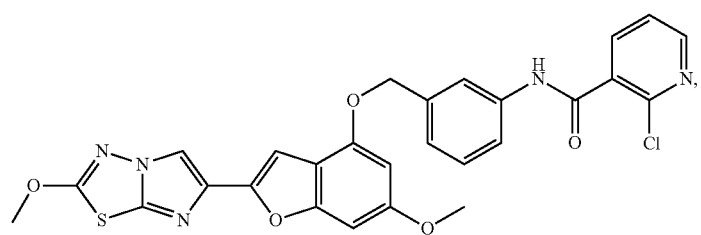

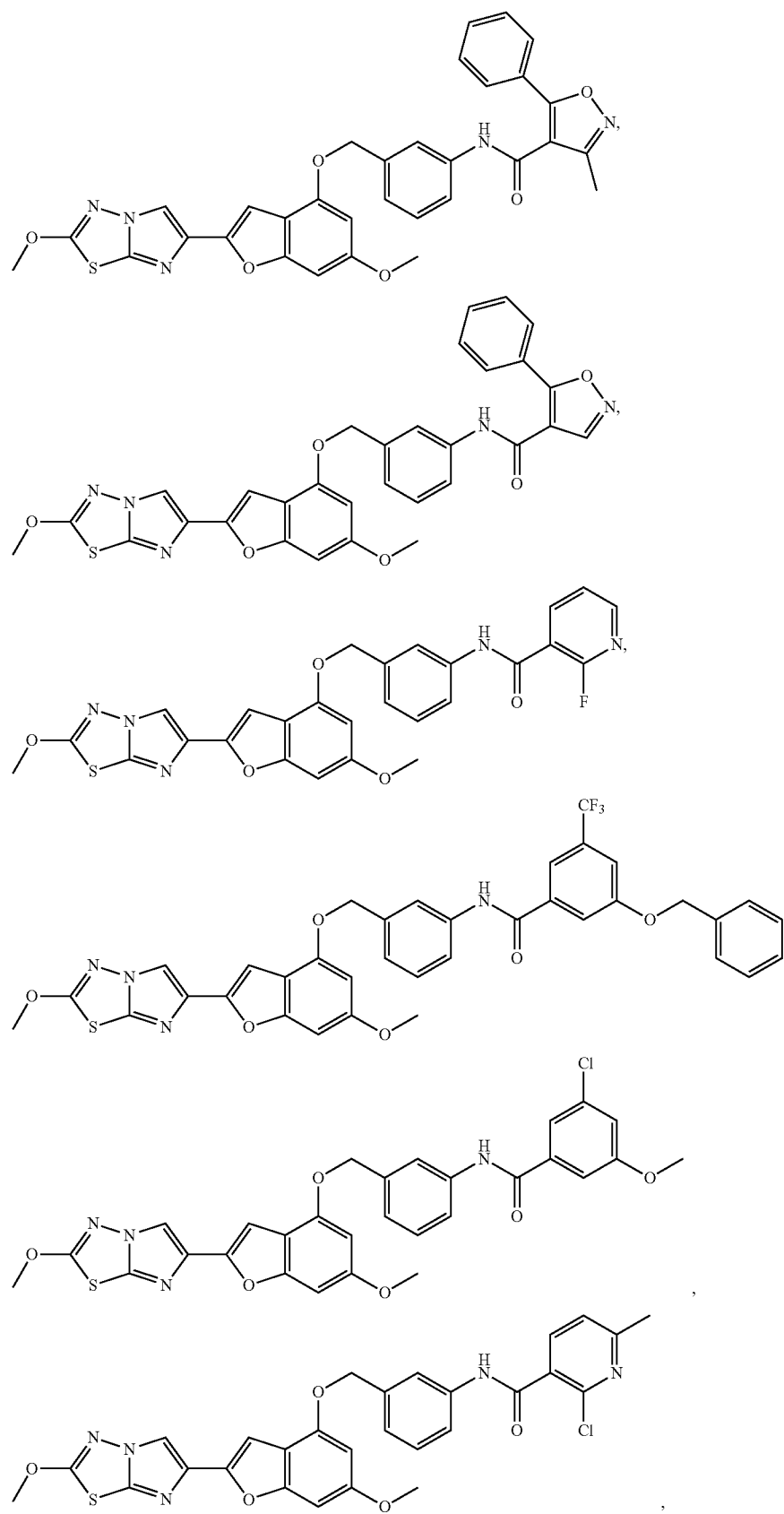

-continued
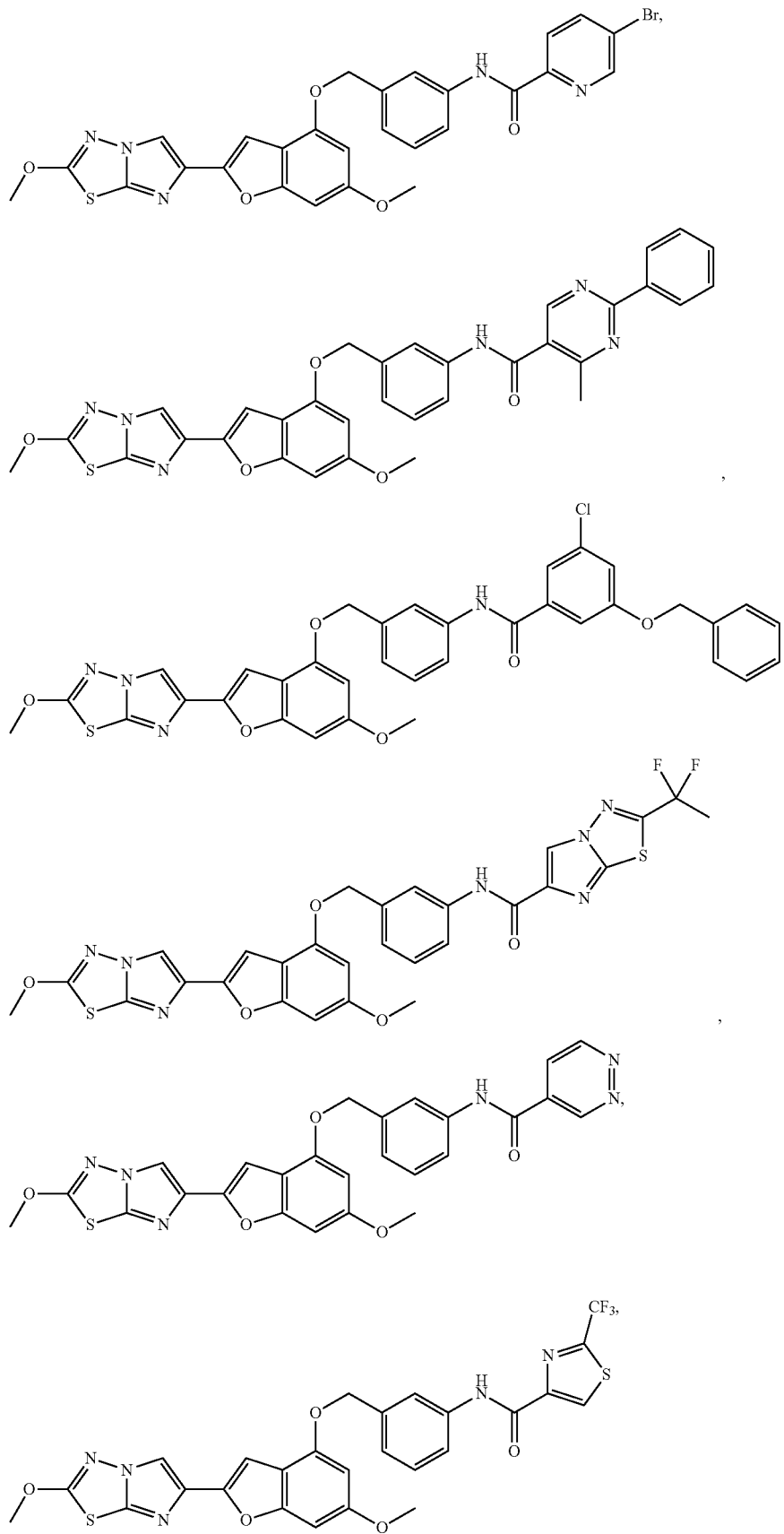

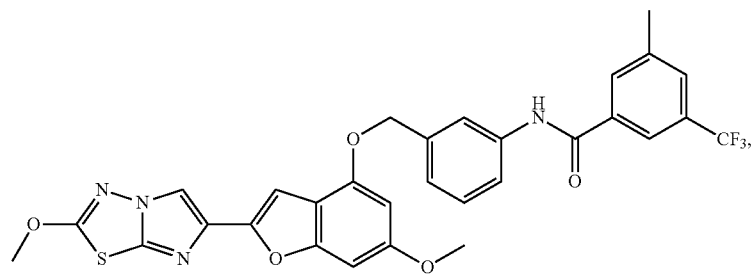
,
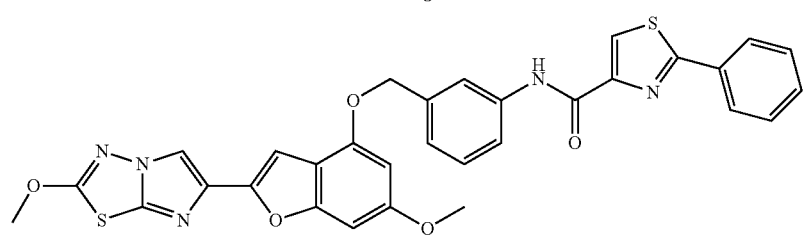
,
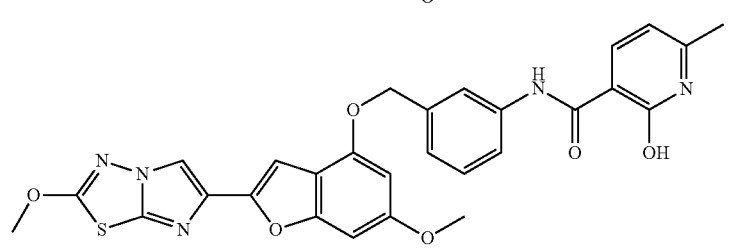
,
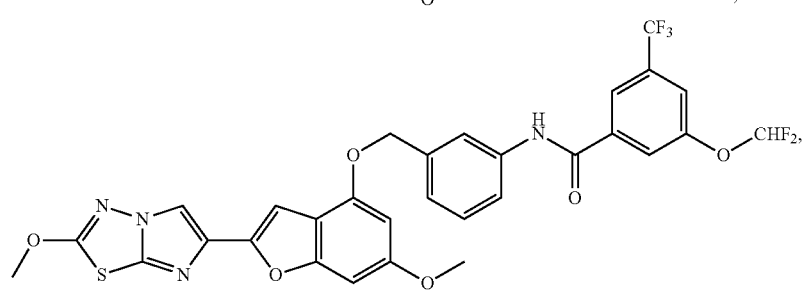
,
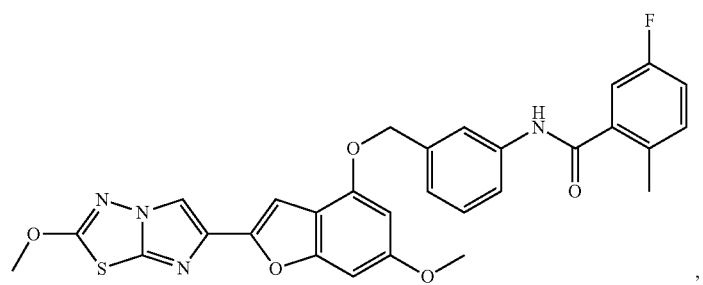
,
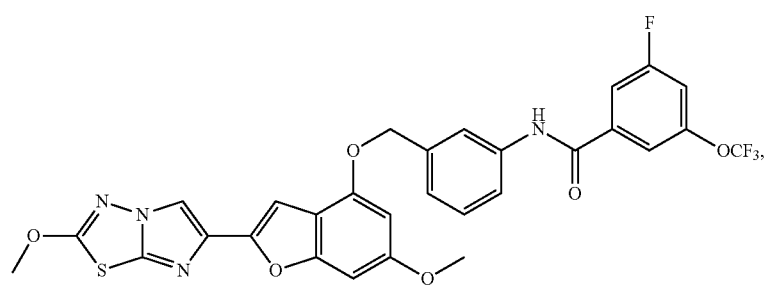
, -continued
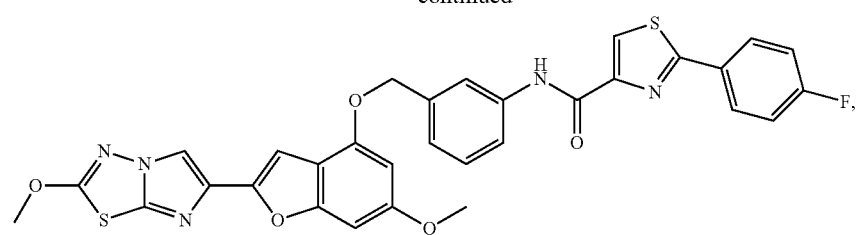
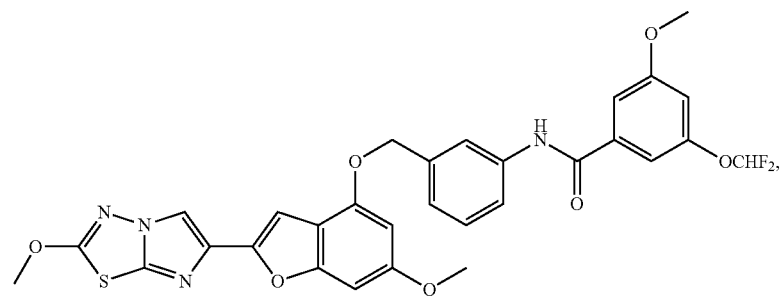
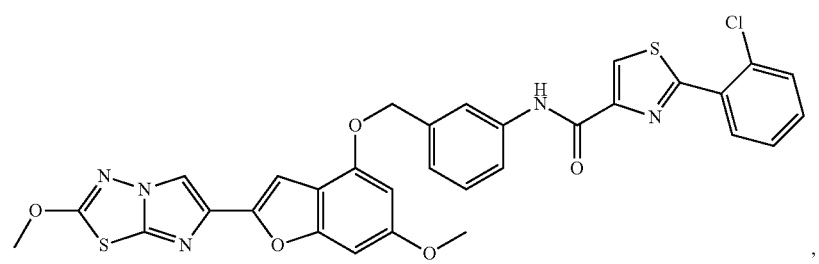
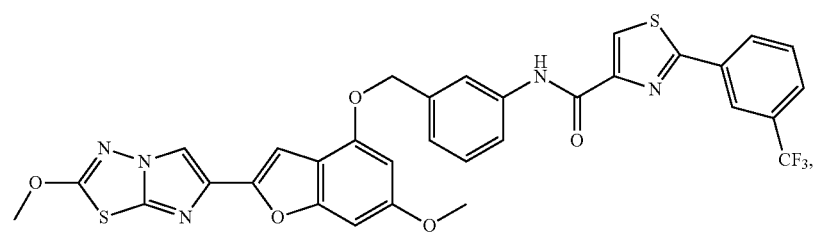
,
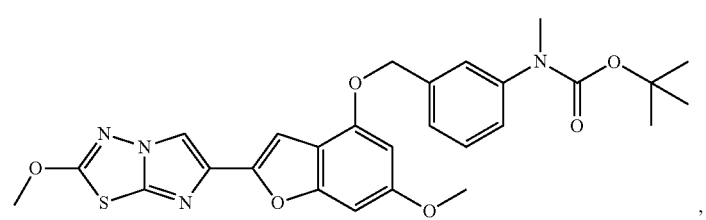
,
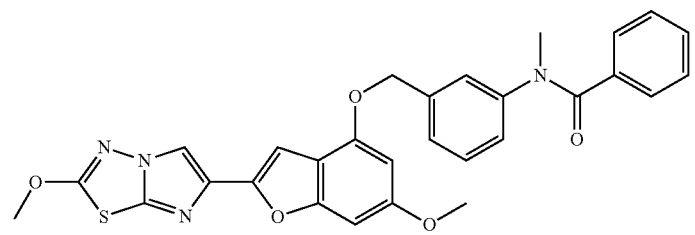
,
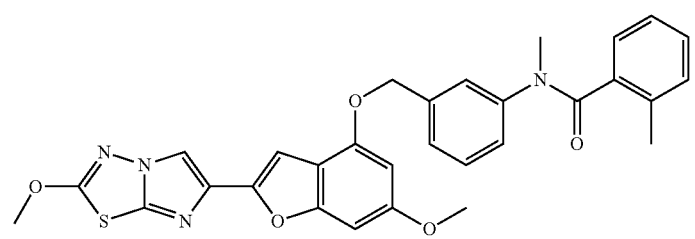
,

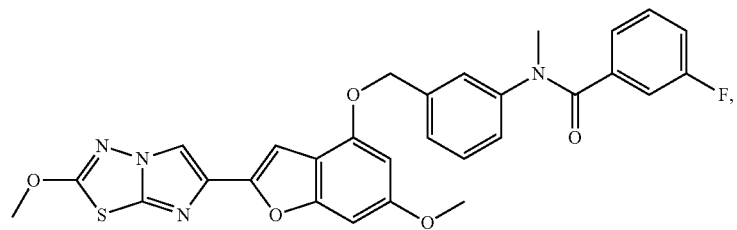
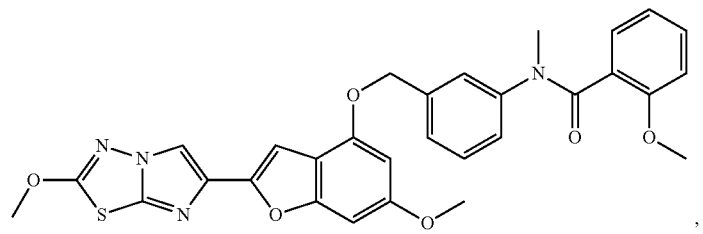,
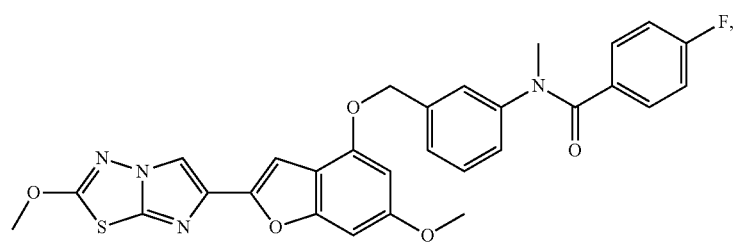
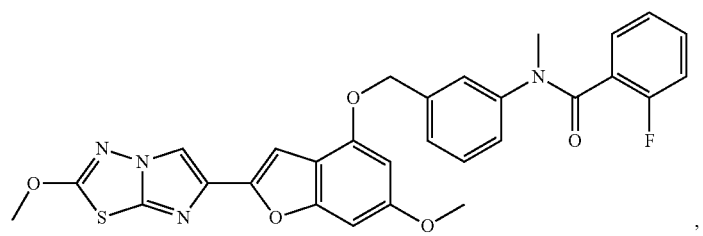,
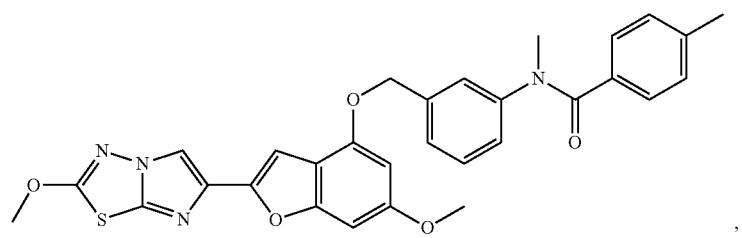
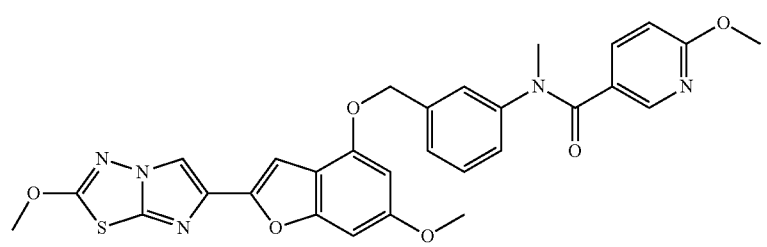,
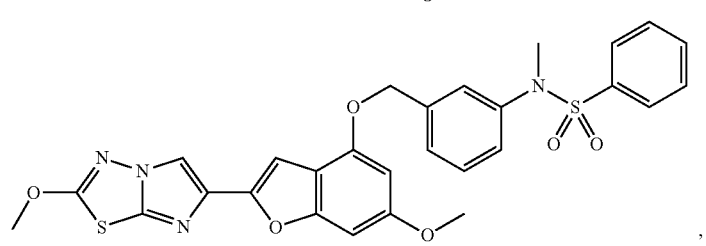,

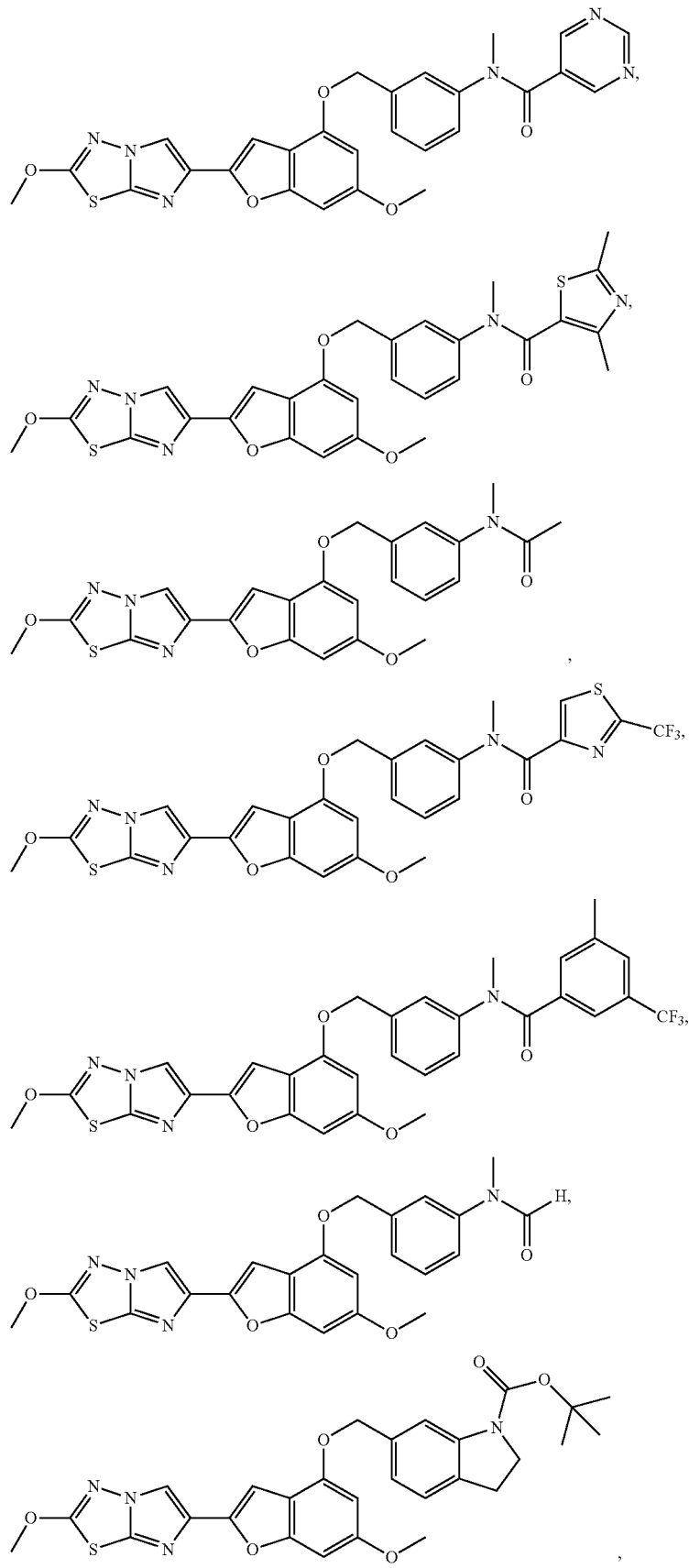

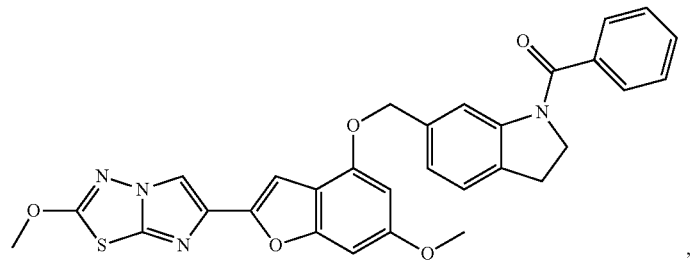,
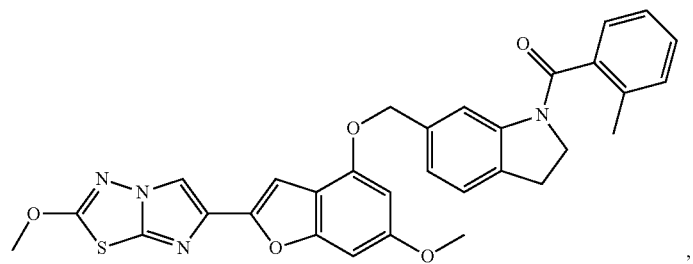,
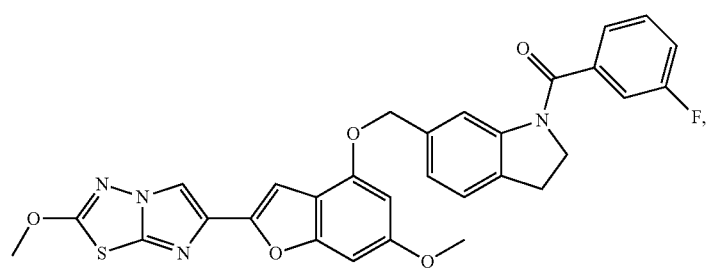,
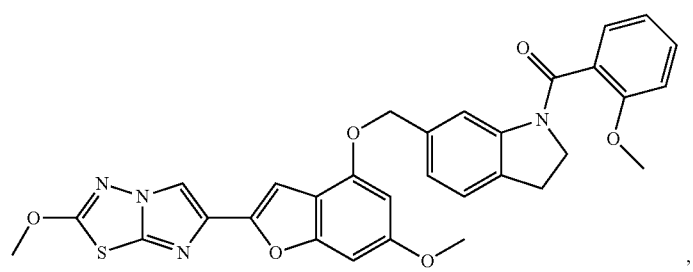,
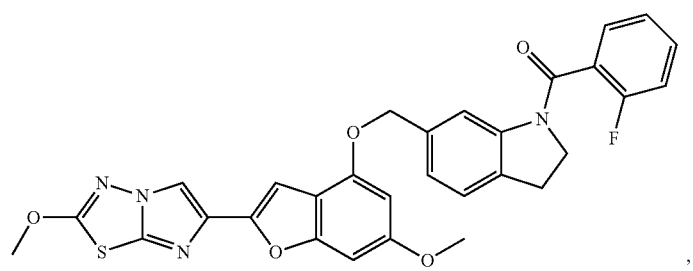,
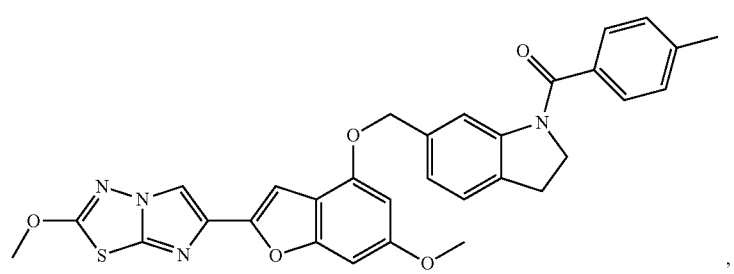,

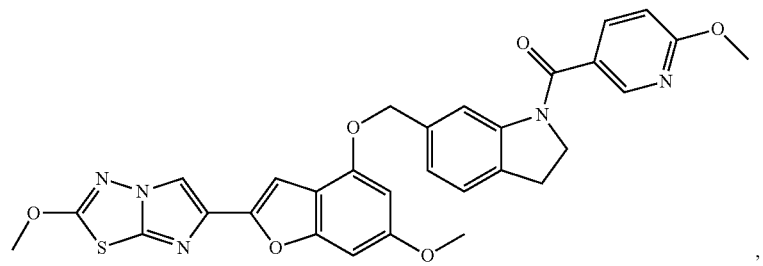,
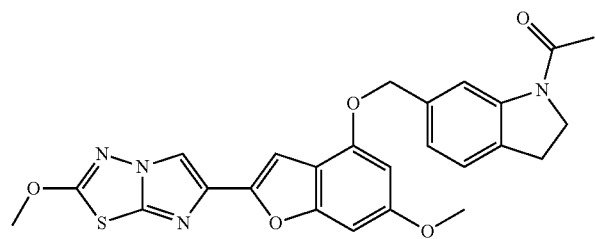,
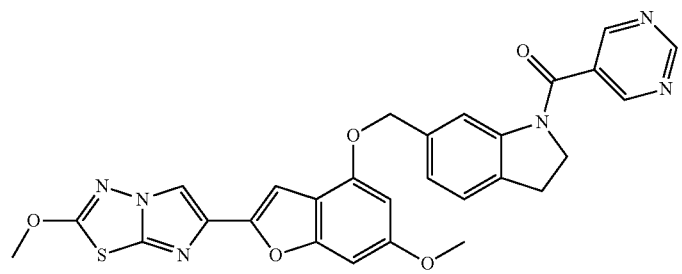,
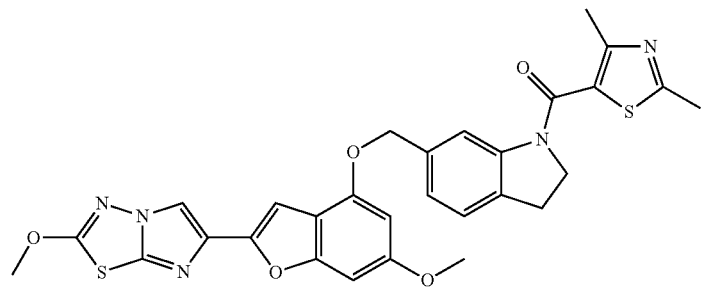,
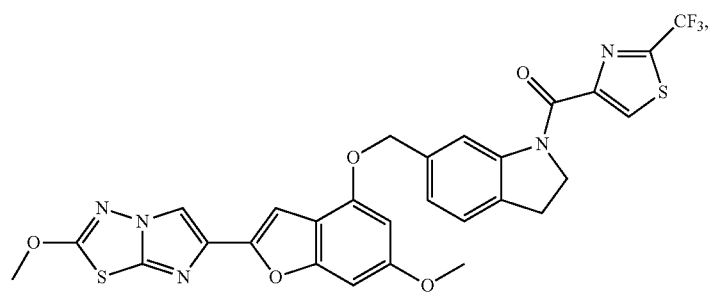,
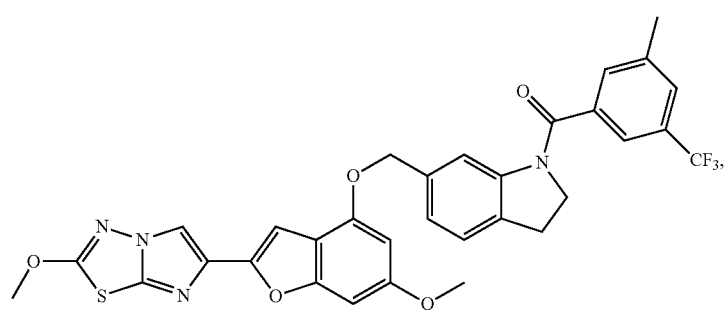,

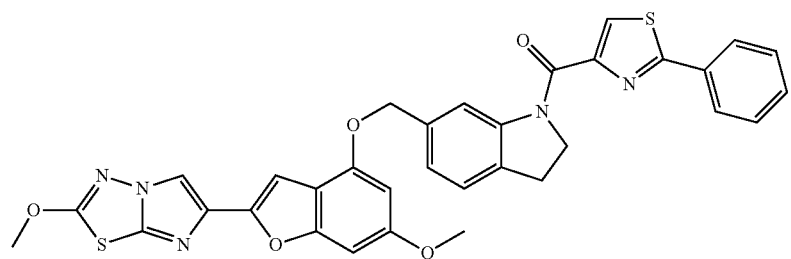,
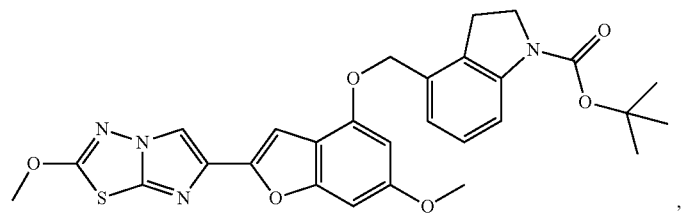,
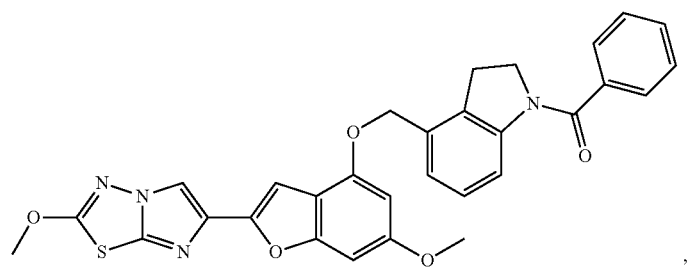,
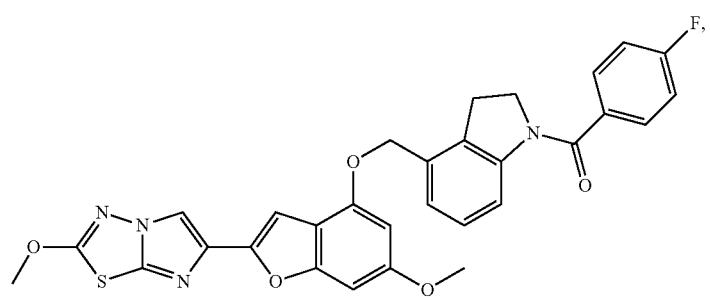,
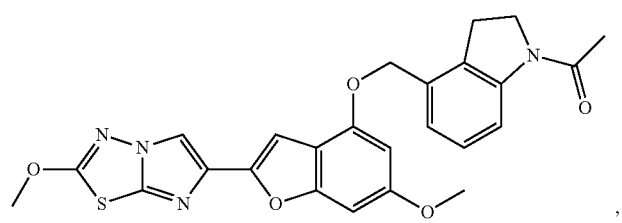,
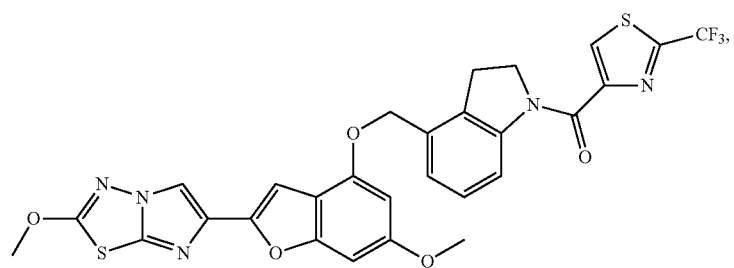

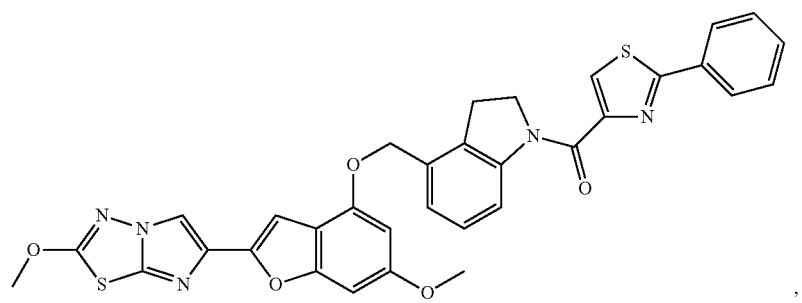,
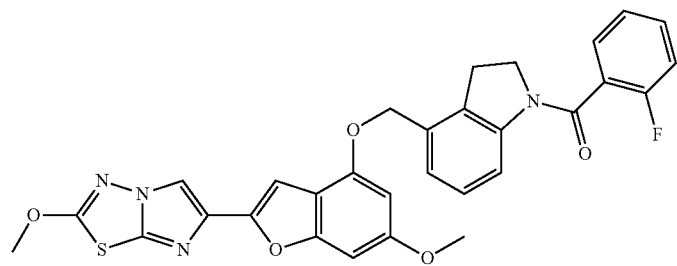,
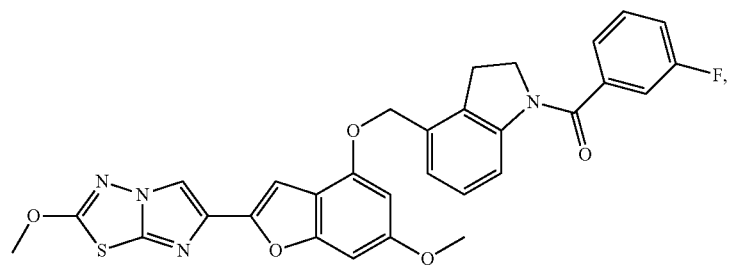,
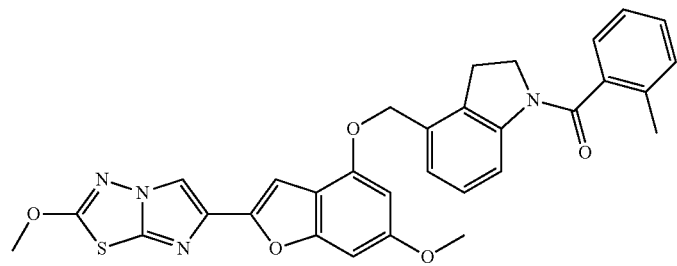,
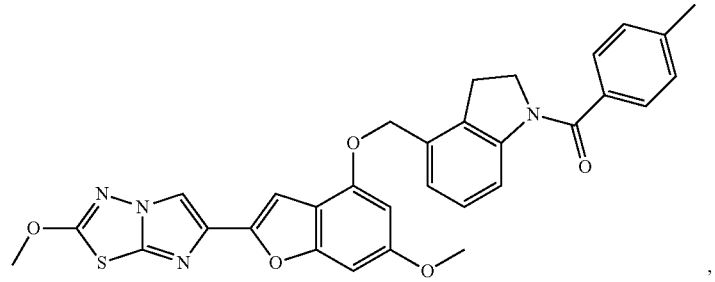,
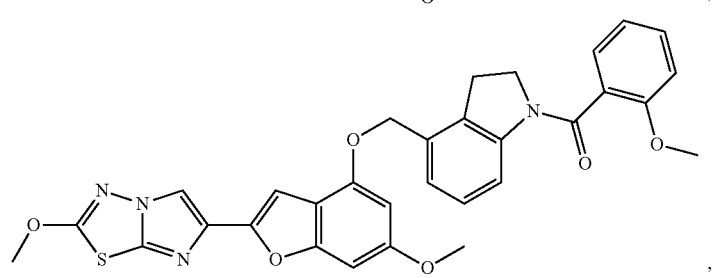,

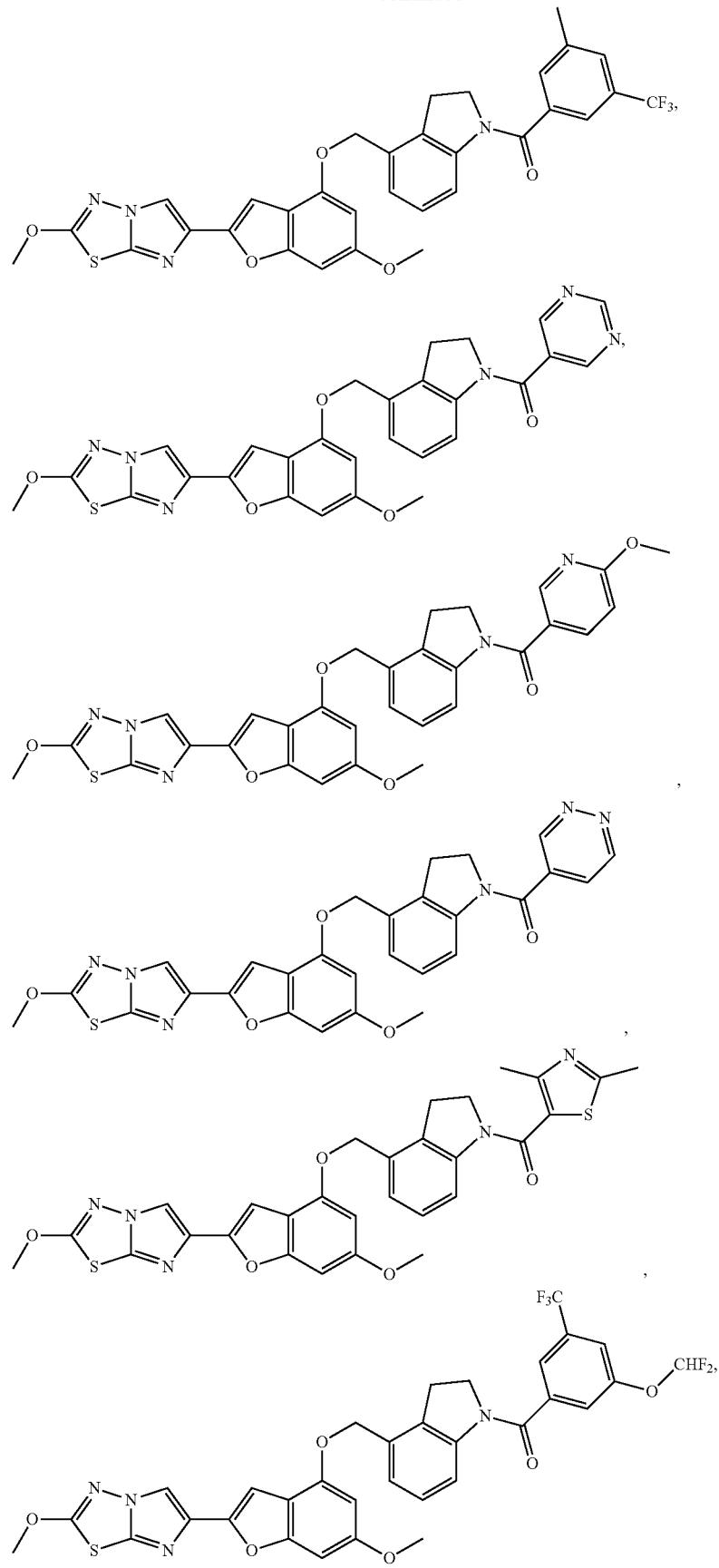

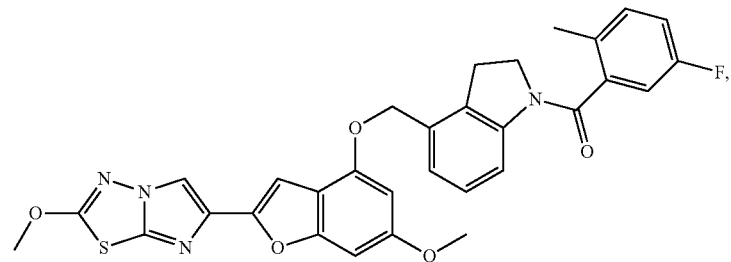
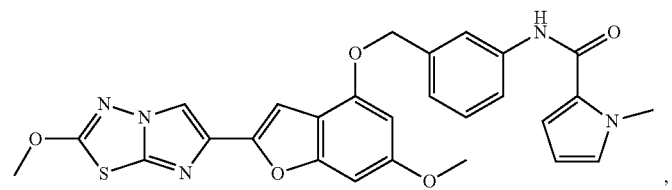
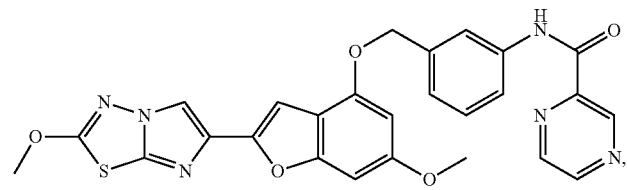
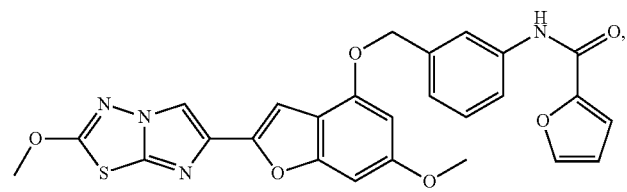
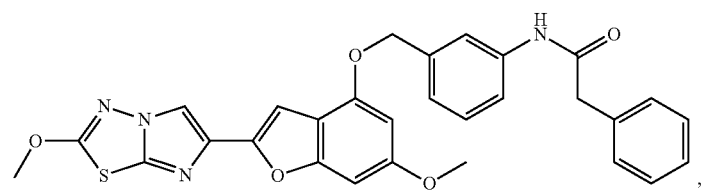
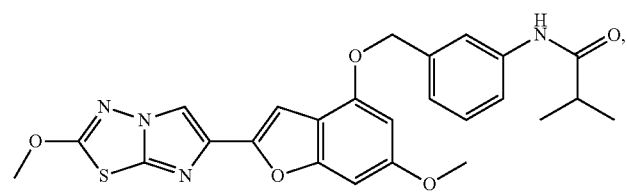
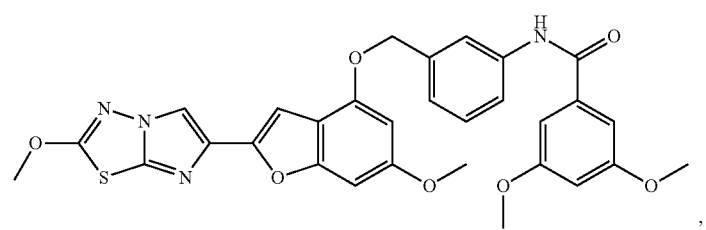
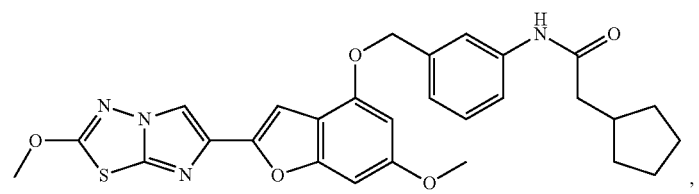

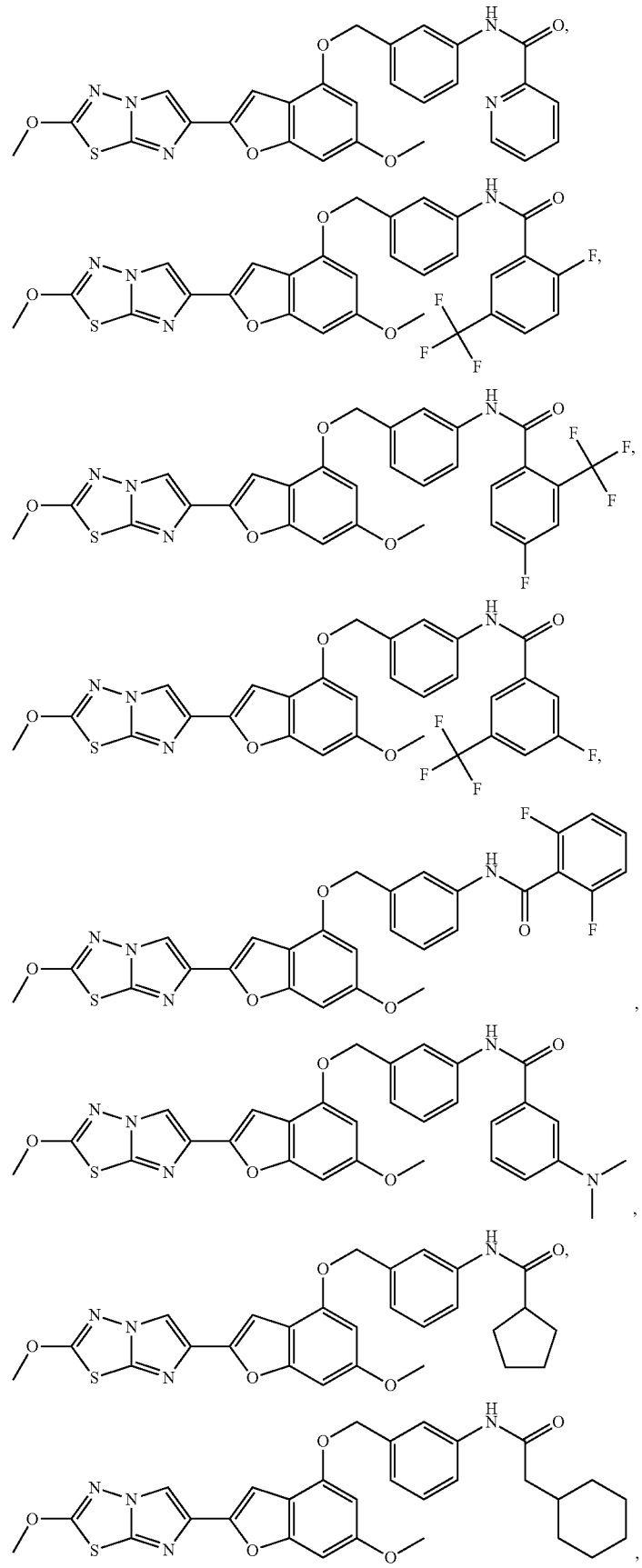

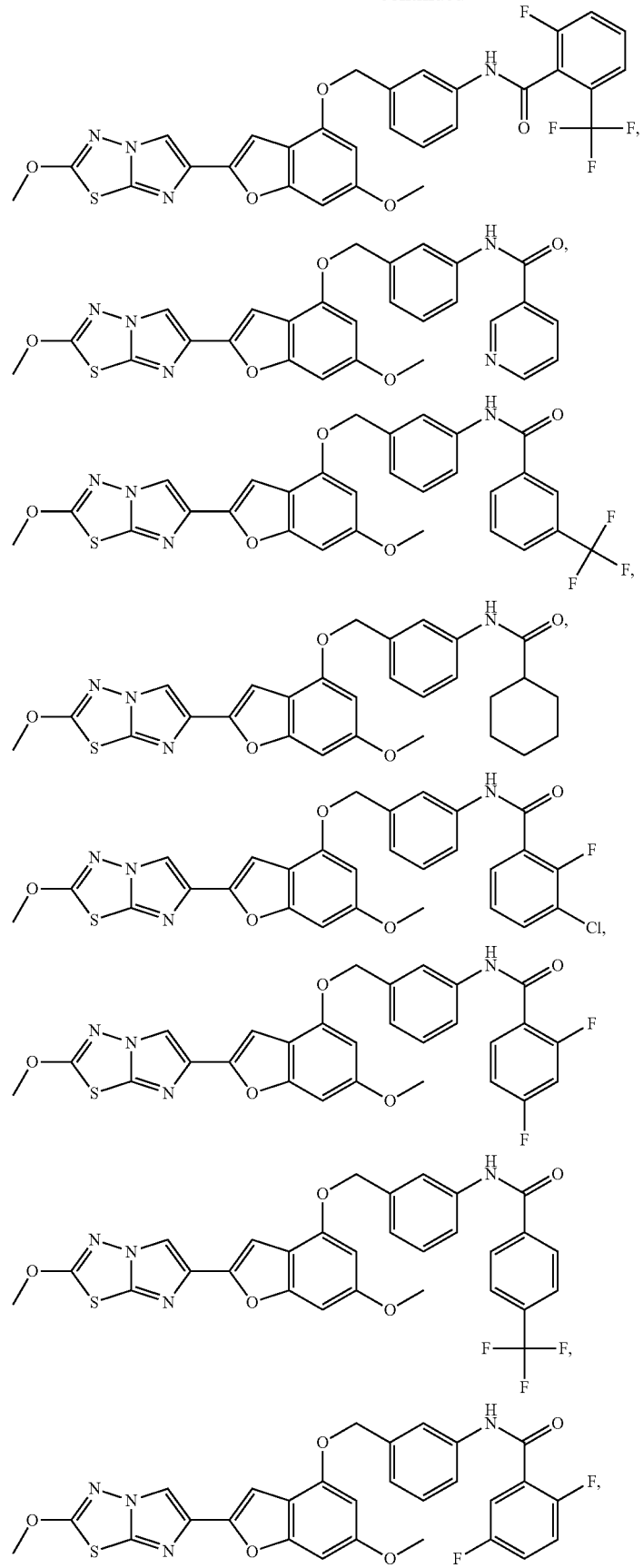

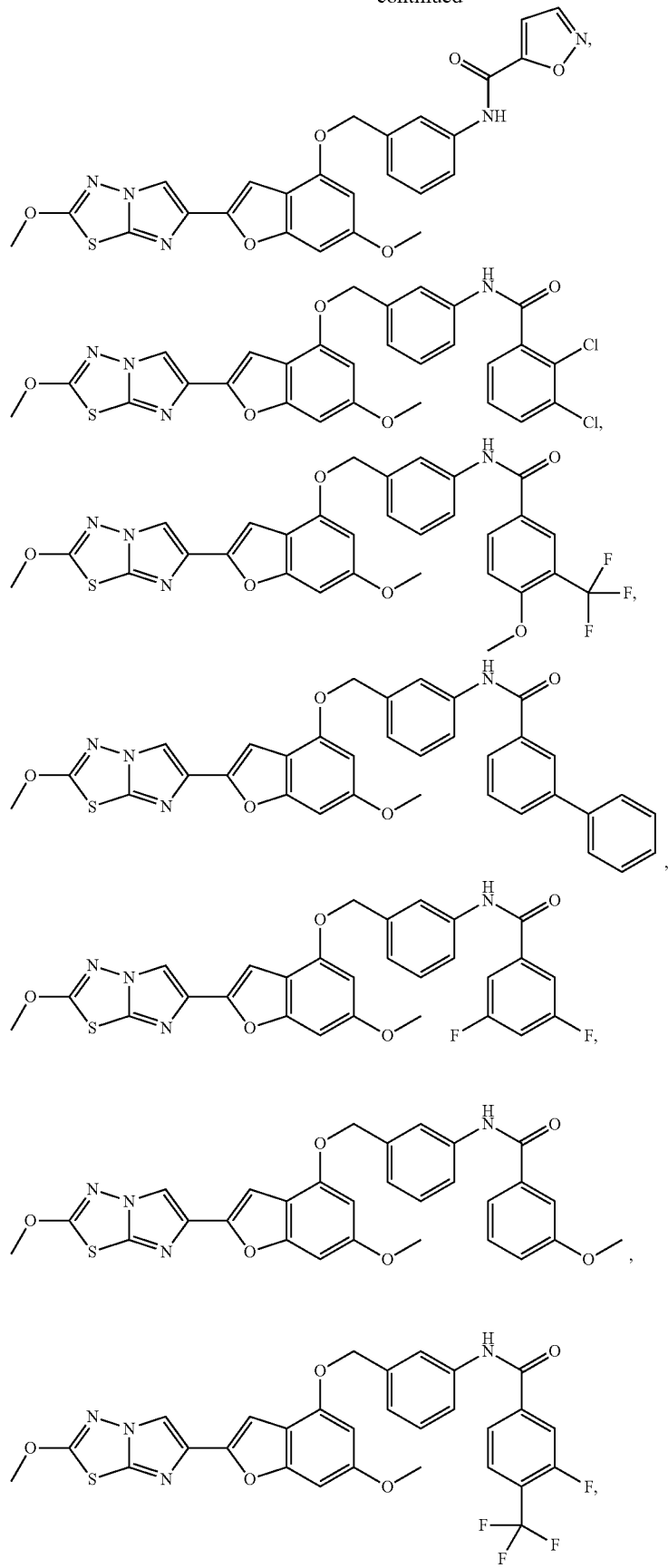

-continued

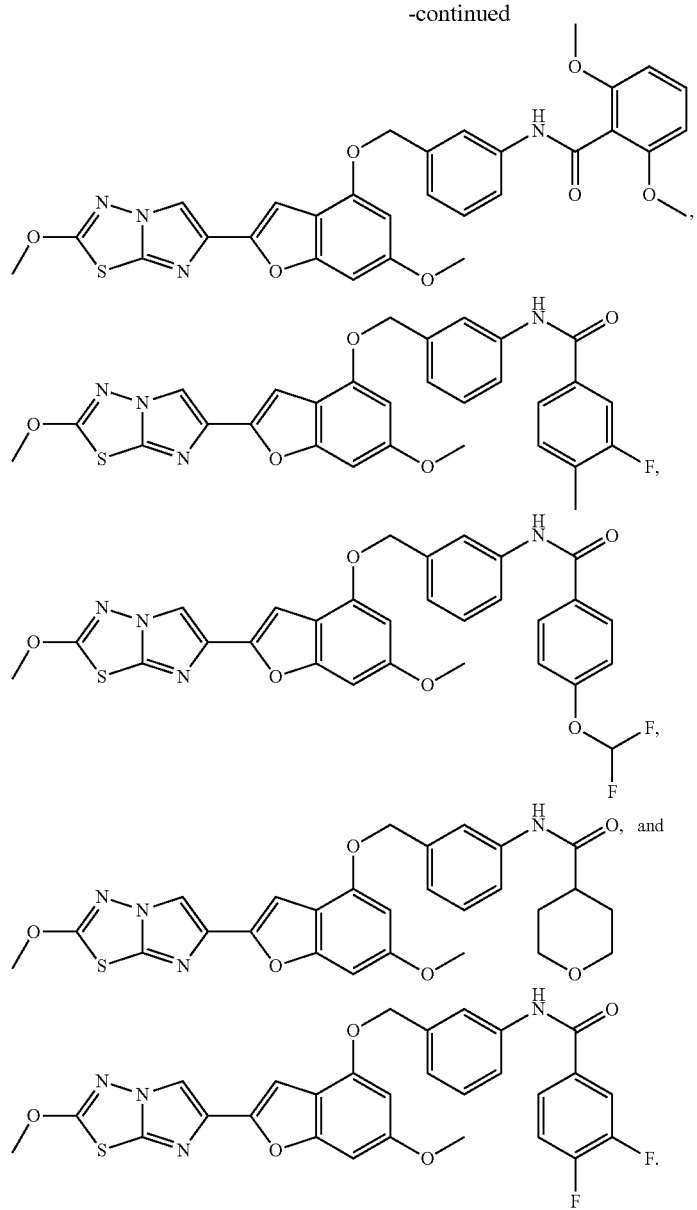

14. A pharmaceutical composition, which comprises a pharmaceutically acceptable carrier and a compound as defined in claim 1, or a stereoisomer, tautomer, or pharmaceutically acceptable salt thereof, alone or in combination with another therapeutic agent.

15. A method of treating a thromboembolic disorder or the primary or secondary prophylaxis of a thromboembolic disorder comprising administering a therapeutically effective amount of a compound as defined in claim 1, or a stereoisomer, tautomer, or pharmaceutically acceptable salt thereof, to a subject in need thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

16. A method of inhibiting or preventing platelet aggregation comprising administering a therapeutically effective amount of a compound as defined in claim 1, or a stereoisomer, tautomer, or pharmaceutically acceptable salt thereof, to a subject in need thereof.

17. A method of treating a thromboembolic disorder or the primary or secondary prophylaxis of a thromboembolic disorder comprising administering the pharmaceutical composition as defined in claim 14, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

18. A method of inhibiting or preventing platelet aggregation comprising administering the pharmaceutical composition as defined in claim 14.

* * * * *